(12) United States Patent
Sharma et al.

(10) Patent No.: US 11,331,140 B2
(45) Date of Patent: May 17, 2022

(54) HEATED VAPOR ABLATION SYSTEMS AND METHODS FOR TREATING CARDIAC CONDITIONS

(71) Applicant: Aqua Heart, Inc., Santa Ana, CA (US)

(72) Inventors: Virender K. Sharma, Paradise Valley, AZ (US); Kevin Holbrook, Los Gatos, CA (US); Holger Friedrich, Meerbusch (DE); Eric Steven Fain, Menlo Park, CA (US)

(*) Notice: Subject to any disclaimer, the term of this patent is extended or adjusted under 35 U.S.C. 154(b) by 211 days.

(21) Appl. No.: 16/567,984

(22) Filed: Sep. 11, 2019

(65) Prior Publication Data

US 2020/0085496 A1 Mar. 19, 2020

Related U.S. Application Data

(63) Continuation-in-part of application No. 15/600,670, filed on May 19, 2017, now Pat. No. 10,695,126.
(Continued)

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/6853* (2013.01); *A61B 2018/00232* (2013.01);
(Continued)

(58) Field of Classification Search
CPC ............. A61B 18/04; A61B 18/1492; A61B 2018/0022; A61B 2018/00232; A61B 2018/00255; A61B 2018/00357; A61B 2018/00375; A61B 2018/00791; A61B 2018/00875; A61B 2018/048;
(Continued)

(56) References Cited

U.S. PATENT DOCUMENTS

| 408,899 A | 8/1889 | Small |
| 697,181 A | 4/1902 | Smith |

(Continued)

FOREIGN PATENT DOCUMENTS

| CN | 2757751 Y | 2/2006 |
| CN | 1803113 A | 7/2006 |

(Continued)

OTHER PUBLICATIONS

International Search Report for PCT/US19/50662, dated Jan. 7, 2020.

(Continued)

*Primary Examiner* — Michael F Peffley
(74) *Attorney, Agent, or Firm* — Novel IP

(57) ABSTRACT

Cardiac ablation catheters include an outer balloon positioned at a distal end of the catheter and configured to have an inner balloon disposed therein. The outer balloon is inflated with a first fluid that has a temperature less than 100 degrees Celsius, while the inner balloon is inflated with heated vapor. An area of contact between the two balloons, comprising a surface area less than the total surface area of either balloon, creates a hot zone for ablating cardiac tissue through the transfer of thermal energy from the contact area to the cardiac tissue.

30 Claims, 141 Drawing Sheets

Related U.S. Application Data

(60) Provisional application No. 62/425,144, filed on Nov. 22, 2016, provisional application No. 62/338,871, filed on May 19, 2016, provisional application No. 62/844,222, filed on May 7, 2019, provisional application No. 62/729,777, filed on Sep. 11, 2018.

(51) Int. Cl.
*A61B 18/04* (2006.01)
*A61B 18/00* (2006.01)

(52) U.S. Cl.
CPC .............. *A61B 2018/00357* (2013.01); *A61B 2018/00791* (2013.01); *A61B 2018/048* (2013.01)

(58) Field of Classification Search
CPC ........ A61B 2090/064; A61B 2090/065; A61B 2090/376; A61B 2218/007; A61B 5/6853
See application file for complete search history.

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,289,138 A | 9/1981 | Halvorsen |
| RE32,204 E | 7/1986 | Halvorsen |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Ins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,147,355 A | 9/1992 | Friedman |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,243,980 A | 9/1993 | Mehra |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,383,852 A | 1/1995 | Stevens-Wright |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,462,527 A | 10/1995 | Stevens-Wright |
| 5,470,308 A | 11/1995 | Edwards |
| 5,470,309 A | 11/1995 | Edwards |
| 5,482,037 A | 1/1996 | Borghi |
| 5,484,400 A | 1/1996 | Edwards |
| 5,500,012 A | 3/1996 | Brucker |
| 5,503,638 A | 4/1996 | Cooper |
| 5,507,784 A | 4/1996 | Hill |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,772 A | 11/1996 | Lennox |
| 5,575,803 A | 11/1996 | Cooper |
| 5,584,872 A | 12/1996 | Lafontaine |
| 5,588,432 A | 12/1996 | Crowley |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,630,837 A | 5/1997 | Crowley |
| 5,667,488 A | 9/1997 | Lundquist |
| 5,669,907 A | 9/1997 | Plattjr |
| 5,672,153 A | 9/1997 | Lax |
| 5,672,290 A | 9/1997 | Levy |
| 5,674,191 A | 10/1997 | Edwards |
| 5,674,217 A | 10/1997 | Wahlstrom |
| 5,681,282 A | 10/1997 | Eggers |
| 5,683,366 A | 11/1997 | Eggers |
| 5,685,878 A | 11/1997 | Falwell |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,715,817 A | 2/1998 | Stevens-Wright |
| 5,720,718 A | 2/1998 | Rosen |
| 5,720,719 A | 2/1998 | Edwards |
| 5,730,719 A | 3/1998 | Edwards |

(56) References Cited

U.S. PATENT DOCUMENTS

| | | |
|---|---|---|
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,759,158 A | 6/1998 | Swanson |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,807,249 A | 9/1998 | Qin |
| 5,810,764 A | 9/1998 | Eggers |
| 5,820,580 A | 10/1998 | Edwards |
| 5,824,703 A | 10/1998 | Clarkjr |
| 5,827,268 A | 10/1998 | Laufer |
| 5,830,179 A | 11/1998 | Mikus |
| 5,836,906 A | 11/1998 | Edwards |
| 5,840,031 A | 11/1998 | Crowley |
| 5,840,079 A | 11/1998 | Warman |
| 5,843,019 A | 12/1998 | Eggers |
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | Mcgaffigan |
| 5,879,295 A | 3/1999 | Li |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,895,417 A | 4/1999 | Pomeranz |
| 5,897,553 A | 4/1999 | Mulier |
| 5,902,272 A | 5/1999 | Eggers |
| 5,913,856 A | 6/1999 | Chia |
| 5,919,188 A | 7/1999 | Shearon |
| 5,931,835 A | 8/1999 | Mackey |
| 5,935,102 A | 8/1999 | Bowden |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | Mcgaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Irq |
| 5,989,212 A | 11/1999 | Sussman |
| 5,989,238 A | 11/1999 | Ginsburg |
| 5,989,249 A | 11/1999 | Kirwanjr |
| 5,989,445 A | 11/1999 | Wise |
| 5,993,462 A | 11/1999 | Pomeranz |
| 5,997,499 A | 12/1999 | Sussman |
| 6,002,955 A | 12/1999 | Willems |
| 6,004,269 A | 12/1999 | Crowley |
| 6,010,500 A | 1/2000 | Sherman |
| 6,014,581 A | 1/2000 | Whayne |
| 6,015,406 A | 1/2000 | Goble |
| 6,015,407 A | 1/2000 | Rieb |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,035,226 A | 3/2000 | Panescu |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,064,902 A | 5/2000 | Haissaguerre |
| 6,066,132 A | 5/2000 | Chen |
| 6,066,134 A | 5/2000 | Eggers |
| 6,068,629 A | 5/2000 | Haissaguerre |
| 6,071,281 A | 6/2000 | Burnside |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | Lafleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,119,041 A | 9/2000 | Pomeranz |
| 6,120,496 A | 9/2000 | Whayne |
| 6,126,682 A | 10/2000 | Sharkey |
| 6,129,669 A | 10/2000 | Dorin |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,152,144 A | 11/2000 | Lesh |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | Lafontaine |
| 6,174,308 B1 | 1/2001 | Goble |
| 6,176,842 B1 | 1/2001 | Tachibana |
| 6,178,354 B1 | 1/2001 | Gibson |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,192,266 B1 | 2/2001 | Dupree |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,217,528 B1 | 4/2001 | Koblish |
| 6,217,607 B1 | 4/2001 | Alt |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 | 5/2001 | Swartz |

(56) References Cited

U.S. PATENT DOCUMENTS

| | | |
|---|---|---|
| 6,238,389 B1 | 5/2001 | Paddock |
| 6,238,391 B1 | 5/2001 | Olsen |
| 6,241,666 B1 | 6/2001 | Pomeranz |
| 6,241,702 B1 | 6/2001 | Lundquist |
| 6,245,065 B1 | 6/2001 | Dorin |
| 6,254,597 B1 | 7/2001 | Rizoiu |
| 6,254,600 B1 | 7/2001 | Willink |
| 6,256,537 B1 | 7/2001 | Stoop |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,267,760 B1 | 7/2001 | Swanson |
| 6,270,476 B1 | 8/2001 | Santoianni |
| 6,270,515 B1 | 8/2001 | Linden |
| 6,277,112 B1 | 8/2001 | Underwood |
| 6,277,114 B1 | 8/2001 | Bullivant |
| 6,277,130 B1 | 8/2001 | Shadduck |
| 6,283,961 B1 | 9/2001 | Underwood |
| 6,283,989 B1 | 9/2001 | Laufer |
| 6,287,274 B1 | 9/2001 | Sussman |
| 6,287,301 B1 | 9/2001 | Thompson |
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,620 B1 | 10/2001 | Shadduck |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,375 B1 | 10/2001 | Glines |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,327,505 B1 | 12/2001 | Medhkour |
| 6,331,171 B1 | 12/2001 | Cohen |
| 6,355,032 B1 | 3/2002 | Hovda |
| 6,356,790 B1 | 3/2002 | Maguire |
| 6,358,248 B1 | 3/2002 | Mulier |
| 6,363,937 B1 | 4/2002 | Hovda |
| 6,364,877 B1 | 4/2002 | Goble |
| 6,369,465 B1 | 4/2002 | Swanson |
| 6,375,635 B1 | 4/2002 | Moutafis |
| 6,379,350 B1 | 4/2002 | Sharkey |
| 6,379,351 B1 | 4/2002 | Thapliyal |
| 6,389,311 B1 | 5/2002 | Whayne |
| 6,391,025 B1 | 5/2002 | Weinstein |
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,505 B1 | 7/2002 | Fleischman |
| 6,416,507 B1 | 7/2002 | Eggers |
| 6,416,508 B1 | 7/2002 | Eggers |
| 6,416,509 B1 | 7/2002 | Goble |
| 6,419,673 B1 | 7/2002 | Edwards |
| 6,423,027 B1 | 7/2002 | Gonon |
| 6,428,537 B1 | 8/2002 | Swanson |
| 6,432,103 B1 | 8/2002 | Ellsberry |
| 6,434,424 B1 | 8/2002 | Igel |
| 6,438,407 B1 | 8/2002 | Ousdigian |
| 6,440,127 B2 | 8/2002 | Mcgovern |
| 6,443,950 B1 | 9/2002 | Sutton |
| 6,458,231 B1 | 10/2002 | Wapner |
| 6,461,296 B1 | 10/2002 | Desai |
| 6,461,350 B1 | 10/2002 | Underwood |
| 6,461,354 B1 | 10/2002 | Olsen |
| 6,461,356 B1 | 10/2002 | Patterson |
| 6,464,694 B1 | 10/2002 | Massengill |
| 6,464,695 B2 | 10/2002 | Hovda |
| 6,464,699 B1 | 10/2002 | Swanson |
| 6,464,700 B1 | 10/2002 | Koblish |
| 6,468,270 B1 | 10/2002 | Hovda |
| 6,468,271 B1 | 10/2002 | Wentzel |
| 6,468,272 B1 | 10/2002 | Koblish |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,488,680 B1 | 12/2002 | Francischelli |
| 6,491,710 B2 | 12/2002 | Satake |
| 6,493,589 B1 | 12/2002 | Medhkour |
| 6,494,880 B1 | 12/2002 | Swanson |
| 6,500,144 B1 | 12/2002 | Russell |
| 6,500,173 B2 | 12/2002 | Underwood |
| 6,508,816 B2 | 1/2003 | Shadduck |
| 6,510,854 B2 | 1/2003 | Goble |
| 6,514,245 B1 | 2/2003 | Holland |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,540,743 B2 | 4/2003 | Olson |
| 6,542,781 B1 | 4/2003 | Koblish |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | Mcgaffigan |
| 6,551,309 B1 | 4/2003 | LePivert |
| 6,557,559 B1 | 5/2003 | Eggers |
| 6,558,314 B1 | 5/2003 | Adelman |
| 6,558,379 B1 | 5/2003 | Batchelor |
| 6,564,098 B1 | 5/2003 | Kerver |
| 6,566,636 B1 | 5/2003 | Bentley |
| 6,569,146 B1 | 5/2003 | Werner |
| 6,569,162 B2 | 5/2003 | He |
| 6,572,611 B1 | 6/2003 | Falwell |
| 6,575,929 B2 | 6/2003 | Sussman |
| 6,575,932 B1 | 6/2003 | Obrien |
| 6,575,968 B1 | 6/2003 | Eggers |
| 6,579,270 B2 | 6/2003 | Sussman |
| 6,579,288 B1 | 6/2003 | Swanson |
| 6,582,423 B2 | 6/2003 | Thapliyal |
| 6,585,639 B1 | 7/2003 | Kotmel |
| 6,585,732 B2 | 7/2003 | Mulier |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,084 B2 | 8/2003 | Acker |
| 6,605,087 B2 | 8/2003 | Swartz |
| 6,607,529 B1 | 8/2003 | Jones |
| 6,610,043 B1 | 8/2003 | Ingenito |
| 6,610,055 B1 | 8/2003 | Swanson |
| 6,613,046 B1 | 9/2003 | Jenkins |
| 6,620,130 B1 | 9/2003 | Ginsburg |
| 6,620,155 B1 | 9/2003 | Underwood |
| 6,620,159 B2 | 9/2003 | Hegde |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,638,278 B2 | 10/2003 | Falwell |

(56) References Cited

U.S. PATENT DOCUMENTS

| | | | |
|---|---|---|---|
| 6,640,120 | B1 | 10/2003 | Swanson |
| 6,647,300 | B1 | 11/2003 | Ian |
| 6,648,847 | B2 | 11/2003 | Sussman |
| 6,650,937 | B2 | 11/2003 | Kerver |
| 6,652,555 | B1 | 11/2003 | VanTassel |
| 6,652,594 | B2 | 11/2003 | Francis |
| 6,653,525 | B2 | 11/2003 | Ingenito |
| 6,656,174 | B1 | 12/2003 | Hegde |
| 6,659,106 | B1 | 12/2003 | Hovda |
| 6,659,981 | B2 | 12/2003 | Stewart |
| 6,666,863 | B2 | 12/2003 | Wentzel |
| 6,666,864 | B2 | 12/2003 | Bencini |
| 6,668,195 | B2 | 12/2003 | Warman |
| 6,669,685 | B1 | 12/2003 | Rizoiu |
| 6,669,693 | B2 | 12/2003 | Friedman |
| 6,669,694 | B2 | 12/2003 | Shadduck |
| 6,673,071 | B2 | 1/2004 | Vandusseldorp |
| 6,676,628 | B2 | 1/2004 | Sussman |
| 6,676,629 | B2 | 1/2004 | Andrew |
| 6,679,264 | B1 | 1/2004 | Deem |
| 6,679,269 | B2 | 1/2004 | Swanson |
| 6,679,879 | B2 | 1/2004 | Shadduck |
| 6,682,520 | B2 | 1/2004 | Ingenito |
| 6,692,491 | B1 | 2/2004 | Phan |
| 6,692,494 | B1 | 2/2004 | Cooper |
| 6,695,785 | B2 | 2/2004 | Brisken |
| 6,695,839 | B2 | 2/2004 | Sharkey |
| 6,699,244 | B2 | 3/2004 | Carranza |
| 6,706,038 | B2 | 3/2004 | Francischelli |
| 6,708,056 | B2 | 3/2004 | Duchon |
| 6,711,444 | B2 | 3/2004 | Koblish |
| 6,712,811 | B2 | 3/2004 | Underwood |
| 6,712,812 | B2 | 3/2004 | Roschak |
| 6,716,190 | B1 | 4/2004 | Glines |
| 6,716,252 | B2 | 4/2004 | Lazarovitz |
| 6,718,206 | B2 | 4/2004 | Casavant |
| 6,719,738 | B2 | 4/2004 | Mehier |
| 6,719,754 | B2 | 4/2004 | Underwood |
| 6,719,755 | B2 | 4/2004 | Sliwajr |
| 6,723,064 | B2 | 4/2004 | Babaev |
| 6,726,684 | B1 | 4/2004 | Woloszko |
| 6,726,696 | B1 | 4/2004 | Houser |
| 6,726,708 | B2 | 4/2004 | Lasheras |
| 6,730,079 | B2 | 5/2004 | Lovewell |
| 6,734,405 | B2 | 5/2004 | Centanni |
| 6,740,082 | B2 | 5/2004 | Shadduck |
| 6,745,080 | B2 | 6/2004 | Koblish |
| 6,746,447 | B2 | 6/2004 | Davison |
| 6,749,604 | B1 | 6/2004 | Eggers |
| 6,755,790 | B2 | 6/2004 | Stewart |
| 6,755,794 | B2 | 6/2004 | Soukup |
| 6,758,846 | B2 | 7/2004 | Goble |
| 6,760,616 | B2 | 7/2004 | Hoey |
| 6,763,836 | B2 | 7/2004 | Tasto |
| 6,764,487 | B2 | 7/2004 | Mulier |
| 6,766,202 | B2 | 7/2004 | Underwood |
| 6,770,070 | B1 | 8/2004 | Balbierz |
| 6,770,071 | B2 | 8/2004 | Woloszko |
| 6,772,012 | B2 | 8/2004 | Ricart |
| 6,773,431 | B2 | 8/2004 | Eggers |
| 6,776,765 | B2 | 8/2004 | Soukup |
| 6,776,780 | B2 | 8/2004 | Mulier |
| 6,780,178 | B2 | 8/2004 | Palanker |
| 6,780,180 | B1 | 8/2004 | Goble |
| 6,788,969 | B2 | 9/2004 | Dupree |
| 6,805,130 | B2 | 10/2004 | Tasto |
| 6,813,520 | B2 | 11/2004 | Truckai |
| 6,814,731 | B2 | 11/2004 | Swanson |
| 6,824,515 | B2 | 11/2004 | Suorsa |
| 6,827,718 | B2 | 12/2004 | Hutchins |
| 6,832,996 | B2 | 12/2004 | Woloszko |
| 6,837,884 | B2 | 1/2005 | Woloszko |
| 6,837,886 | B2 | 1/2005 | Collins |
| 6,837,887 | B2 | 1/2005 | Woloszko |
| 6,837,888 | B2 | 1/2005 | Ciarrocca |
| 6,852,108 | B2 | 2/2005 | Barry |
| 6,860,847 | B2 | 3/2005 | Alferness |
| 6,860,868 | B1 | 3/2005 | Sussman |
| 6,875,194 | B2 | 4/2005 | Mackool |
| 6,887,238 | B2 | 5/2005 | Jahns |
| 6,893,438 | B2 | 5/2005 | Hall |
| 6,896,672 | B1 | 5/2005 | Eggers |
| 6,896,674 | B1 | 5/2005 | Woloszko |
| 6,896,675 | B2 | 5/2005 | Leung |
| 6,901,291 | B2 | 5/2005 | Stoop |
| 6,901,927 | B2 | 6/2005 | Deem |
| 6,904,909 | B2 | 6/2005 | Andreas |
| 6,905,475 | B2 | 6/2005 | Hauschild |
| 6,905,496 | B1 | 6/2005 | Ellman |
| 6,907,881 | B2 | 6/2005 | Suki |
| 6,908,464 | B2 | 6/2005 | Jenkins |
| 6,911,028 | B2 | 6/2005 | Shadduck |
| 6,913,604 | B2 | 7/2005 | Mihalik |
| 6,915,806 | B2 | 7/2005 | Pacek |
| 6,916,317 | B2 | 7/2005 | Falwell |
| 6,916,318 | B2 | 7/2005 | Francischelli |
| 6,917,834 | B2 | 7/2005 | Koblish |
| 6,918,903 | B2 | 7/2005 | Bass |
| 6,921,385 | B2 | 7/2005 | Clements |
| 6,926,712 | B2 | 8/2005 | Phan |
| 6,926,714 | B1 | 8/2005 | Sra |
| 6,929,640 | B1 | 8/2005 | Underwood |
| 6,929,642 | B2 | 8/2005 | Xiao |
| 6,939,350 | B2 | 9/2005 | Phan |
| 6,949,096 | B2 | 9/2005 | Davison |
| 6,949,097 | B2 | 9/2005 | Stewart |
| 6,949,098 | B2 | 9/2005 | Mulier |
| 6,950,689 | B1 | 9/2005 | Willis |
| 6,952,615 | B2 | 10/2005 | Satake |
| 6,955,674 | B2 | 10/2005 | Eick |
| 6,955,675 | B2 | 10/2005 | Jain |
| 6,960,182 | B2 | 11/2005 | Moutafis |
| 6,960,203 | B2 | 11/2005 | Xiao |
| 6,960,204 | B2 | 11/2005 | Eggers |
| 6,969,376 | B2 | 11/2005 | Takagi |
| 6,972,014 | B2 | 12/2005 | Eum |
| 6,974,464 | B2 | 12/2005 | Quijano |
| 6,978,184 | B1 | 12/2005 | Marcus |
| 6,979,329 | B2 | 12/2005 | Burnside |
| 6,986,769 | B2 | 1/2006 | Nelson |
| 6,989,010 | B2 | 1/2006 | Francischelli |
| 6,991,028 | B2 | 1/2006 | Comeaux |
| 6,991,631 | B2 | 1/2006 | Woloszko |
| 6,994,092 | B2 | 2/2006 | Erik |
| 7,004,940 | B2 | 2/2006 | Ryan |
| 7,004,941 | B2 | 2/2006 | Tvinnereim |
| 7,008,401 | B2 | 3/2006 | Thompson |
| 7,008,417 | B2 | 3/2006 | Eick |
| 7,011,655 | B2 | 3/2006 | Thompson |
| 7,011,671 | B2 | 3/2006 | Welch |
| 7,014,652 | B2 | 3/2006 | Cioanta |
| 7,022,088 | B2 | 4/2006 | Keast |
| 7,025,762 | B2 | 4/2006 | Johnston |
| 7,031,504 | B1 | 4/2006 | Argiro |
| 7,047,068 | B2 | 5/2006 | Haissaguerre |
| 7,047,074 | B2 | 5/2006 | Connelly |
| 7,058,443 | B2 | 6/2006 | Struble |
| 7,079,892 | B2 | 7/2006 | Dahl |
| 7,081,115 | B2 | 7/2006 | Taimisto |
| 7,082,330 | B2 | 7/2006 | Stadler |
| 7,083,612 | B2 | 8/2006 | Littrup |
| 7,083,614 | B2 | 8/2006 | Fjield |
| 7,087,040 | B2 | 8/2006 | Mcguckinjr |
| 7,089,064 | B2 | 8/2006 | Manker |
| 7,094,215 | B2 | 8/2006 | Davison |
| 7,101,367 | B2 | 9/2006 | Xiao |
| 7,101,368 | B2 | 9/2006 | Lafontaine |
| 7,104,986 | B2 | 9/2006 | Hovda |
| 7,105,007 | B2 | 9/2006 | Hibler |
| 7,107,098 | B2 | 9/2006 | Sharma |
| 7,112,198 | B2 | 9/2006 | Satake |
| 7,113,838 | B2 | 9/2006 | Funk |
| RE39,358 | E | 10/2006 | Goble |
| 7,128,748 | B2 | 10/2006 | Mooradian |

(56) References Cited

U.S. PATENT DOCUMENTS

| | | |
|---|---|---|
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuesteriii |
| 7,144,588 B2 | 12/2006 | Oray |
| 7,153,301 B2 | 12/2006 | Swartz |
| 7,166,105 B2 | 1/2007 | Mulier |
| 7,169,143 B2 | 1/2007 | Eggers |
| 7,169,164 B2 | 1/2007 | Borillo |
| 7,172,589 B2 | 2/2007 | Lafontaine |
| 7,175,619 B2 | 2/2007 | Koblish |
| 7,175,734 B2 | 2/2007 | Stewart |
| 7,179,255 B2 | 2/2007 | Lettice |
| 7,181,273 B2 | 2/2007 | Havel |
| 7,182,764 B2 | 2/2007 | Jenkins |
| 7,186,234 B2 | 3/2007 | Dahla |
| 7,186,250 B2 | 3/2007 | Koblish |
| 7,189,227 B2 | 3/2007 | Lafontaine |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,255,695 B2 | 8/2007 | Falwell |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,285,119 B2 | 10/2007 | Stewart |
| 7,297,143 B2 | 11/2007 | Woloszko |
| 7,297,145 B2 | 11/2007 | Woloszko |
| 7,303,558 B2 | 12/2007 | Swanson |
| 7,311,705 B2 | 12/2007 | Sra |
| 7,318,821 B2 | 1/2008 | Lalonde |
| 7,320,325 B2 | 1/2008 | Duchon |
| 7,321,794 B2 | 1/2008 | Thacker |
| 7,322,973 B2 | 1/2008 | Nahon |
| 7,331,958 B2 | 2/2008 | Falwell |
| 7,335,195 B2 | 2/2008 | Mehier |
| 7,335,197 B2 | 2/2008 | Sage |
| 7,338,434 B1 | 3/2008 | Haarstad |
| 7,340,307 B2 | 3/2008 | Maguire |
| 7,347,856 B2 | 3/2008 | Wittenberger |
| 7,347,858 B2 | 3/2008 | Francischelli |
| 7,347,859 B2 | 3/2008 | Garabedian |
| 7,357,800 B2 | 4/2008 | Swanson |
| 7,364,546 B2 | 4/2008 | Dorin |
| 7,364,578 B2 | 4/2008 | Francischelli |
| 7,364,579 B2 | 4/2008 | Mulier |
| 7,367,972 B2 | 5/2008 | Francischelli |
| 7,371,233 B2 | 5/2008 | Swanson |
| 7,410,486 B2 | 8/2008 | Fuimaono |
| 7,419,500 B2 | 9/2008 | Marko |
| 7,422,588 B2 | 9/2008 | Mulier |
| 7,422,591 B2 | 9/2008 | Phan |
| 7,429,262 B2 | 9/2008 | Woloszko |
| 7,435,250 B2 | 10/2008 | Francischelli |
| 7,438,714 B2 | 10/2008 | Phan |
| 7,450,996 B2 | 11/2008 | Macdonald |
| 7,455,669 B2 | 11/2008 | Swanson |
| 7,470,228 B2 | 12/2008 | Connors |
| 7,470,272 B2 | 12/2008 | Mulier |
| 7,474,909 B2 | 1/2009 | Phan |
| 7,488,289 B2 | 2/2009 | Suorsa |
| 7,503,904 B2 | 3/2009 | Choi |
| 7,512,445 B2 | 3/2009 | Truckai |
| 7,517,315 B2 | 4/2009 | Willis |
| 7,549,987 B2 | 6/2009 | Shadduck |
| 7,549,988 B2 | 6/2009 | Eberl |
| 7,559,367 B2 | 7/2009 | Vinegar |
| 7,582,084 B2 | 9/2009 | Swanson |
| 7,585,295 B2 | 9/2009 | Ben-Nun |
| 7,585,310 B2 | 9/2009 | Phan |
| 7,597,147 B2 | 10/2009 | Vitek |
| 7,597,704 B2 | 10/2009 | Frazier |
| 7,608,072 B2 | 10/2009 | Swanson |
| 7,610,078 B2 | 10/2009 | Willis |
| 7,633,502 B2 | 12/2009 | Willis |
| 7,647,124 B2 | 1/2010 | Williams |
| 7,650,186 B2 | 1/2010 | Hastings |
| 7,662,151 B2 | 2/2010 | Crompton, Jr. |
| 7,674,256 B2 | 3/2010 | Marrouche |
| 7,674,259 B2 | 3/2010 | Shadduck |
| 7,678,108 B2 | 3/2010 | Chrisitian |
| 7,678,111 B2 | 3/2010 | Mulier |
| 7,706,860 B2 | 4/2010 | Mcgee |
| 7,706,882 B2 | 4/2010 | Francischelli |
| 7,711,421 B2 | 5/2010 | Shafer |
| 7,713,282 B2 | 5/2010 | Frazier |
| 7,720,520 B2 | 5/2010 | Willis |
| 7,722,604 B2 | 5/2010 | Brown, III |
| 7,727,228 B2 | 6/2010 | Abboud |
| 7,727,231 B2 | 6/2010 | Swanson |
| 7,734,346 B2 | 6/2010 | Van Bolhuis |
| 7,735,493 B2 | 6/2010 | Erik |
| 7,740,623 B2 | 6/2010 | Nayak |
| 7,740,627 B2 | 6/2010 | Gammie |
| 7,753,871 B2 | 7/2010 | Mehier |
| 7,758,580 B2 | 7/2010 | Rothstein |
| 7,785,289 B2 | 8/2010 | Rios |
| 7,785,323 B2 | 8/2010 | Jenkins |
| 7,792,580 B2 | 9/2010 | Borowitz |
| 7,794,454 B2 | 9/2010 | Abboud |
| 7,794,460 B2 | 9/2010 | Mulier |
| 7,818,039 B2 | 10/2010 | Jahns |
| 7,824,399 B2 | 11/2010 | Francischelli |
| 7,831,133 B2 | 11/2010 | Vinegar |
| 7,837,676 B2 | 11/2010 | Sinelnikov |
| 7,846,157 B2 | 12/2010 | Kozel |
| 7,850,685 B2 | 12/2010 | Kunis |
| 7,861,725 B2 | 1/2011 | Swanson |
| 7,862,561 B2 | 1/2011 | Swanson |
| 7,862,562 B2 | 1/2011 | Eberl |
| 7,871,409 B2 | 1/2011 | Briscoe |
| 7,877,137 B2 | 1/2011 | Whitehurst |
| 7,892,229 B2 | 2/2011 | Shadduck |
| 7,896,871 B2 | 3/2011 | Bhushan |
| 7,913,698 B2 | 3/2011 | Barry |
| 7,922,714 B2 | 4/2011 | Stevens-Wright |
| 7,937,161 B2 | 5/2011 | Hastings |
| 7,938,828 B2 | 5/2011 | Koblish |
| 7,953,475 B2 | 5/2011 | Harlev |
| 7,955,325 B2 | 6/2011 | Wittenberger |
| 7,959,630 B2 | 6/2011 | Taimisto |
| 7,963,963 B2 | 6/2011 | Francischelli |
| 7,972,327 B2 | 7/2011 | Eberl |
| 7,972,359 B2 | 7/2011 | Kreidler |
| 7,975,703 B2 | 7/2011 | Jahns |
| 7,976,541 B2 | 7/2011 | Mcgee |
| 7,993,323 B2 | 8/2011 | Barry |
| 8,002,738 B2 | 8/2011 | White |
| 8,007,497 B2 | 8/2011 | Young |
| RE42,724 E | 9/2011 | Falwell |
| 8,014,711 B2 | 9/2011 | Ito |
| 8,016,822 B2 | 9/2011 | Swanson |
| 8,016,823 B2 | 9/2011 | Shadduck |
| 8,027,791 B2 | 9/2011 | Soykan |
| 8,050,774 B2 | 11/2011 | Kveen |
| 8,052,676 B2 | 11/2011 | Swanson |
| 8,052,715 B2 | 11/2011 | Quinn |
| 8,055,357 B2 | 11/2011 | Swanson |
| 8,057,466 B2 | 11/2011 | Soykan |
| RE43,007 E | 12/2011 | Lalonde |
| 8,080,006 B2 | 12/2011 | Lafontaine |
| 8,086,293 B2 | 12/2011 | Boseck |
| 8,092,444 B2 | 1/2012 | Lentz |
| 8,116,884 B2 | 2/2012 | Jung |

(56) References Cited

U.S. PATENT DOCUMENTS

| | | |
|---|---|---|
| 8,123,741 B2 | 2/2012 | Marrouche |
| 8,142,424 B2 | 3/2012 | Swanson |
| 8,142,470 B2 | 3/2012 | Quinn |
| 8,145,113 B2 | 3/2012 | Murakami |
| 8,147,532 B2 | 4/2012 | Barry |
| 8,162,929 B2 | 4/2012 | Lentz |
| 8,162,941 B2 | 4/2012 | Christian |
| 8,165,691 B2 | 4/2012 | Ellingson |
| 8,172,837 B2 | 5/2012 | Rothstein |
| 8,187,269 B2 | 5/2012 | Shadduck |
| 8,197,496 B2 | 6/2012 | Roue |
| 8,197,527 B2 | 6/2012 | Borillo |
| 8,216,224 B2 | 7/2012 | Morris |
| 8,221,402 B2 | 7/2012 | Francischelli |
| 8,221,411 B2 | 7/2012 | Francischelli |
| 8,221,445 B2 | 7/2012 | Van Tassel |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,235,976 B2 | 8/2012 | Lafontaine |
| 8,251,985 B2 | 8/2012 | Hoey |
| 8,260,422 B2 | 9/2012 | Ellingson |
| 8,272,383 B2 | 9/2012 | Hoey |
| 8,273,079 B2 | 9/2012 | Hoey |
| 8,273,084 B2 | 9/2012 | Kunis |
| 8,290,600 B2 | 10/2012 | Hastings |
| 8,298,219 B2 | 10/2012 | Lalonde |
| 8,306,612 B2 | 11/2012 | Macadam |
| 8,313,485 B2 | 11/2012 | Shadduck |
| 8,322,335 B2 | 12/2012 | Barry |
| 8,332,035 B2 | 12/2012 | Iaizzo |
| 8,333,757 B2 | 12/2012 | Mazzone |
| 8,333,764 B2 | 12/2012 | Francischelli |
| 8,353,900 B2 | 1/2013 | Jung |
| 8,355,623 B2 | 1/2013 | Vinegar |
| 8,361,059 B2 | 1/2013 | Abboud |
| 8,372,065 B2 | 2/2013 | Hoey |
| 8,388,611 B2 | 3/2013 | Shadduck |
| 8,401,644 B2 | 3/2013 | Gunderson |
| 8,414,573 B2 | 4/2013 | Francischelli |
| 8,419,723 B2 | 4/2013 | Shadduck |
| 8,425,456 B2 | 4/2013 | Mihalik |
| 8,437,840 B2 | 5/2013 | Patel |
| 8,437,870 B2 | 5/2013 | Tsai |
| 8,444,636 B2 | 5/2013 | Shadduck |
| 8,454,587 B2 | 6/2013 | Lalonde |
| 8,460,282 B2 | 6/2013 | Mcauley |
| 8,465,481 B2 | 6/2013 | Mazzone |
| 8,475,440 B2 | 7/2013 | Abboud |
| 8,480,664 B2 | 7/2013 | Watson |
| 8,504,132 B2 | 8/2013 | Friedman |
| 8,512,326 B2 | 8/2013 | Shadduck |
| 8,512,337 B2 | 8/2013 | Francischelli |
| 8,521,074 B2 | 8/2013 | Murakami |
| 8,521,281 B2 | 8/2013 | Patel |
| 8,527,027 B2 | 9/2013 | Falwell |
| 8,556,892 B2 | 10/2013 | Hong |
| 8,571,626 B2 | 10/2013 | Lau |
| 8,574,226 B2 | 11/2013 | Shadduck |
| 8,579,888 B2 | 11/2013 | Hoey |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,591,504 B2 | 11/2013 | Tin |
| 8,606,369 B2 | 12/2013 | Williams |
| 8,615,287 B2 | 12/2013 | Harlev |
| 8,617,149 B2 | 12/2013 | Lafontaine |
| 8,617,152 B2 | 12/2013 | Werneth |
| 8,623,010 B2 | 1/2014 | Ocel |
| 8,632,529 B2 | 1/2014 | Bencini |
| 8,632,530 B2 | 1/2014 | Hoey |
| 8,641,711 B2 | 2/2014 | Kelly |
| 8,642,747 B2 | 2/2014 | Sharma |
| 8,644,932 B2 | 2/2014 | Seifert |
| 8,647,336 B2 | 2/2014 | Werneth |
| 8,647,339 B2 | 2/2014 | Satake |
| 8,663,245 B2 | 3/2014 | Francischelli |
| 8,679,104 B2 | 3/2014 | Abboud |
| 8,682,436 B2 | 3/2014 | Ghosh |
| 8,685,055 B2 | 4/2014 | Vantassel |
| 8,688,469 B2 | 4/2014 | Ziegler |
| 8,700,120 B2 | 4/2014 | Koblish |
| 8,702,693 B2 | 4/2014 | Subramaniam |
| 8,702,696 B2 | 4/2014 | White |
| 8,706,260 B2 | 4/2014 | Stewart |
| 8,715,274 B2 | 5/2014 | Watson |
| 8,721,632 B2 | 5/2014 | Hoey |
| 8,727,983 B2 | 5/2014 | Kinnison |
| 8,734,380 B2 | 5/2014 | Barry |
| 8,744,578 B2 | 6/2014 | Ellingson |
| 8,744,601 B2 | 6/2014 | Spotnitz |
| 8,747,352 B1 | 6/2014 | Lalonde |
| 8,758,341 B2 | 6/2014 | Shadduck |
| 8,761,626 B2 | 6/2014 | Seo |
| 8,764,740 B2 | 7/2014 | Watson |
| 8,764,745 B2 | 7/2014 | Malewicz |
| 8,774,909 B2 | 7/2014 | Patel |
| 8,790,300 B2 | 7/2014 | Tun |
| 8,795,271 B2 | 8/2014 | Koblish |
| 8,798,706 B2 | 8/2014 | Kim |
| 8,801,702 B2 | 8/2014 | Hoey |
| 8,805,466 B2 | 8/2014 | Salahieh |
| 8,805,496 B2 | 8/2014 | Ellingson |
| 8,821,484 B2 | 9/2014 | Ingle |
| 8,821,485 B2 | 9/2014 | Heberer |
| 8,821,488 B2 | 9/2014 | Stewart |
| 8,827,952 B2 | 9/2014 | Subramaniam |
| 8,838,254 B2 | 9/2014 | Mcclure |
| 8,845,558 B2 | 9/2014 | Macadam |
| 8,849,400 B2 | 9/2014 | Gunderson |
| 8,858,549 B2 | 10/2014 | Shadduck |
| 8,870,859 B2 | 10/2014 | Swanson |
| 8,886,296 B2 | 11/2014 | Patel |
| 8,900,223 B2 | 12/2014 | Shadduck |
| 8,911,430 B2 | 12/2014 | Hoey |
| 8,911,434 B2 | 12/2014 | Wittenberger |
| 8,926,602 B2 | 1/2015 | Pageard |
| 8,926,635 B2 | 1/2015 | Francischelli |
| 8,929,969 B2 | 1/2015 | Gillis |
| 8,945,116 B2 | 2/2015 | Macadam |
| 8,951,247 B2 | 2/2015 | Ding |
| 8,968,354 B2 | 3/2015 | Wang |
| 8,974,451 B2 | 3/2015 | Smith |
| 8,983,606 B2 | 3/2015 | Ellingson |
| 8,992,519 B2 | 3/2015 | Kim |
| 9,002,454 B2 | 4/2015 | Ghosh |
| 9,005,194 B2 | 4/2015 | Oral |
| 9,008,788 B2 | 4/2015 | Jenison |
| 9,028,486 B2 | 5/2015 | Collins |
| 9,034,006 B2 | 5/2015 | Quinn |
| 9,039,687 B2 | 5/2015 | Condie |
| 9,039,712 B2 | 5/2015 | Abboud |
| 9,050,074 B2 | 6/2015 | Joye |
| 9,061,155 B2 | 6/2015 | Gillberg |
| 9,072,516 B2 | 7/2015 | Sherman |
| 9,072,911 B2 | 7/2015 | Hastings |
| 9,089,272 B2 | 7/2015 | Thakur |
| 9,089,314 B2 | 7/2015 | Wittenberger |
| 9,095,321 B2 | 8/2015 | Phelan |
| 9,095,350 B2 | 8/2015 | Condie |
| 9,095,715 B2 | 8/2015 | Gillberg |
| 9,096,685 B2 | 8/2015 | Sharma |
| 9,113,858 B2 | 8/2015 | Barry |
| 9,113,911 B2 | 8/2015 | Sherman |
| 9,113,944 B2 | 8/2015 | Shadduck |
| 9,119,636 B2 | 9/2015 | Venkata |
| 9,125,667 B2 | 9/2015 | Stone |
| 9,125,668 B2 | 9/2015 | Subramaniam |
| 9,149,198 B2 | 10/2015 | Werneth |
| 9,149,320 B2 | 10/2015 | Kuck |
| 9,155,590 B2 | 10/2015 | Mathur |
| 9,161,801 B2 | 10/2015 | Hoey |

(56) References Cited

U.S. PATENT DOCUMENTS

| | | |
|---|---|---|
| 9,168,080 B2 | 10/2015 | Wittenberger |
| 9,179,973 B2 | 11/2015 | Nabutovsky |
| 9,186,080 B2 | 11/2015 | Shuros |
| 9,198,708 B2 | 12/2015 | Hoey |
| 9,204,889 B2 | 12/2015 | Shadduck |
| 9,205,268 B2 | 12/2015 | Yoon |
| 9,211,156 B2 | 12/2015 | Kim |
| 9,233,193 B2 | 1/2016 | Truckai |
| 9,289,145 B2 | 3/2016 | Grenz |
| 9,295,513 B2 | 3/2016 | Watson |
| 9,314,612 B2 | 4/2016 | Dollimer |
| 9,320,564 B2 | 4/2016 | Avitall |
| 9,326,815 B2 | 5/2016 | Watson |
| 9,332,920 B2 | 5/2016 | Thakur |
| 9,333,023 B2 | 5/2016 | Wittenberger |
| 9,339,657 B2 | 5/2016 | Stanger |
| 9,345,507 B2 | 5/2016 | Hoey |
| 9,345,528 B2 | 5/2016 | Laske |
| 9,345,529 B2 | 5/2016 | Mihalik |
| 9,345,540 B2 | 5/2016 | Mallin |
| 9,351,783 B2 | 5/2016 | Jannicke |
| 9,351,789 B2 | 5/2016 | Novichenok |
| 9,370,329 B2 | 6/2016 | Tun |
| 9,387,032 B2 | 7/2016 | Martin |
| 9,387,310 B2 | 7/2016 | Satake |
| 9,433,457 B2 | 9/2016 | Shadduck |
| 9,456,867 B2 | 10/2016 | Lawrence |
| 9,463,064 B2 | 10/2016 | Subramaniam |
| 9,468,487 B2 | 10/2016 | Shadduck |
| 9,474,467 B2 | 10/2016 | Harlev |
| 9,474,516 B2 | 10/2016 | Clark |
| 9,486,280 B2 | 11/2016 | Koblish |
| 9,517,017 B2 | 12/2016 | Shuros |
| 9,526,434 B2 | 12/2016 | Harlev |
| 9,526,435 B2 | 12/2016 | Ghosh |
| 9,526,555 B2 | 12/2016 | Hoey |
| 9,532,725 B2 | 1/2017 | Laughner |
| 9,532,828 B2 | 1/2017 | Condie |
| 9,539,046 B2 | 1/2017 | Wittenberger |
| 9,554,848 B2 | 1/2017 | Stewart |
| 9,561,043 B2 | 2/2017 | Warnking |
| 9,566,113 B2 | 2/2017 | Werneth |
| 9,572,536 B2 | 2/2017 | Abboud |
| 9,579,034 B2 | 2/2017 | Thakur |
| 9,597,140 B2 | 3/2017 | Mihalik |
| 9,603,651 B2 | 3/2017 | Ghosh |
| 9,603,659 B2 | 3/2017 | Subramaniam |
| 9,610,045 B2 | 4/2017 | Du |
| 9,615,875 B2 * | 4/2017 | Shadduck ............ A61B 17/122 |
| 9,615,879 B2 | 4/2017 | Kim |
| 9,622,806 B2 | 4/2017 | Mihalik |
| 9,636,032 B2 | 5/2017 | Thakur |
| 9,636,172 B2 | 5/2017 | Hu |
| 9,642,555 B2 | 5/2017 | Bonner |
| 9,642,675 B2 | 5/2017 | Werneth |
| 9,643,024 B2 | 5/2017 | Reinke |
| 9,649,040 B2 | 5/2017 | Laughner |
| 9,655,666 B2 | 5/2017 | Markowitz |
| 9,655,667 B2 | 5/2017 | Hon |
| 9,655,668 B2 | 5/2017 | Ingle |
| 9,656,063 B2 | 5/2017 | Kelley |
| 9,662,470 B2 | 5/2017 | Roman |
| 9,675,263 B2 | 6/2017 | Deac |
| 9,675,270 B2 | 6/2017 | Sarkar |
| 9,675,806 B2 | 6/2017 | Ellingson |
| 9,681,817 B2 | 6/2017 | Maskara |
| 9,687,166 B2 | 6/2017 | Subramaniam |
| 9,693,819 B2 | 7/2017 | Francischelli |
| 9,730,600 B2 | 8/2017 | Thakur |
| 9,730,602 B2 | 8/2017 | Harlev |
| 9,737,223 B2 | 8/2017 | Du |
| 9,743,972 B2 | 8/2017 | Wittenberger |
| 9,743,973 B2 | 8/2017 | Pageard |
| 9,744,023 B2 | 8/2017 | Wang |
| 9,744,364 B2 | 8/2017 | Gordon |
| 9,750,556 B2 | 9/2017 | Lafontaine |
| 9,750,567 B2 | 9/2017 | Falwell |
| 9,750,570 B2 | 9/2017 | Condie |
| 9,757,191 B2 | 9/2017 | Avitall |
| 9,757,194 B2 | 9/2017 | Werneth |
| 9,757,535 B2 | 9/2017 | Rajagopalan |
| 9,763,625 B2 | 9/2017 | Laughner |
| 9,795,314 B2 | 10/2017 | Laughner |
| 9,814,523 B2 | 11/2017 | Condie |
| 9,844,641 B2 | 12/2017 | Rajagopalan |
| 9,848,795 B2 | 12/2017 | Marecki |
| 9,848,946 B2 | 12/2017 | Edmunds |
| 9,861,370 B2 | 1/2018 | Clark |
| 9,861,422 B2 | 1/2018 | Hareland |
| 9,861,423 B2 | 1/2018 | Lalonde |
| 9,872,717 B2 | 1/2018 | Bencini |
| 9,883,936 B2 | 2/2018 | Sutton |
| 9,907,599 B2 | 3/2018 | Hoey |
| 9,919,158 B2 | 3/2018 | Ellingson |
| 9,925,359 B2 | 3/2018 | Lalonde |
| 9,931,134 B2 | 4/2018 | Hissong |
| 9,931,152 B2 | 4/2018 | Wittenberger |
| 9,936,996 B2 | 4/2018 | Zachman |
| 9,936,999 B2 | 4/2018 | Lalonde |
| 9,956,401 B2 | 5/2018 | Hastings |
| 9,958,515 B2 | 5/2018 | Ellingson |
| 9,974,607 B2 | 5/2018 | Stone |
| 9,993,279 B2 | 6/2018 | Avitall |
| 10,010,368 B2 | 7/2018 | Laske |
| 10,010,716 B2 | 7/2018 | Ellingson |
| 10,022,538 B2 | 7/2018 | Drasler |
| 10,034,708 B2 | 7/2018 | Zarins |
| 10,039,467 B2 | 8/2018 | Stewart |
| 10,064,697 B2 * | 9/2018 | Sharma ................ A61B 18/04 |
| 10,179,019 B2 | 1/2019 | Chee |
| 10,299,857 B2 | 5/2019 | Rajagopalan |
| 10,864,352 B2 | 12/2020 | Rajagopalan |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1 | 6/2002 | Shadduck |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0156470 A1 | 10/2002 | Shadduck |
| 2002/0161326 A1 | 10/2002 | Sussman |
| 2002/0177846 A1 | 11/2002 | Mulier |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |

(56) References Cited

U.S. PATENT DOCUMENTS

| | | |
|---|---|---|
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | Mcgurk |
| 2006/0036237 A1 | 2/2006 | Davison |
| 2006/0041277 A1 | 2/2006 | Deem |
| 2006/0047291 A1 | 3/2006 | Barry |
| 2006/0085054 A1 | 4/2006 | Zikorus |
| 2006/0089636 A1 | 4/2006 | Christopherson |
| 2006/0095032 A1 | 5/2006 | Jackson |
| 2006/0100619 A1 | 5/2006 | Mcclurken |
| 2006/0130830 A1 | 6/2006 | Barry |
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0264832 A1 | 11/2006 | Skwarek |
| 2006/0276871 A1 | 12/2006 | Lamson |
| 2007/0032785 A1 | 2/2007 | Diederich |
| 2007/0036417 A1 | 2/2007 | Irq |
| 2007/0049920 A1 | 3/2007 | Mcclurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1 | 9/2007 | Ren |
| 2007/0239197 A1 | 10/2007 | Dubey |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | Mclean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | Mclean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | LePivert |
| 2009/0018553 A1 | 1/2009 | Mclean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0082837 A1 | 3/2009 | Gellman |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0221998 A1 | 9/2009 | Epstein |
| 2009/0227998 A1 | 9/2009 | Aljuri |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1 | 3/2010 | Hoey |
| 2010/0094270 A1 | 4/2010 | Sharma |
| 2010/0114082 A1 | 5/2010 | Sharma |
| 2010/0114083 A1 | 5/2010 | Sharma |
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0168624 A1 | 7/2010 | Sliwa |
| 2010/0179416 A1 | 7/2010 | Hoey |
| 2010/0179528 A1 | 7/2010 | Shadduck |
| 2010/0204688 A1 | 8/2010 | Hoey |
| 2010/0262133 A1 | 10/2010 | Hoey |
| 2010/0274260 A1 | 10/2010 | Darpiany |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0172654 A1 | 7/2011 | Barry |
| 2011/0184400 A1 | 7/2011 | Pageard |
| 2011/0190751 A1 | 8/2011 | Ingle |
| 2011/0238144 A1 | 9/2011 | Hoey |
| 2011/0264090 A1 | 10/2011 | Shadduck |
| 2011/0276046 A1 | 11/2011 | Heimbecher |
| 2012/0065632 A1 | 3/2012 | Shadduck |
| 2012/0078078 A1 | 3/2012 | Macadam |
| 2012/0101413 A1 | 4/2012 | Beetel |
| 2012/0116376 A1 | 5/2012 | Hoey |
| 2012/0232409 A1 | 9/2012 | Stahmann |
| 2012/0259271 A1 | 10/2012 | Shadduck |
| 2012/0323167 A1 | 12/2012 | Hoey |
| 2013/0006231 A1 | 1/2013 | Sharma |
| 2013/0030410 A1 | 1/2013 | Drasler |
| 2013/0074847 A1 | 3/2013 | Hoey |
| 2013/0079772 A1 | 3/2013 | Shadduck |
| 2013/0116683 A1 | 5/2013 | Shadduck |
| 2013/0165914 A1 | 6/2013 | Satake |
| 2013/0172867 A1 | 7/2013 | Shadduck |
| 2013/0197555 A1 | 8/2013 | Schaer |
| 2013/0237978 A1 | 9/2013 | Shadduck |
| 2013/0267939 A1 | 10/2013 | Barry |
| 2013/0296837 A1 | 11/2013 | Burnett |
| 2013/0345670 A1 | 12/2013 | Rajagopalan |
| 2014/0025057 A1 | 1/2014 | Hoey |
| 2014/0031805 A1 | 1/2014 | Shadduck |
| 2014/0107637 A1 | 4/2014 | Hoey |
| 2014/0114306 A1 | 4/2014 | Harada |
| 2014/0200569 A1 | 7/2014 | Shadduck |
| 2014/0200570 A1 | 7/2014 | Hoey |

(56) References Cited

U.S. PATENT DOCUMENTS

| | | | |
|---|---|---|---|
| 2014/0276713 A1 | 9/2014 | Hoey | |
| 2014/0288543 A1 | 9/2014 | Hoey | |
| 2014/0324037 A1 | 10/2014 | Hoey | |
| 2014/0357956 A1 | 12/2014 | Salahieh | |
| 2014/0358137 A1 | 12/2014 | Hu | |
| 2014/0371736 A1 | 12/2014 | Levin | |
| 2015/0025515 A1 | 1/2015 | Hoey | |
| 2015/0025516 A1 | 1/2015 | Hoey | |
| 2015/0080883 A1 | 3/2015 | Haverkost | |
| 2015/0126990 A1* | 5/2015 | Sharma | A61B 18/1492 606/30 |
| 2015/0265329 A1 | 9/2015 | Lalonde | |
| 2016/0220297 A1 | 8/2016 | Kroon | |
| 2016/0354140 A1 | 12/2016 | Sharma | |
| 2016/0354144 A1 | 12/2016 | Caplan | |
| 2017/0165002 A1 | 6/2017 | Sharma | |
| 2017/0231678 A1 | 8/2017 | Sharma | |
| 2017/0367755 A1* | 12/2017 | Sharma | A61B 18/04 |
| 2019/0110830 A1 | 4/2019 | Hastings | |
| 2019/0269449 A1 | 9/2019 | Hastings | |
| 2019/0388133 A1 | 12/2019 | Sharma | |

FOREIGN PATENT DOCUMENTS

| | | |
|---|---|---|
| CN | 102238920 | 9/2011 |
| CN | 102238920 A | 11/2011 |
| CN | 103582463 A | 2/2014 |
| CN | 105228547 A | 1/2016 |
| EP | 1602338 B1 | 12/2005 |
| EP | 2341859 | 7/2011 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 02069821 | 9/2002 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 | 4/2010 |
| WO | 2010042461 A1 | 4/2010 |
| WO | 2012167213 | 12/2012 |
| WO | 2012167213 A2 | 12/2012 |
| WO | 2013086461 A1 | 6/2013 |
| WO | 2013152119 A1 | 10/2013 |
| WO | 2014113724 | 7/2014 |
| WO | 2014113724 A2 | 7/2014 |
| WO | 2017201504 A1 | 11/2017 |

OTHER PUBLICATIONS

Written Opinion of the International Searching Authority for PCT/US19/50662, dated Jan. 7, 2020.
Tanaka, et al. "A New Radiofrequency Thermal Balloon Catheter for Pulmonary Vein Isolation", Journal of the American College of Cargiology, 2001, vol. 38, No. 7, Dec. 2001: 2079-86; ISSN 0735-109, Ph S0735-1097.
Microsulis America, Inc.; Instructions for Use, Microsulis Microwave Endometrial Ablation (MEA) System; Microsulis Americas, Inc. - MEA System Instructions for Use; Dec. 2002; 62795/09/038 Issue 1; pp. 16-35; Microsulis Americas.
International Search Report for PCT/US2017/033693, dated Oct. 2, 2017.
Thibeau; AW-06995-001; Text, Manual, Novasure, V1, En, US; Aug. 26, 2011; pp. 1-23; Hologic, Inc.
Sharma et al.; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.
Sharma et al.; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.
Sanfilippo et al.; Update: Options in Endometrial Ablation; Supplement to OBG Management; Dec. 2009; pp. S1-S24; Dowden Health Media.
United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; heroption office cryoablation therapy Resource Guide; 2007; pp. 1-29; American Medical Systems, Inc.. 10700 Bren Road West, Minnetonka, MN 55343 USA.
Boston Scientific; Hta System Endometrial Ablation System; 2006; BVU 1090 Rev. A 10M 9/Jun. 9, 08; Boston Scientific Corporation, One Boston Scientific Place, Natick, MA 01760-1537.
Ethicon Women's Health & UROLOGY; Instructions for Use, Gynecare Thermachoice HI Uterine Balloon Therapy System, Thermal Balloon Ablation Silicone Catheter and Syringe (SingleUse); Mar. 26, 2008; pp. 1-156; TCIII_389630.R06_Main.indd; Gynecare, a division of Ethicon, Inc. a Johnson & Johnson company, Sommerville, NJ, 08876-0151 USA.
Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.
Carter; Endometrial Ablation: More Choices, More Options; The Female Patient; 2005; pp. 35-40; 30(12).
International Search Report for PCT/US2009/059609, dated Mar. 5, 2010.
International Search Report for PCT/US2012/040639, dated Dec. 18, 2012.
International Search Report for PCT/US2014/012131, dated Jul. 30, 2014.
"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.
Hai; Photoselective Vaporization Prostatectomy: A Palliative Treatment Option for Men with Urinary Obstruction Secondary to Prostate Cancer; PCRI Prost. Cancer Rsrch. Inst. Reprint, from PCRI Insights Nov. 2005, vol. 8(4); p. 4.
Van De Velde; Vapo-cauterization of the uterus; Amer. J. Med. Sci.; vol. CXVII; 1899.
Blacker; Vaporization of the uterus; J. Obstet. & Gyn.; pp. 488-511; 1901.
Neuwirth et al.; The endometrial ablator: a new instrument; Obst. & Gyn.; vol. 83; No. 5; part 1; pp. 792-796; 1994.
Prior et al.; Treatment of mennorrhagia by radiofrequency heating; Int. J. Hyperthermia; vol. 7; No. 2; pp. 213-220; 1991.
International Search Report for PCT/US2016/012840, dated Aug. 18, 2016.
International Search Report for PCT/US21/13582, dated May 13, 2021.
Written Opinion of the International Searching Authority for PCT/US21/13582, dated May 13, 2021.
International Search Report for PCT/US20/48419, dated Dec. 18, 2020.
Written Opinion of the International Searching Authority for PCT/US20/48419, dated Dec. 18, 2020.

* cited by examiner

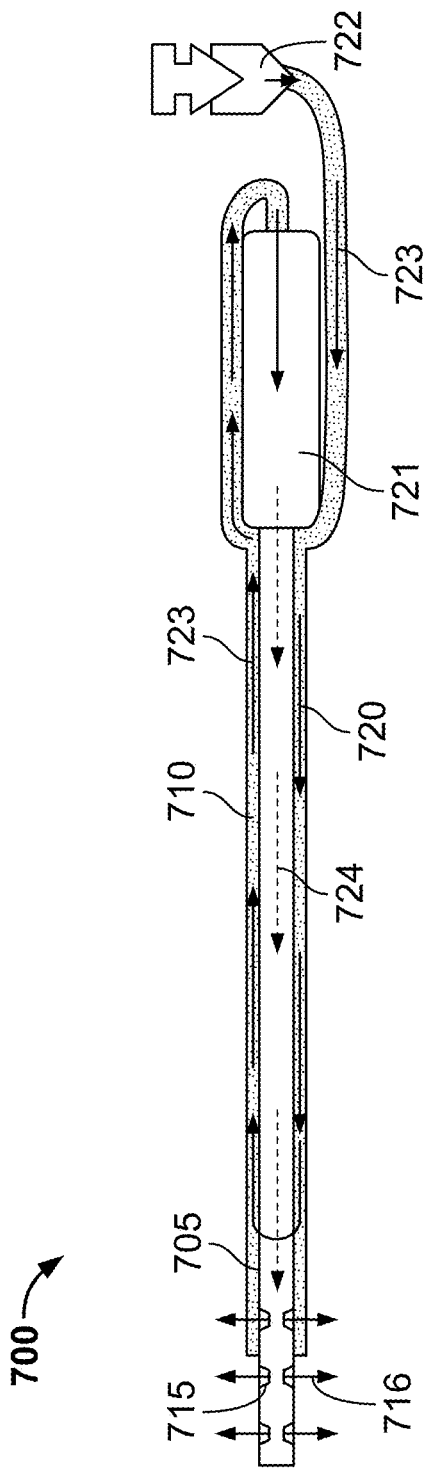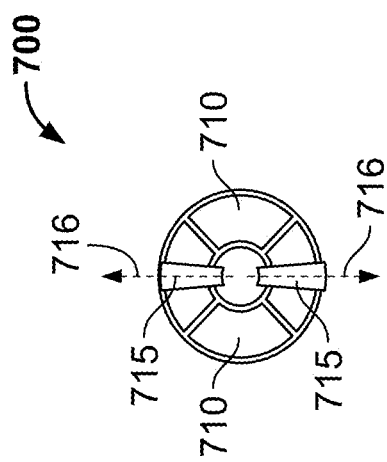
FIG. 7A
FIG. 7B

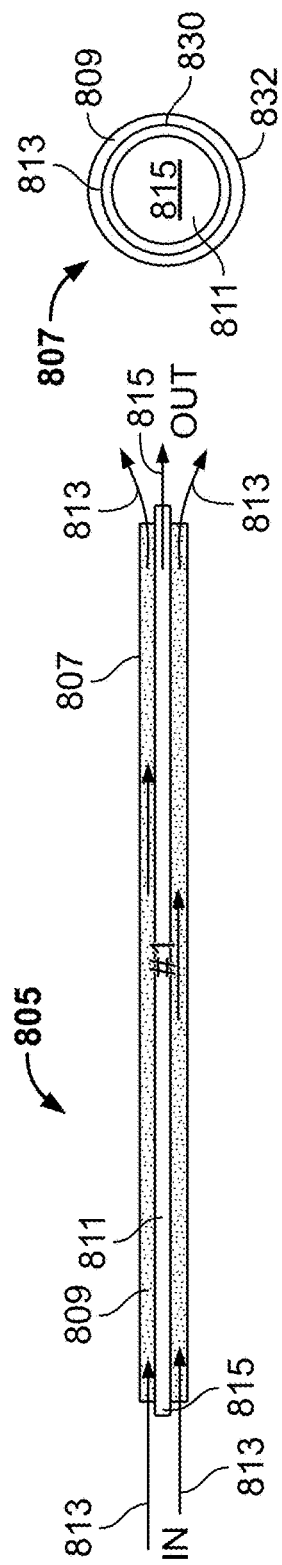
FIG. 8A
FIG. 8B
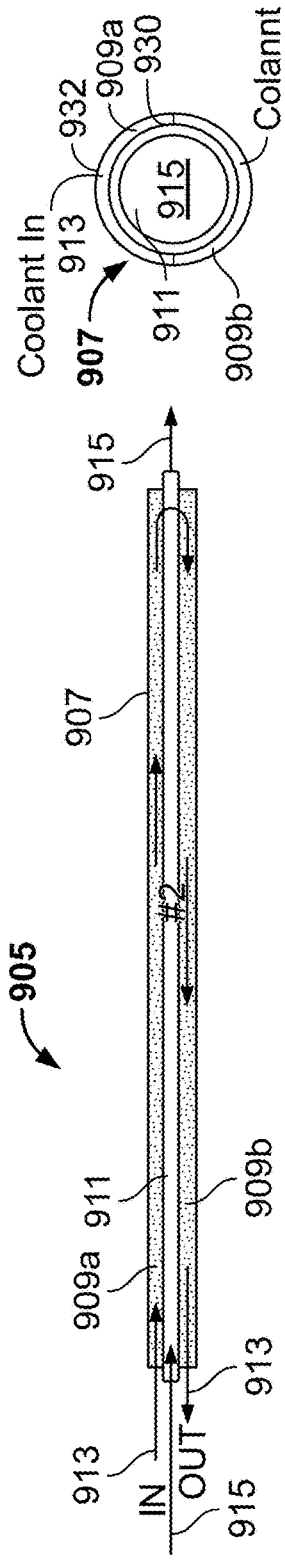
FIG. 9A
FIG. 9B
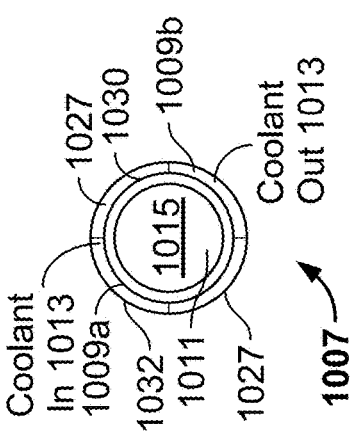
FIG. 10A
FIG. 10B

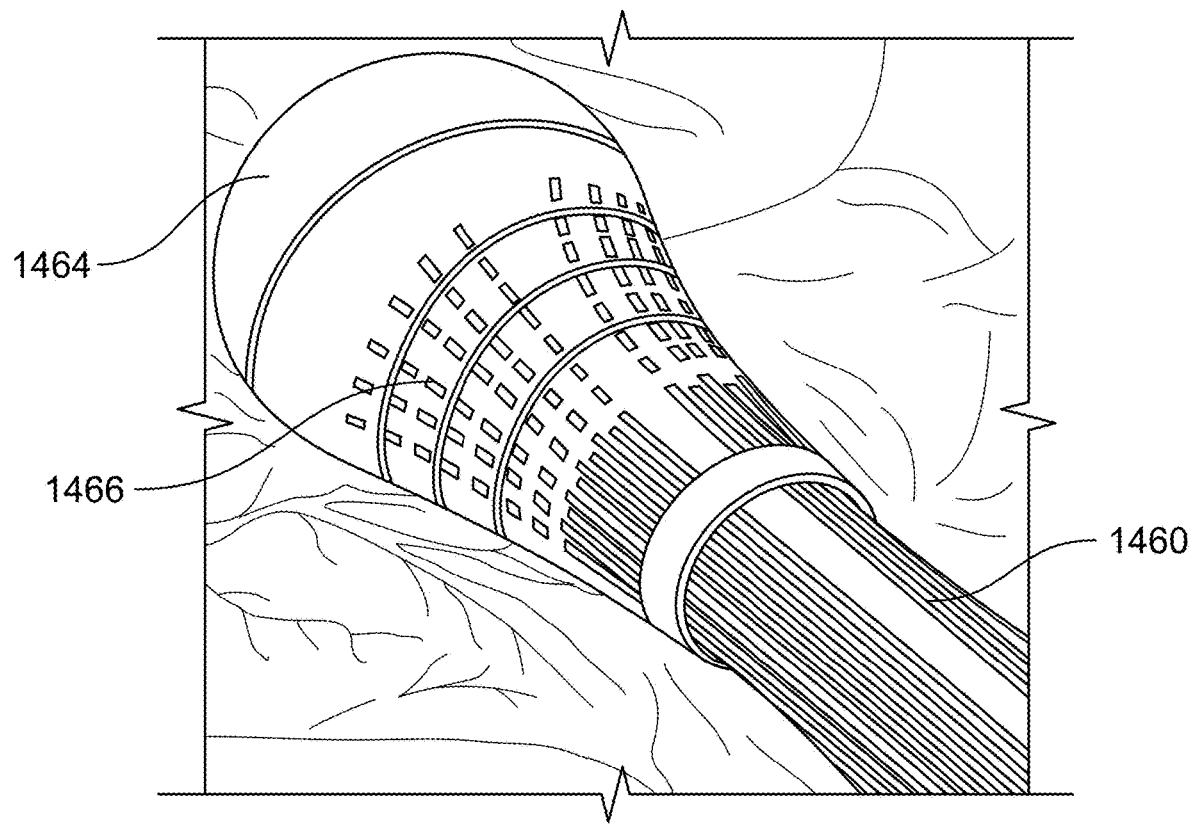
FIG. 14E
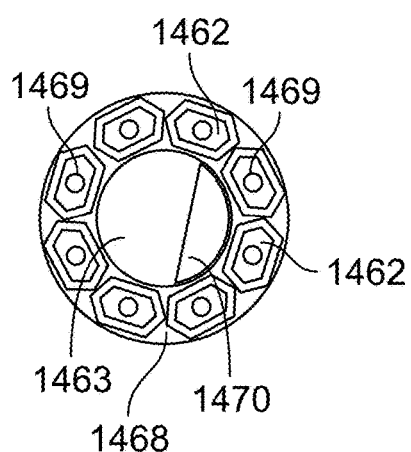 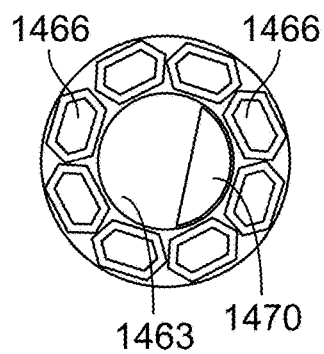
FIG. 14F     FIG. 14G

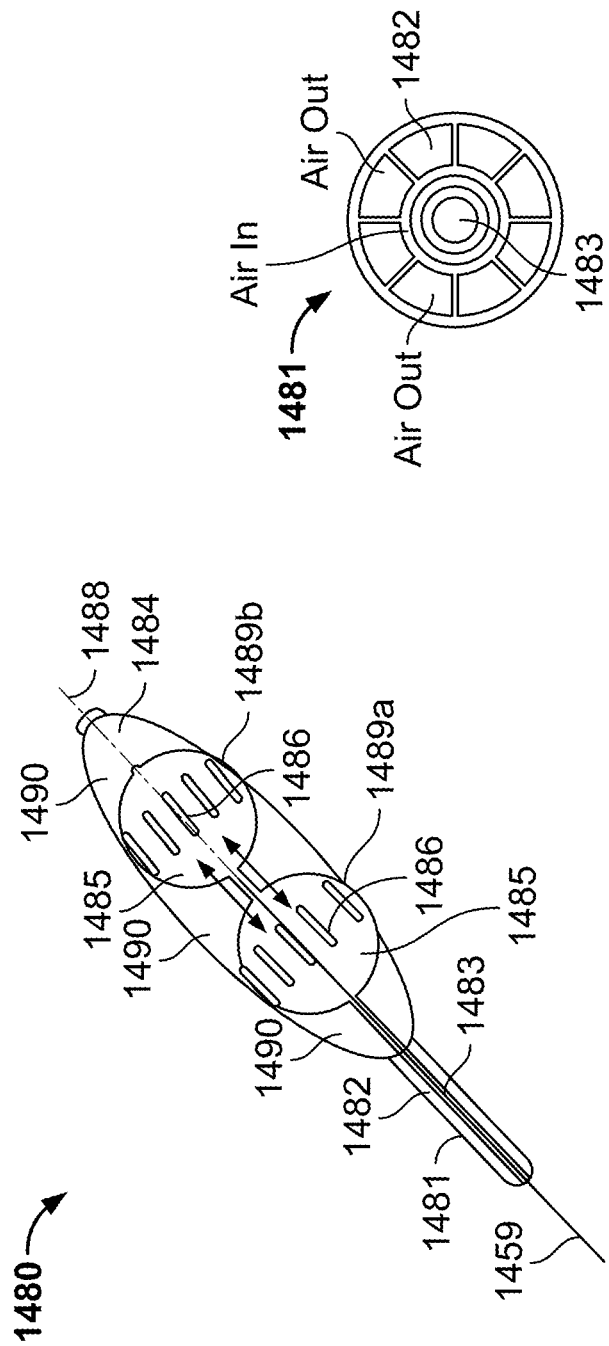

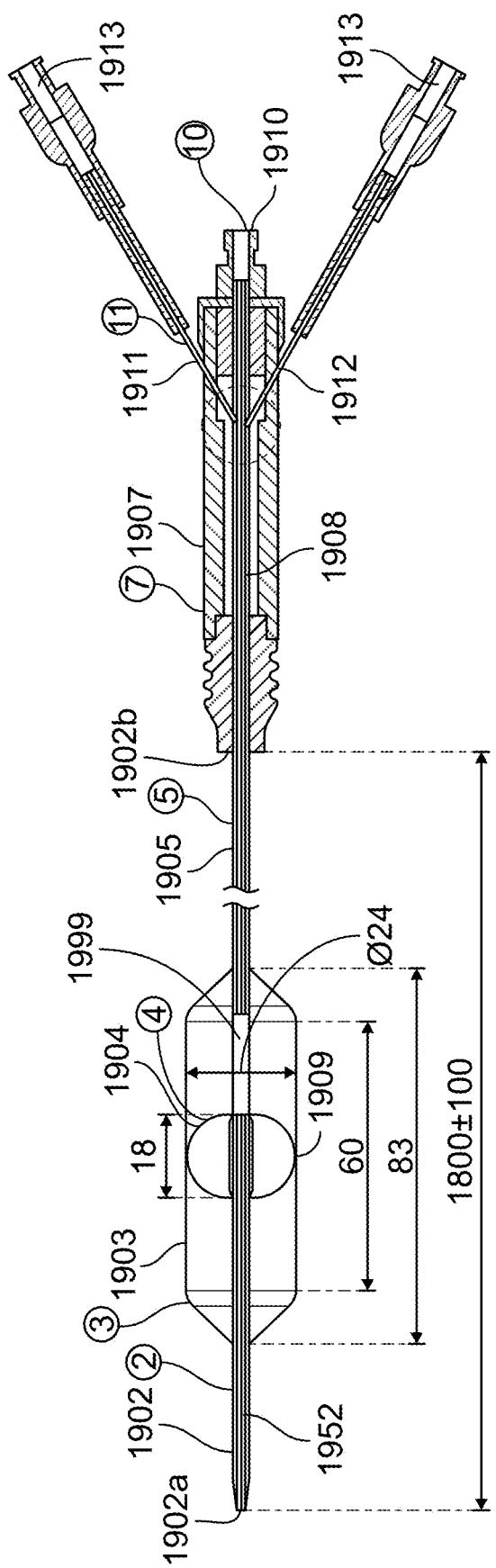
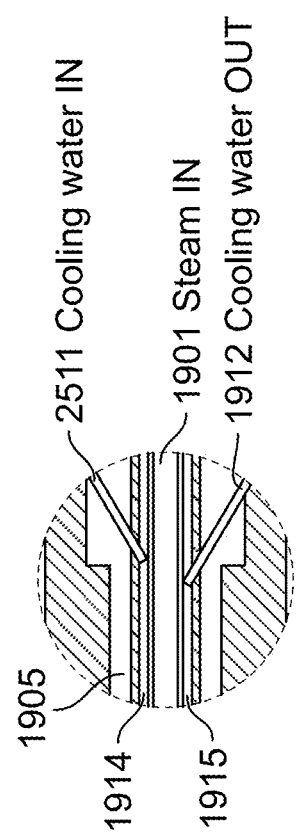
FIG. 19A
FIG. 19B

Section A-A

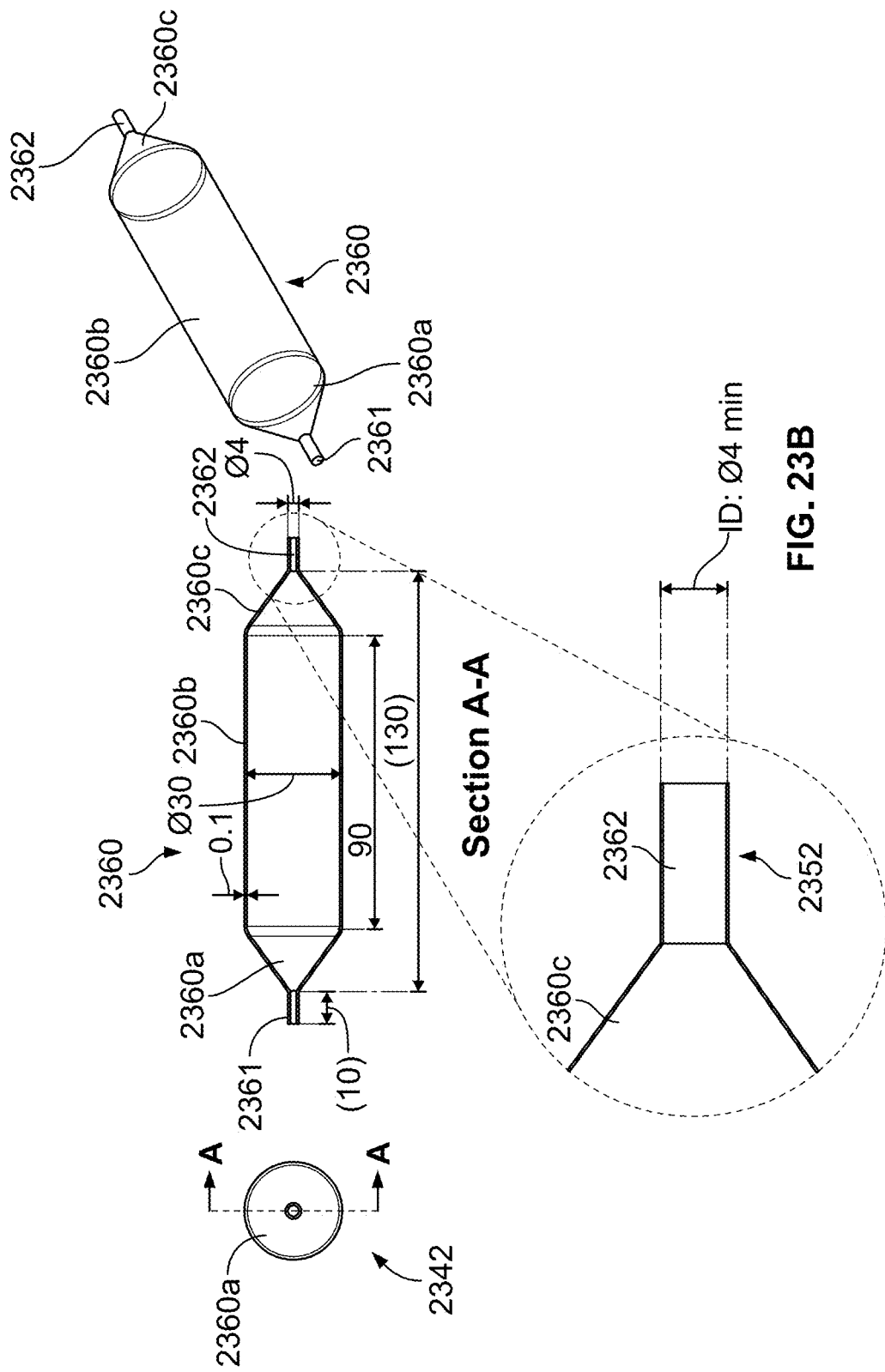

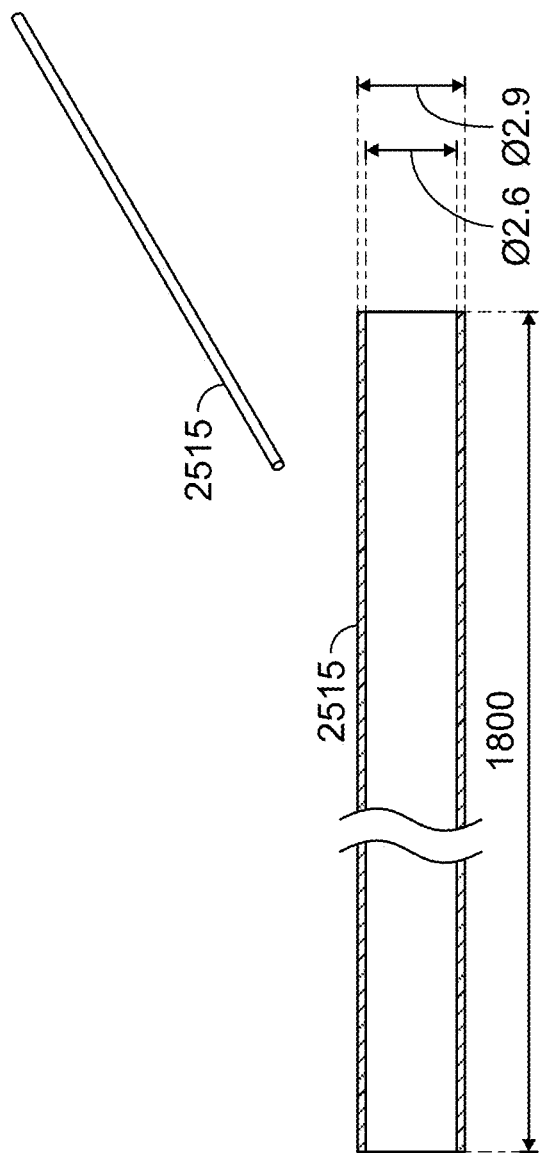
SECTION A-A
FIG. 25D
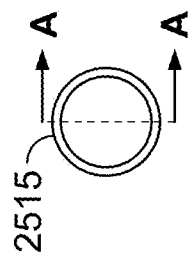

SECTION A-A

SECTION A-A

SECTION A-A

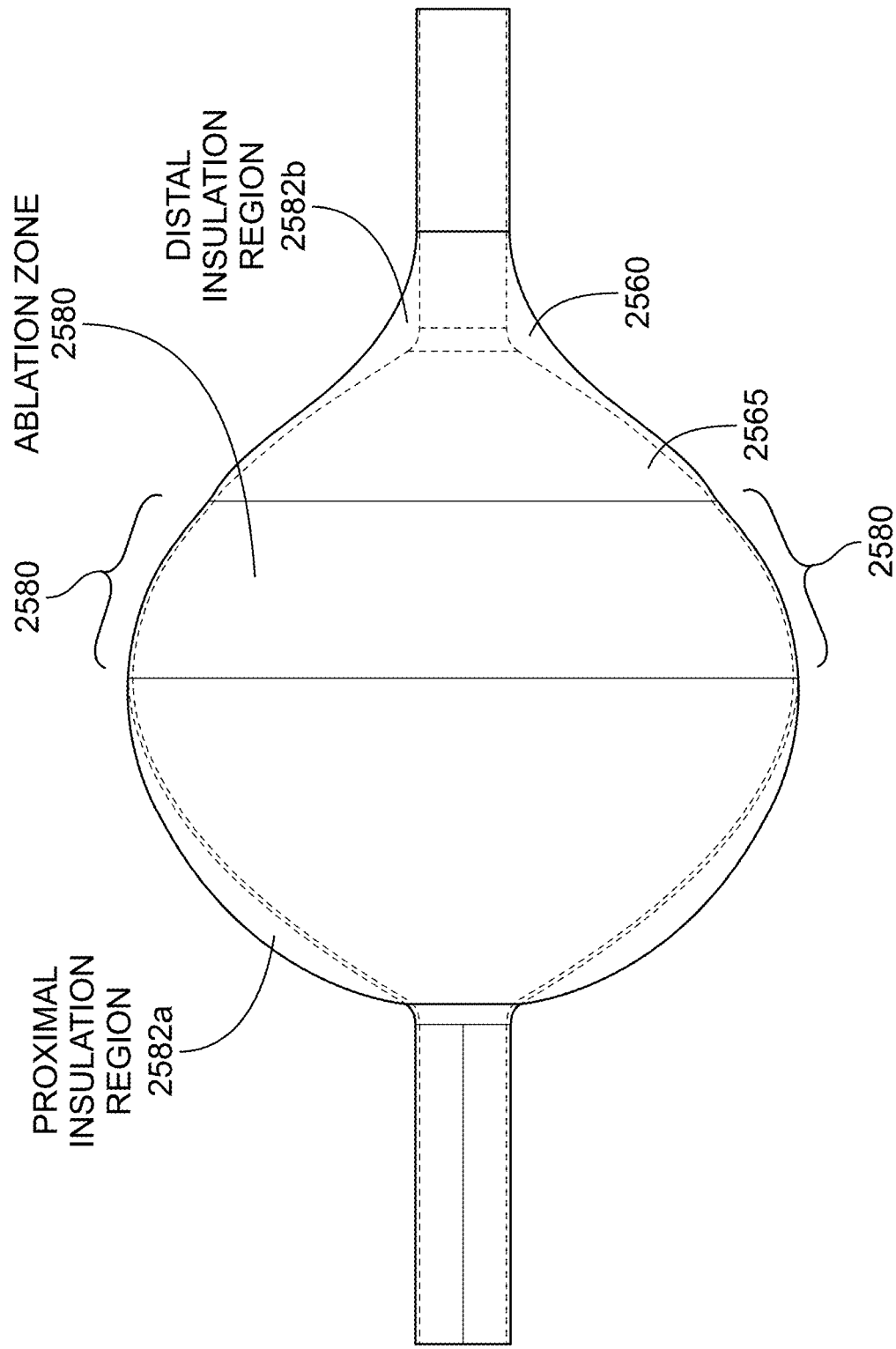

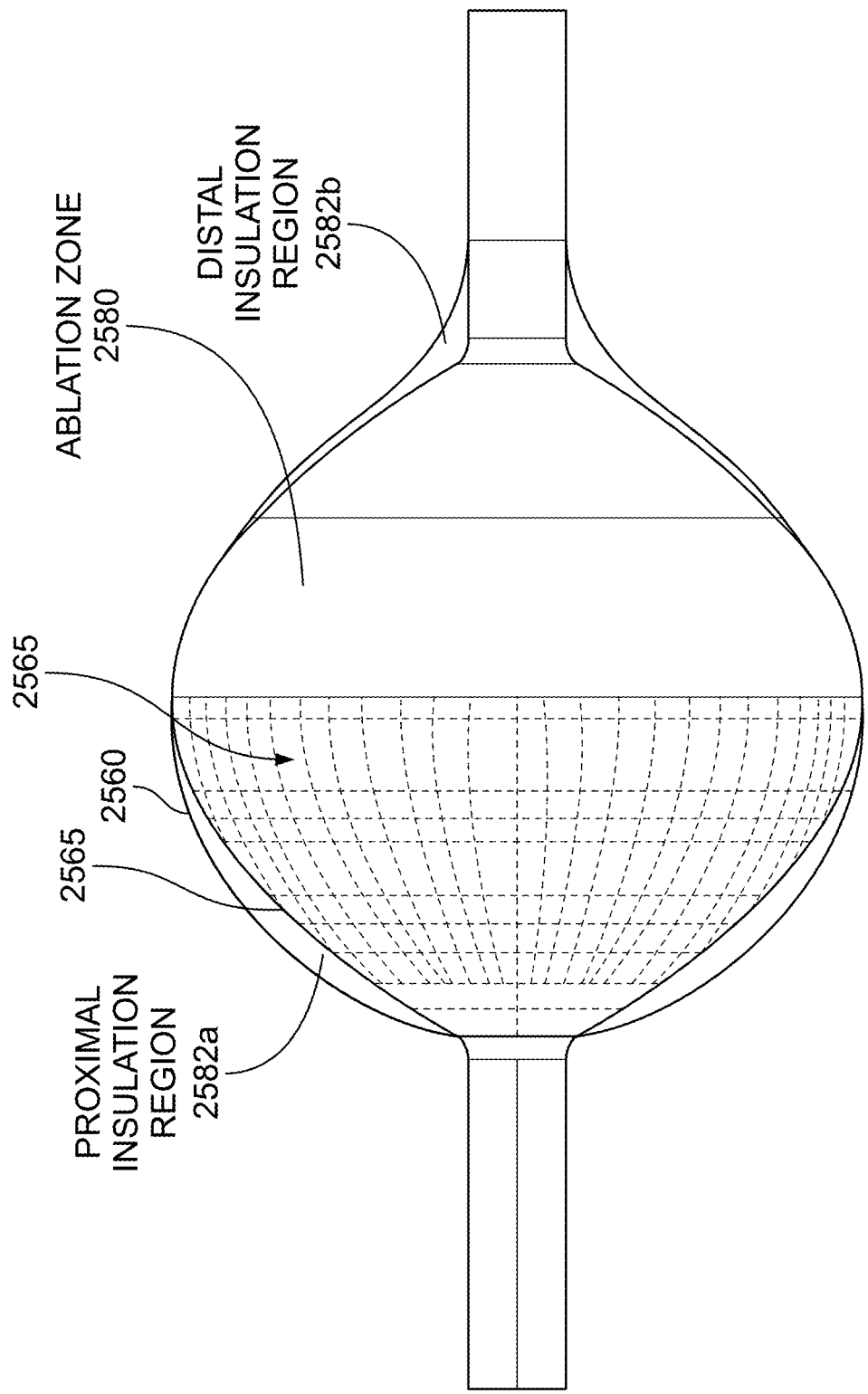

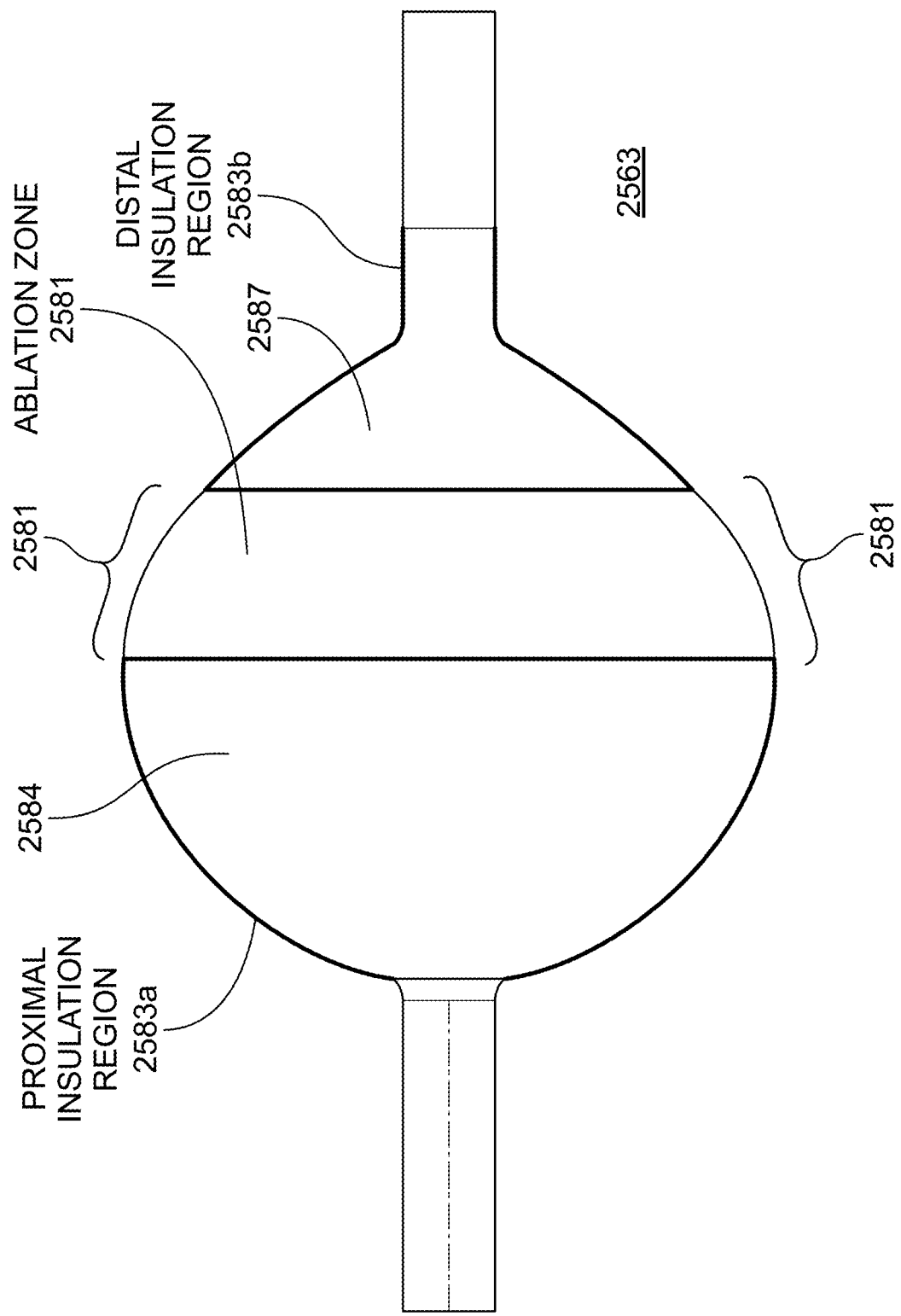

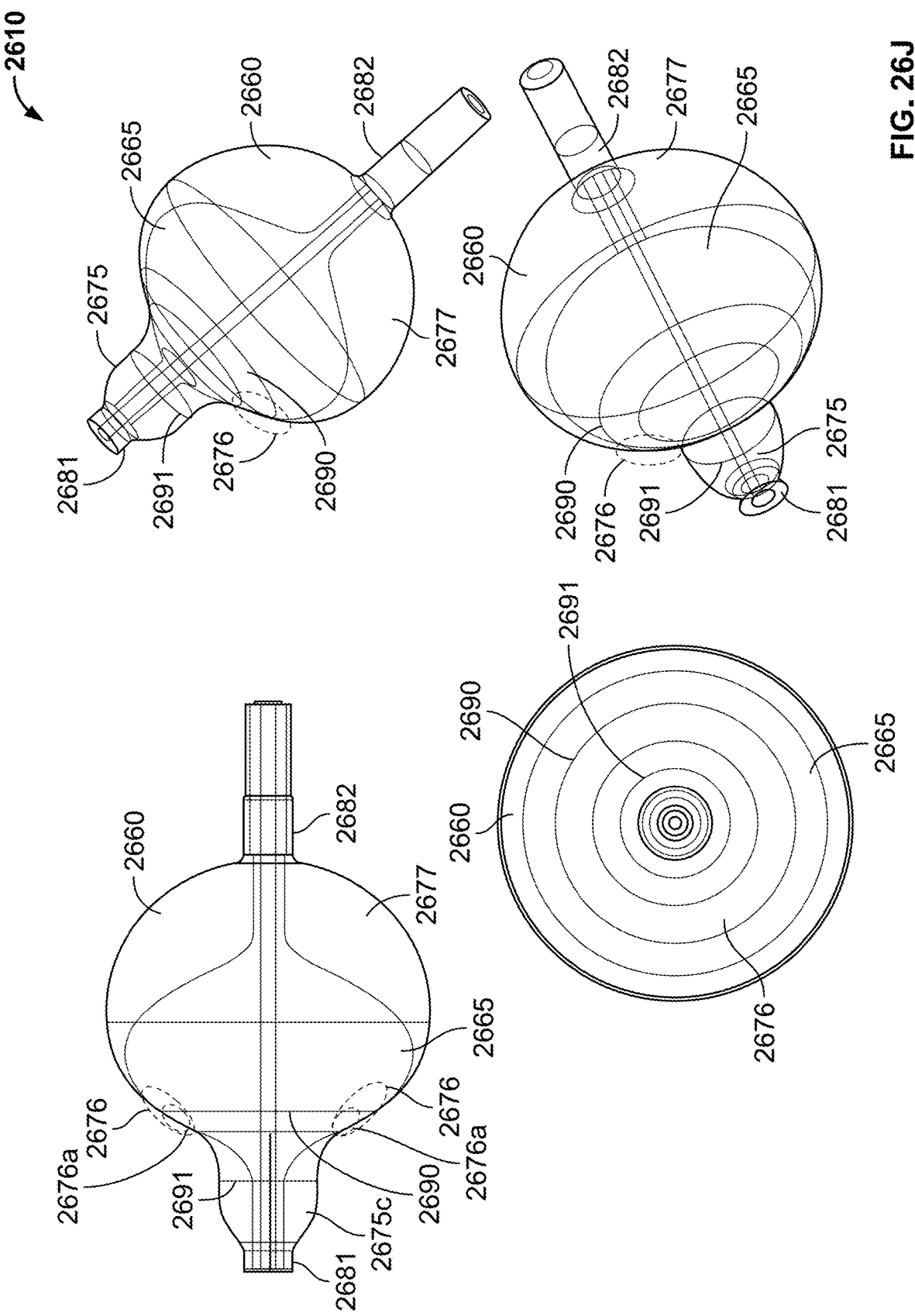

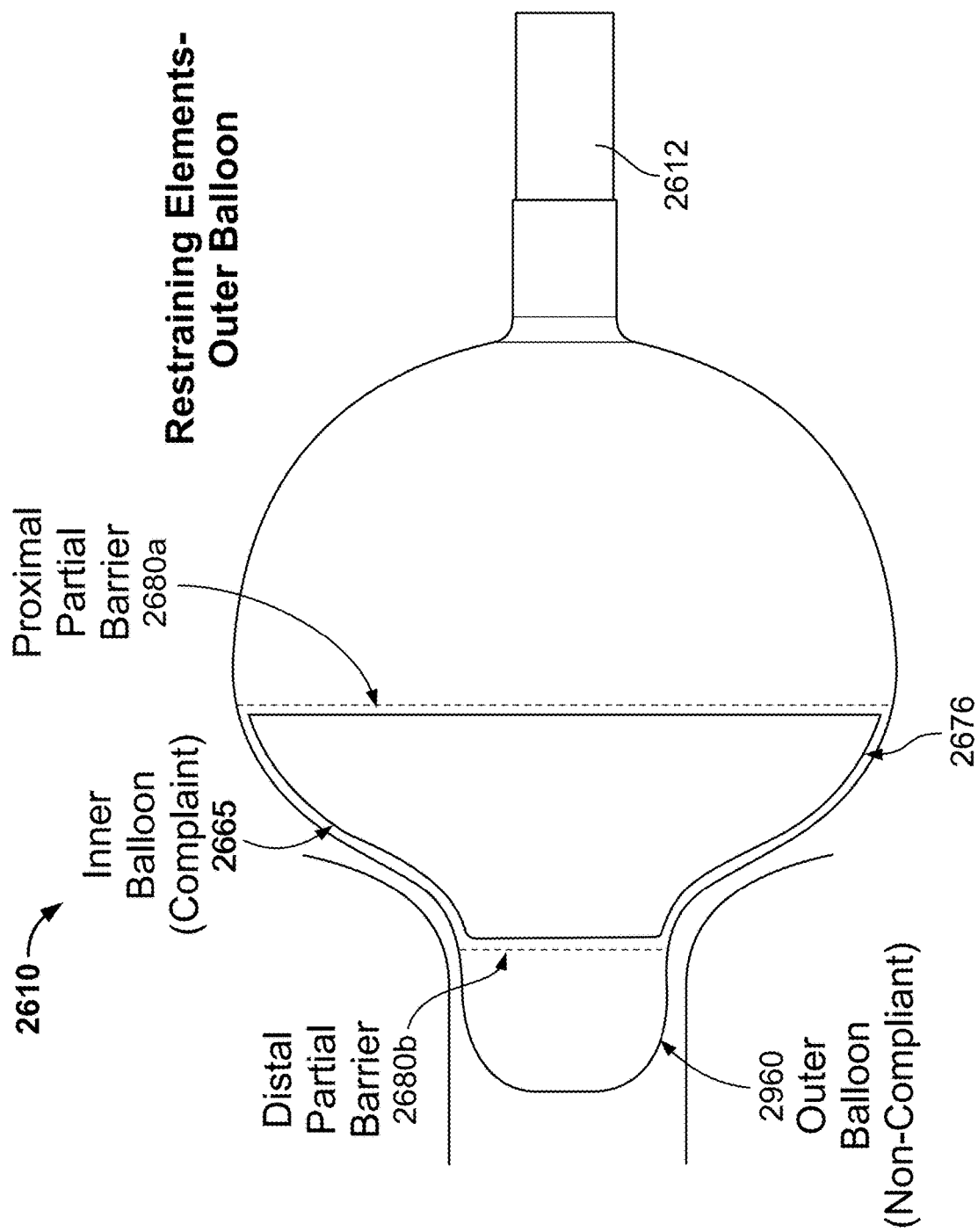

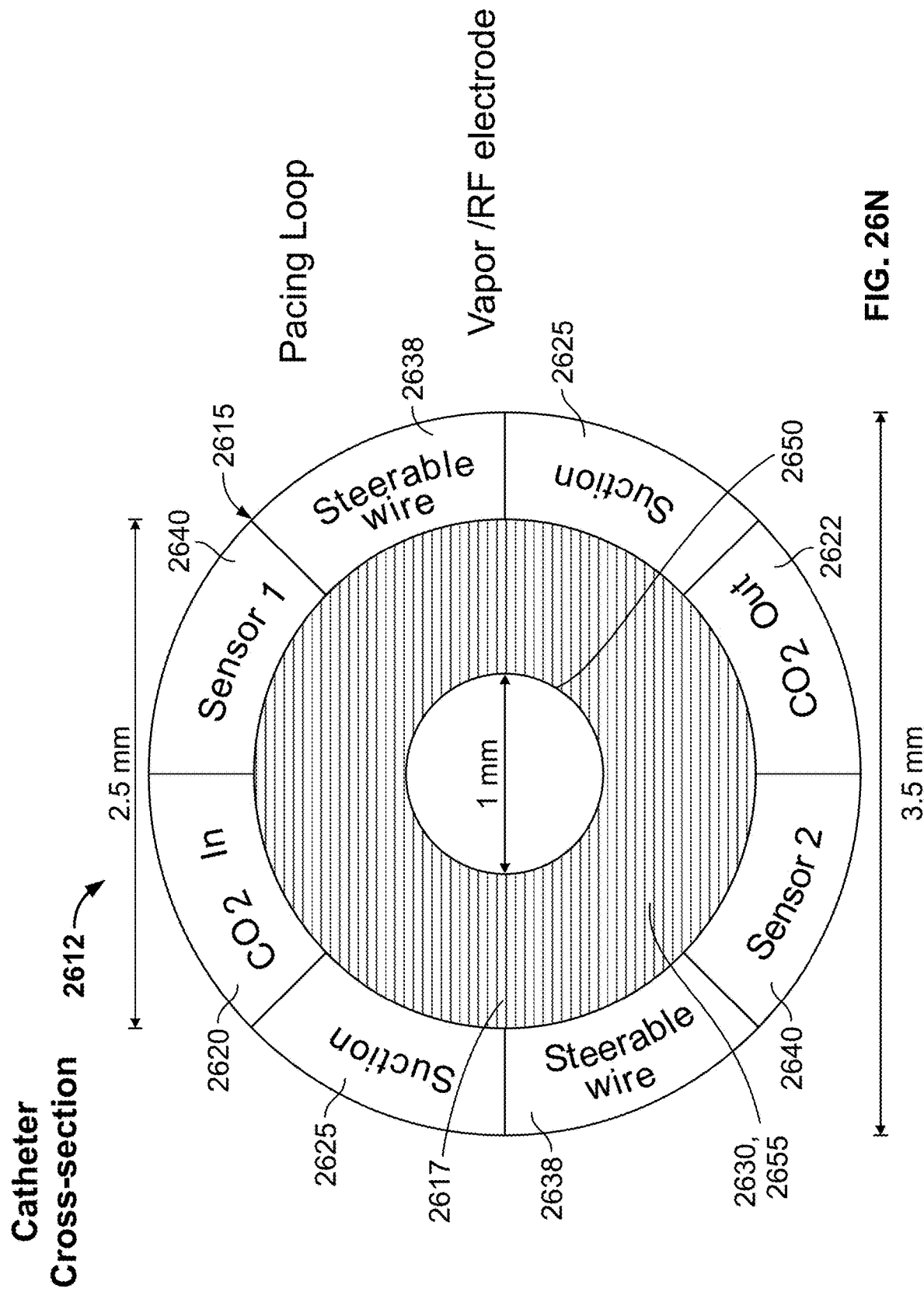

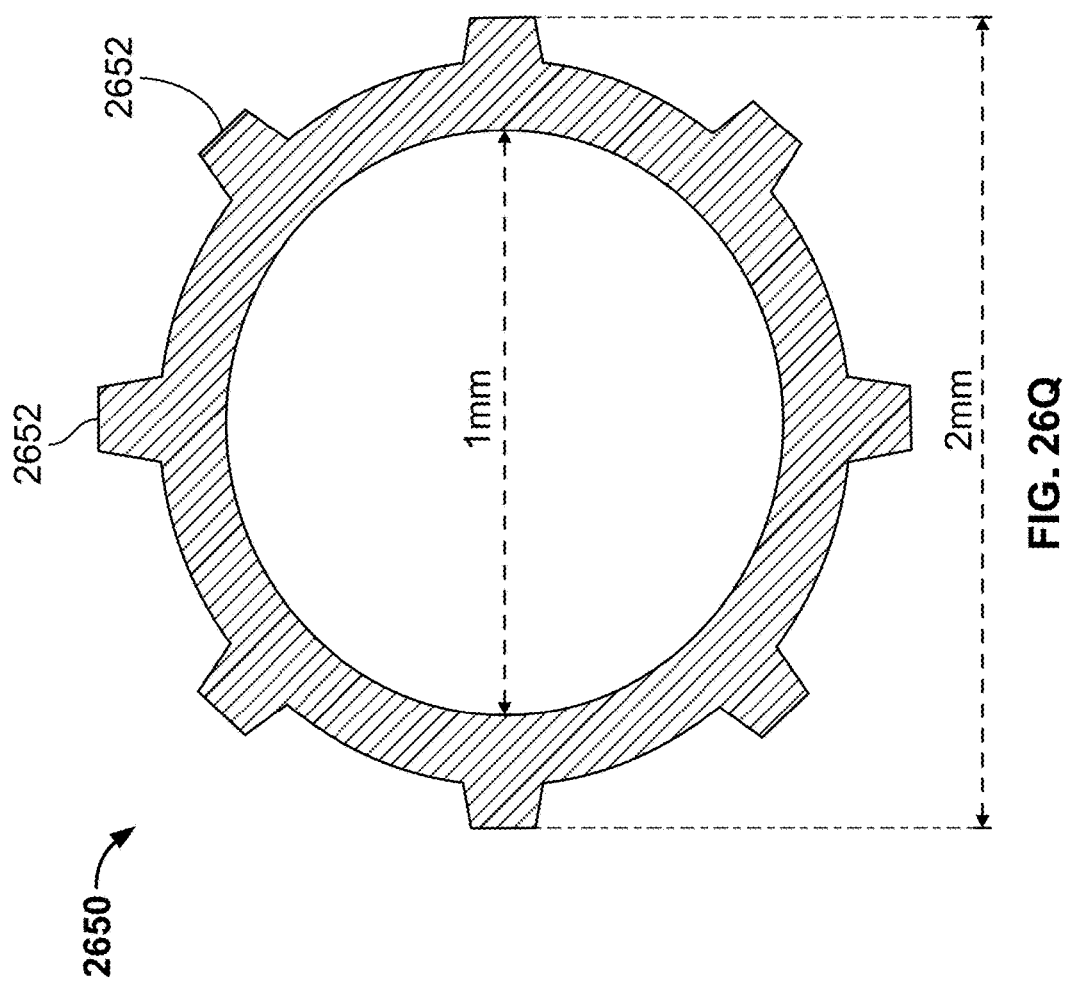

This circumferential channel, concentrically positioned around the MLE, passes CO2 to inflate the outer ballon and also is the channel for deflating the outer ballon. It connects to the outer ballon via a valve.

3662
Place a guidewire or pacing catheter into a left atrial appendage

3664
Place a double balloon catheter over the guidewire or pacing catheter into the left atrial appendage 3666
Inflate an outer balloon with insulating fluid to occlude left atrial appendage 3668
Inflate an inner balloon with vapor to contact the outer balloon in an ablation zone 3670
Transmit heat from inside the inner balloon through the outer balloon to ablate the left atrial appendage 3672
Fill the left atrial appendage with an acellular matrix to promote cell growth and occlusion of the left atrial appendage

FIG. 36D

3695a
Place a guidewire into a target vessel or organ (such as, for example, a pulmonary artery or a lung)

3695b
Place a balloon catheter over the guidewire or through an endoscope into the target organ

3695c
Inflate a balloon of the balloon catheter with an insulating fluid to obtain contact with and occlusion of a target site

3695d
Pass vapor through a channel in the wall of the balloon to create ablation in the targeted tissue in a desired pattern

3695e
Optionally repeating the ablation, if required

FIG. 36F

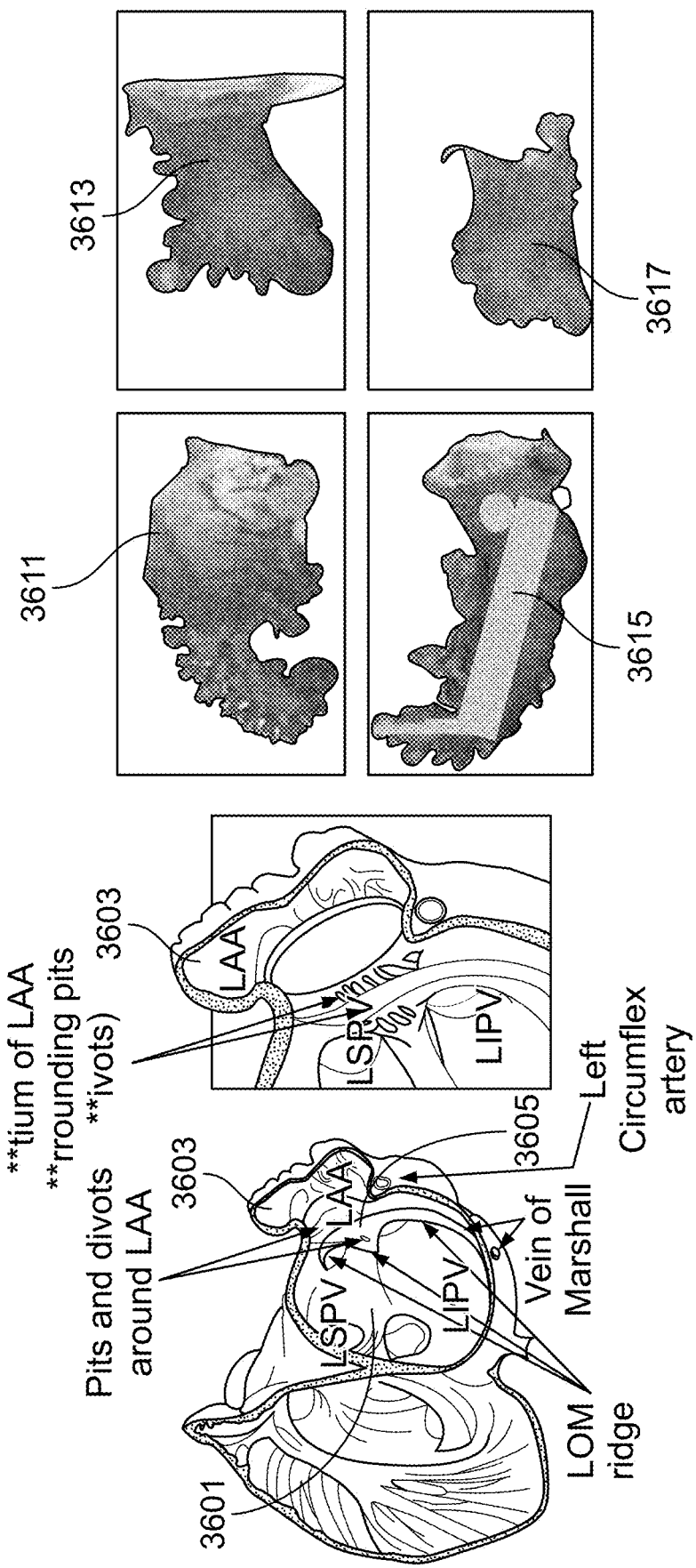

HEATED VAPOR ABLATION SYSTEMS AND METHODS FOR TREATING CARDIAC CONDITIONS

CROSS-REFERENCE

The present application is a continuation-in-part application of U.S. patent application Ser. No. 15/600,670, entitled "Ablation Catheter with Integrated Cooling" and filed on May 19, 2017, now U.S. Pat. No. 10,695,126, which relies on U.S. Provisional Patent Application No. 62/425,144, entitled "Methods and Systems for Ablation" and filed on Nov. 22, 2016, and U.S. Provisional Patent Application No. 62/338,871, entitled "Cooled Coaxial Ablation Catheter" and filed on May 19, 2016, for priority.

The present application also relies on U.S. Patent Provisional Application No. 62/729,777, entitled "Cardiac Ablation Systems and Methods" and filed on Sep. 11, 2018, for priority and further relies on U.S. Provisional Patent Application No. 62/844,222, entitled "Vapor Ablation Systems and Methods for Treating Cardiac Conditions" and filed on May 7, 2019, for priority.

All of the above referenced applications are herein incorporated by reference in their entirety.

FIELD

The present specification relates to systems and methods configured to generate and deliver vapor for ablation therapy. More particularly, the present specification relates to a novel catheter and vapor generation system for delivering vapor-based ablation therapy to cardiac tissue to treat cardiac conditions such as arrhythmias and atrial fibrillation via pulmonary vein ablation and left atrial appendage (LAA) disorder by LAA ablation.

BACKGROUND

Ablation, as it pertains to the present specification, relates to the removal or destruction of a body tissue, via the introduction of a destructive agent, such as radiofrequency energy, electroporation, laser energy, ultrasonic energy, cyroagents, or steam. Ablation is commonly used to eliminate diseased or unwanted tissues, such as, but not limited to cysts, polyps, tumors, hemorrhoids, and other similar lesions including arrhythmia generating cardiovascular tissue, or eliminate certain entities of certain tissues, in particular electrical conductivity.

Atrial fibrillation (A-fib) refers to a condition of abnormal heart rhythm originating in a top chamber of the heart, also known as atria. In cases of a normal heartbeat, electrical impulses in the heart originate at the sinoatrial (SA or sinus) node in the right atrium of the heart. These electrical impulses set the rate and rhythm of the heartbeat. In patients with atrial fibrillation, the heart's electrical rhythm is not directed by the SA node, and instead, many different impulses rapidly fire at once, thereby causing a very fast, chaotic rhythm in the atria. There are different methods to treat A-fib, including medications that slow the heart rate, antiarrhythmic drugs, and anticoagulants that may reduce the risk of a resulting stroke. However, one of the effective methods of treating atrial fibrillation is pulmonary vein ablation (also called pulmonary vein antrum isolation or PVAI). PVAI comprises an ablation of a portion of the patient's pulmonary vein including a PV ostium or the atrial tissue at the junction of the left atrium and the pulmonary vein. PVAI is most suitable for patients with paroxysmal and in some cases persisting symptom of A-fib even after treatment with medications, and also for patients who are prone to complications from antiarrhythmic drugs. It has been observed that nearly 80% of paroxysmal A-fib patients with no other heart diseases can be completely cured with a single PVAI procedure. Patients, after treatment, are considered cured of A-fib when they have normal sinus rhythms without any dependence on medications. Even patients with long-standing A-fib have been noted to be cured with a success rate of 50 to 70%, with the aid of PVAI, depending on their underlying heart disease and other factors.

During the PVAI procedure, an ablation device is directed to precise location(s) in the. These points are then isolated and destroyed. This ensures that the certain heart muscle cells in the border zone distal from the insulation line cannot re-trigger A-fib. However, it is difficult to locate and therefore isolate the locations in order to complete a coherent lesion. It is known that most A-fib signals come from the openings (ostia) of the four pulmonary veins in the left atrium. The PVAI procedure isolates these veins from the rest of the heart and prevents any pulses from these veins from getting into the heart.

Multiple methods to locate and isolate A-fib signals are known in the art. One of the methods involves making circular radiofrequency (RF) ablation lines around each pulmonary vein opening so as to isolate the pulmonary veins. It is difficult and time-consuming, however, to make circular lesions to achieve complete isolation. Delivering ablative energy through freezing, laser, or ultrasound based catheters are sometimes used to encircle the vein opening and make the circular lesions. Another method, known as segmental catheter ablation, uses pulmonary vein potentials to locate and eliminate A-fib signals. Once the area in the pulmonary vein identified with any potential is ablated, the potential disappears. Usually, the pathways taken by the A-fib signals from the pulmonary veins are located and ablated outside of the pulmonary vein openings. One more procedures, known as 'anatomically-based circumferential pulmonary vein ablation' or 'left atrial ablation' emphasizes on creating blocking lesions in the left atrium, similar to circumferential ablation. A large diameter catheter at a high wattage is dropped and dragged to make circular linear lesions. Other balloon-based methodology, such as cryoballoon ablation, laser ablation and high-intensity focused ultrasound (HIFU) ablation may be used to ablate cardiac tissue. Electroporation using pulsed field ablation has also been used to achieve pulmonary vein isolation.

Idiopathic pulmonary arterial hypertension (IPAH) is known to be characterized by elevations of mean pulmonary artery (PA) pressure (PAP) and pulmonary vascular resistance (PVR). PA denervation (PADN) is sometimes used for patients with IPAH, so as to abolish the increment of PAP, by inducing local injury to the baroreceptor or sympathetic nervous fibers. PADN is also known to have been used for patients with combined pre- and post-capillary pulmonary hypertension (CpcPH). PADN procedures also involve location and ablation of targets within the PA using catheter ablation methods stated above.

A left atrial appendage (LAA), comprising a small sac in a wall of a left atrium, can be a source of both atrial arrhythmias as well as emboli which can cause strokes. Left atrial appendage occlusion and ligation devices are used to eliminate atrial arrhythmias and emboli from clots in the atrial appendage. While methods exist for closure of an LAA, ablation using any modality to control LAA emboli by decreasing or obliterating the lumen of the LAA has not been described in the prior art.

Steam-based ablation systems, such as the ones disclosed in U.S. Pat. Nos. 9,615,875, 9,433,457, 9,376,497, 9,561,068, 9,561,067, and 9,561,066, disclose ablation systems that controllably deliver steam through one or more lumens toward a tissue target. One problem that all such steam-based ablation systems have is the potential overheating or burning of healthy tissue. Steam passing through a channel within a body cavity heats up surfaces of the channel and may cause exterior surfaces of the medical tool, other than the operational tool end itself, to become excessively hot. As a result, physicians may unintentionally burn healthy tissue when external portions of the device, other than the distal operational end of the tool, accidentally contacts healthy tissue. U.S. Pat. Nos. 9,561,068, 9,561,067, and 9,561,066 are hereby incorporated herein by reference.

Double balloon ablation catheters having inner and outer balloons, such as the ones disclosed in U.S. Pat. Nos. 7,727,228, 7,850,685, 8,425,456, and 8,679,104, maintain the outer balloon under a vacuum with almost no space between the inner and outer balloons. The purpose of such a construction is to provide a backup covering (the outer balloon) in case of a catastrophic failure of the inner balloon. Hence, during operation, the dimensions of the inner and outer balloons and shape of the inner and outer balloons are substantially the same and, during operation of the catheter, the outer balloon fits on the inner balloon like a glove.

What is needed is a catheter configured to concurrently direct ablative vapor heat toward cardiac tissue, firmly position the catheter in the right cardiac tissue location, avoid burning healthy, or non-targeted tissue, including blood, and controllably deliver ablative energy to the target location. It would be further desirable to have steam-based ablation devices that integrate into the catheter safety mechanisms which prevent unwanted thermal injury to the patient and the operator during use. It is further desirable to be able to provide a way to increase, or augment, a natural cooling process to thereby decrease treatment time. It is also desirable to create dynamic or variable ablation (hot) and cooling zones that can vary with, and accommodate to, a patient's anatomy. Finally, it is desirable to provide an easy to implement heated ablation zone and cooling mechanism that does not rely on a separate medical tool to deliver fluid to cool the treatment area.

SUMMARY

The present specification discloses a method of ablating cardiac tissue, the method comprising: positioning a catheter proximate a cardiac tissue of a patient, wherein the catheter comprises an elongate body having a lumen, a proximal end and a distal end and wherein an outer balloon and an inner balloon are positioned at the distal end such that the inner balloon is positioned within the outer balloon; inflating the outer balloon with a first fluid to increase a pressure of the outer balloon to a first outer balloon pressure; infusing heated vapor into the inner balloon to increase a pressure of the inner balloon to a first inner balloon pressure, wherein infusing heated vapor into the inner balloon creates an ablation zone and wherein a surface area of the ablation zone is defined by a portion of the inner balloon contacting a portion of the outer balloon to thereby allow for heat transfer from the heated vapor in the inner balloon through the ablation zone to the cardiac tissue; maintaining the first inner balloon pressure for a first pre-determined period of time to ablate the cardiac tissue to a predetermined extent; stopping the infusion of heated vapor, wherein stopping the infusion of heated vapor causes the pressure of the inner balloon to decrease to a second inner balloon pressure; and deflating the outer balloon to a second outer balloon pressure.

The cardiac tissue may be a pulmonary vein, a portion of a pulmonary vein, a pulmonary vein ostium, an atrium, tissue proximate to a pulmonary vein antrum, or a left atrial appendage. Optionally, the method further comprises documenting a degree of pulmonary vein occlusion achieved by inflating the outer balloon.

The first outer balloon pressure may be between 0.01 atm and 5 atm and preferably between 0.1 atm and 5 atm or any range or increment therein.

Optionally, the method further comprises inflating the inner balloon with a second fluid prior to infusing the heated vapor into the inner balloon, wherein the second fluid is air or $CO_2$.

Optionally, the first pre-determined period of time is between 1 second and 5 minutes. The first outer balloon pressure may be maintained for the first pre-determined period of time.

Optionally, the surface area of the ablation zone is a function of a surface area of tissue positioned at a junction between the patient's pulmonary vein and the patient's left atrium.

Optionally, the method further comprises removing a fluid created by a condensation of the heated vapor in the inner balloon, wherein the removal of the fluid decreases the pressure of the inner balloon to a third inner balloon pressure and wherein the third inner balloon pressure is less than or equal to the first inner balloon pressure.

Optionally, the catheter comprises a plurality of electrodes positioned proximate the distal end and the heated vapor is generated by directing saline through the lumen and over the plurality of electrodes.

Optionally, the method further comprises documenting a degree of removing an occlusion of the pulmonary vein after deflating the outer balloon.

The first fluid may be air or $CO_2$.

Optionally, the heated vapor comprises steam and a temperature of the heated vapor is at least 100° C.

Optionally, the method further comprises placing a guide wire or pacing catheter into a heart of the patient and placing the catheter over the guide wire or pacing catheter.

Optionally, the method further comprises sensing or stimulating a pulmonary vein using the guide wire or pacing catheter to determine a degree of pulmonary vein isolation.

Optionally, a distal tip of the catheter is configured to deflect from a linear configuration to a curved configuration, wherein the curved configuration is defined by the distal tip being adapted to turn up to 150 degrees through a radius ranging from 0.5 to 2.5 inches.

Optionally, the inflated outer balloon is in contact with a portion of an ostium of a pulmonary vein and occludes at least a portion of the pulmonary vein 2 mm to 15 mm distal to the pulmonary vein ostium.

Optionally, the ablation zone has a width of 2 mm to 15 mm and a curved length at least partially defined by an extent of contact between the inflated outer balloon and a surface of the cardiac tissue.

Optionally, a distance between an outer surface of the inflated outer balloon and an outer surface of the uninflated inner balloon is in a range of 1 mm to 25 mm.

Optionally, the method further comprises using at least one of fluoroscopy, three dimensional mapping, or an endoscopic procedure to determine an extent of contact of between at least two of the inner balloon, the outer balloon, and the cardiac tissue.

Optionally, the catheter further comprises at least one sensor. Optionally, the at least one sensor is configured to monitor contact of the inner balloon with the outer balloon or configured to monitor a temperature or pressure of the outer balloon or a temperature or pressure of the inner balloon.

Optionally, the method further comprises introducing the catheter through a venous puncture in a femoral vein of the patient and advancing the catheter into a left atrium of the patient and into a pulmonary vein or left atrial appendage through a trans-septal puncture.

Optionally, the ablation zone is positioned away from a source of production of the heated vapor no further than 100 mm.

Optionally, the ablation zone is only created when a pressure opposing a surface of the outer balloon is greater than 0.1 psi.

Optionally, the method further comprises repeating steps to ablate cardiac tissue for a second pre-determined period of time, wherein the second pre-determined period of time is equal to 50% to 250% of the first pre-determined period of time.

Optionally, the ablation is performed to treat atrial fibrillation or ablate a left atrial appendage in the patient.

Optionally, upon being inflated, the outer balloon has a pear-shaped configuration, wherein the pear-shaped configuration comprises a proximal body that narrows into a tapered distal end.

Optionally, upon being inflated, a shape of the outer balloon is defined by a curve of a surface of the outer balloon that is further defined by a plane intersecting an entire length of the catheter, wherein the curve is characterized by a first point, a second point, and a third point sequentially positioned, and extending along the length of the catheter, between a proximal point and a distal point, wherein a first slope between the proximal point and first point has a first value, a second slope between the first point and second point has a second value, a third slope between the second point and the third point has a third value, a fourth slope between the third point and distal point has a fourth value, and wherein an absolute value of the first value is greater than an absolute value of the second value, an absolute value of the third value or an absolute value of the fourth value, the absolute value of the second value is greater than the absolute value of the third value, and the absolute value of the fourth value is greater than the absolute value of the third value; and, when inflated, the inner balloon has the shape of an oblate spheroid where the minor axis, or short axis, coincides with the longitudinal axis of the catheter and the major axis, or long axis, is perpendicular to the catheter.

Optionally, upon being inflated, a shape of the outer balloon may be defined by a first distance from a central axis of the outer balloon to a first proximal point on an outer surface of the outer balloon, a second distance from the central axis to a second proximal point on the outer surface of the outer balloon, a third distance from the central axis to a third point on the outer surface of the outer balloon, a fourth distance from the central axis to a first distal point on the outer surface of the outer balloon, and a fifth distance from the central axis to a second distal point on the outer surface of the outer balloon, wherein each of the first proximal point, the second proximal point, the third point, the first distal point, and the second distal point are sequentially positioned along a length of the central axis starting from a proximal position and extending distally, wherein the second distance is greater than the first distance, the third distance, and the fifth distance and wherein the fourth distance is greater than the first distance, the second distance, the third distance, and the fifth distance.

Optionally, upon the inner balloon and outer balloon being inflated, the ablation zone has a width and curved length defined by an extent of contact between the outer balloon and a portion of the cardiac tissue.

The present specification also discloses a system for ablating cardiac tissue comprising: a catheter adapted to be positioned proximate a cardiac tissue of a patient, wherein the catheter comprises: a distal end; a proximal end; a first lumen; a second lumen comprising a heating element; an inner balloon positioned at the distal end of the catheter and in fluid communication with the second lumen; and an outer balloon positioned at the distal end of the catheter and enclosing the inner balloon, wherein the outer balloon is in fluid communication with a first fluid source via the first lumen and wherein, upon inflation of the outer balloon with a first fluid and inflation of the inner balloon with a heated vapor, an ablation zone is formed at a contact area of the inner balloon with the outer balloon; and a controller, wherein the controller comprises programmatic instructions that, when executed, cause: the first fluid to be infused into the outer balloon; and a second fluid to be directed through the second lumen and placed in contact with the heating element to form the heated vapor.

Optionally, the outer balloon is not fixedly attached to the inner balloon in said contact area.

Optionally, a contour of a surface area of the ablation zone is a function of, and dependent on, a portion of the pulmonary vein of the patient.

Optionally, the ablation zone is defined by a surface area and a size of the surface area ranges from 5% to 95% of a surface area of at least one of the inner balloon or outer balloon.

Optionally, the ablation zone has a width in a range of 1 mm to 20 mm.

Optionally, the first fluid is air or $CO_2$.

Optionally, the second fluid is saline or carbonated saline, the heated vapor is steam, and the heated vapor has a temperature of at least 100° C.

Optionally, the heating element is flexible and comprises a plurality of electrodes positioned within the second lumen. Optionally, the heating element is defined by a distal end wherein the distal end is positioned at a distance in a range of 0 mm to 80 mm from a proximal end of the outer balloon.

Optionally, the heating element comprises a plurality of electrodes configured to receive an electrical current activated by the controller. Optionally, each of the plurality of electrodes comprises at least one edge adapted to be exposed to fluid present in the second lumen.

Optionally, the system further comprises one or more insulation zones, wherein each of the one or more insulation zones is defined by a surface area of the outer balloon that is proximal or distal to the ablation zone and wherein each of the one or more insulation zones has an average temperature that is less than an average temperature of the ablation zone. Optionally, each of the one or more insulation zones has a width of at least 0.1 mm and extends along a curved length in a range of 1 mm to a circumference of the outer balloon.

Optionally, the inner balloon is configured to be movable along a horizontal longitudinal axis within the outer balloon and the catheter further comprises a mechanism configured to move the inner balloon within the outer balloon.

Optionally, the controller further comprises programmatic instructions that, when executed, cause the outer balloon to be inflated to a first pressure and maintained at the first pressure during ablation. Optionally, the controller further comprises programmatic instructions that, when executed, cause the inner balloon to be inflated to a second pressure during ablation, wherein the first pressure is equal to or less than the second pressure. Optionally, the first pressure is between 0.01 atm and 5 atm and preferably between 0.1 atm and 5 atm or any range or increment therein.

Optionally, the system further comprises one or more pressure valves in fluid communication with the first lumen, wherein each of the one or more pressure valves is configured to control a movement of fluid into, or out of, the outer balloon based upon a predetermined pressure level.

Optionally, the controller further comprises programmatic instructions that, when executed, cause the ablation zone to be maintained for a period of time between 1 second and 5 minutes.

Optionally, the controller further comprises programmatic instructions that, when executed, cause the outer balloon to be inflated to a first volume and the inner balloon to be inflated to a second volume and wherein the first volume is at least 10% greater than the second volume.

Optionally, the system further comprises a mapping member positioned at a distal end of the catheter and configured to map an area of cardiac tissue responsible for a cardiac arrhythmia, wherein the mapping member comprises a plurality of sensors, detectors, or electrodes. Optionally, the mapping member comprises a range of 1 to 64 electrodes configured to record signals form the pulmonary vein or pacing in the pulmonary vein.

Optionally, the system further comprises at least one sensor, wherein the at least one sensor is positioned at the distal end of the catheter or at the proximal end of the catheter. Optionally, the sensor comprises a temperature sensor configured to monitor a delivery of thermal energy to the cardiac tissue. Optionally, the sensor comprises a pressure sensor configured to measure a pressure inside the inner balloon.

Optionally, the outer balloon is defined by a pear shape and configured to be positioned in the pulmonary vein of the patient to occlude the pulmonary vein.

Optionally, when inflated, the outer balloon has an axis that extends along a length of the outer balloon and through the center of the outer balloon and a distance from the axis to an outer surface of the outer balloon changes along said length.

Optionally, upon being inflated, a shape of the outer balloon is defined by a curve of a surface of the outer balloon that is further defined by a plane intersecting an entire length of the catheter, wherein the curve is characterized by a first point, a second point, and a third point sequentially positioned, and extending along the length of the catheter, between a proximal point and a distal point, wherein a first slope between the proximal point and first point has a first value, a second slope between the first point and second point has a second value, a third slope between the second point and the third point has a third value, a fourth slope between the third point and distal point has a fourth value, and wherein an absolute value of the first value is greater than an absolute value of the second value, an absolute value of the third value or an absolute value of the fourth value, the absolute value of the second value is greater than the absolute value of the third value, and the absolute value of the fourth value is greater than the absolute value of the third value; and, when inflated, the inner balloon has the shape of an oblate spheroid where the minor axis, or short axis, coincides with the longitudinal axis of the catheter and the major axis, or long axis, is perpendicular to the catheter.

Optionally, upon being inflated, a shape of the outer balloon may be defined by a first distance from a central axis of the outer balloon to a first proximal point on an outer surface of the outer balloon, a second distance from the central axis to a second proximal point on the outer surface of the outer balloon, a third distance from the central axis to a third point on the outer surface of the outer balloon, a fourth distance from the central axis to a first distal point on the outer surface of the outer balloon, and a fifth distance from the central axis to a second distal point on the outer surface of the outer balloon, wherein each of the first proximal point, the second proximal point, the third point, the first distal point, and the second distal point are sequentially positioned along a length of the central axis starting from a proximal position and extending distally, wherein the second distance is greater than the first distance, the third distance, and the fifth distance and wherein the fourth distance is greater than the first distance, the second distance, the third distance, and the fifth distance.

Optionally, the inner balloon has a spherical, ovoid, conical, disc, elliptical, rectangular prism, or triangular prism shape.

Optionally, when inflated, the outer balloon is characterized by at least one first radial length extending from a central point on an axis extending longitudinally along the catheter and through the outer balloon to a point on a surface of the outer balloon, wherein, when inflated, the inner balloon, is characterized by at least one second radial length extending from a central point on an axis extending longitudinally along the catheter and through the inner balloon to a point on a surface of the inner balloon, and wherein the at least one first radial length is different than the at least one second radial length. Optionally, the at least one first radial length is greater than the at least one second radial length by any amount or by at least 10%.

Optionally, upon the inner balloon and outer balloon being inflated, the ablation zone has a width and curved length defined by an extent of contact between the outer balloon and the cardiac tissue.

The present specification also discloses a method of treating atrial fibrillation, the method comprising: positioning a catheter in a pulmonary vein leading to a left atrium of a heart of a patient, said catheter comprising an elongate body with proximal and distal ends, wherein an outer balloon and an inner balloon are positioned at the distal end such that the inner balloon lies within the outer balloon; inflating the outer balloon to a first pressure to occlude blood flow in the pulmonary vein; beginning vapor flow to the inner balloon to inflate said inner balloon, wherein upon full expansion the inner balloon contacts with a predetermined circumferential area of the outer balloon so that thermal energy is transmitted from within the inner balloon through the outer balloon into surrounding cardiac tissue which is in contact with the predetermined circumferential area of the outer balloon; stopping delivery of vapor to the inner balloon after a predetermined time thereby causing the inner balloon to deflate and disconnect from the outer balloon; and deflating the outer balloon.

Optionally, vapor is supplied to the inner balloon by a flexible heating chamber positioned inline within the body at a position proximate and proximal to the outer balloon. Optionally, the first pressure is greater than a mean pulmonary vein pressure and less than 5 atm.

Optionally, vapor flow to the inner balloon raises a temperature within the inner balloon to equal to or greater than 100 degrees Celsius and the pressure between the inner balloon is greater than the pressure in the outer balloon.

Optionally, after vapor flow to the inner balloon, air or $CO_2$ is circulated into and out of the outer balloon to maintain a temperature of a portion of the outer balloon below 60 degrees Celsius.

Optionally, after vapor flow to the inner balloon, air or $CO_2$ is suctioned out of the outer balloon to maintain pressure within the outer balloon at the first pressure.

Optionally, said transmission of thermal energy causes a temperature of a portion of said cardiac tissue to be raised to at least 60 degrees Celsius.

Optionally, the inner balloon is moved along a length of the body, within the outer balloon, to better position the inner balloon at a target range of circumferential areas of the outer balloon.

Optionally, upon inflation, a length of the outer balloon is greater than a length of the inner balloon and a diameter of the inner balloon approximates a diameter of the outer balloon and a volume of the outer balloon is greater than the volume of the inner balloon.

The present specification also discloses a method of ablating cardiac tissue, the method comprising: positioning a catheter in a pulmonary vein of a patient's heart, said catheter comprising an elongate body with proximal and distal ends, wherein an outer balloon and an inner balloon are positioned at the distal end such that the inner balloon lies within the outer balloon; inflating the outer balloon to a first pressure to occlude blood flow in the pulmonary vein; beginning vapor flow to the inner balloon to inflate said inner balloon and raise a temperature within the inner balloon to greater than or equal to 100 degrees Celsius, and a second pressure within the inner balloon to greater than or equal to a first pressure wherein upon full expansion the inner balloon contacts with a circumferentially-defined target region of the outer balloon so that thermal energy is transmitted from within the inner balloon through the outer balloon into said cardiac tissue which is in contact with the predetermined circumferential area of the outer balloon; suctioning air or $CO_2$ or a coolant out of the outer balloon to maintain pressure within the outer balloon to the first pressure; stopping delivery of vapor to the inner balloon after a predetermined time thereby causing the inner balloon to deflate and disconnect from the outer balloon; deflating the outer balloon; and removing the catheter from the pulmonary vein.

Optionally, vapor is supplied to the inner balloon by a flexible heating chamber positioned inline within the body at a position proximate and proximal to the outer balloon.

Optionally, the first pressure is greater than a mean pulmonary vein pressure and less than 5 atm and the second pressure is greater or equal to a first pressure.

Optionally, after vapor flow to the inner balloon, air or $CO_2$ or a coolant is circulated into and out of the outer balloon to maintain a temperature of a portion of the outer balloon below 60 degrees Celsius.

Optionally, said transmission of thermal energy causes a temperature of a portion of said cardiac tissue to be raised to at least 60 degrees Celsius.

Optionally, the inner balloon is moved along a length of the body, within the outer balloon, to better position the inner balloon at a circumferentially defined target area of the outer balloon.

Optionally, prior to removal of the catheter and during the ablation, the pulmonary vein is electrically paced to confirm achievement of at least one therapeutic objective. In some embodiments, the therapeutic objective is electrical isolation of one or more of the pulmonary veins.

Optionally, said at least one therapeutic objective comprises raising a temperature of 25% of an endocardium around a circumference to at least 60 degrees Celsius and maintaining said temperature for greater than 10 seconds.

The present specification also discloses a method of ablating cardiac tissue to treat an arrhythmia, the method comprising: positioning a catheter in a pulmonary vein of a patient's heart, said catheter comprising an elongate body with proximal and distal ends, wherein an outer balloon and an inner balloon are positioned at the distal end such that the inner balloon lies within the outer balloon; inflating the outer balloon to a first pressure to occlude blood flow in the pulmonary vein, wherein the first pressure is greater than a mean pulmonary vein pressure and less than 5 atm; beginning vapor flow to the inner balloon to inflate said inner balloon and raise a temperature within the inner balloon to greater than or equal to 100 degrees Celsius, wherein upon full expansion the inner balloon contacts the outer balloon to create an ablation zone, and wherein thermal energy is transmitted from within the inner balloon through the outer balloon into said cardiac tissue which is in contact with the ablation zone; circulating air or $CO_2$ or a coolant in to and out of the outer balloon to maintain a temperature of a portion of the outer balloon below 60 degrees Celsius; stopping delivery of vapor to the inner balloon after a predetermined time thereby causing the inner balloon to deflate and disconnect from the outer balloon; deflating the outer balloon by suctioning out air or $CO_2$ or coolant from the outer balloon; and removing the catheter from the pulmonary vein.

Optionally, vapor is supplied to the inner balloon by a flexible heating chamber positioned inline within the body at a position proximate and proximal to the outer balloon.

Optionally, after vapor flow to the inner balloon, air, $CO_2$ or a coolant is suctioned out of the outer balloon to maintain pressure within the outer balloon at the first pressure.

Optionally, said transmission of thermal energy causes a temperature of a portion of said cardiac tissue to be raised to at least 60 degrees Celsius.

Optionally, the inner balloon is moved along a length of the body, within the outer balloon, to better position the inner balloon at said ablation zone.

Optionally, the inner balloon is pre-inflated with air or $CO_2$ prior to instilling vapor. Optionally, prior to removal of the catheter, the pulmonary vein is electrically paced to confirm achievement of at least one therapeutic objective. Optionally, said at least one therapeutic objective comprises raising a temperature of 25% or more of an endocardium around a circumference to at least 60 degrees Celsius and maintaining said temperature for greater than 10 seconds.

The present specification also discloses a method of ablating cardiac tissue to treat atrial fibrillation and meet at least one therapeutic objective, the method comprising: positioning a catheter in a pulmonary vein of a patient's heart, said catheter comprising an elongate body with proximal and distal ends, wherein an outer balloon and an inner balloon are positioned at the distal end such that the inner balloon lies within the outer balloon, and wherein at least one flexible heating chamber is positioned inline within the body proximate and proximal to the outer balloon; inflating the outer balloon to a first pressure to occlude blood flow in the pulmonary vein; beginning vapor flow to the inner balloon to inflate said inner balloon and raise a temperature within the inner balloon to greater than or equal to 100 degrees Celsius, wherein upon full expansion the inner balloon is moved along a length of the catheter to contact the outer balloon at a desired position thereby creating an ablation zone at said desired position, and wherein thermal energy is transmitted from within the inner balloon through the outer balloon into said cardiac tissue which is in contact with the ablation zone so that a temperature of a portion of said cardiac tissue is raised to at least 60 degrees Celsius; circulating air or $CO_2$ or a coolant in to and out of the outer balloon to maintain a temperature of the outer balloon, at locations away from the ablation zone, below 60 degrees Celsius; stopping delivery of vapor to the inner balloon thereby causing the inner balloon to deflate and disconnect from the outer balloon; deflating the outer balloon; and removing the catheter from the pulmonary vein.

Optionally, after vapor flow to the inner balloon, air is suctioned out of the outer balloon to maintain pressure within the outer balloon to the first pressure.

Optionally, prior to removal of the catheter, the pulmonary vein is electrically paced to confirm achievement of said at least one therapeutic objective. Optionally, the therapeutic objective is electrical isolation of a pulmonary vein. Optionally, said at least one therapeutic objective comprises raising a temperature of 25% or more of an endocardium around a circumference to at least 60 degrees Celsius and maintaining said temperature for greater than 10 seconds.

Optionally, upon inflation, a length of the outer balloon is greater than a length of the inner balloon and a diameter of the inner balloon approximates a diameter of the outer balloon and a volume of the outer balloon is greater than the volume of the inner balloon.

The present specification also discloses a method of ablating cardiac tissue to treat atrial fibrillation and meet at least one therapeutic objective, the method comprising: positioning a catheter in a pulmonary vein of a patient's heart, said catheter comprising an elongate body with proximal and distal ends, wherein an outer balloon and an inner balloon are positioned at the distal end such that the inner balloon lies within the outer balloon, and wherein at least one flexible heating chamber is positioned inline within the body proximate and proximal to the outer balloon; inflating the inner balloon to a first pressure to occlude blood flow in the pulmonary vein; inflating the outer balloon to a second pressure to displace the blood away from the first balloon wherein the second pressure is equal to or less than the first pressure, beginning vapor flow to the inner balloon to heat said inner balloon and raise a temperature within the inner balloon to greater than or equal to 100 degrees Celsius and a third pressure wherein the third pressure is same or higher than the first pressure, wherein the inner balloon contacts the outer balloon at a desired position thereby creating an ablation zone at said desired position, and wherein thermal energy is transmitted from within the inner balloon through the outer balloon into said cardiac tissue which is in contact with the ablation zone so that a temperature of a portion of said cardiac tissue is raised to at least 60 degrees Celsius; circulating air or $CO_2$ or a coolant into and out of the outer balloon to maintain a temperature of the outer balloon, at locations away from the ablation zone, below 60 degrees Celsius; stopping delivery of vapor to the inner balloon thereby causing the inner balloon to deflate and disconnect from the outer balloon; deflating the outer balloon; and removing the catheter from the pulmonary vein.

Optionally, after vapor flow to the inner balloon, air is suctioned out of the outer balloon to maintain pressure within the outer balloon at the first pressure.

Optionally, prior to removal of the catheter, the pulmonary vein is electrically paced to confirm achievement of said at least one therapeutic objective. Optionally, the therapeutic objective is electrical isolation of a pulmonary vein.

Optionally, said at least one therapeutic objective comprises raising a temperature of 25% of an endocardium around a circumference to at least 60 degrees Celsius and maintaining said temperature for greater than 10 seconds.

Optionally, upon inflation, a length of the outer balloon is greater than a length of the inner balloon and a diameter of the inner balloon approximates a diameter of the outer balloon and a volume of the outer balloon is greater than the volume of the inner balloon.

Optionally, an intersection of the shapes of the inner balloon and the outer balloon determine a shape and/or size of the ablation zone.

Optionally a durometer of an inner balloon is different from a durometer of the outer balloon.

The present specification also discloses a method of ablating a left atrial appendage tissue to treat an left atrial appendage disorder including atrial fibrillation and meet at least one therapeutic objective, the method comprising: positioning a catheter in a left atrial appendage of a patient's heart, said catheter comprising an elongate body with proximal and distal ends, wherein an outer balloon and an inner balloon are positioned at the distal end such that the inner balloon lies within the outer balloon and a third balloon is positioned distal to the outer balloon, and wherein at least one flexible heating chamber is positioned inline within the body proximate and proximal to the outer balloon; inflating the outer balloon to a first pressure to occlude blood flow to the left atrial appendage; inflating the third balloon to a second pressure to displace the blood out of the left atrial appendage; beginning irrigation with a fluid through the catheter distal to the third balloon into the left atrial appendage to irrigate any remaining blood between the third balloon and the left atrial appendage out of the left atrial appendage, followed by applying suction through the lumen in the catheter to aspirate any excess fluid and blood and to oppose the left atrial appendage against the third balloon; beginning vapor flow to the third balloon to heat said third balloon and raise a temperature within the third balloon to greater than or equal to 100 degrees Celsius and a third pressure wherein the third pressure is equal to or greater than the second pressure, wherein the third balloon contacts at least 10% of the left atrial appendage creating a transmural ablation to at least 10% of the left atrial appendage. Optionally, the method further comprises delivering vapor to the inner balloon wherein thermal energy is transmitted from within the inner balloon through the outer balloon into said cardiac tissue at the opening of the left atrial appendage which is in contact with the ablation zone so that a temperature of a portion of said cardiac tissue is raised to at least 60 degrees Celsius; circulating air or $CO_2$ or a coolant in to and out of the outer balloon to maintain a temperature of the outer balloon, at locations away from the ablation zone, below 60 degrees Celsius; stopping delivery of vapor to the third balloon and the inner balloon thereby causing the third balloon and the inner balloon to deflate and the inner balloon to disconnect from the outer balloon while the outer balloon maintains contact with a left atrial appendage ostium and preventing blood from flowing into the left atrial ostium; deflating the outer balloon; and removing the catheter from the left atrial appendage. Optionally, the method further comprises insertion of an acellular matrix or a scaffolding into the left atrial appendage to promote tissue growth in the left atrial appendage to decrease the surface area or a circumference of a left atrial appendage.

Optionally, after vapor flow to the inner balloon, air is suctioned out of the outer balloon to maintain a pressure within the outer balloon at the first pressure.

Optionally, prior to removal of the catheter, the left atrial appendage is electrically paced to confirm achievement of said at least one therapeutic objective. Optionally, the therapeutic objective is electrical isolation of a left atrial appendage. Optionally, said at least one therapeutic objective comprises raising a temperature of 25% of an endocardium around a circumference to at least 60 degrees Celsius and maintaining said temperature for greater than 10 seconds.

Optionally, upon inflation, a length of the outer balloon is greater than a length of the inner balloon and a diameter of the inner balloon approximates a diameter of the outer balloon and a volume of the outer balloon is greater than the volume of the inner balloon.

Optionally, an intersection of the shapes of the inner balloon and the outer balloon determine a shape and/or size of an ablation zone.

Optionally, the durometer of an inner balloon is different from the durometer of the outer balloon. Optionally, the durometer of the outer balloon is same as the durometer of the third balloon.

Optionally, a different ablation modality, such as a cryoablation, an RF ablation or an electroporation using the above methodology or using any commercially available ablation catheter can be used for the ablation of a left atrial appendage to treat a condition of a left atrial appendage.

In one embodiment, 25% or more of a surface area of a left atrial appendage is ablated. In another embodiment, 25% or more of a thickness of a left atrial appendage is ablated.

The present specification also discloses an ablation catheter comprising: a shaft having multiple separate channels extending there through; an inner balloon having a first inflated volume in fluid communication with a first one of the multiple separate channels; an outer balloon having a second inflated volume in fluid communication with a second one of the multiple separate channels, wherein, when inflated, the outer balloon's inflated volume is equal to or greater than 105% of the inner balloon's inflated volume, wherein, when inflated, the inner balloon is positioned entirely within the outer balloon's inflated volume, wherein, when inflated, the outer balloon is configured to occlude a pulmonary vein of the patient, wherein the inner balloon is configured to receive steam and wherein, when inflated, an exterior surface of the inner balloon contacts an interior surface of the outer balloon to form an ablation zone on a surface of the outer balloon.

Optionally, a surface area of the ablation zone is less than 50% of the total surface area of the outer balloon.

Optionally, the ablation zone is positioned closer to a distal end of the outer balloon than a proximal end of the outer balloon.

Optionally, a position of the ablation zone changes based on an anatomy of the patient.

Optionally, a location of the ablation zone is based upon a physiology of a patient. Optionally, the shaft, each of the multiple separate channels, the inner balloon, and the outer balloon are made of a same material. Optionally, the same material is Arnitel. Optionally, the same material has a softening temperature of 100° C. or greater.

Optionally, a circumference of the inner balloon at its inflated volume, does not change more than 10% after one use.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 7A is an illustration of a cooled catheter, in accordance with one embodiment of the present specification;

FIG. 7B is a cross-section view of the shaft of the cooled catheter of FIG. 7A;

FIG. 8A illustrates a first ablation catheter in accordance with an embodiment of the present specification;

FIG. 8B is a cross sectional view of a shaft or elongate body of the catheter of FIG. 8A;

FIG. 9A illustrates a second ablation catheter in accordance with an embodiment of the present specification;

FIG. 9B is a cross sectional view of a shaft or elongate body of the catheter of FIG. 9A;

FIG. 10A illustrates a third ablation catheter in accordance with an embodiment of the present specification;

FIG. 10B is a cross sectional view of a shaft or elongate body of the catheter of FIG. 10A;

FIG. 14E illustrates the mapping balloon with mapping electrodes of the catheter of FIG. 14D;

FIG. 14F illustrates a cross sectional view of a mid-shaft portion of the catheter of FIG. 14D;

FIG. 14G illustrates a cross sectional view of a distal tip portion of the catheter of FIG. 14D;

FIG. 14I illustrates a cardiac ablation catheter in accordance with yet another embodiment of the present specification;

FIG. 14J is a cross sectional view of a mid-shaft portion of the catheter of FIG. 14I;

FIG. 19A illustrates a side cross section view of an embodiment of a cardiac ablation catheter, where the distal attachment comprises an inner balloon lying within an outer balloon;

FIG. 19B illustrates the channels within the catheter of FIG. 19A, in accordance with one embodiment;

FIG. 23B illustrates a plurality of views of an outer balloon of the catheter of FIG. 23A, in accordance with some embodiments of the present specification;

FIG. 25D illustrates transverse cross-sectional, longitudinal cross-sectional and perspective views of an outer catheter of the catheter of FIG. 25A, in accordance with some embodiments of the present specification;

FIG. 25K illustrates an exemplary double balloon embodiment with insulation regions, in accordance with some embodiments of the present specification;

FIG. 25L illustrates an exemplary double balloon embodiment with insulation regions, in accordance with some embodiments of the present specification;

FIG. 25M illustrates an exemplary embodiment of a double balloon configuration where the outer balloon has thicker areas along insulation zones, and is relatively thinner along the ablation zone where heat transfer is required, so as to create a relative degree of insulation, in accordance with some embodiments of the present specification;

FIG. 26J illustrates a plurality of perspective views of the catheter of FIG. 26B wherein the inner balloon is substantially conical in shape, in accordance with some embodiments of the present specification;

FIG. 26M illustrates proximal and distal constraining elements in an outer balloon of the catheter of FIG. 26B, in accordance with some embodiments of the present specification;

FIG. 26N illustrates a transverse cross-sectional view of an elongate body of the catheter of FIG. 26B, in accordance with some embodiments of the present specification;

FIG. 26Q illustrates a transverse cross-sectional view of an inner catheter of the catheter of FIG. 26B, in accordance with some embodiments of the present specification;

FIG. 28 shows a second plurality of double balloon configurations, in accordance with some embodiments of the present specification;

FIG. 29 shows a plurality of exemplary shapes of an outer or inner balloon of a dual balloon catheter, in accordance with some embodiments of the present specification;

FIG. 30 shows a plurality of exemplary balloon ends or corners, in accordance with some embodiments of the present specification;

FIG. 31 shows a plurality of balloon shapes having at least one substantially tapering or conical end, in accordance with some embodiments of the present specification;

FIG. 32 shows a double balloon catheter having an inflatable dilation balloon, in accordance with an embodiment of the present specification;

FIG. 33 illustrates a balloon catheter to measure geometry (shape and size) of a body lumen, in accordance with some embodiments of the present specification;

FIG. 34 illustrates relative flow paths of cooling and ablation fluids in an ablation catheter, in accordance with some embodiments of the present specification;

FIG. 35A illustrates a bicornuate cardiac ablation catheter, in accordance with some embodiments of the present specification;

FIG. 35B illustrates a plurality of patterns of ablation fluid channels defined in a multilayered balloon of an ablation catheter, in accordance with various embodiments of the present specification;

FIG. 36A is a flowchart of a plurality of exemplary steps of inflating the balloons of a cardiac ablation catheters and managing pressure within the balloons during an ablation procedure, in accordance with an embodiment of the present specification;

FIG. 36B is a flowchart of a plurality of exemplary steps of a method of performing atrial fibrillation ablation, in accordance with some embodiments of the present specification;

FIG. 36C is a flowchart of a plurality of exemplary steps of another method of performing atrial fibrillation ablation, in accordance with some embodiments of the present specification;

Figure 36A:
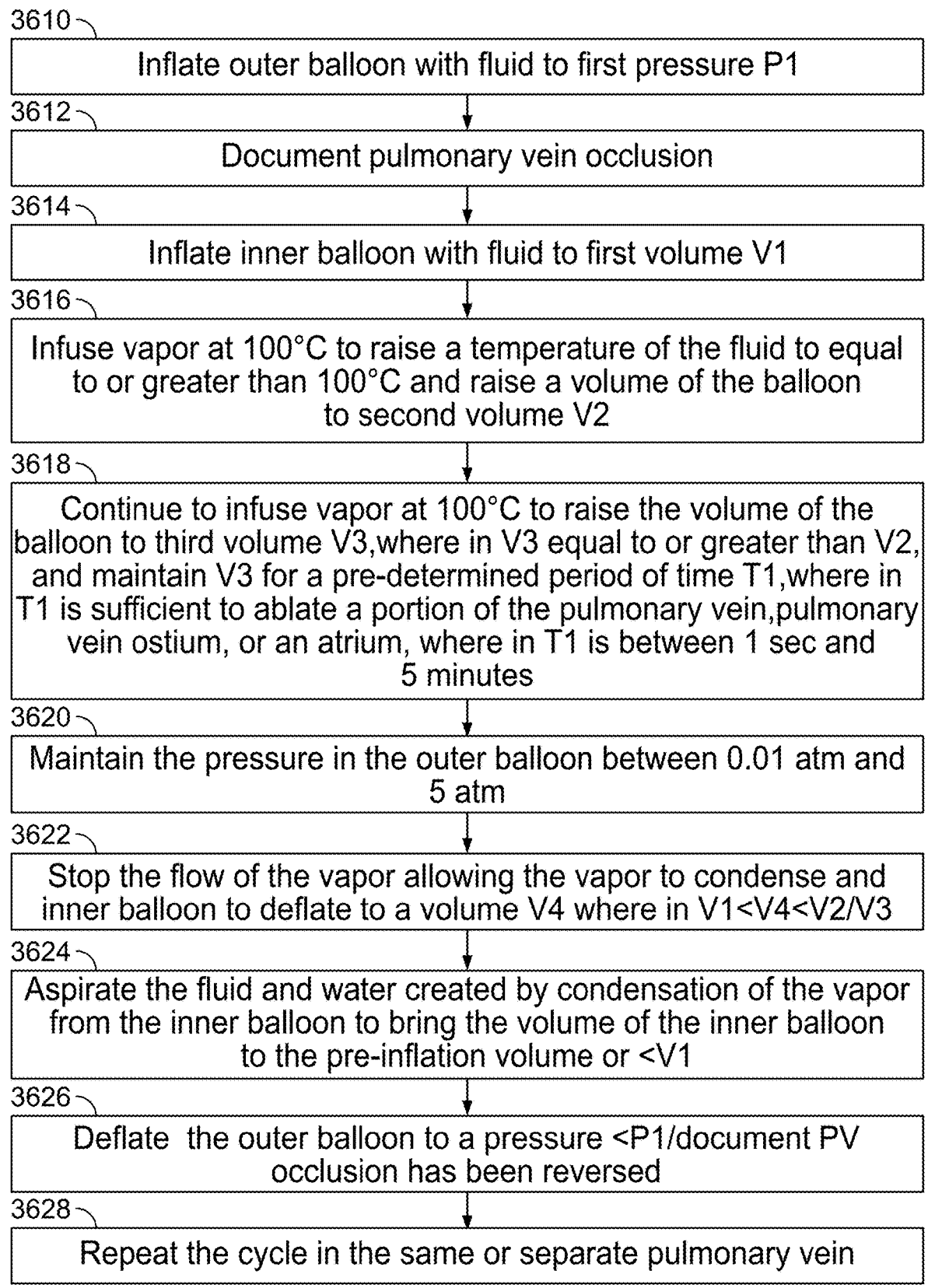
Figure 36B:
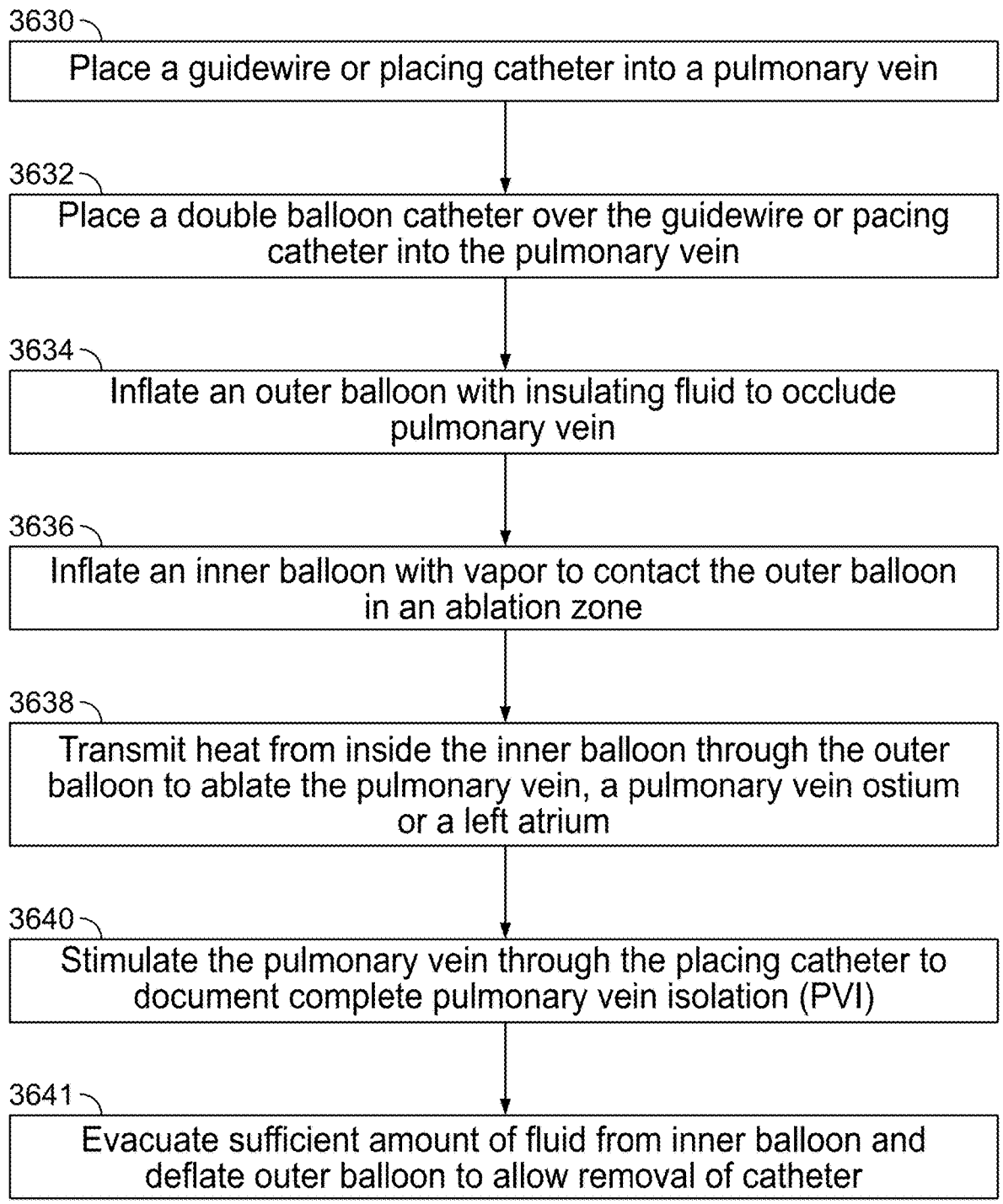
Figure 36C:
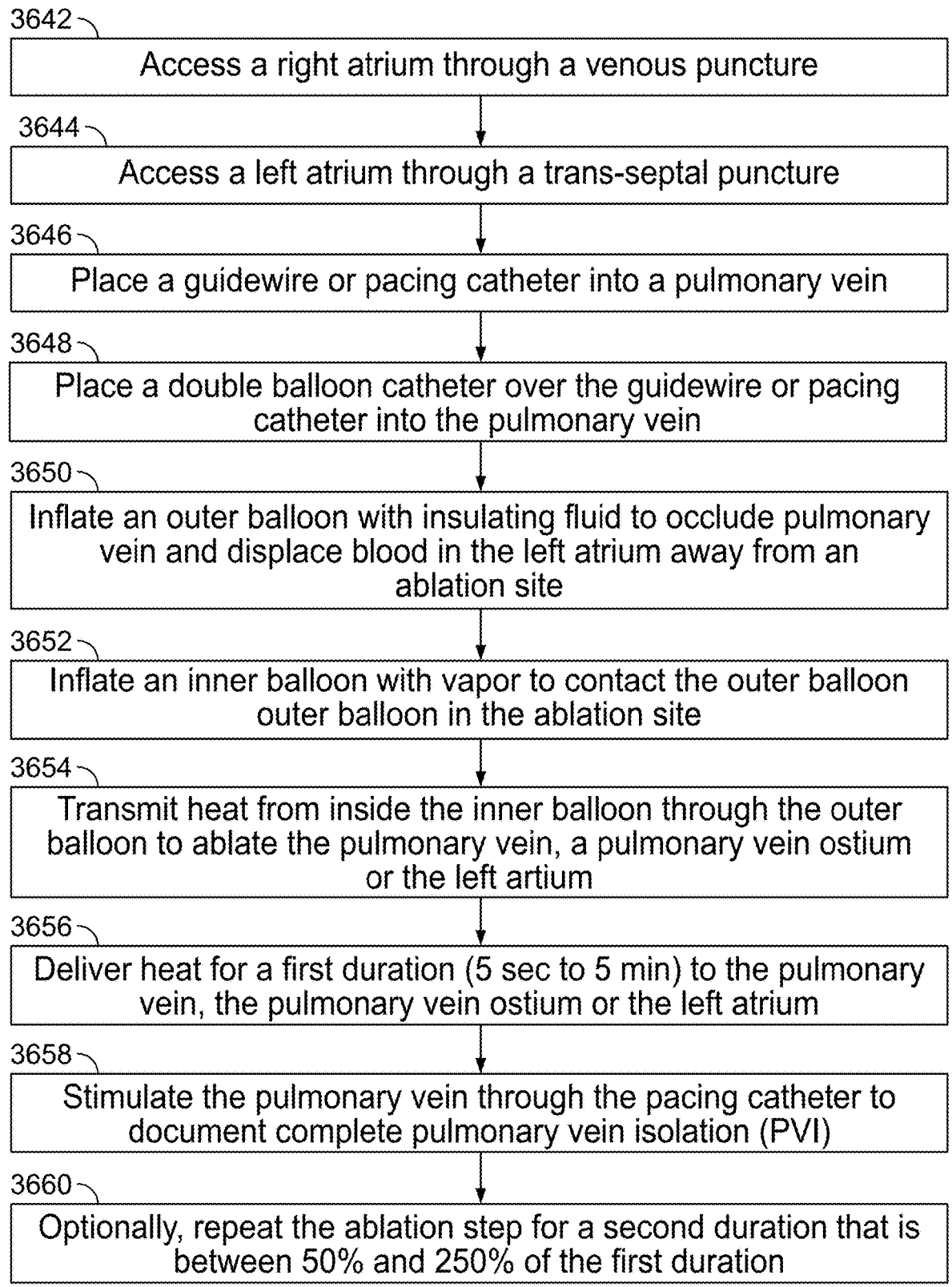
Figure 36E:
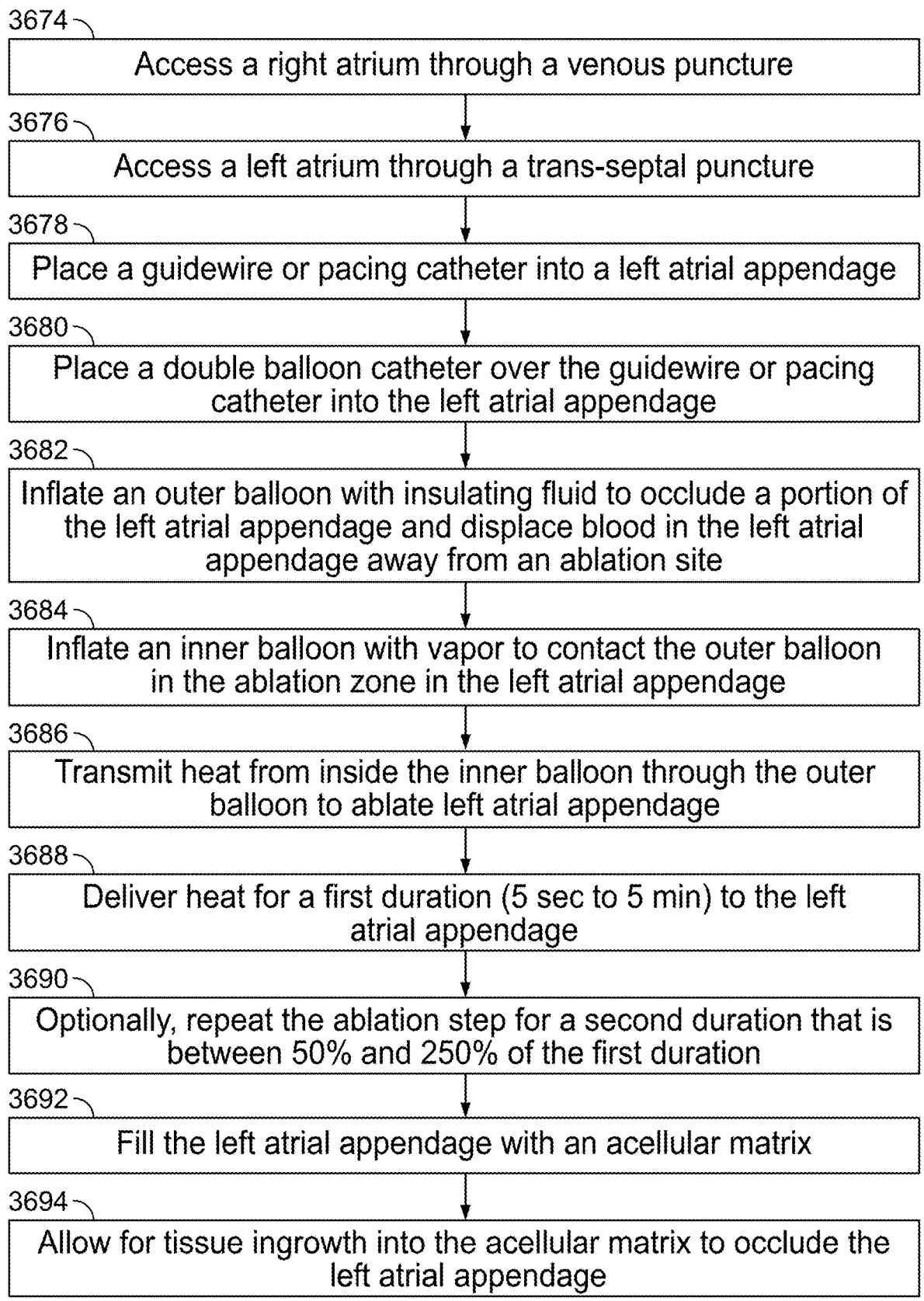
Figure 36G:
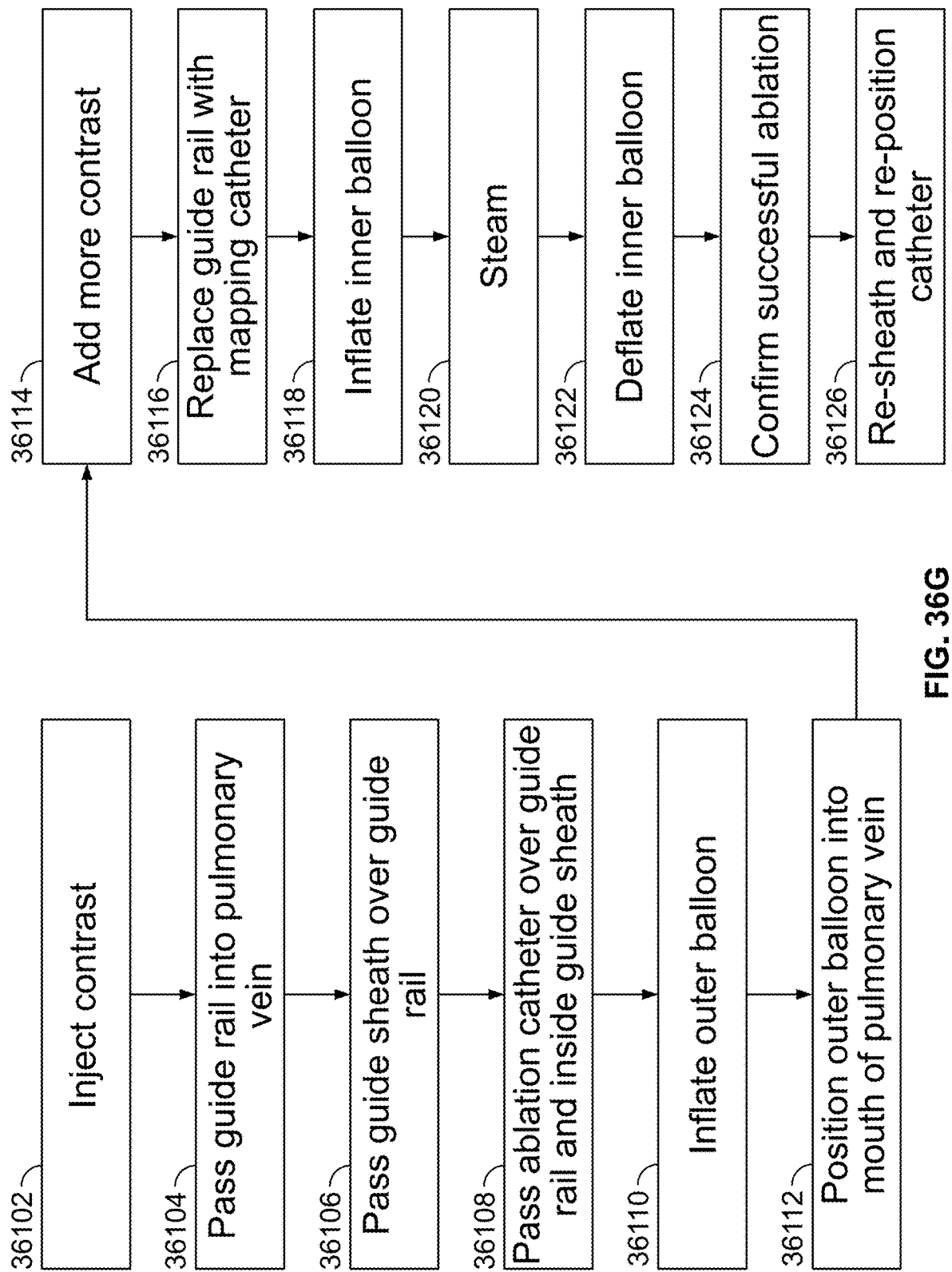
Figure 36H:
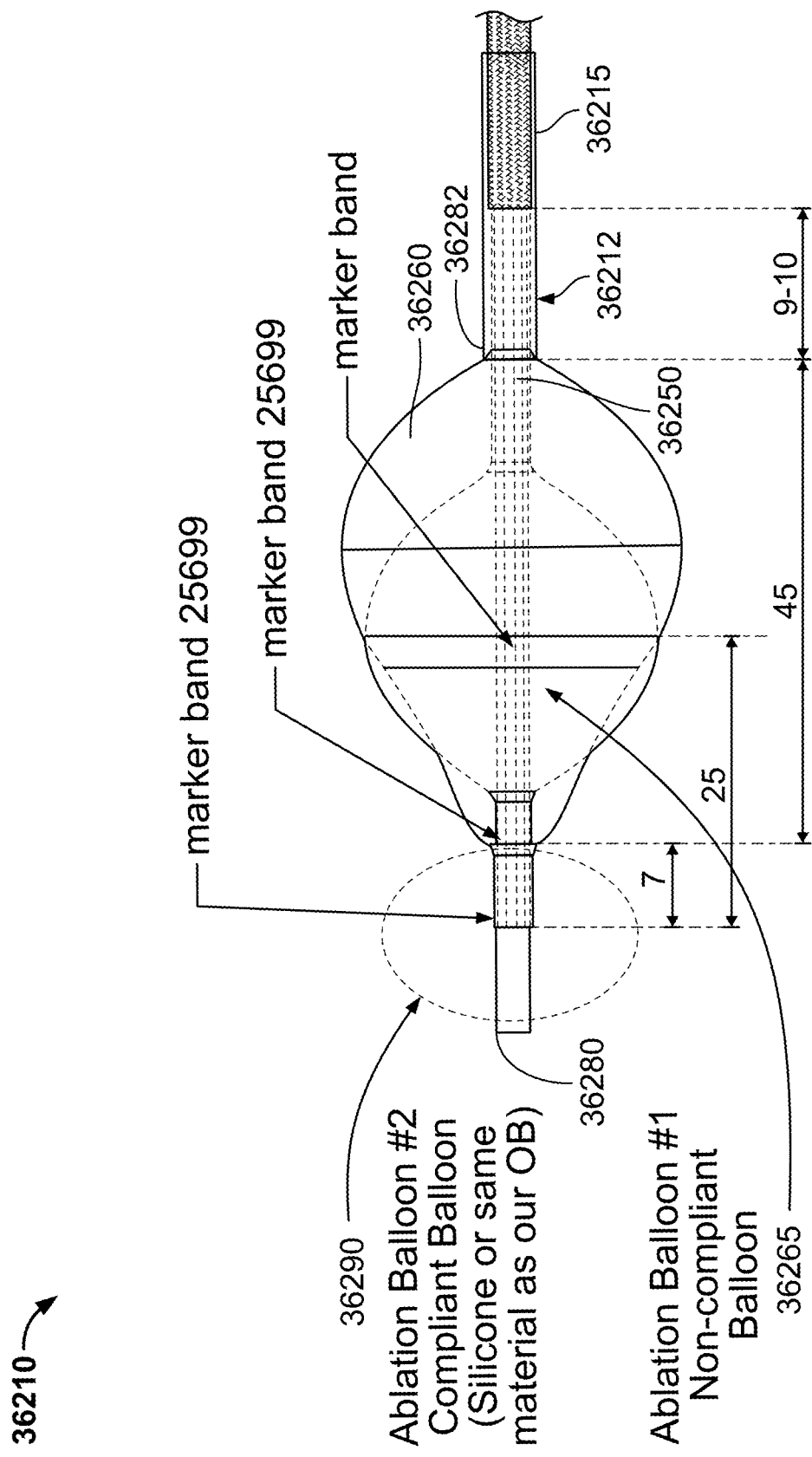
Figure 37A:
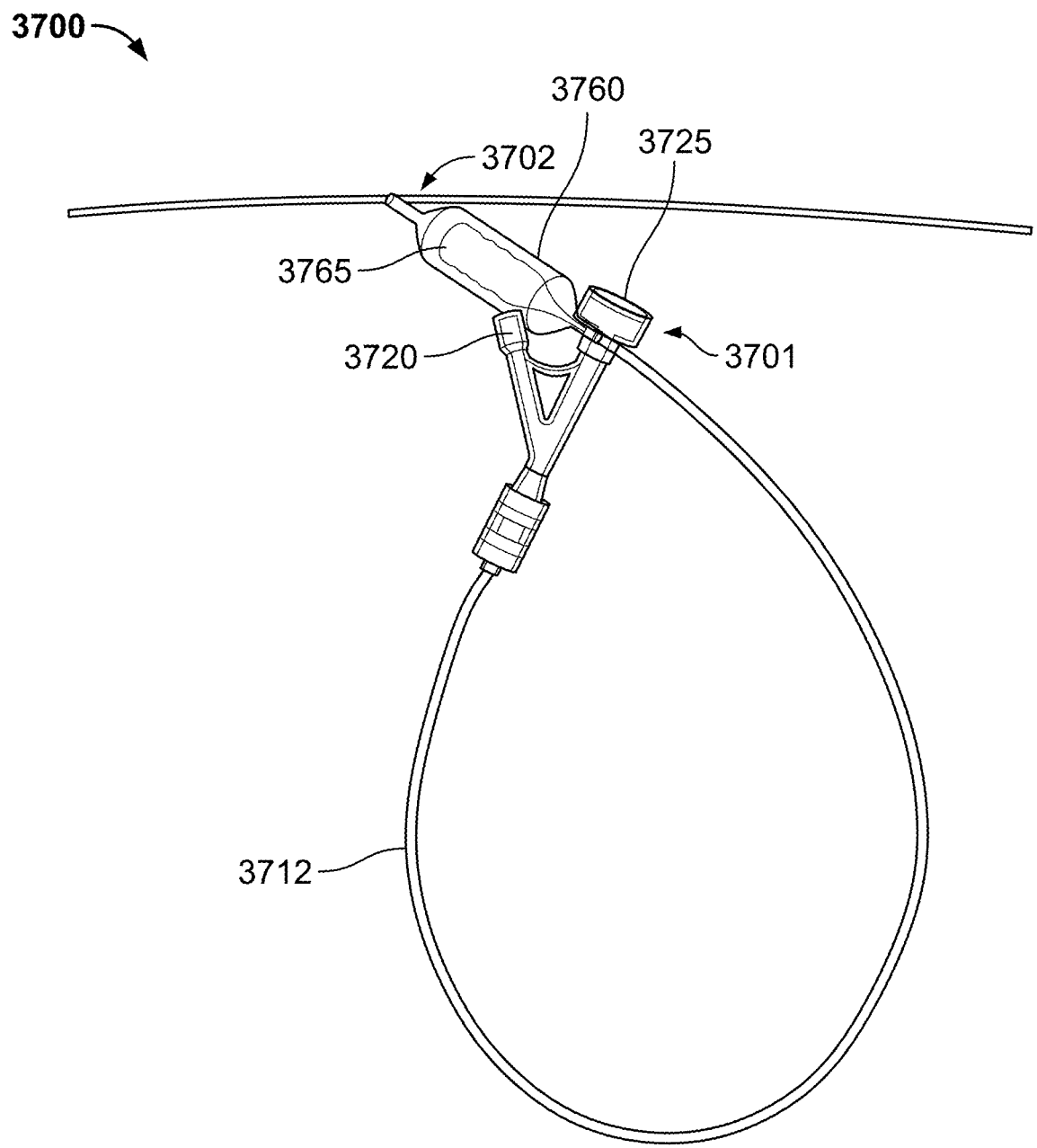
Figure 37B:
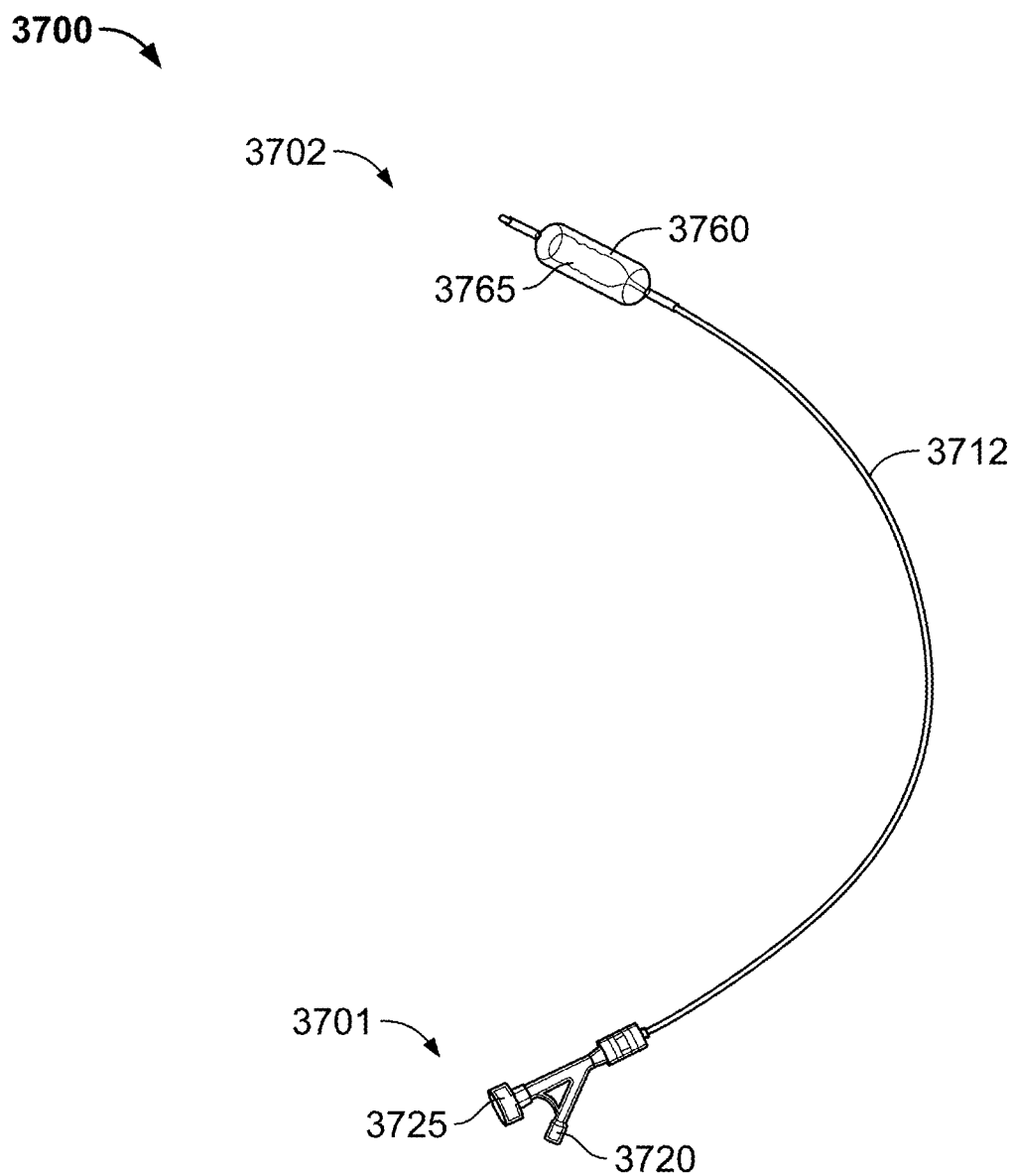
Figure 37C:
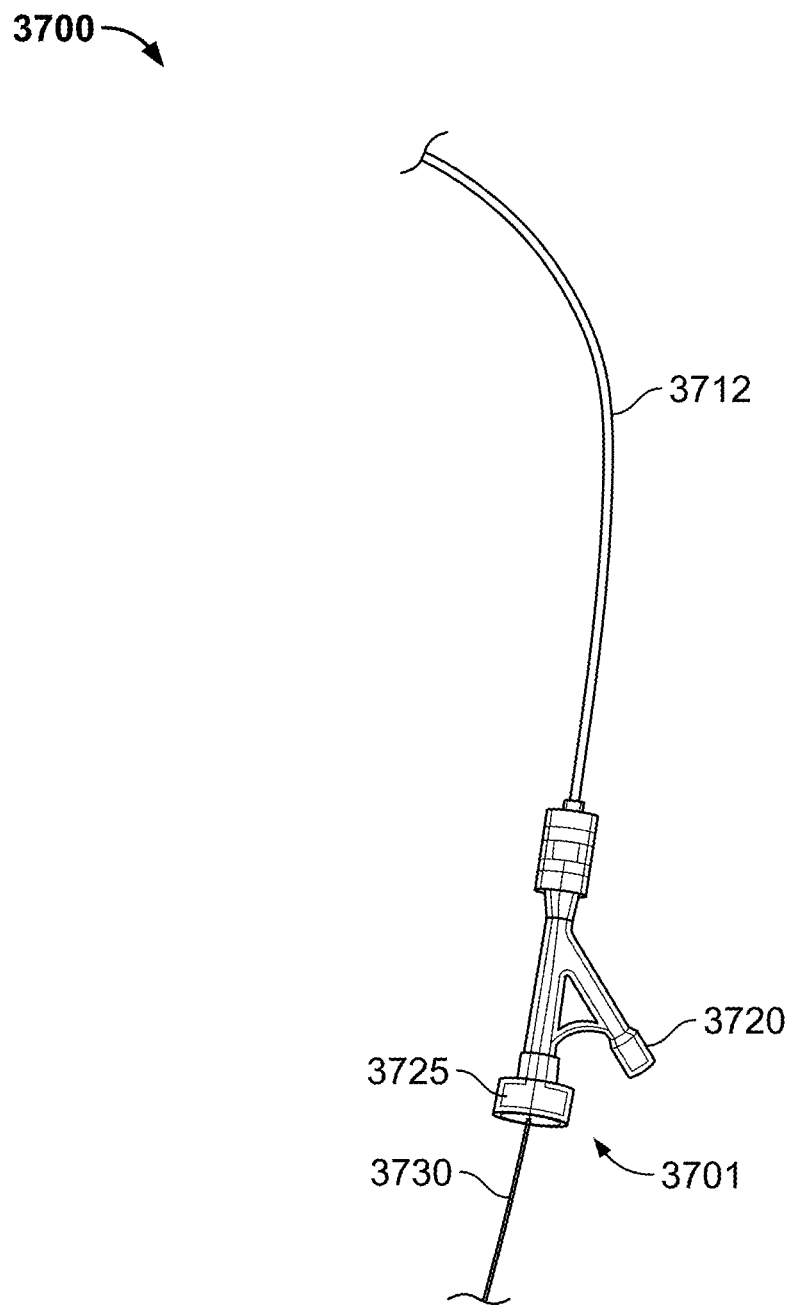
Figure 37D:
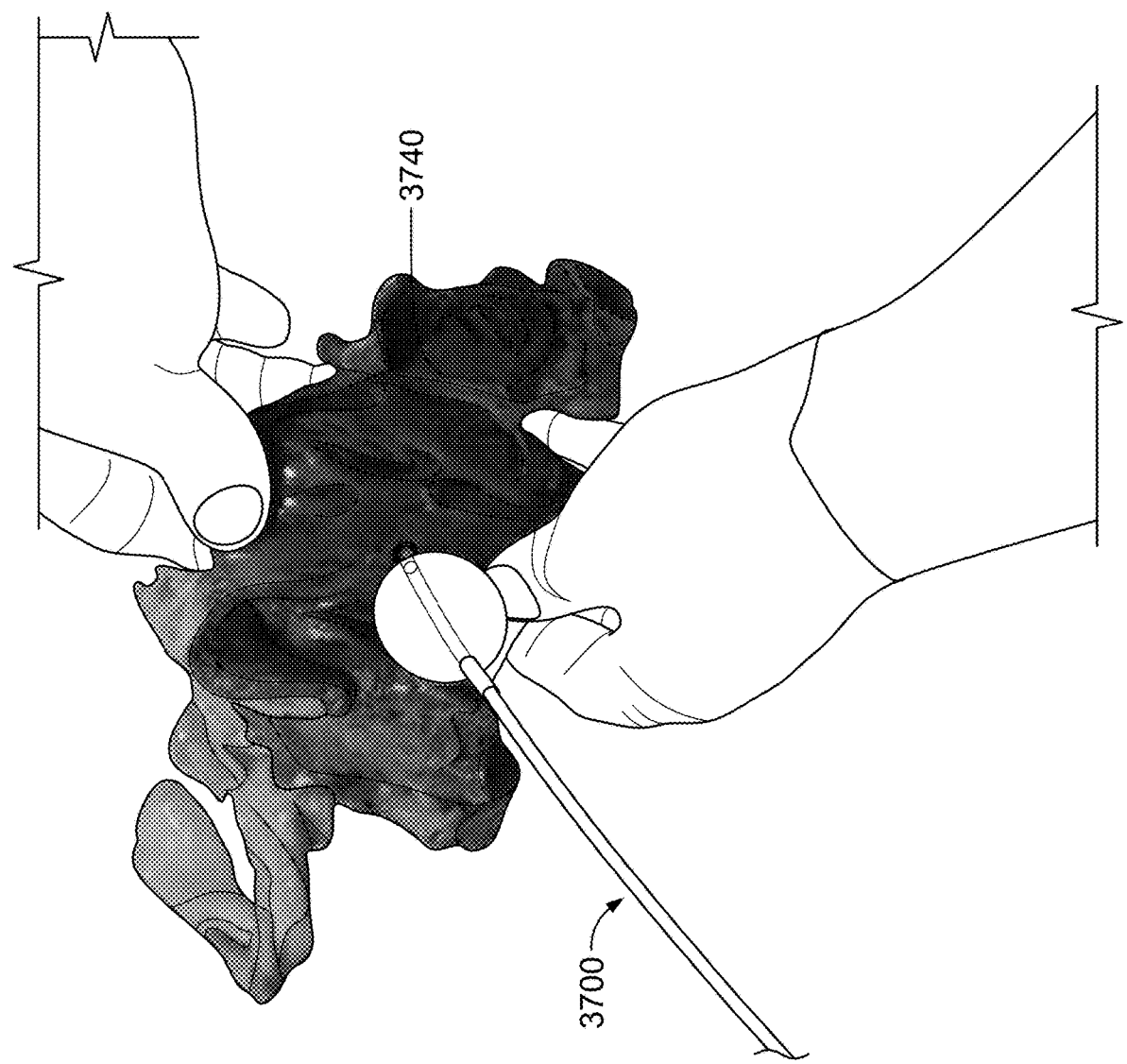
Figure 37E:
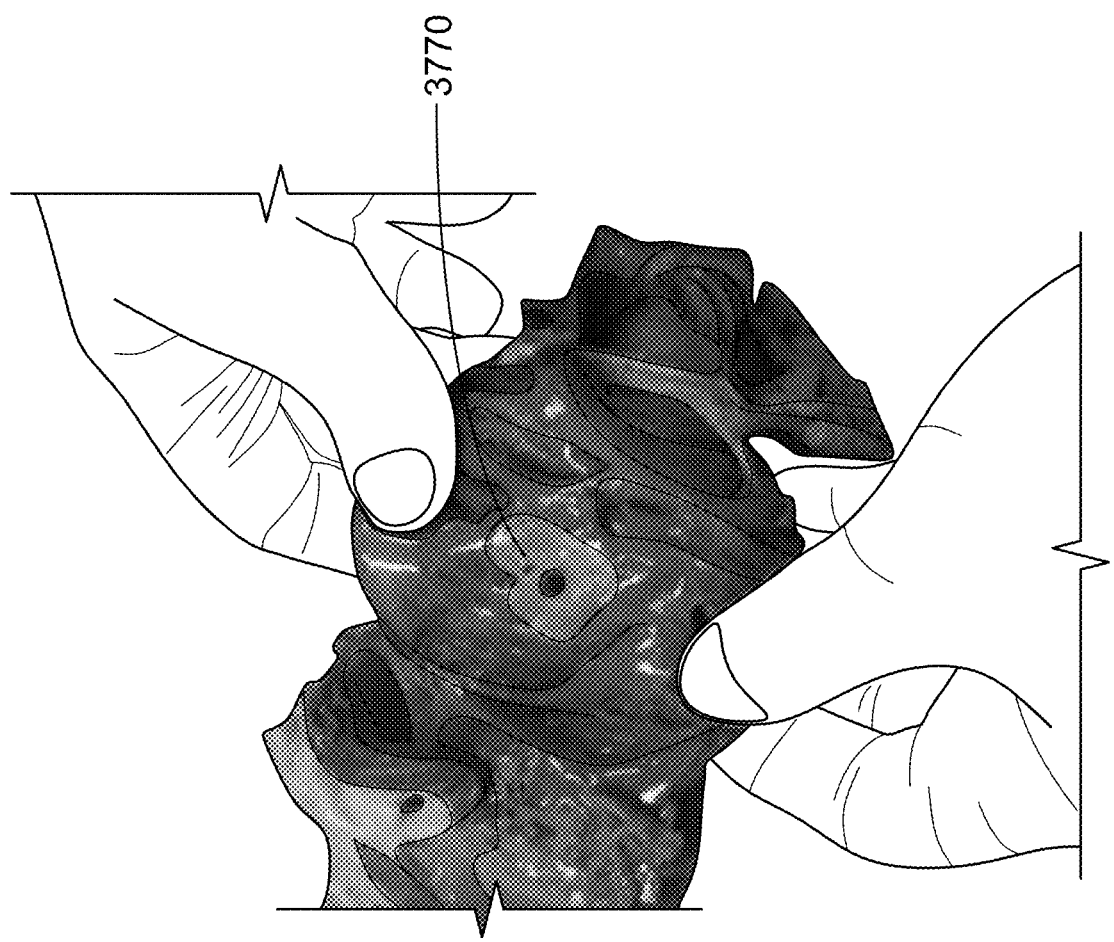
Figure 38:
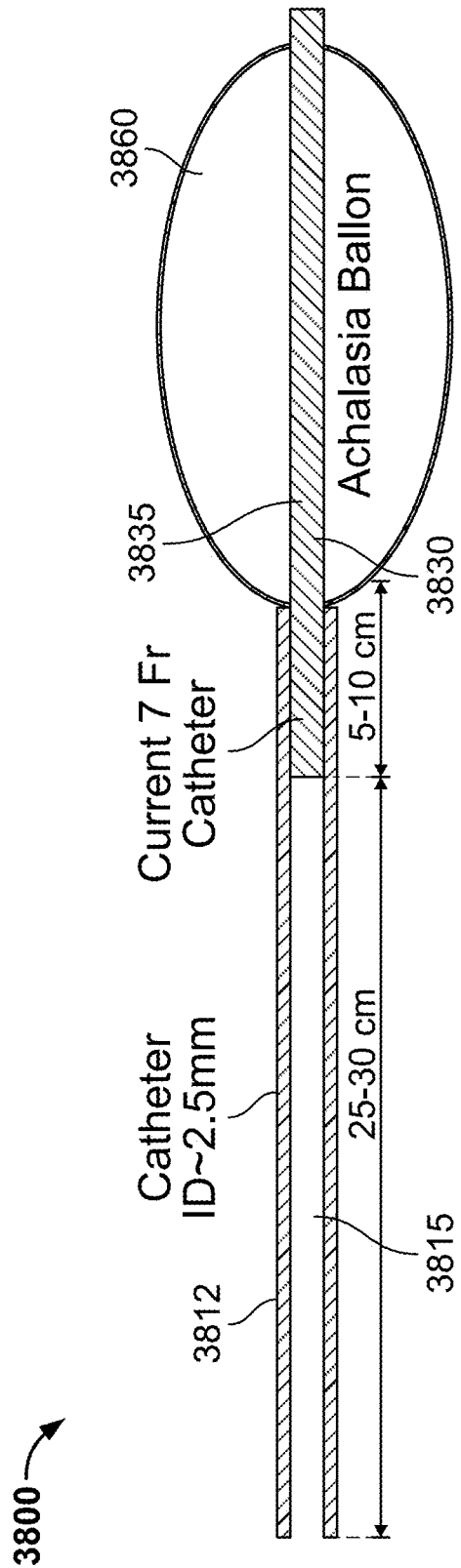
Figure 39:
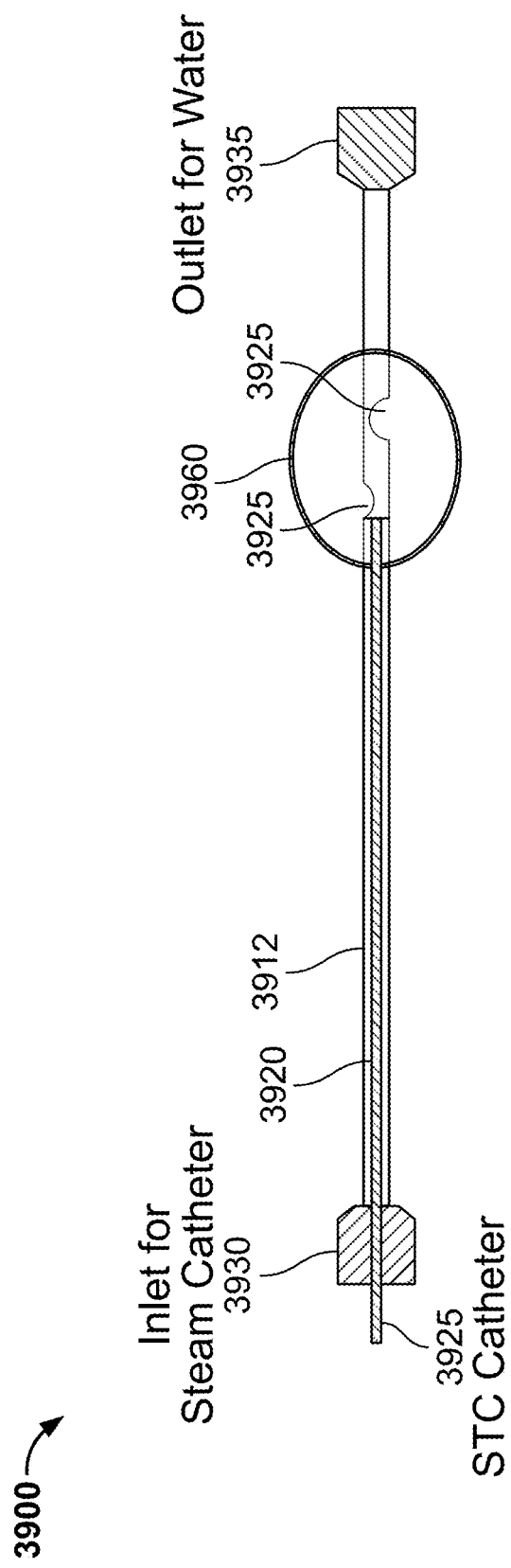
Figure 40:
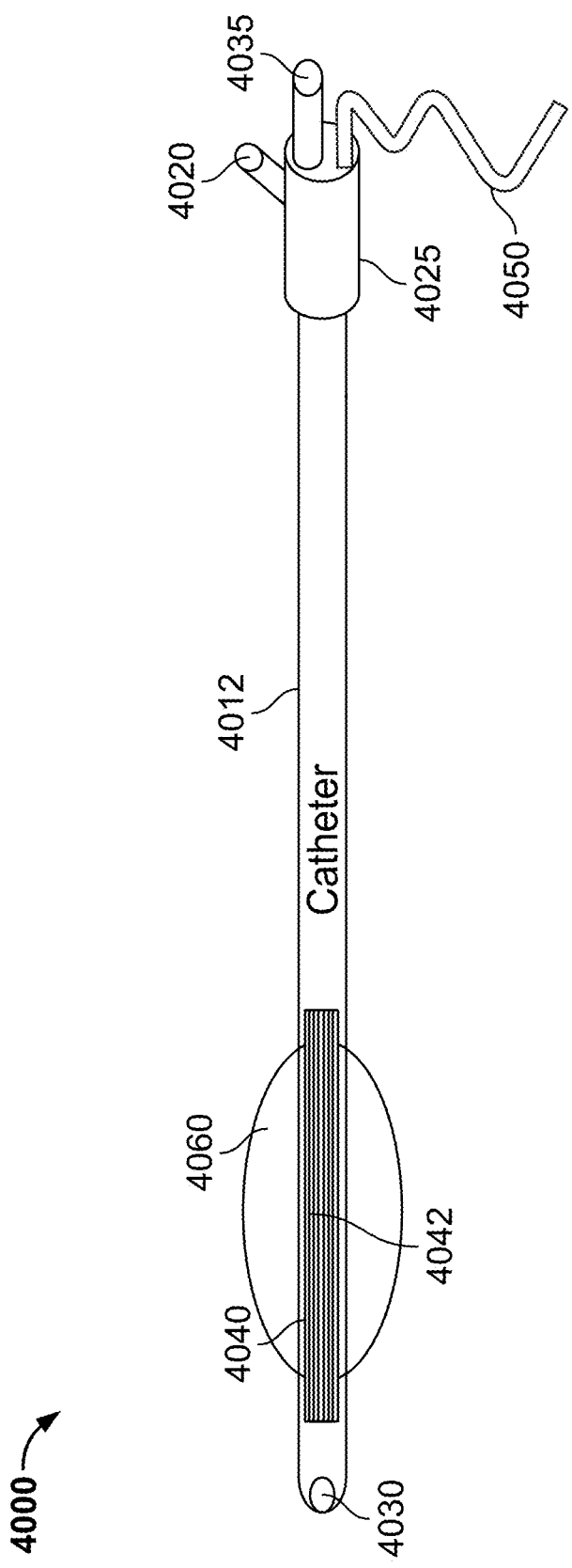
Figure 41A:
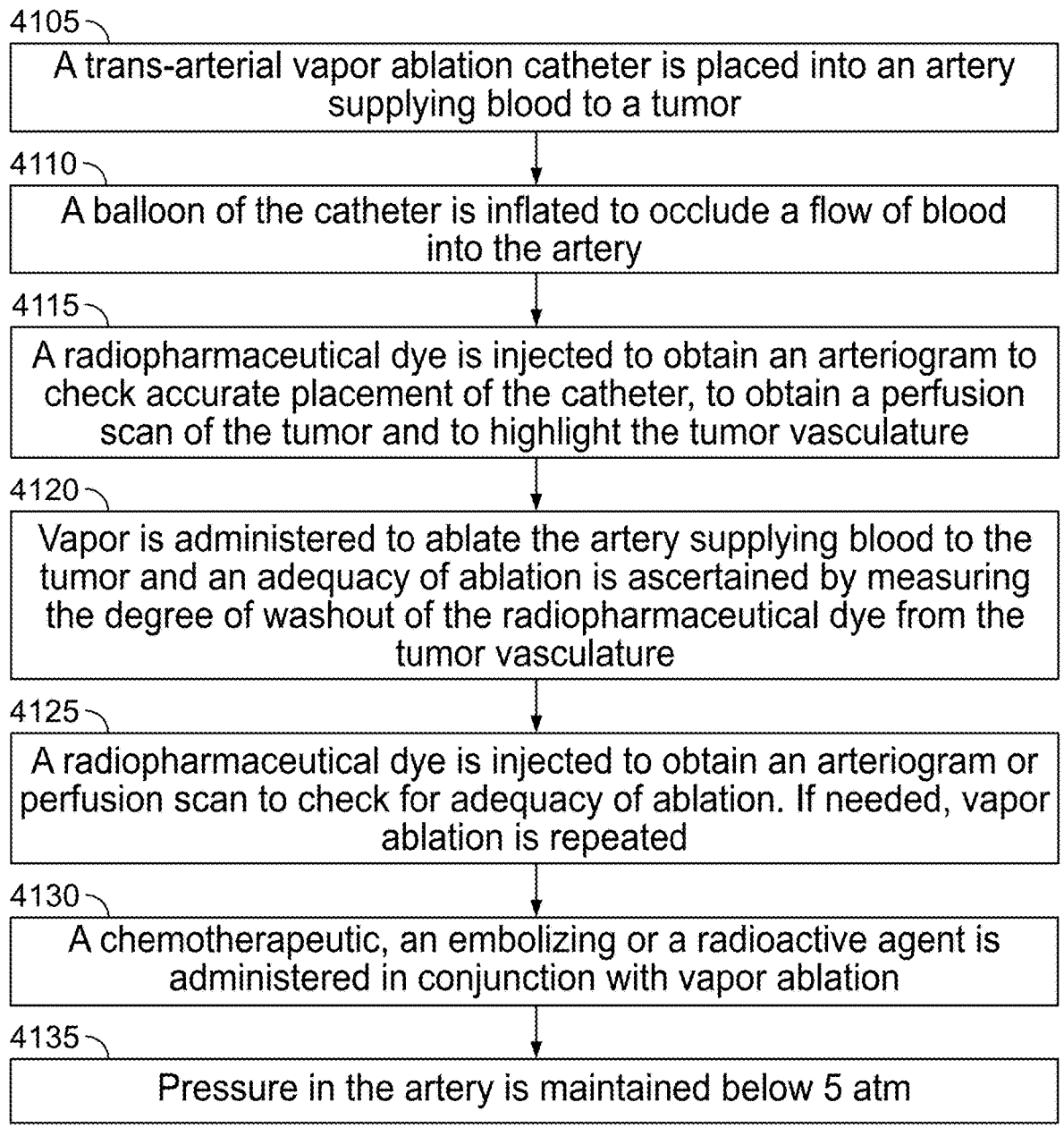
Figure 41B:
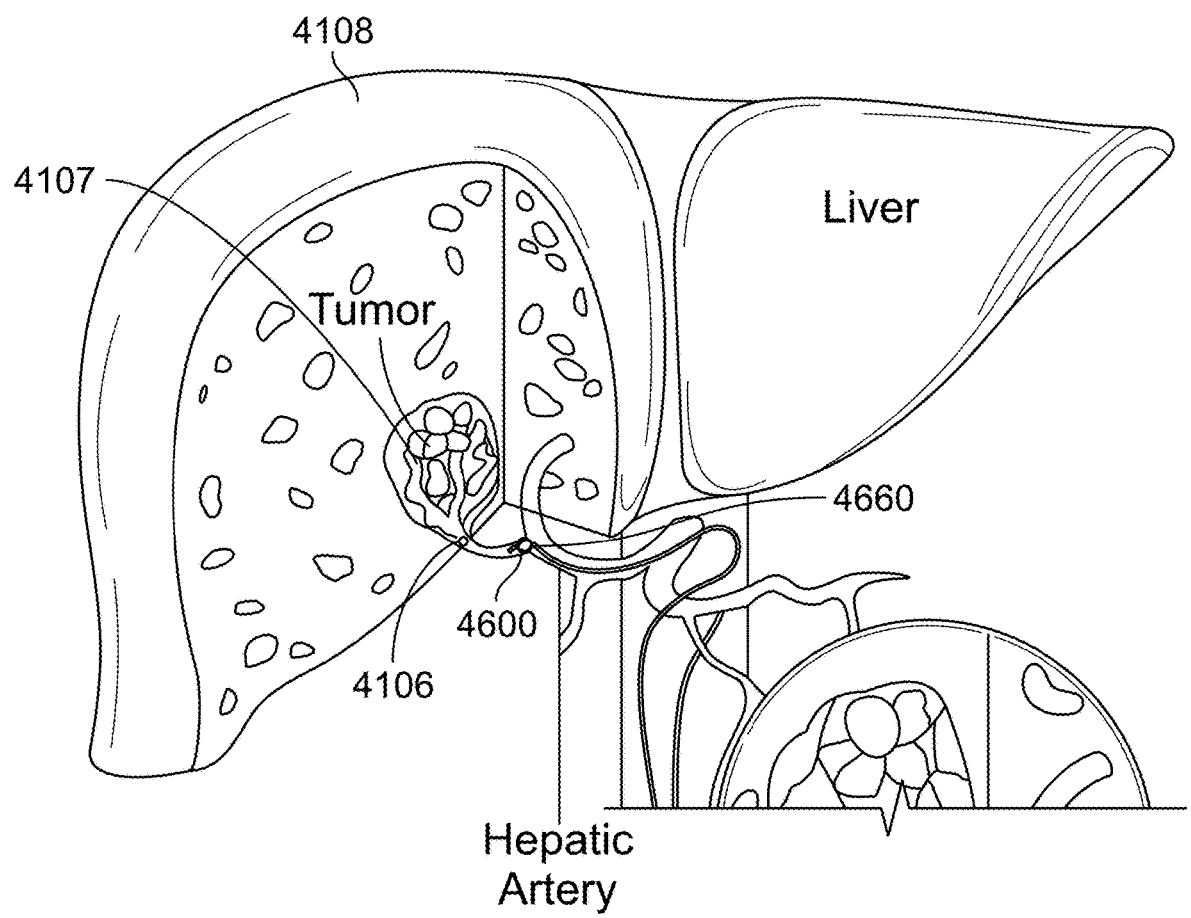
Figure 42A:
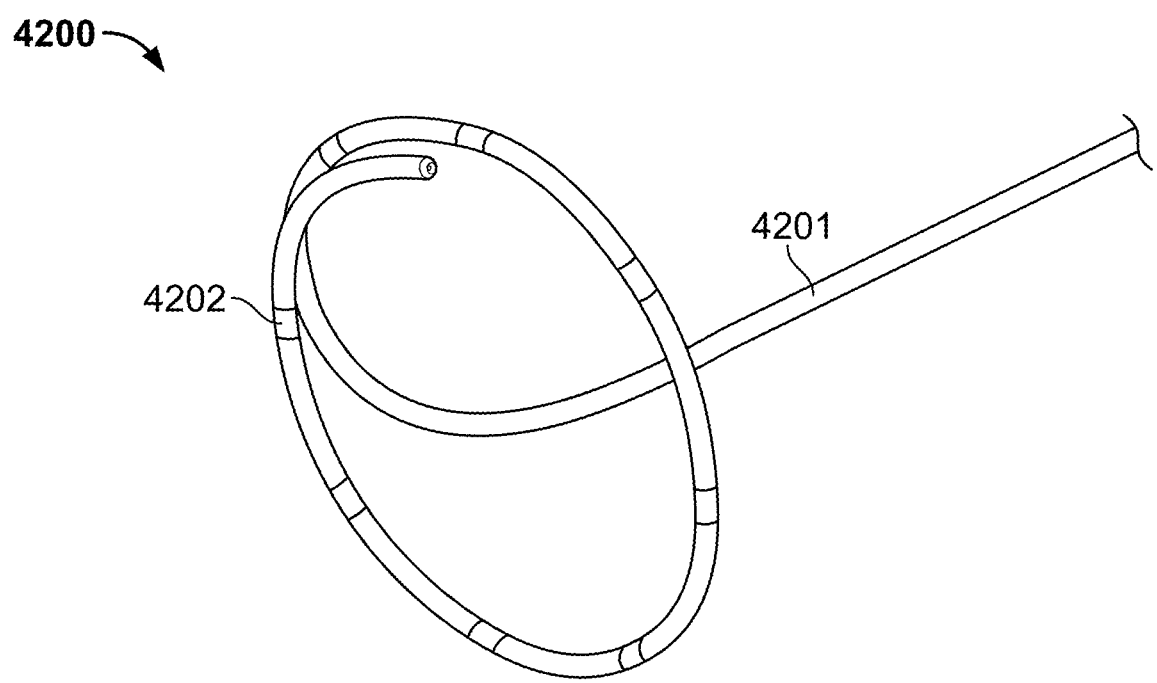
Figure 42B:
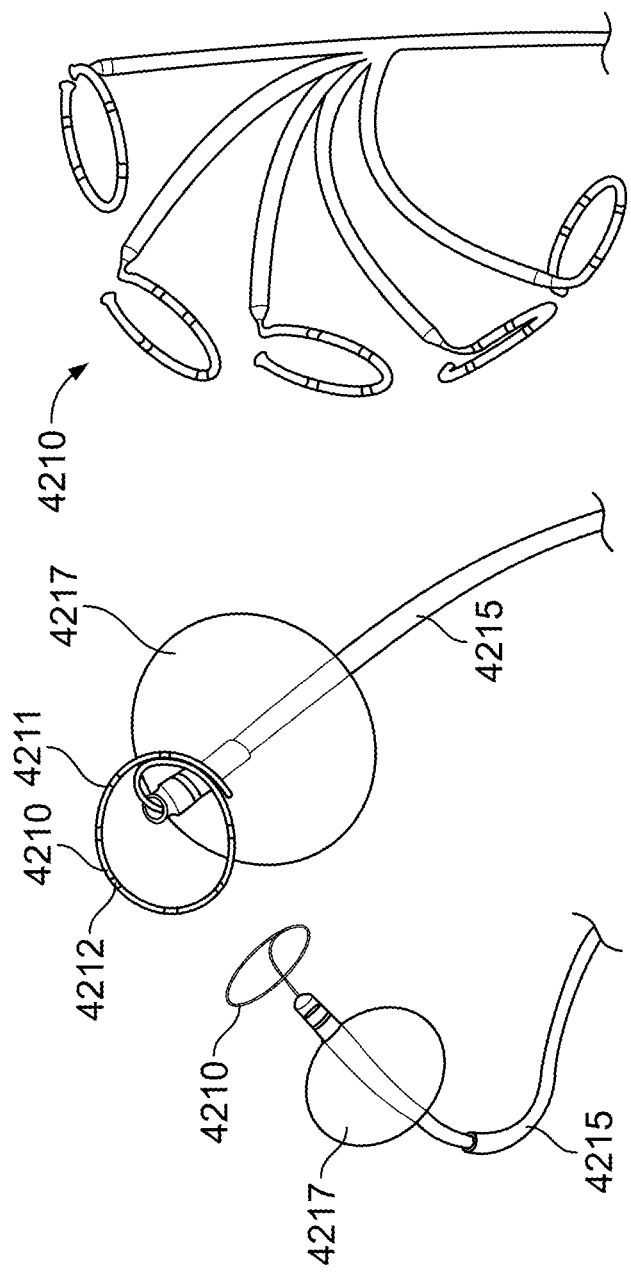
Figure 42C:
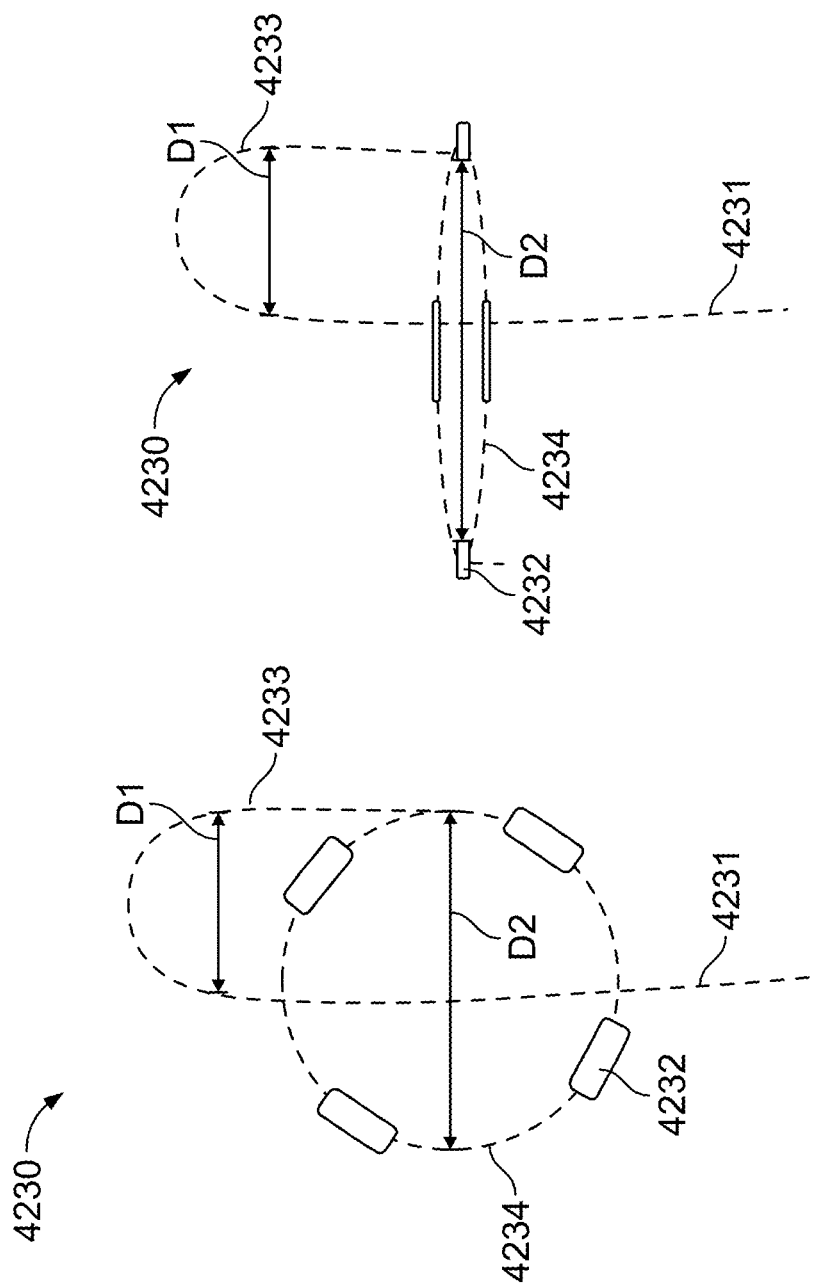
Figure 42D:
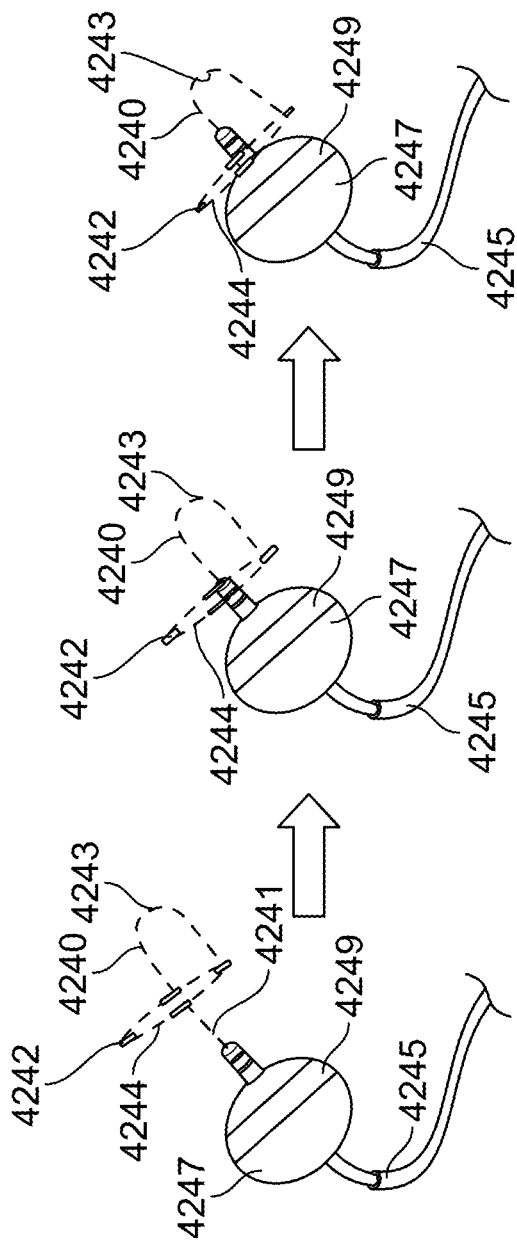
Figure 42E:
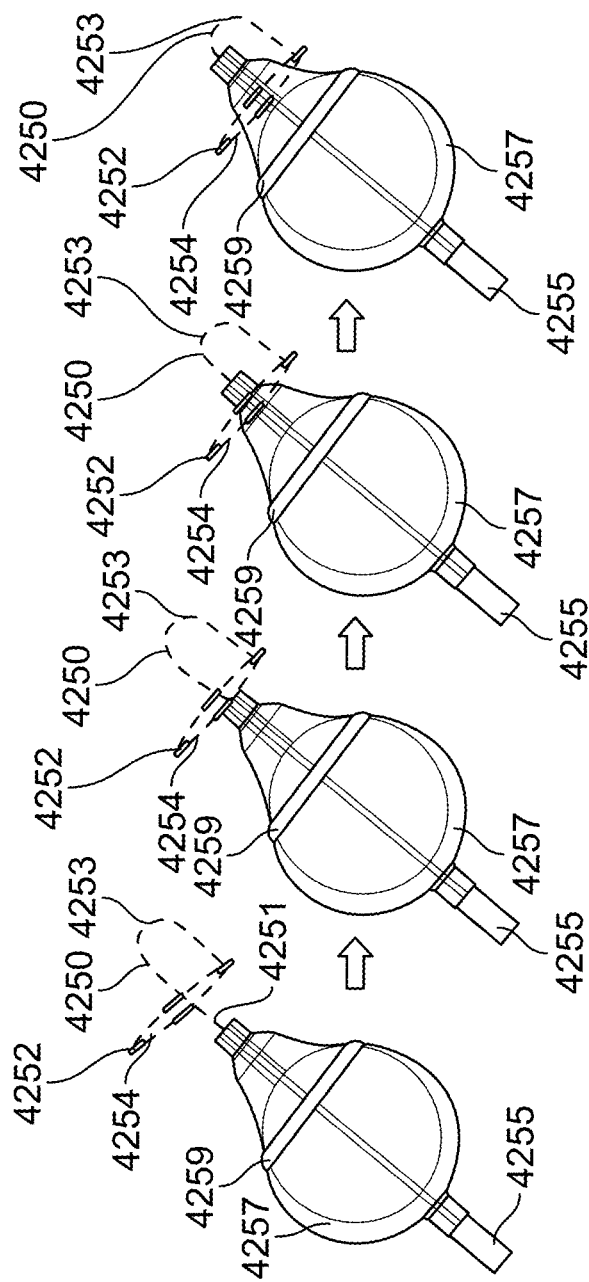

FIG. 36D is a flowchart of a plurality of exemplary steps of a method of performing left atrial appendage ablation, in accordance with some embodiments of the present specification;

FIG. 36E is a flowchart of a plurality of exemplary steps of another method of performing left atrial appendage ablation, in accordance with some embodiments of the present specification;

FIG. 36F is a flowchart of a plurality of exemplary steps of a method of performing vessel or bronchus ablation, in accordance with some embodiments of the present specification;

FIG. 36G is a flow chart illustrating exemplary steps under each of these tasks, which may be performed to implement a process of using the double balloon cardiac ablation catheter in accordance with the various embodiments of the present specification;

FIG. 36H depicts a triple balloon configuration with a plurality of marker bands in accordance with the various embodiments of the present specification for left atrial appendage ablation;

FIG. 36I illustrates a left atrium depicting a left atrial appendage in a wall of the left atrium;

FIG. 36J illustrates a plurality of left atrial appendages depicting a variety of shapes of the left atrial appendages;

FIG. 37A illustrates a first perspective view of a double balloon test catheter for performing ablation in a pig heart, in accordance with some embodiments of the present specification;

FIG. 37B illustrates a second perspective view of the test catheter of FIG. 37A, in accordance with some embodiments of the present specification;

FIG. 37C illustrates a third perspective view of the test catheter of FIG. 37A, in accordance with some embodiments of the present specification;

FIG. 37D shows ablation being carried out in a frozen pig heart using the test catheter of FIG. 37A, in accordance with some embodiments of the present specification;

FIG. 37E shows a circumferential ablated tissue as a result of an ablation treatment using the test catheter of FIG. 37A, in accordance with some embodiments of the present specification;

FIG. 38 illustrates another test catheter for performing ablation in a pig heart, in accordance with some embodiments of the present specification;

FIG. 39 illustrates a catheter, in accordance with some embodiments of the present specification;

FIG. 40 illustrates a trans-arterial vapor ablation catheter, in accordance with some embodiments of the present specification;

FIG. 41A is a flowchart of a plurality of exemplary steps of a method of performing trans-arterial vapor ablation of a tumor, in accordance with some embodiments of the present specification;

FIG. 41B illustrates trans-arterial vapor ablation of a tumor being performed in a liver, in accordance with some embodiments of the present specification;

FIG. 42A illustrates a mapping member in a loop configuration in accordance with some embodiments of the present specification;

FIG. 42B illustrates a flexible, loop shaped mapping member extending from a distal end of a double balloon catheter, in accordance with some embodiments of the present specification;

FIG. 42C illustrates a flexible mapping member having a vertical loop and a horizontal loop with a plurality of electrodes, in accordance with some embodiments of the present specification;

FIG. 42D illustrates a flexible mapping member having a vertical loop and a horizontal loop with a plurality of electrodes extending from a distal end of a double balloon catheter, in accordance with some embodiments of the present specification; and FIG. 42E illustrates a flexible mapping member having a vertical loop and a horizontal loop with a plurality of electrodes being pulled down onto a distal end of a double balloon catheter, in accordance with some embodiments of the present specification.

DETAILED DESCRIPTION

In various embodiments, the ablation devices and catheters described in the present specification are used in conjunction with any one or more of the heating systems described in U.S. patent application Ser. No. 14/594,444, entitled "Method and Apparatus for Tissue Ablation", filed on Jan. 12, 2015 and issued as U.S. Pat. No. 9,561,068 on Feb. 7, 2017, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. The terms "comprises" and variations thereof do not have a limiting meaning where these terms appear in the description and claims. It should be noted herein that any feature or component described in association with a specific embodiment may be used and implemented with any other embodiment unless clearly indicated otherwise.

Unless otherwise specified, "a," "an," "the," "one or more," and "at least one" are used interchangeably and mean one or more than one.

The term "controller" refers to an integrated hardware and software system defined by a plurality of processing elements, such as integrated circuits, application specific integrated circuits, and/or field programmable gate arrays, in data communication with memory elements, such as random access memory or read only memory where one or more processing elements are configured to execute programmatic instructions stored in one or more memory elements.

The term "vapor generation system" refers to any or all of the heater or induction-based approaches to generating steam from water described in this application.

The terms "coolant", "cooling agent", and "insulating agent" may be used interchangeably and may refer to air, water, or $CO_2$.

The term "cardiac tissue" refers to a portion of the pulmonary vein, a pulmonary vein ostium, a junction between the left atrium and pulmonary vein, an atrium, a left atrial appendage, tissue adjacent thereto, or other parts of the heart and adjacent tissue.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used for the treatment of cardiac arrhythmias, atrial fibrillation, ventricular fibrillation, atrial appendage reduction or closure, hypertension, diabetes, nonalcoholic steatohepatitis/nonalcoholic fatty liver disease (NASH/NAFLD), asthma, and for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of a vascular structure such as blood vessels, heart tissue, pulmonary artery or vein, pulmonary vein ostium, left atrium, ventricular tissue, left atrial appendage, renal artery/vein/nerve, hepatic artery/vein/nerve or portal vein and bronchus or bronchial nerve. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferromagnetic materials can be incorporated into the catheter to help with magnetic navigation.

Ablative agents such as steam, heated gas or cryogens, such as, but not limited to, liquid nitrogen and liquid $CO_2$ are inexpensive and readily available and are directed via the infusion port onto the tissue, held at a fixed and consistent distance, targeted for ablation. This allows for uniform distribution of the ablative agent on the targeted tissue. With respect to the present specification, the preferred ablative agent is hot vapor generated from a source of saline or carbonated saline. In some embodiments, the ablative agent comprises electrical energy delivered as radiofrequency or as electrical pulses to achieve electroporation.

The flow of the ablative agent is controlled by a microprocessor according to a predetermined method based on the characteristic of the tissue to be ablated, required depth of ablation, and distance of the port from the tissue. The microprocessor may use temperature, pressure, electrical or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
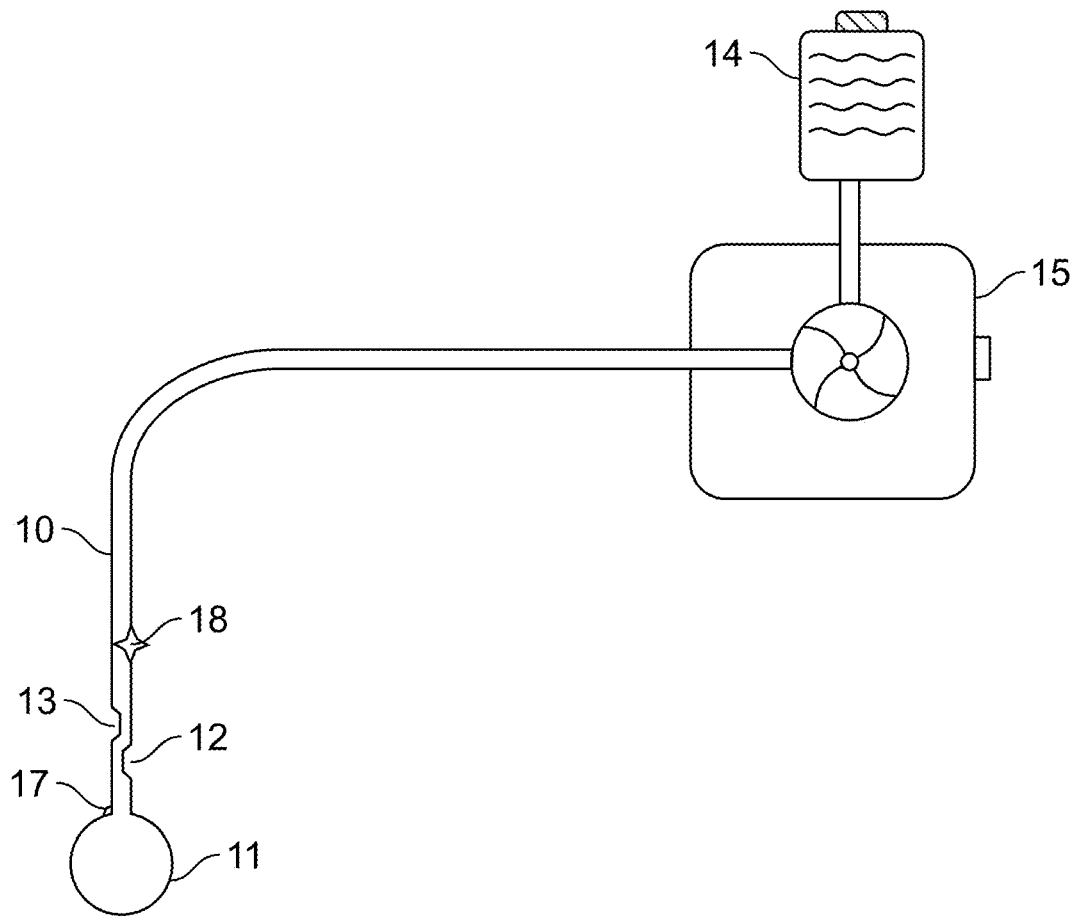
FIG. 1 illustrates an ablation device, in accordance with an embodiment of the present specification.

Ablation Controller for the Delivery of Fluid to a Catheter and Heating of the Fluid Therein FIG. 1 illustrates an ablation device, in accordance with an embodiment of the present specification. The ablation device comprises a catheter 10 having a distal centering or positioning attachment, together with an ablation agent control attachment, which are preferably inflatable balloons 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. In one embodiment, the infusion ports 12 can direct the ablative agent at different angles. In one embodiment, the infusion ports 12 reside inside the inflatable balloon 11.

Ablative agent is stored in a reservoir 14 connected to the catheter 10. Delivery of the ablative agent is controlled by a controller 15. In various embodiments, the controller 15 comprises a machine that controllably delivers a flow of fluid to the catheter 10. Optional sensor 17 monitors changes in an ablative tissue or its vicinity to guide flow of ablative agent. In one embodiment, optional sensor 17 also includes a temperature sensor. Optional infrared, electromagnetic, acoustic or radiofrequency energy emitters and sensors 18 measure the dimensions of the hollow organ. In one embodiment, the ablative agent is saline which is converted to vapor along the length of the catheter 10.

In one embodiment, a user interface included with the controller 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool/room temperature air or fluid flush, cool/room temperature water flush, and alarms/tones to indicate start and stop of treatment.

General Ablation Catheters and Methods

Figure 2:
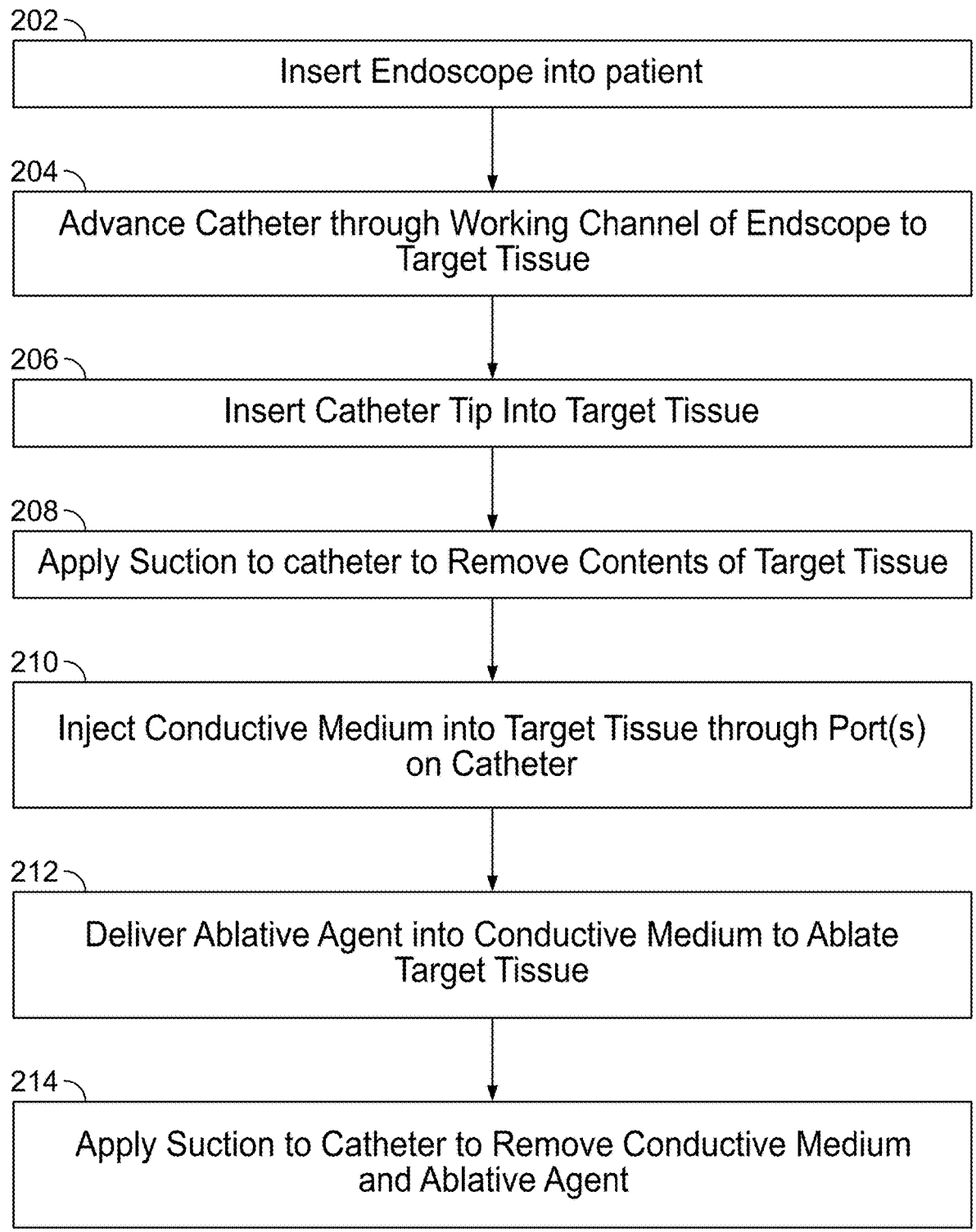
FIG. 2 is a flow chart listing the steps involved in a hollow tissue or organ ablation process using an ablation device, in accordance with one embodiment of the present specification.

FIG. 2 is a flow chart listing the steps involved in a hollow tissue or organ ablation process using the ablation device, in accordance with one embodiment of the present specification. At step 202, an endoscope is inserted into a patient. An ablation device comprising a catheter in accordance with one embodiment of the present specification, is advanced through a working channel of the endoscope and to a target tissue at step 204. At step 206, the distal end or tip of the catheter is inserted into the target hollow tissue or organ. Then, at step 208, suction is applied at the proximal end of the catheter to remove the natural contents of the hollow tissue or organ. A conductive medium is then injected, at step 210, into the hollow tissue or organ via at least one port on the distal end of the catheter. At step 212, an ablative agent is delivered into the conductive medium for ablation of the target tissue. At step 214, the remaining contents of the tissue, including conductive medium and ablative agent, are removed via suction using the catheter. In another embodiment, step 214 is optional, and the remaining contents of the hollow tissue or organ are reabsorbed by the body. In another embodiment, the removal of the natural contents of the hollow tissue or organ at step 208 is optional, and the procedure moves directly to the injection of conductive medium at step 210 from entering the target tissue with the catheter at step 206. Optionally, in some embodiments, the natural contents of the hollow organ can be used as the conductive media.

In various embodiments, ablation therapy provided by the vapor ablation systems of the present specification is delivered to achieve the following general therapeutic endpoints: maintain a tissue temperature between 45° C. and 100° C. for a time period lasting longer than 1 sec; maintain a tissue temperature at 100° C. or less to cause coagulation of intracellular proteins without carbonization of intracellular sugars; exert a pressure on a tissue to be ablated equal to or less than 125% of a pre-treatment pressure of the tissue; and exert a pressure on a tissue to be ablated which is less than a patient's mean arterial pressure so as not to impede perfusion to the tissue.

Figure 3:
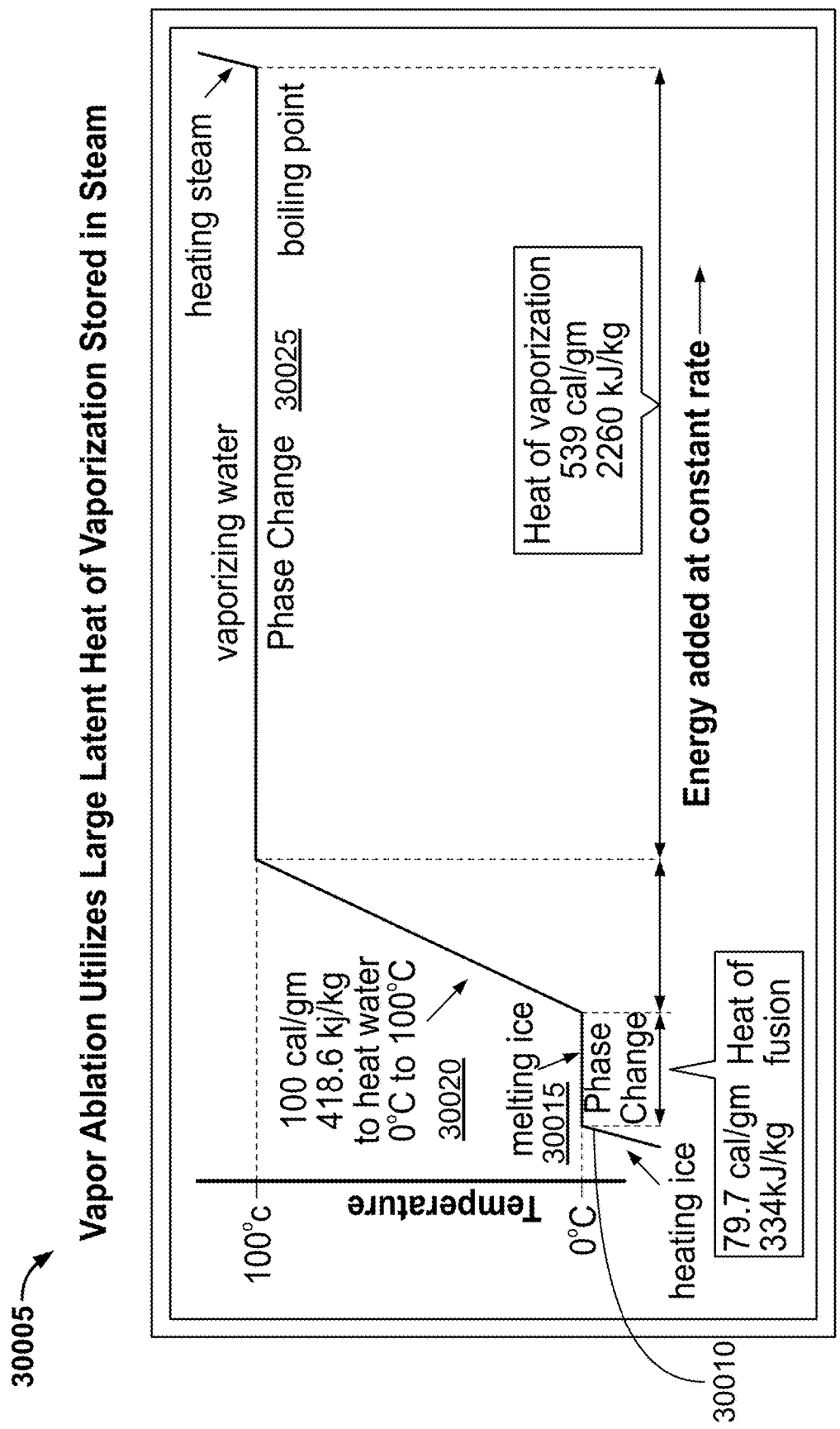
FIG. 3 shows a graph illustrating the latent heat of vaporization and fusion of water, in accordance with an embodiment of the present specification.

FIG. 3 shows a graph 30005 illustrating the latent heat of vaporization and fusion of water, in accordance with an embodiment of the present specification. The graph 30005 shows heat energy input or added on the X-axis and a corresponding rise in temperature of water on the Y-axis. The graph 30005 illustrates various phase changes as heat energy is added to an ice phase of water through to a steam phase. A first phase 30010 corresponds to ice, below 0 degrees Celsius, being heated to attain a temperature of 0 degrees Celsius. A second phase 30015 corresponds to melting of ice at 0 degrees Celsius without any change in temperature. The latent heat of fusion added in the second phase 30015 is 79.7 calories/gm or 334 kJ/kg. A third phase 30020 corresponds to temperature of water rising from 0 to 100 degrees Celsius. The amount of heat needed in the third phase 30020 is 100 calories/gm or 418.6 kJ/kg. A fifth phase 30025 corresponds to boiling of water at 100 degrees Celsius to convert into steam at 100 degrees Celsius without any change in temperature. The latent heat of vaporization added in the fifth phase 30025 is 539 calories/gm or 2260 kJ/kg. In accordance with an aspect of the present specification, ablation using steam or vapor utilizes the large latent heat of vaporization stored in steam.

Figure 4A:
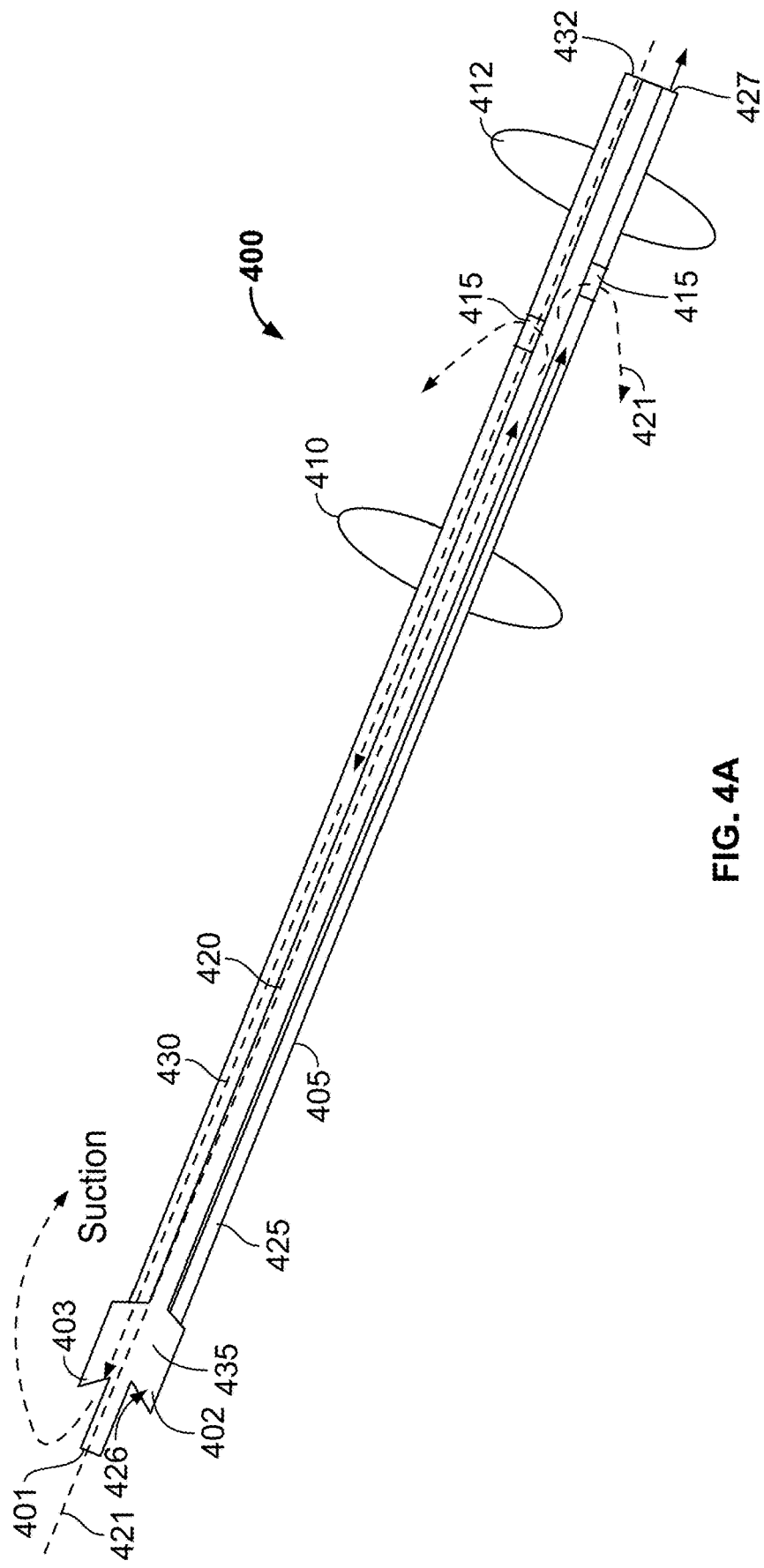
FIG. 4A illustrates a multi-lumen ablation catheter, in accordance with an embodiment.

FIG. 4A illustrates a multiple lumen ablation catheter 400 in accordance with an embodiment of the present specification. The catheter 400 includes an elongate body 405 with a proximal end and a distal end. The catheter 400 includes at least one positioning element proximate its distal end. In various embodiments, the positioning element is a balloon. In some embodiments, the catheter includes more than one positioning element.

In the embodiment depicted in FIG. 4A, the catheter 400 includes two positioning balloons 410, 412 proximate its distal end with a plurality of infusion ports 415 located on the body 405 between the two balloons 410, 412. A fluid delivery port 427 and a suction port 432 are located at the distal end of the body 405. The body 405 includes a first lumen 420 in fluid communication with the plurality of infusion ports 415, a second lumen 425 in fluid communication with the fluid delivery port 427, and a third lumen 430 in fluid communication with the suction port 432. The first, second and third lumens 420, 425, 430 extend along the length of the body 405 through a handle 435 at the proximal end to the distal end. An ablative agent 421 is introduced into the first lumen 420 at an ablative agent input port 401 at the proximal end of the catheter 400 and exits through the infusion ports 415 for ablation. In one embodiment, the ablative agent 421 is vapor or steam.

A fluid 426 is introduced into the second lumen 425 at a fluid input port 402 at the proximal end of the catheter 400 and exits through the fluid delivery port 427. In one embodiment, the fluid 426 is a coolant. In one embodiment, the coolant is water and is in a temperature range of 0 degrees C. to 60 degrees C. Negative pressure is applied, using a pump, to the third lumen 430 at a suction input port 403 at the proximal end of the catheter 400 to enable suction of the fluid, delivered from the fluid delivery port 427 and the infusion ports 415 respectively, via the suction port 432. In various embodiments, the fluid delivery port 427 and a suction port 432 can be located at various locations along the length of the catheter 400 distal to positioning balloon 412 or proximal to positioning balloon 410.

Figure 4B:
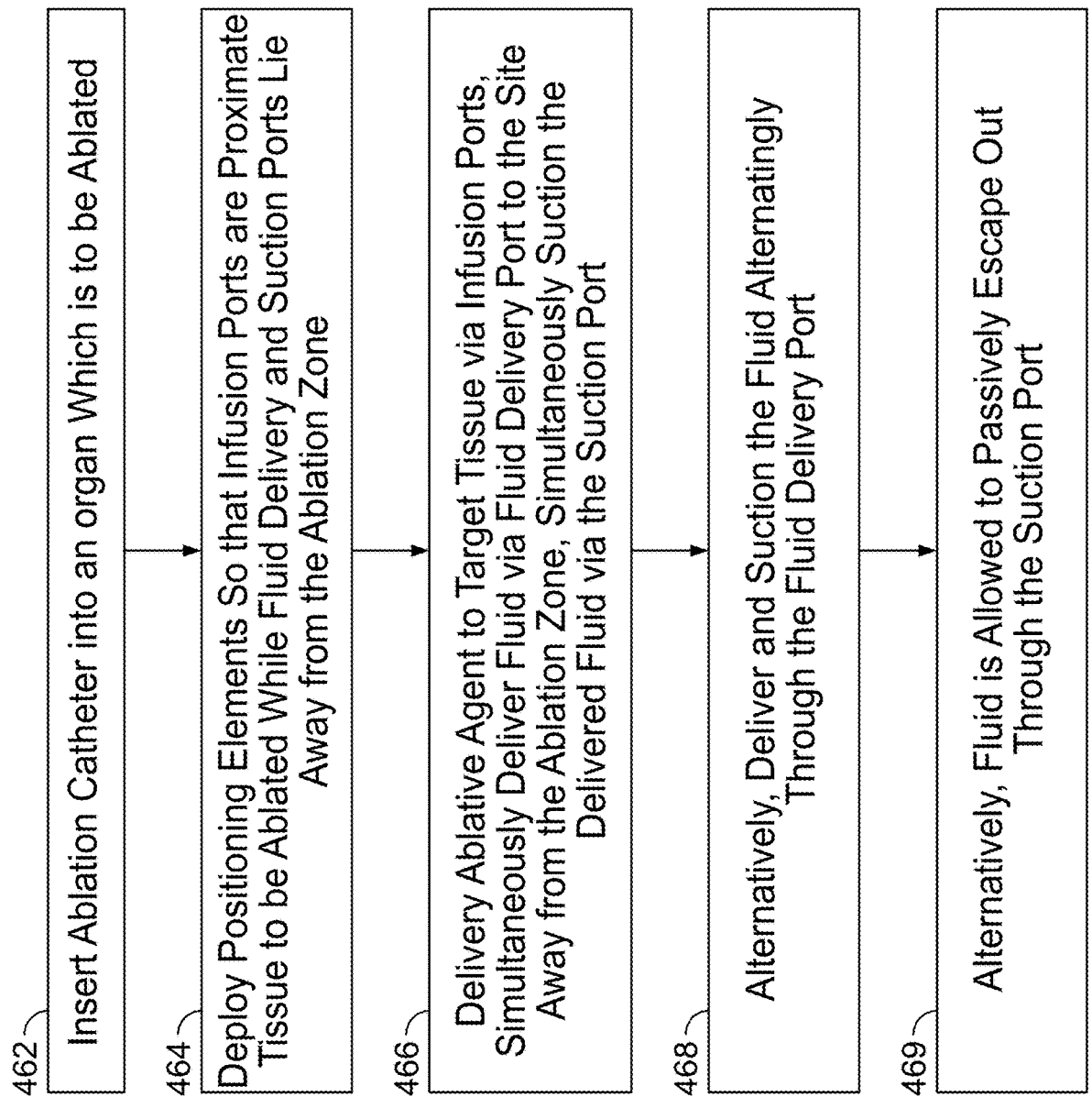
FIG. 4B is a flowchart illustrating the basic procedural steps for using the ablation catheter of FIG. 4A, in accordance with an embodiment of the present specification.

FIG. 4B is a flowchart illustrating the basic procedural steps for using the ablation catheter 400 of FIG. 4A, in accordance with an embodiment of the present specification. Referring now to FIGS. 4A and 4B, at step 462, the body 405 of the ablation catheter 400 is inserted into an organ which is to be ablated. For example, in order to perform ablation in a Barrett's esophagus of a patient, the catheter is inserted into the Barrett's esophagus via the esophagus of the patient.

At step 464, the positioning elements or balloons 410, 412 are deployed such that the plurality of infusion ports 415 lie proximate to the tissue to be ablated while the fluid delivery port 427 and the suction port 432 are positioned at a site away from the ablation zone. Thereafter, at step 466, an ablative agent (such as steam) is delivered through a first lumen, via infusion ports 415, to the target tissue to be ablated while simultaneously a fluid is delivered through a second lumen, via fluid delivery port 427, at the site away from the tissue being ablated such that the delivery of the fluid does not significantly interfere with the delivery of the ablative agent. In accordance with some embodiments, the fluid is delivered at a temperature ranging from 0 to 60° C. Also, simultaneously, the delivered fluid is suctioned out through the suction port 432 and third lumen 430 from the site away from the tissue being ablated such that the suction of the fluid does not result in suction of the delivered ablative agent. In accordance with alternative embodiments, at step 468, the fluid is alternatingly delivered and suctioned, respectively, through the fluid delivery port 427 and second lumen 425. In another embodiment, at step 469, the fluid is allowed to passively escape out through suction port 432.

In one embodiment, the first positioning balloon 410 is inside the second positioning balloon 412 and the vapor delivery ports 415 reside within the first positioning balloon 410 while the cooling fluid delivery ports 427 and cooling fluid suction ports 432 reside in the second positioning balloon 412.

Figure 5A:
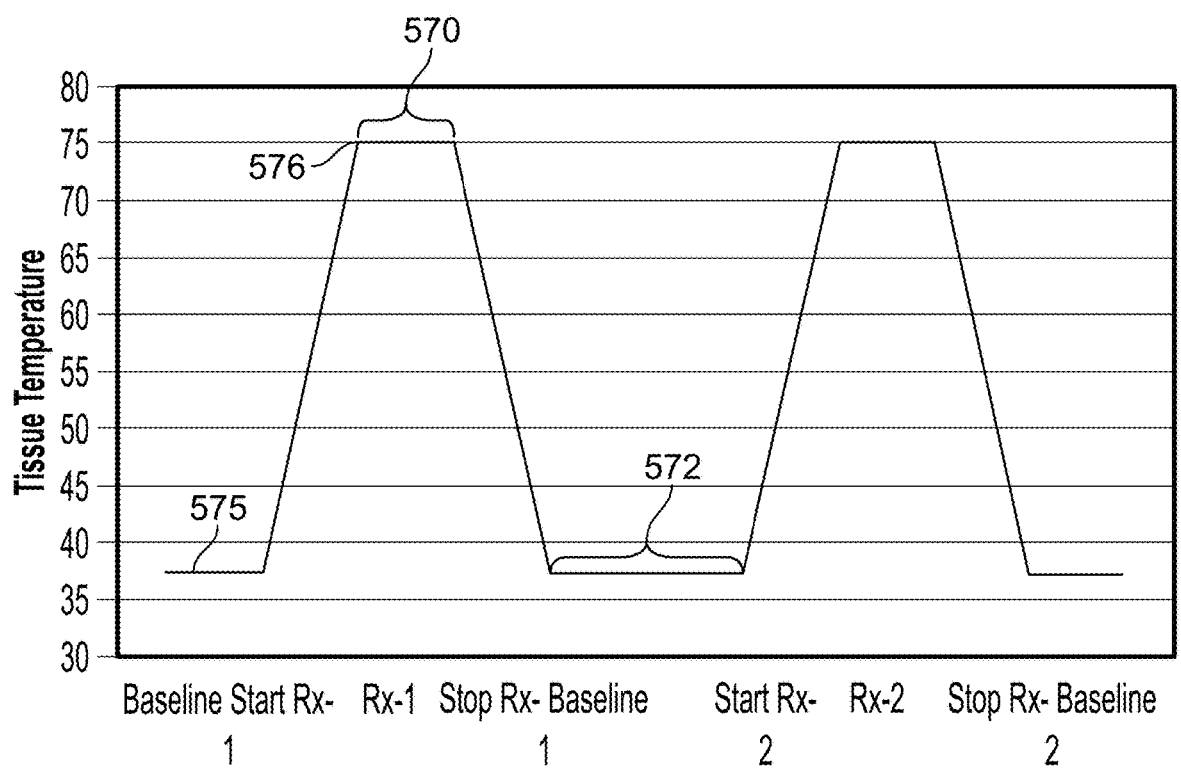
FIG. 5A is a first graph illustrating a process of ablating tissue in accordance with an embodiment.

FIG. 5A is a first graph illustrating a process of ablating tissue in accordance with an embodiment. As shown in FIG. 5A, ablative agent, such as vapor, is delivered to a target tissue for a first period of time 570 as a result of which the temperature of the target tissue rises to a first temperature 576. The target tissue temperature is maintained at the first temperature 576 for the first period of time 570. After completion of the first period of time 570, the delivery of vapor is turned off and the target tissue temperature is allowed to cool down to a base temperature 575. After a second period of time 572, the vapor delivery is resumed to the target tissue and the ablation process cycle is repeated.

Figure 5B:
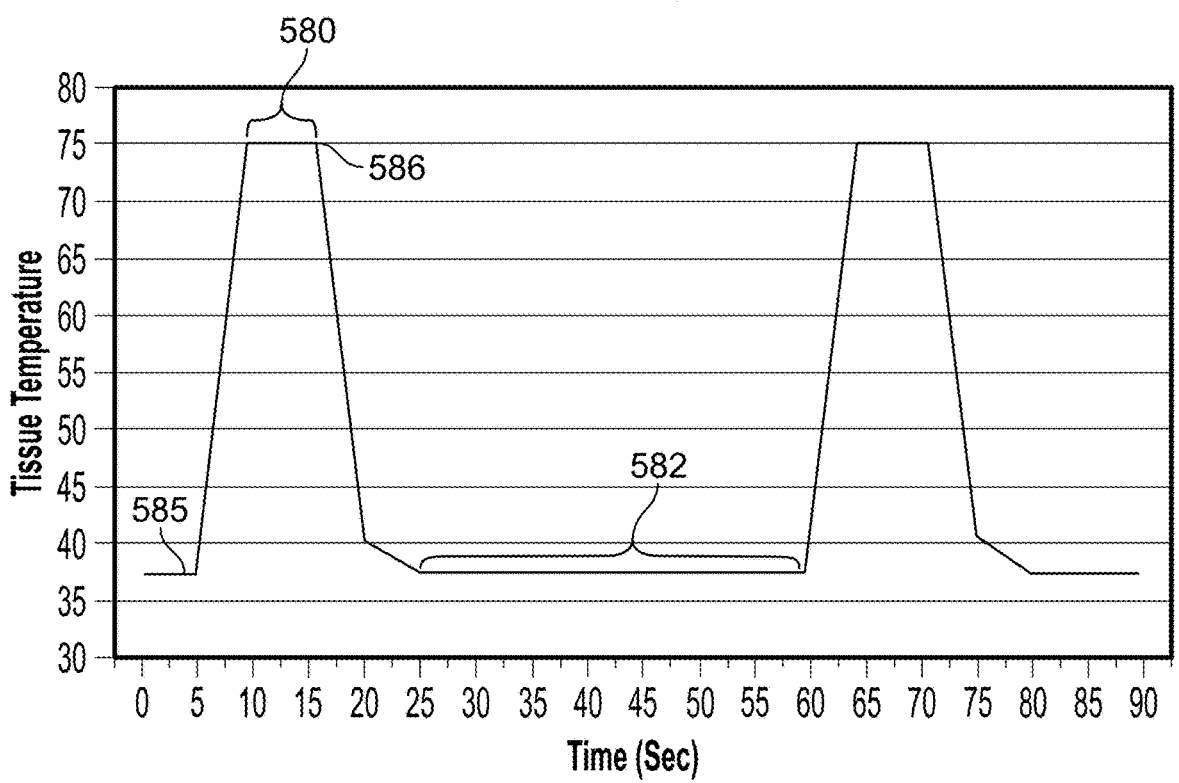
FIG. 5B is a second graph illustrating a process of ablating tissue in accordance with another embodiment.

FIG. 5B is a second graph illustrating a process of ablating tissue in accordance with another embodiment. As shown in FIG. 5B, ablative agent, such as vapor, is delivered to a target tissue for a third period of time 580 as a result of which the temperature of the target tissue rises to a second temperature 586. The target tissue temperature is maintained at the second temperature 586 for the third period of time 580. After completion of the third period of time 580, the delivery of vapor is turned off and the target tissue temperature is allowed to cool down to a base temperature 585. After a fourth period of time 582, the vapor delivery is resumed to the target tissue and the ablation process cycle is repeated, if desired. In various embodiments, the first and second periods of time 570, 572 may or may not be equal. Similarly, in various embodiments, the third and fourth periods of time 580, 582 may or may not be equal. In still other embodiments, the first and third periods of time 570 and 580 are not equal and the second and fourth periods of time 572 and 582 are also not equal.

In various embodiments, the first and third time periods 570, 580 range from 1 to 1800 seconds while the second and fourth time periods 572, 582 range from 0 to 1800 seconds. Also, in various embodiments, the base temperature 575, 585 ranges from 37 to 45 degree C. while the first and second temperatures 576, 586 range from 60 to 110 degrees C.

Figure 5C:
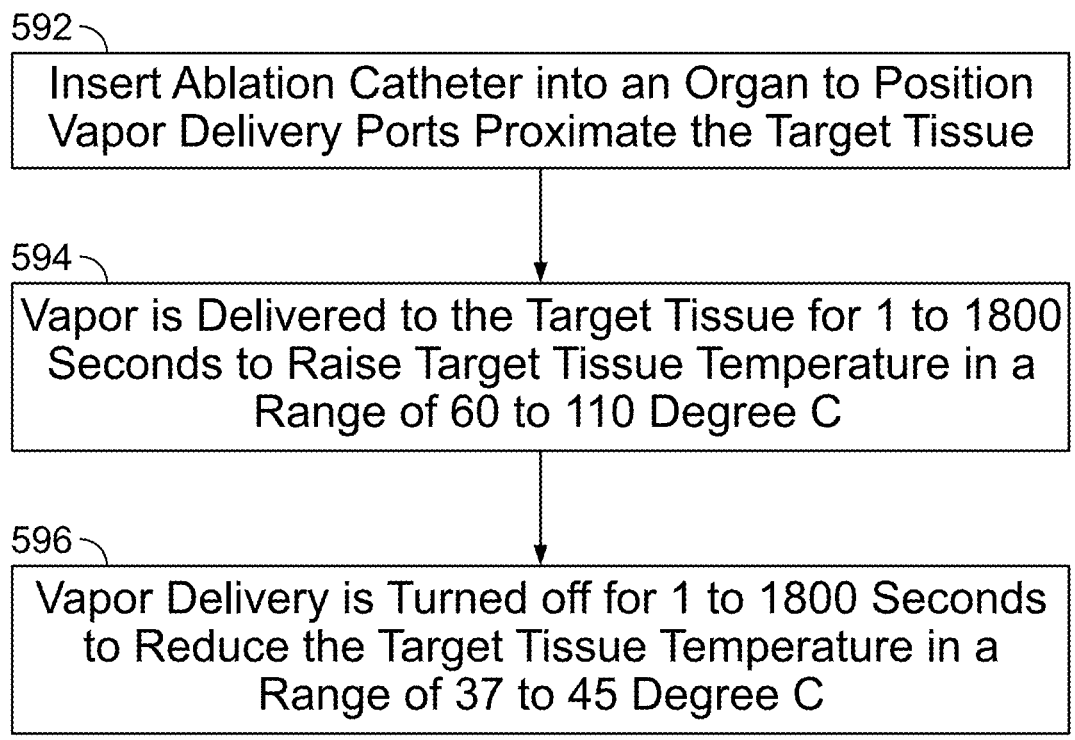
FIG. 5C is a flow chart illustrating a plurality of steps associated with the ablation processes of FIGS. 5A and 5B.

FIG. 5C is a flow chart illustrating a plurality of steps associated with the ablation processes of FIGS. 5A and 5B. At step 592, an ablation catheter is inserted into an organ so that the vapor delivery ports are positioned proximate the target tissue for ablation. At step 594, vapor is delivered to the target tissue for a heating period of time, ranging from 1 to 1800 seconds, as a result of which the target tissue temperature rises, in a range of 60 to 110 degrees C. At step 596, the vapor delivery is turned off for a cooling off period of time, ranging from 1 to 1800 seconds, as a result of which the target tissue temperature reduces to be in a range of 37 to 45 degree C. After completion of the cooling off period of time, the steps 592 and 594 are repeated.

Figure 6:
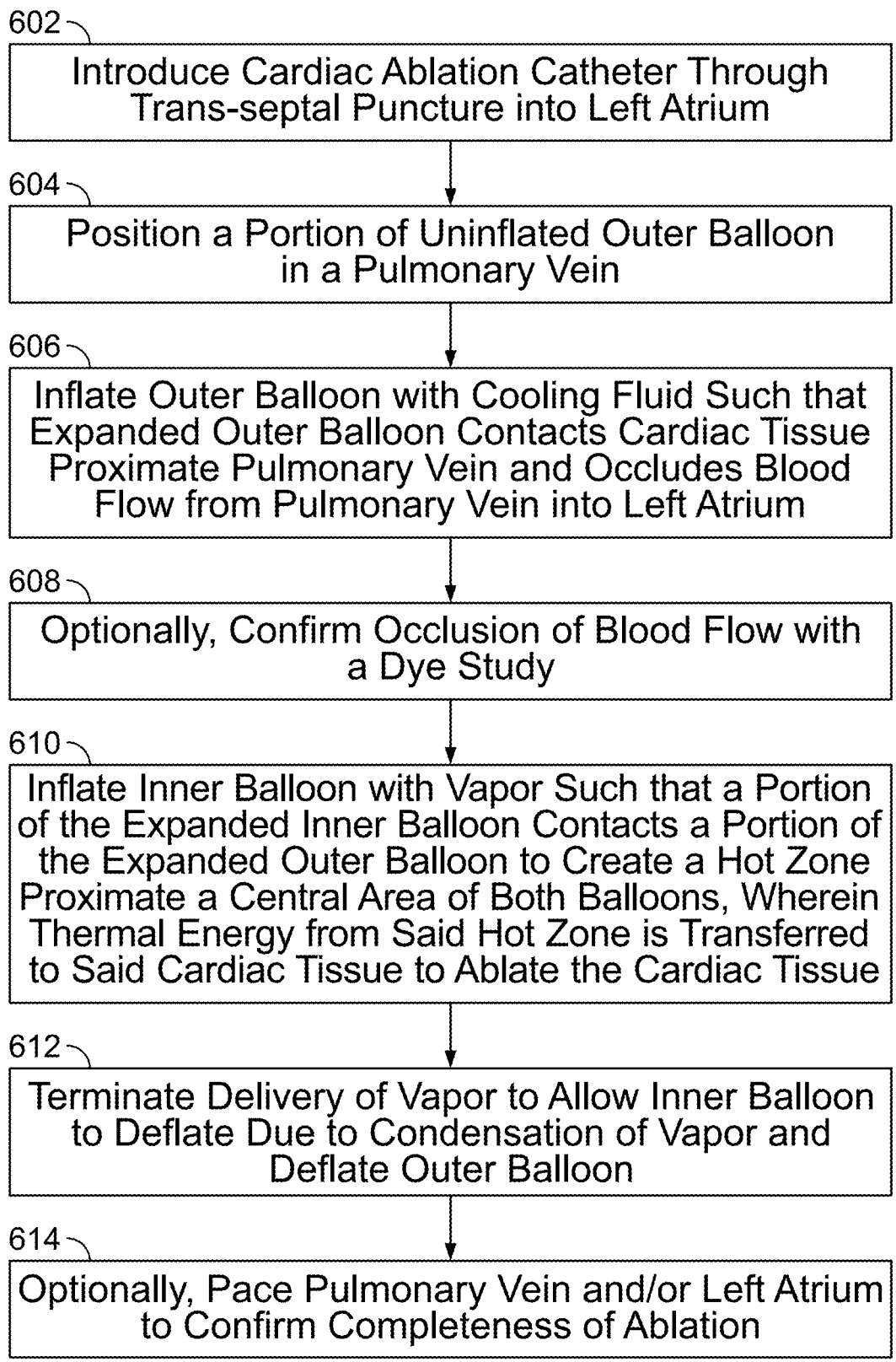
FIG. 6 is a flowchart illustrating a method of ablation for a cardiac tissue, according to some embodiments of the present specification.

FIG. 6 is a flowchart illustrating a method of ablation of a cardiac tissue according to some embodiments of the present specification. At step 602, a cardiac ablation catheter in accordance with the embodiments of the present specification is introduced through a trans-septal puncture into a left atrium of a patient. An uninflated outer balloon of the catheter is positioned in a pulmonary vein at step 604. At step 606, the outer balloon is inflated with a cooling fluid such that the outer balloon, once expanded, contacts a cardiac tissue proximate said pulmonary vein and occludes blood flow from the pulmonary vein into the left atrium. Optionally, the occlusion of blood flow is confirmed with a dye study at step 608. At step 610, an inner balloon of the cardiac ablation catheter is inflated with vapor such that a portion of the inner balloon, once expanded, contacts a portion of the expanded outer balloon to create a hot zone proximate a central area of both balloons, wherein thermal energy from the hot zone is transferred to said cardiac tissue to ablate the cardiac tissue. The delivery of vapor is terminated at step 612 to allow the inner balloon to deflate due to the condensation of vapor and the outer balloon is deflated. Optionally, at step 614, pacing of the pulmonary vein and/or left atrium is performed to confirm the completeness of the ablation. In one embodiment, the inner balloon is pre-inflated with air or $CO_2$. In embodiments, the hot (ablation zone) resides on the distal hemispheres of the two balloons.

FIG. 7A is an illustration of a water or saline cooled catheter 700, in accordance with one embodiment of the present specification, and FIG. 7B is a cross-section view of the shaft of the water cooled catheter of FIG. 7A. The catheter 700 comprises an elongate body 705 having a proximal end and a distal end. The distal end includes a plurality of infusion ports 715 for the delivery of an ablative agent 716, such as steam or vapor for tissue ablation. A sheath 710 comprising cooling channels extends along the body 705 of the catheter 700. In some embodiments, the sheath 710 extends along the catheter body 705 to a point distal to or proximate the ports 715. In these embodiments, the sheath 710 is positioned such that it does not cover the ports 715, allowing ablative agent 716 to exit the catheter 700 through said ports 715, as depicted in FIG. 7B. In other embodiments, the sheath extends along the catheter body to a point proximal to the ports. During use, water 720 from a water source 722 is circulated through the sheath 710 to cool the catheter 700. The water 710 for cooling is then fed into chamber 721 where it is heated to turn into vapor 716 to be delivered through the elongate body 705 and through the infusion ports 715. Vapor 716 for ablation and water 720 for cooling are supplied to the catheter 700 at its proximal end. Arrows 723 show the path of water 710 through the sheath and into the chamber 721. Arrows 724 show the path of vapor 716 through the elongate body 705 and out the infusion ports 715. In embodiments, chamber 721 is positioned anywhere along the length of catheter 700.

FIG. 8A illustrates an ablation catheter 805 while FIG. 8B is a cross-sectional view of an elongate body or shaft 807 of the catheter 805, in accordance with an embodiment of the present specification. The elongate body or shaft 807 has a distal end, a proximal end and includes an outer lumen 809 and a coaxial inner lumen 811. In accordance with an aspect, a coolant 813, such as, but not limited to, air, $CO_2$ water or saline, passes from the proximal end of the body or shaft 807 into the outer lumen 809 and is discharged through the distal end of the body or shaft 807. Similarly, vapor 815 passes from the proximal end of the body or shaft 807 into the inner lumen 811 to emanate from the distal end of the body or shaft 807 while the body or shaft 807 is kept cooled by the circulating coolant 813.

FIG. 9A illustrates an ablation catheter 905 while FIG. 9B is a cross-sectional view of an elongate body or shaft 907 of the catheter 905, in accordance with an embodiment of the present specification. The elongate body or shaft 907 has a distal end, a proximal end and includes first and second outer lumens 909a, 909b and a coaxial inner lumen 911. In accordance with an aspect, a coolant 913, such as, but not limited to, air, $CO_2$, water or saline, passes from the proximal end of the body or shaft 907 into the first outer lumen 909a and is discharged through the second outer lumen 909b, also at the proximal end of the body or shaft 907, after having been circulated through the body or shaft 907. Vapor 915 passes from the proximal end of the body or shaft 907 into the inner lumen 911 to emanate from the distal end of the body or shaft 907 while the body or shaft 907 is kept cooled by the recirculating coolant 913. In embodiments, where the coolant 913 is air or $CO_2$, the air or $CO_2$ may be released or discharged via a handle attached at the proximal end of the body or shaft 907 thereby cooling the handle. In embodiments, where the coolant 913 is water or saline, the water enters the shaft 907 through the first outer lumen 909a and is fed, through the second outer lumen 909b, into a heating chamber enclosed within the handle attached at the proximal end of the body or shaft 907 or placed anywhere along the length of catheter 905. The water fed into the heating chamber is converted into vapor 915 that then enters the inner lumen 911.

FIG. 10A illustrates an ablation catheter 1005 while FIG. 10B is a cross-sectional view of an elongate body or shaft 1007 of the catheter 1005, in accordance with an embodiment of the present specification. The elongate body or shaft 1007 has a distal end, a proximal end and includes first and second outer lumens 1009a, 1009b and a coaxial inner lumen 1011. At least one balloon 1025 is attached at the distal end of the body or shaft 1007 and is in fluid communication with the first and second outer lumens 1009a, 1009b. In some embodiments, the elongate body or shaft 1007 optionally includes one or more additional outer lumens 1027 (FIG. 10B) to function as accessory channels such as for various sensors. In accordance with an aspect, a coolant 1013, preferably air or $CO_2$, passes from the proximal end of the body or shaft 1007 into the first outer lumen 1009a and is discharged through the second outer lumen 1009b, also at the proximal end of the body or shaft 1007, after having inflated the balloon 1025 to a desired pressure while maintaining the air or $CO_2$ circulation in the body or shaft 1007 to maintain the shaft temperature below 60 degrees C., and preferably below 45 degrees C. The desired pressure, within the balloon 1025, is maintained by a pressure valve (or an e-valve controlled by a micro-controller) positioned at the proximal end of the second outer lumen 1009b wherein the pressure valve maintains air flow and opens when the desired pressure is rated. Similarly, vapor 1015 passes from the proximal end of the body or shaft 1007 into the inner lumen 1011 to emanate from the distal end of the body or shaft 1007 while the body or shaft 1007 is kept cooled by the circulating coolant 1013. It should be appreciated that in some embodiments the inner lumen 1011 is in fluid communication with another balloon positioned and freely movable within the balloon 1025 and the vapor is delivered into the second balloon. In another embodiment, the inner lumen is in fluid communication with another balloon positioned and freely movable distal to the balloon 1025 and the vapor is delivered into the second balloon.

Thus, in accordance with an aspect, a coolant, such as water, circulates within the outer lumen of the elongate body and is then fed into a heating chamber for conversion to vapor—as described with reference to FIGS. 9A, 9B. In accordance with another aspect a coolant, such as air, is circulated in a balloon back and forth through the outer lumen of the elongate body to cool the elongate body or shaft—as described with reference to FIGS. 10A, 10B. In various embodiments, the heating chamber is positioned anywhere along the length of the catheter. In one embodiment, a portion of the heating chamber is at the distal tip inside the balloon 125. In various embodiments, additional cooling fluid is delivered along the length of the catheter outside the catheter body to achieve the therapeutic cooling objective.

Referring now to FIGS. 8B, 9B and 10B, in accordance with an aspect of the present specification, an inner layer 830, 930, 1030 of the catheter shaft 807, 907, 1007 is thicker in comparison to an outer layer 832, 932, 1032 to prevent heat loss or minimize energy transfer from inside to the outside of the catheter. This is in contrast to prior art cooled shaft catheters where the purpose is to maximize transfer of cold temperature from inside the catheter to the outside of the catheter.

Figure 11:
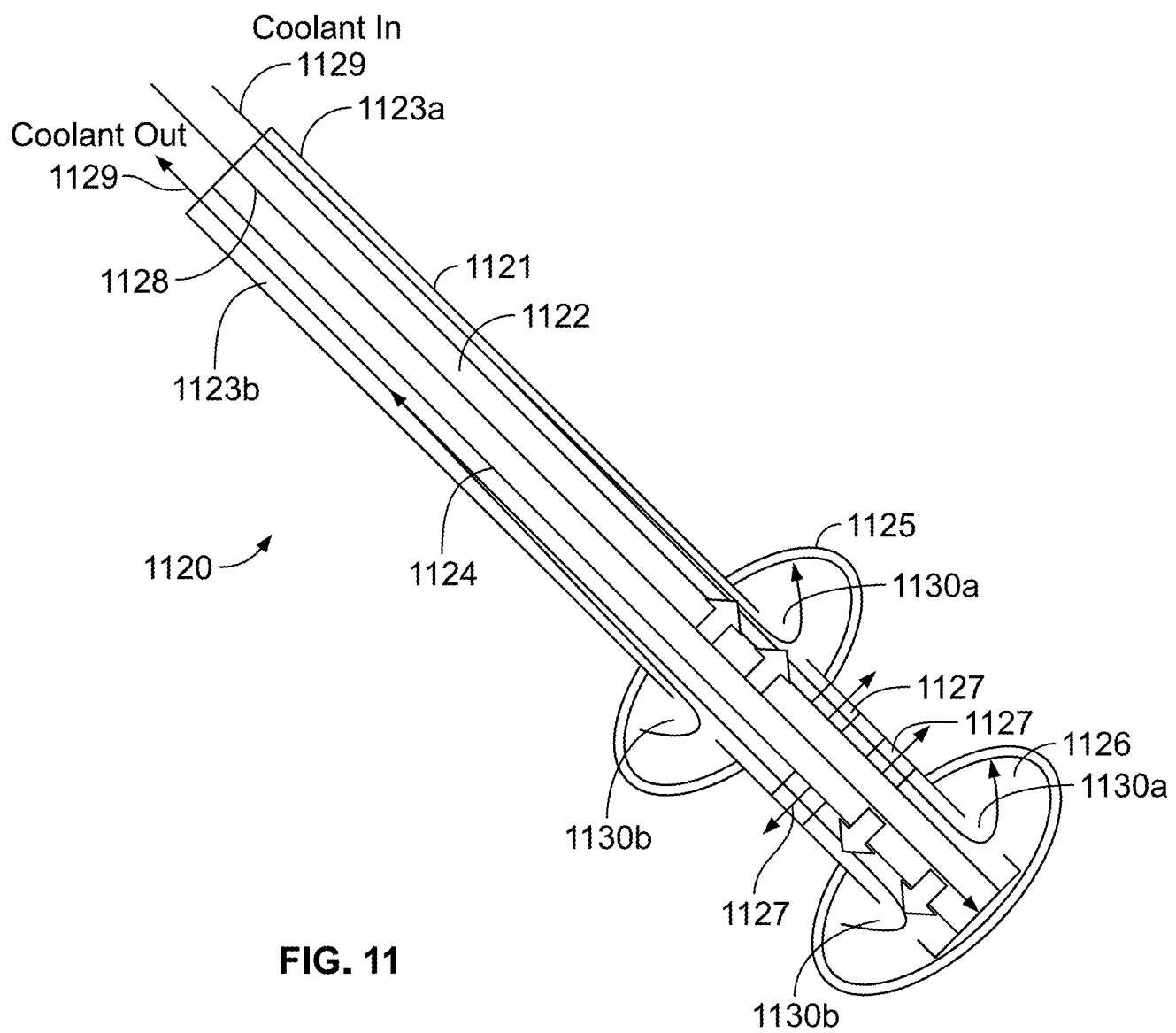
FIG. 11 illustrates an ablation catheter is accordance with an embodiment of the present specification.

FIG. 11 illustrates an ablation catheter 1120 in accordance with one embodiment of the present specification. The catheter 1120 includes an elongate body 1121 with a proximal end and a distal end. In one embodiment, the catheter body 1121 includes an inner lumen 1122, a first outer lumen 1123a and a second outer lumen 1123b. The inner lumen 1122 is separated from the outer lumens 1123a, 1123b by a thermally semi-permeable wall 1124 which allows a portion of the thermal energy to pass from the inner lumen 1122 to the outer lumens 1123a, 1123b. The catheter also includes at least one positioning element or balloon at its distal end. In the embodiment depicted in FIG. 11, the catheter 1120 includes two positioning balloons 1125, 1126 at its distal end with a plurality of delivery ports 1127 located on the catheter body 1121 between the two balloons 1125, 1126. The delivery ports 1127 are in fluid communication with the inner lumen 1122. An ablative agent 1128 is introduced into the inner lumen 1122 at the proximal end of the catheter 1120 and exits through the delivery ports 1127 into an organ, such as an esophagus, for ablation. In one embodiment, the ablative agent 1128 is steam. Coolant, such as air or $CO_2$ 1129, is introduced into the first outer lumen 1123a at the proximal end of the catheter 1120 and travels through inflation ports 1130a into the balloons 1125, 1126 to inflate said balloons 1125, 1126 and thereafter exits the balloons 1125, 1126 via exit ports 1130b into the second outer lumen 1123b and finally exits at the proximal end of the catheter, allowing for the air or $CO_2$ 1129 to circulate a length of the catheter 1120 and through one or more of the balloons 1125, 1126. In one embodiment, the air or $CO_2$ circulates through the first balloon 1125 and the ablative agent is released into the second balloon 1126.

Figure 12:
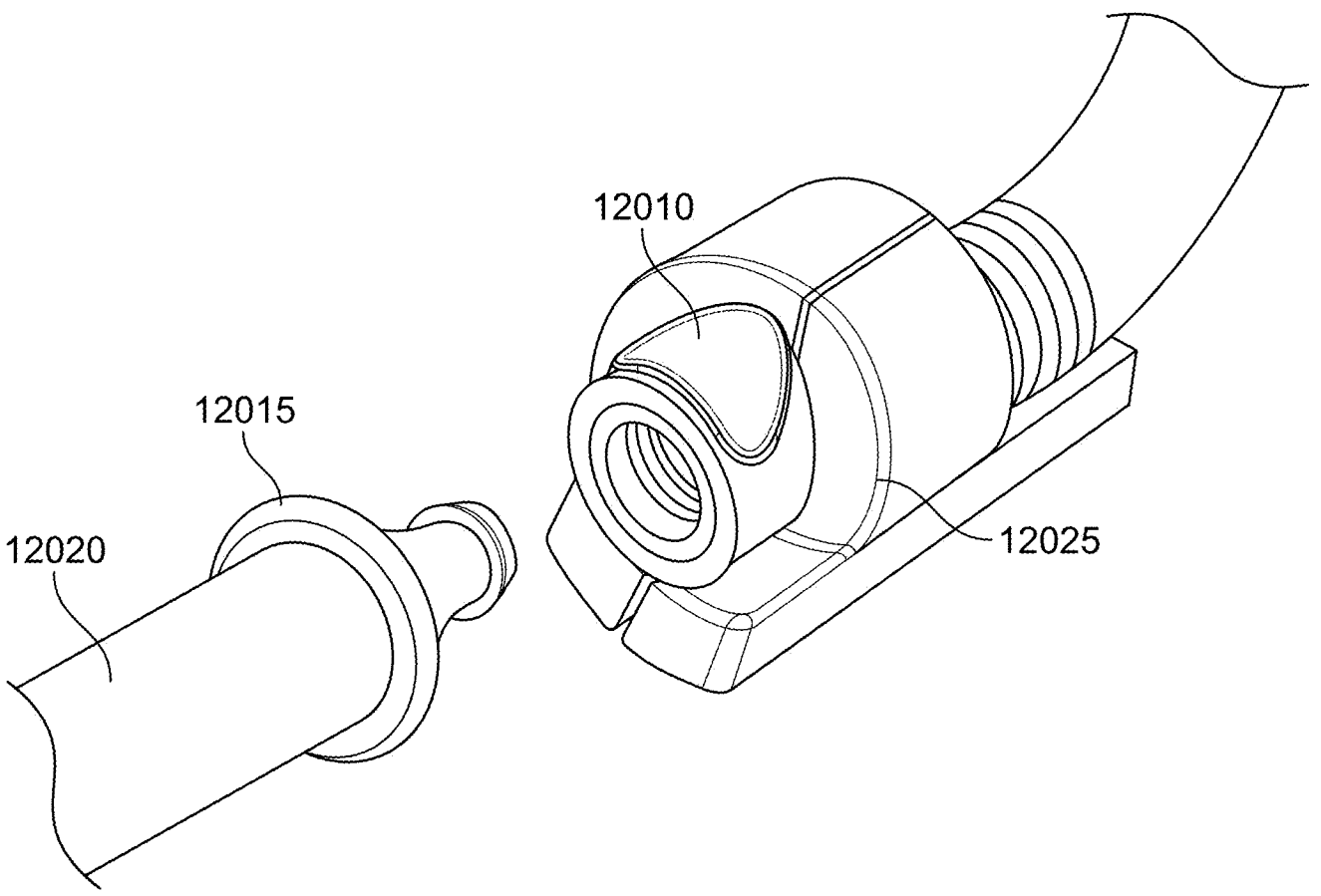
FIG. 12 illustrates a connection between a syringe and a catheter, in accordance with an embodiment of the present specification.

FIG. 12 illustrates a connection between a syringe 12020 and a catheter 12010, in accordance with an embodiment. As shown in FIG. 12, a proximal end of a catheter 12010 is configured to receive a distal end of a connector component 12015 in order to form a fluid seal when the distal end of the connector component 12015 is inserted into the proximal end of the catheter 12010. A syringe 12020 is coupled to a proximal end of the connector component 12015 to supply water or saline to the catheter 12010 through the connector component 12015 coupled to the catheter 12010. In various embodiments, a radio frequency identification component 12025 is included at the proximal end of the catheter 12010 to communicate successful fluid connection between the catheter 12010 and the syringe 12020.

In various embodiments, the connectors described in the present specification are composed of thermoplastics including ABS, acetal, nylon (polyamide), and polyetheretherketone (PEEK), and fluoropolymers including polyvinylidene difluoride (PVDF). In various embodiments, the O-rings are composed of fluorocarbon (FKM) or silicone.

Figure 13A:
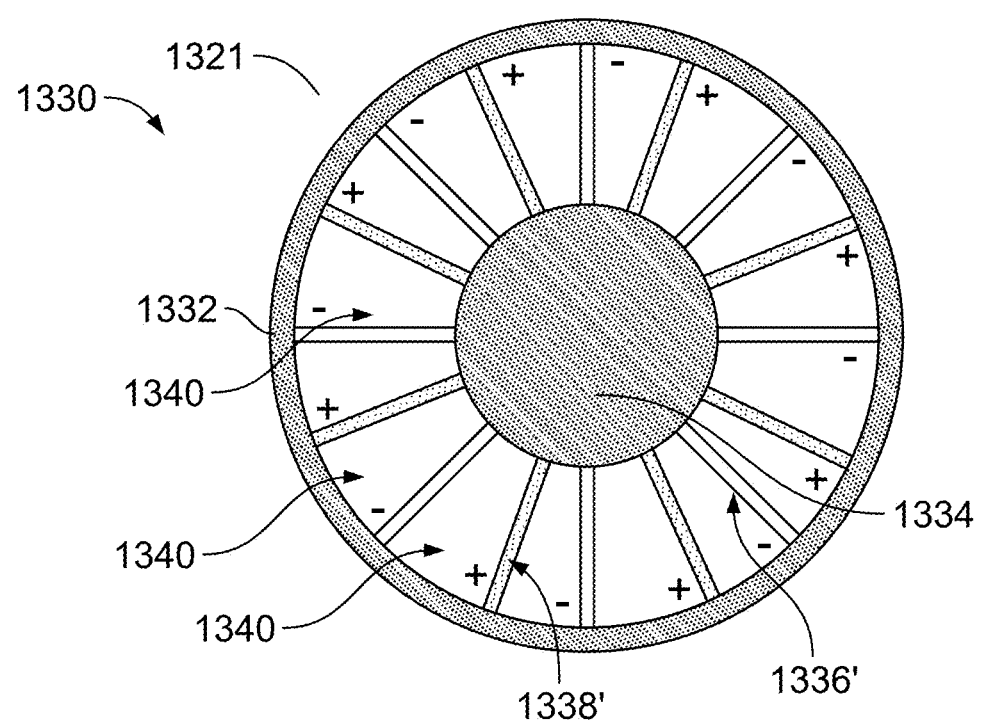
FIG. 13A is a transverse cross-section view of a flexible heating chamber, in accordance with an embodiment of the present specification.
Figure 13B:
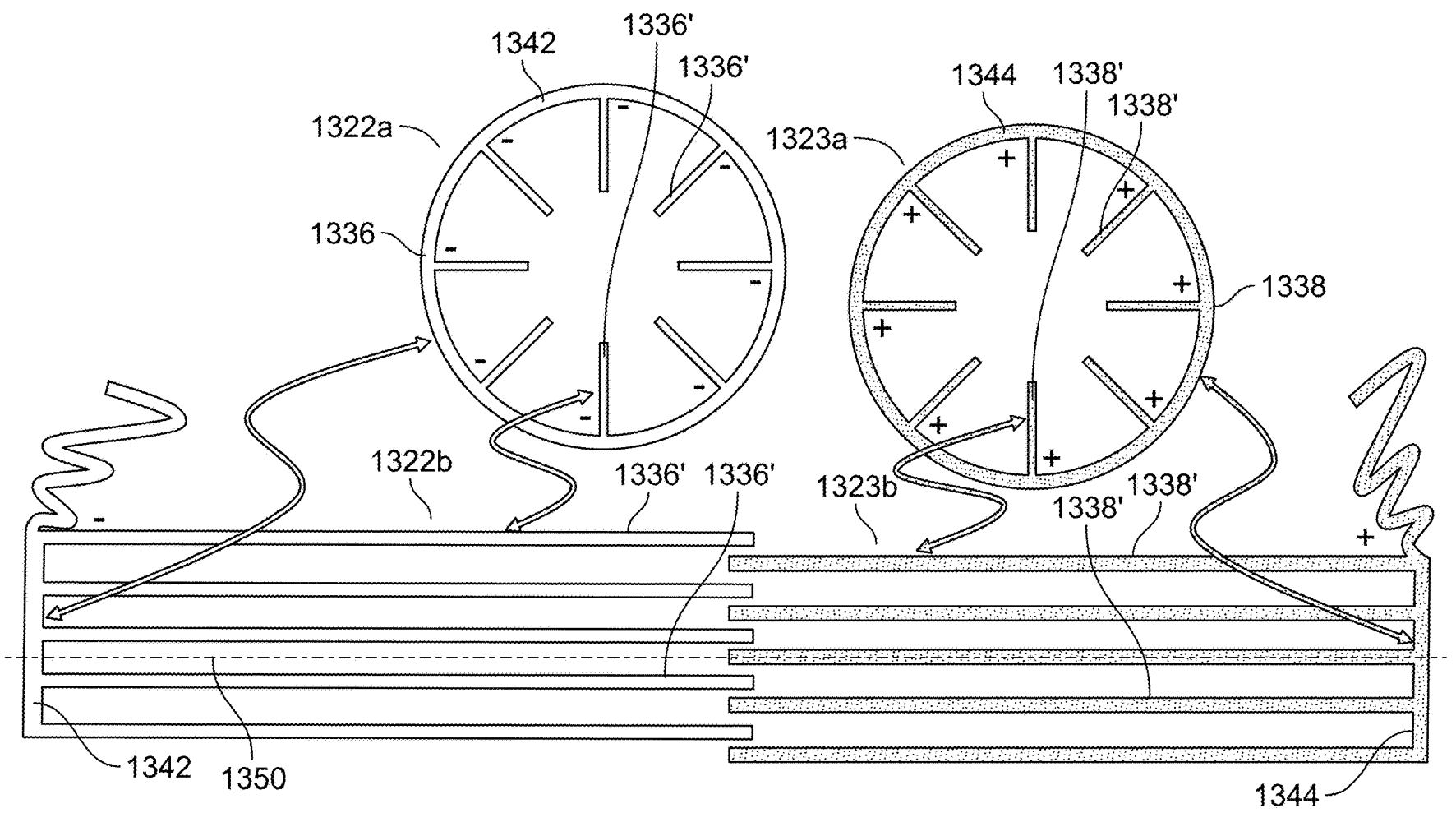
FIG. 13B illustrates transverse and longitudinal cross-section views of first and second arrays of electrodes of a flexible heating chamber, in accordance with an embodiment of the present specification.
Figure 13C:
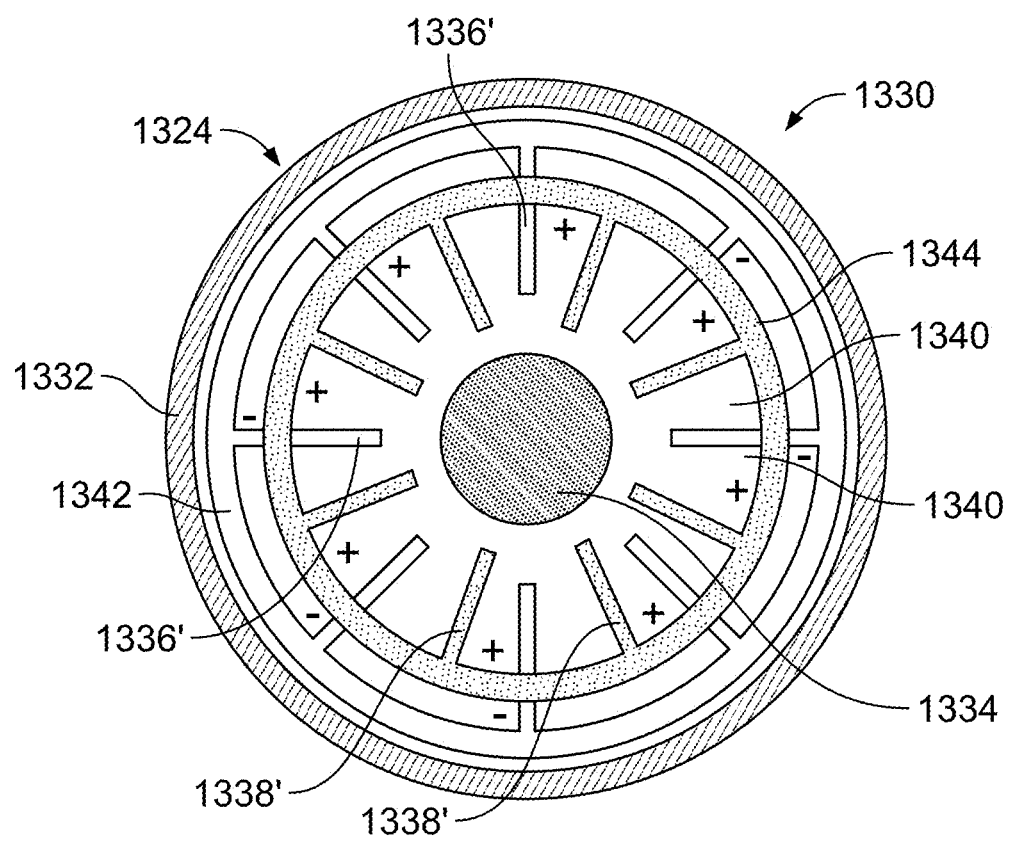
FIG. 13C is a transverse cross-section view of the heating chamber of FIG. 13A, including assembled first and second arrays of electrodes, in accordance with an embodiment of the present specification.
Figure 13D:
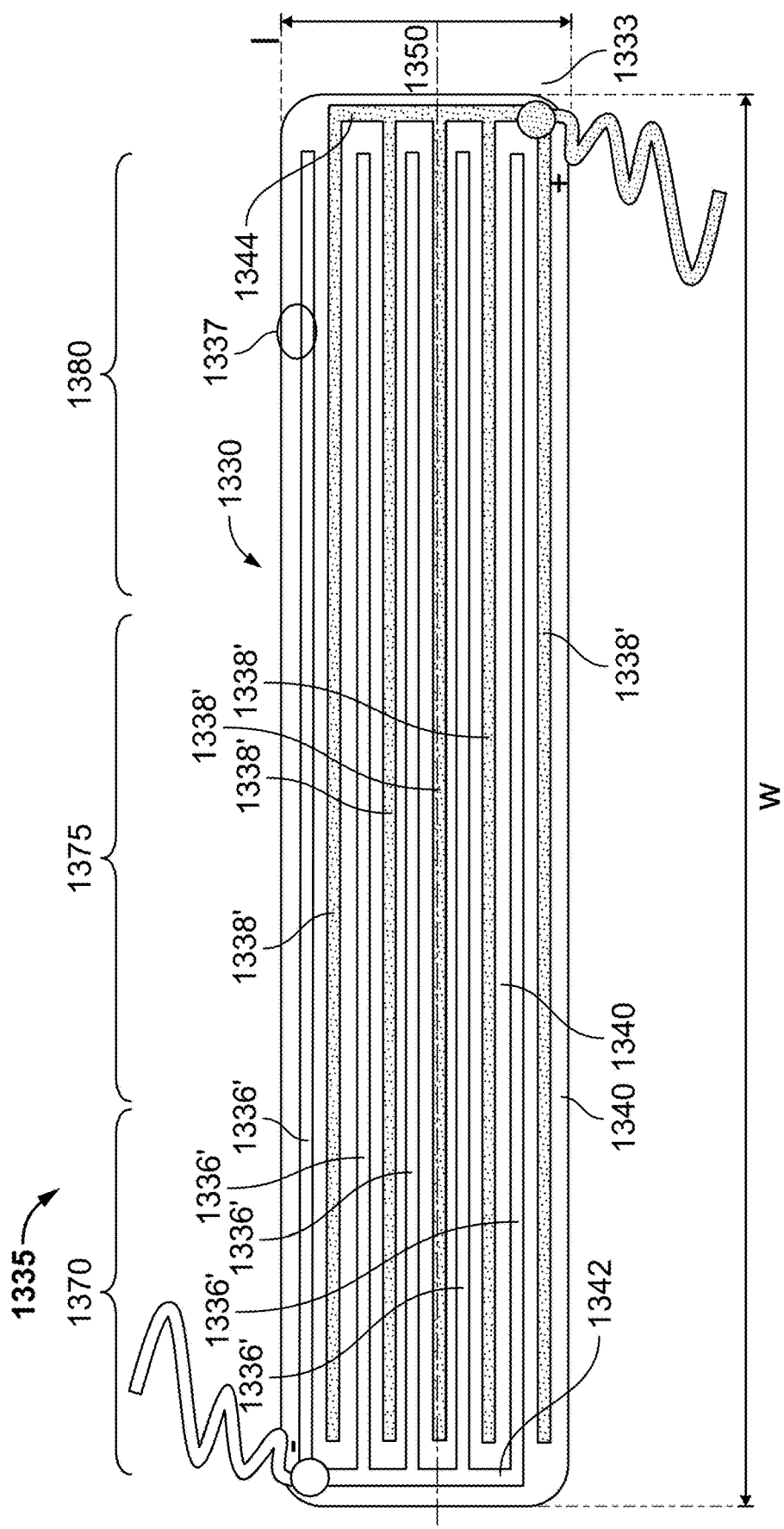
FIG. 13D is a longitudinal cross-section view of the heating chamber of FIG. 13A, including assembled first and second arrays of electrodes, in accordance with an embodiment of the present specification.

Heating Chambers FIG. 13A is a transverse cross-section view 1321 of a flexible heating chamber 1330 configured to be incorporated at or into a distal portion or tip of a catheter, in accordance with an embodiment of the present specification. FIG. 13B illustrates a transverse cross-section view 1322a and a longitudinal cross-section view 1322b of a first array of electrodes 1336 along with a transverse cross-section view 1323a and a longitudinal cross-section view 1323b of a second array of electrodes 1338 of a flexible heating chamber for a catheter, in accordance with an embodiment of the present specification. FIGS. 13C and 13D are, respectively, transverse and longitudinal cross-section views 1324, 1325 of the heating chamber 1330 including assembled first and second electrodes 1336, 1338.

Referring now to FIGS. 13A, 13B, 13C, and 13D simultaneously, the heating chamber 1330 comprises an outer covering 1332 and a coaxial inner core 1334. A plurality of electrodes, configured as first and second arrays of electrodes 1336, 1338, is disposed between the outer covering 1332 and the inner core 1334. In some embodiments, the first and second array of electrodes 1336, 1338 respectively comprise metal rings 1342, 1344 from which a plurality of electrode fins or elements 1336', 1338' extend radially into the space between the outer covering 1332 and inner core 1334 (see views 1322a, 1323a). The electrode fins or elements 1336', 1338' also extend longitudinally along a longitudinal axis 1350 of the heating chamber 1330 (see views 1322b, 1323b). In other words, each of the electrode fins 1336', 1338' have a first dimension along a radius of the heating chamber 1330 and a second dimension along a longitudinal axis 1350 of the heating chamber 1330. The electrode fins or elements 1336', 1338' define a plurality of segmental spaces 1340 there-between through which saline/water flows and is vaporized into steam. Electrical current is provided to the electrodes 1336, 1338 which causes the fins or elements 1336', 1338' to generate heat which is then transferred to the saline/water to convert said saline/water to steam. The first and second dimensions enable the electrodes 1336, 1338 to have increased surface area for heating the saline/water flowing in the spaces 1340. In accordance with an embodiment, the first electrodes 1336 have a first polarity and the second electrodes 1338 have a second polarity opposite said first polarity. In an embodiment, the first polarity is negative (cathode) while the second polarity is positive (anode).

In embodiments, the outer covering 1332 and the inner core 1334 are comprised of silicone, Teflon, ceramic or any other suitable thermoplastic elastomer known to those of ordinary skill in the art. The inner core 1334, outer covering 1332, electrodes 1336, 1338 (including rings 1342, 1344 and fins or elements 1336', 1338') are all flexible to allow for bending of the distal portion or tip of the catheter to provide better positioning of the catheter during ablation procedures. In embodiments, the inner core 1334 stabilizes the electrodes 1336, 1338 and maintains the separation or spacing 1340 between the electrodes 1336, 1338 while the tip of the catheter flexes or bends during use.

As shown in FIGS. 13C and 13D, when the heating chamber 1330 is assembled, the electrode fins or elements 1336', 1338' interdigitate or interlock with each other (similar to fingers of two clasped hands) such that a cathode element is followed by an anode element which in turn is followed by a cathode element that is again followed by an anode element and so on, with a space 1340 separating each cathode and anode element. In various embodiments, each space 1340 has a distance from a cathode element to an anode element ranging from 0.01 mm to 1 mm. In some embodiments, the first array of electrodes 1336 has a range of 1 to 50 electrode fins 1336', with a preferred number of 8 electrode fins 1336', while the second array of electrodes 1338 has a range of 1 to 50 electrode fins 1338', with a preferred number of 8 electrode fins 1338'. In various embodiments, the heating chamber 1330 has a width w in a range of 1 to 5 mm and a length/in a range of 1 to 150 mm.

Figure 13E:
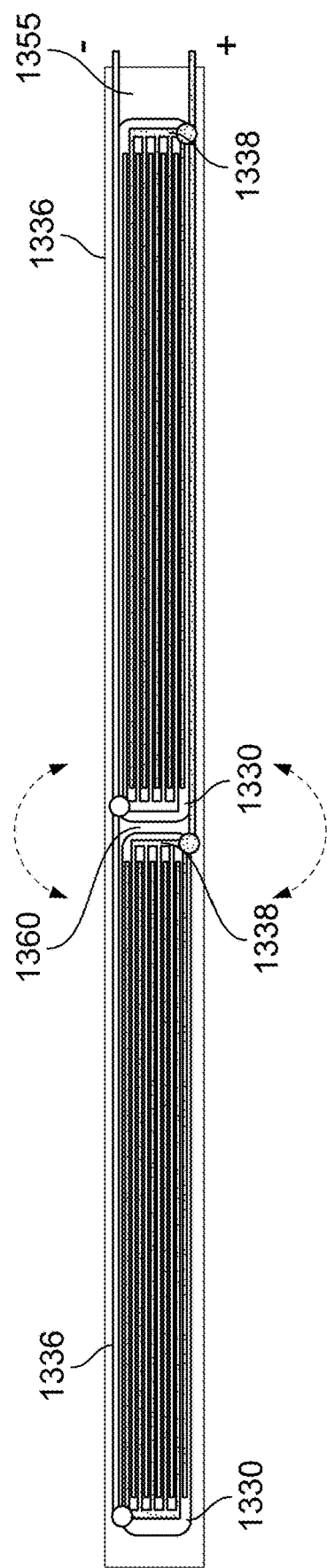
FIG. 13E is a first longitudinal view of two heating chambers of FIG. 13A arranged in series in a catheter tip, in accordance with an embodiment of the present specification.
Figure 13F:
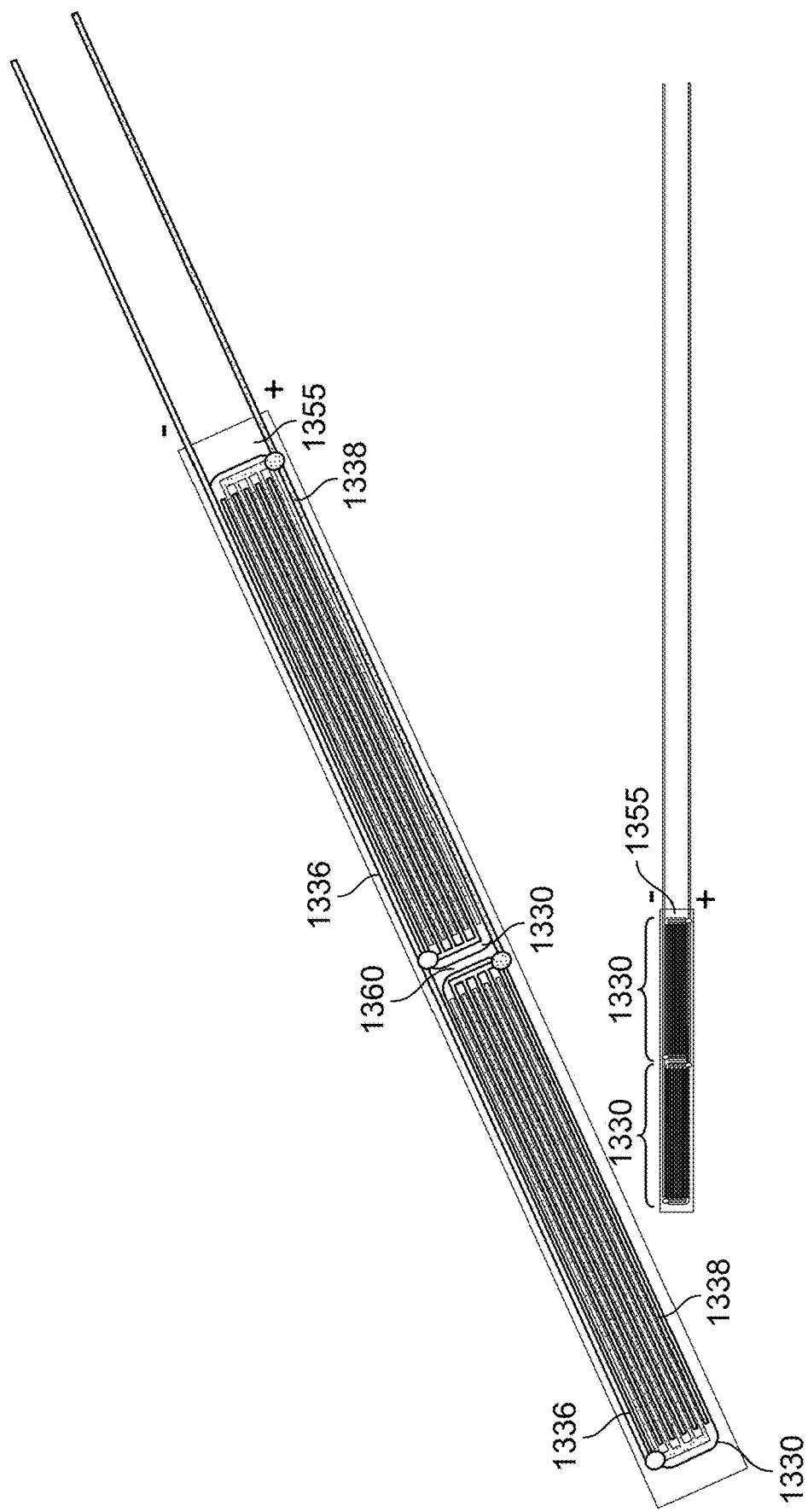
FIG. 13F is a second longitudinal view of two heating chambers of FIG. 13A arranged in series in a catheter tip, in accordance with an embodiment of the present specification.

In accordance with an aspect of the present specification, multiple heating chambers 1330 can be arranged in the catheter tip. FIGS. 13E and 13F are longitudinal cross-section views of a catheter tip 1355 wherein two heating chambers 1330 are arranged in series, in accordance with an embodiment of the present specification. Referring to FIGS. 13E and 13l, the two heating chambers 1330 are arranged in series such that a space 1360 between the two heating chambers 1330 acts as an area of lower rigidity, thereby imparting added flexibility to the catheter tip 1355 to allow it to bend. The two heating chambers 1330 respectively comprise interdigitated first and second arrays of electrodes 1336, 1338. Use of multiple, such as two, heating chambers 1330 enables a further increase in the surface area of the electrodes 1336, 1338 while maintaining flexibility of the catheter tip 1355.

Referring now to FIGS. 13A through 13F, for generating steam, fluid is delivered from a reservoir to the heating chamber 1330 by a pump or any other pressurization means. In embodiments, the fluid is sterile saline or water that is delivered at a constant or variable fluid flow rate. An RF generator, connected to the heating chamber 1330, provides power to the first and second arrays of electrodes 1336, 1338. As shown in FIG. 13D, during vapor generation, as the fluid flows through spaces 1340 in the heating chamber 1330 and power is applied to the electrodes 1336, 1338 causing the electrodes to heat, the fluid is warmed in a first proximal region 1370 of the heating chamber 1330. When the fluid is heated to a sufficient temperature, such as 100 degrees Centigrade at atmospheric pressure, the fluid begins to transform into a vapor or steam in a second middle region 1375. All of the fluid is transformed into vapor by the time it reaches a third distal region 1380, after which it can exit a distal end 1333 of the heating chamber 1330 and exit the catheter tip 1355. If the pressure in the heating chamber is greater than atmospheric pressure, higher temperatures will be required and if it is lower than atmospheric pressure, lower temperatures will generate vapor. A standard circular or rectangular electrode positioned in the catheter tip may have dimensions that prevent effective bending of the catheter tip. Specifically, electrodes are printed on to Kapton and then rolled into a cylinder, thereby making them rigid. Embodiments of the catheter tip in accordance with the present specification have a bend radius in a range of 3 to 0.15 inches, and preferably within a range of 1 to 0.5 inches. There is a need for another design of the electrodes so as to incorporate electrode lengths that are greater than the bend radius.

Figure 13G:
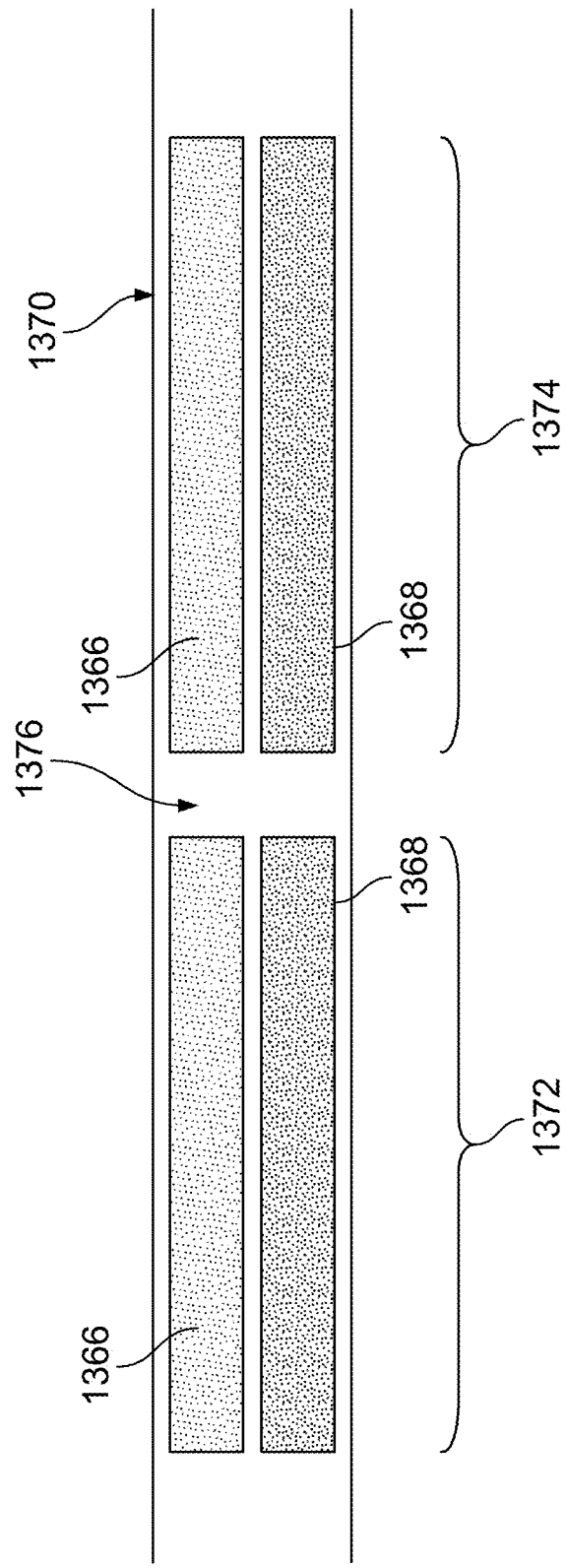
FIG. 13G illustrates discontinuous electrodes, such that they could be longer than the bend radius but flexible at the point of discontinuity, in accordance with an embodiment of the present specification.

Due to the bend radius at the tip, the size of the electrodes becomes significant. The electrodes need to be less than or equal to 2.5 inches, preferably less than or equal to 1 inch, in order to allow for the needed bend radius. In one embodiment, the bend radius of the guide sheath is 180 degrees around a 1 inch radius. In one embodiment, the maximum length of a continuous electrode is equal to the bend radius. FIG. 13G illustrates discontinuous electrodes 1366 and 1368, such that they could be longer than the bend radius but flexible at the point of discontinuity, in accordance with an embodiment of the present specification. Therefore, in one embodiment, a hot fluid channel 1370 comprises two or more electrode segments 1372 and 1374, wherein each electrode segment is separated by a space 1376 and wherein each electrode segment is no longer than a bend radius of the catheter or wherein each electrode segment has a length that is equal to or less than 2.5 inches, preferably 1 inch.

For an optimal positioning of the electrode, a primary requirement is that the electrode is positioned proximal to the output of the hot fluid channel into the inner balloon. At the same time, it is desirable that the electrode is not too proximal, because steam quality (the amount of condensed water in the steam) decreases. In some embodiments, electrode is positioned within the inner balloon. In some embodiments, the electrode is positioned a distance in a range of 0 mm to 500 mm proximal to the output of the hot fluid channel into the inner balloon. In some embodiments, the electrode is positioned a distance in a range of 1 mm to 150 mm proximal to the output of the hot fluid channel into the inner balloon.

In some embodiments, the electrode is made of a plurality of segments which are electrically connected to each other and housed in a flexible section of a catheter body with a desired bend radius wherein the length of each segment of the electrode is less than four times the bend radius of the catheter, thereby providing sufficient length coverage.

Figure 13H:
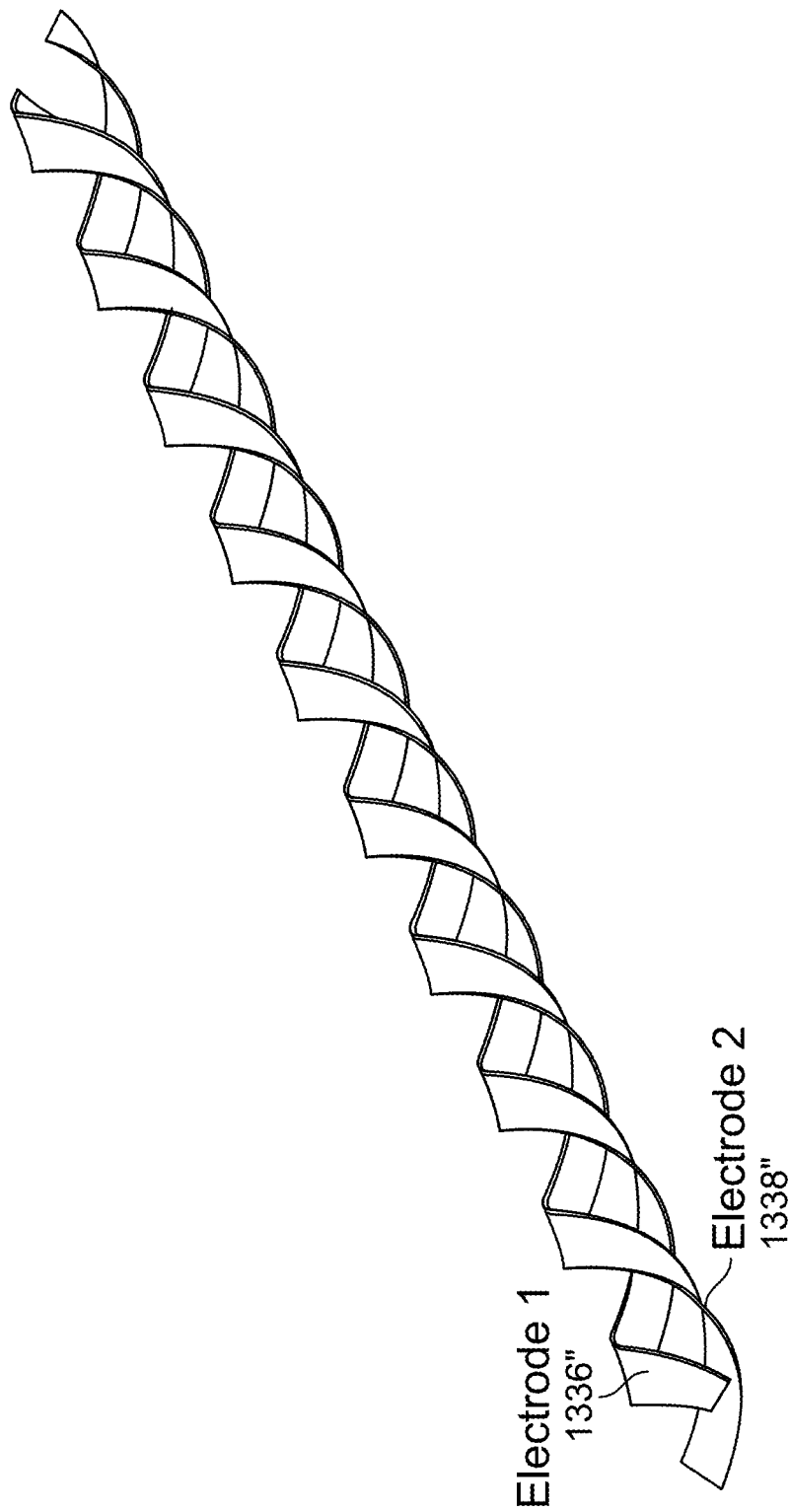
FIG. 13H illustrates another embodiment of arrangement of electrodes that may be configured within a flexible heating chamber for incorporation at or into a distal portion or tip of a catheter, in accordance with an embodiment of the present specification.

FIG. 13H illustrates another embodiment of arrangement of electrodes 1336", 1338" that may be configured within a flexible heating chamber for incorporation at or into a distal portion or tip of a catheter, in accordance with an embodiment of the present specification. Electrodes 1336" and 1338" represent the two poles (ends of electrodes 1336 and 1338 seen in FIGS. 13A to 13F) are rectangular and are arranged in a double-helix configuration. Use of the double helix structure enhances flexibility of the catheter tip and enables ease of bending the catheter tip. In some embodiments, a radial dimension of electrodes 1336" and 1338" is within a range of 0.5 mm to 5 mm, and the axial dimension is within 5 mm to 150 mm.

Additionally, in some embodiments the electrodes are manufactured using Nitinol-based material, thereby ensuring that the mounting process is simple.

Figure 13I:
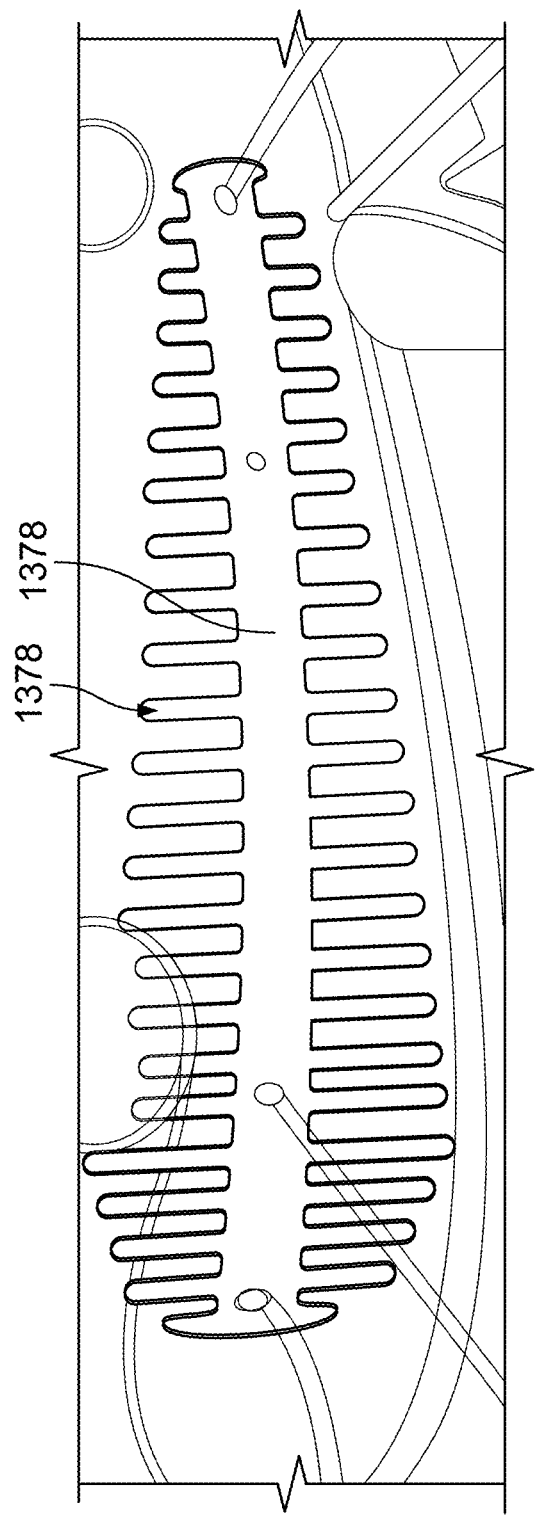
FIG. 13I illustrates another embodiment of a serrated configuration of electrodes that may be configured within a flexible heating chamber for incorporation at or into a distal portion or tip of a catheter, in accordance with an embodiment of the present specification.

FIG. 13I illustrates another embodiment of a serrated configuration of electrodes 1378 that may be configured within a flexible heating chamber for incorporation at or into a distal portion or tip of a catheter, in accordance with an embodiment of the present specification. Electrodes 1378 are designed with jagged edges and are arranged longitudinally around a circumference around a tip of a catheter. The serrated pattern of the electrode results in high current density at the edges of the electrode resulting in increased heating or an increased edge effect. This increases the power efficiency of the system by requiring less power generation to create steam required for therapy. The electrode, in one embodiment, has a perimeter which is greater than 2×(length+breadth) of the electrode. In another embodiment, the electrodes are configured as a flattened structure. The flattened electrode configuration comprises an elongated linear member having a first side and an opposing second side that are both planar. The flattened electrode configuration may comprise a bipolar array defined by a plurality of printed or deposited electrode fins. Saline is configured to flow equally over the top and bottom surfaces of the flattened electrode configuration. In embodiments, the catheter lumen that houses the flattened electrode configuration has an elliptical geometry that centers the electrode configuration within the larger radius of the elliptical lumen in order to ensure consistent steam quality on both sides of the electrode configuration.

During vapor generation, a signal can be sensed to determine if the fluid has fully developed into vapor before exiting the distal end of the heating chamber. In some embodiments, the signal is sensed by a controller. Sensing whether the vapor is fully developed can be particularly useful for many surgical applications, such as in the ablation of various tissues, where delivering high quality fully developed vapor results in more effective treatment. In some embodiments, the heating chamber includes at least one sensor 1337. In various embodiments, said at least one sensor 1337 comprises an impedance, temperature, pressure or flow sensor. In one embodiment, the electrical impedance of the electrode arrays 1336, 1338 can be sensed. In other embodiments, the temperature of the fluid, temperature of the electrode arrays, fluid flow rate, pressure, or similar parameters can be sensed.

It should be appreciated that any ablation catheter or system of the present specification, used to ablate tissue in an organ, may be used with a controller, wherein the controller is configured to limit a pressure generated by ablation fluid, such as steam/vapor, within the organ to less than 5 atm or 100 psi.

Cardiac Ablation Catheters and Methods

In various embodiments, cardiac ablation catheters, having one or more inflatable balloons, are disclosed. In various embodiments, as detailed in Table 1 below, the one or more balloons are of the following types and specifications:

TABLE 1

| Balloon Types and Specifications | |
|---|---|
| Non-compliant Dilatation Balloons | |
| Characteristics | Ultrahigh strength, thin walls |
| Materials | PET |
| Compliance Range | 0%-10% (typical) |
| Sizes | Diameter: 0.5 mm-80 mm |
| | Length: Virtually any (15" max) |
| Burst pressures | 15 psi-400 psi (1 atm-27 atm) |
| Semi-compliant Dilatation Balloons | |
| Characteristics | High strength, thin walls |
| Materials | Nylon, Polyurethane, other thermoplastic elastomers |
| Compliance Range | 10%-20% (typical) |
| Sizes | Diameter: 0.5 mm-50 mm |
| | Length: 15" max |
| Burst pressures | 15 psi-375 psi (1 atm-25.5 atm) |
| Compliant Balloons | |
| Characteristics | Low pressure, thin and thick walls |
| Materials | Polyurethane, Nylon elastomers, and other thermoplastic elastomers |
| Compliance Range | 20%-200% or more |
| Sizes | Diameter: 0.5 mm-80 mm |
| | Length: Virtually any (15" max) |
| Burst pressures | 0 psi-30 psi (0 atm-2 atm) |
| | Balloons can be designed for volume |

Following are some definitions with reference to balloon types and specifications:

Balloon Diameter—refers to nominal inflated balloon diameter measured at a specified pressure.

Balloon Length—typically refers to the working length or the length of the straight body section.

Burst Pressure—refers to an average pressure required to rupture a balloon; usually measured at body temperature.

Rated Burst Pressure—refers to a maximum statistically guaranteed pressure to which a balloon can be inflated without failing. For PTCA and PTA catheters, this is normally 95% confidence/99.9% guarantee.

Balloon Profile—refers to the maximum diameter of the balloon when mounted on a catheter in its deflated and wrapped condition or the smallest hole through which the deflated wrapped balloon catheter can pass.

Balloon Compliance—refers to change in balloon diameter as a function of inflation pressure.

In various embodiments, when inflated, the one or more balloons may have a shape such as, but not limited to, conical, square, spherical, elliptical, conical-square, long conical-square, conical-spherical, long spherical, tapered, dog bone, stepped, offset and conical-offset.

Again, in various embodiments, an end (distal and/or proximal) of the one or more balloons may have a shape such as, but not limited to, conical sharp corner, conical radius corner, square end, spherical end and offset neck.

Table 2 provides a comparison of a plurality of balloons made with various materials:

TABLE 2

| Materials | Tensile Strength | Compliance | Stiffness | Profile | Max. Rated Pressure for PTCA* | | Sterilization Methods |
|---|---|---|---|---|---|---|---|
| | | | | | ATM | PSI | |
| PET | High-Very High | Low-Medium | High | Low | 20 | 294 | EtO or Radiation |
| Nylons | Medium-High | Medium | Medium | Low-Medium | 16 | 235 | EtO |
| PE (crosslinked) and other polyolefins | Low | High | Low | High | 10 | 147 | EtO or Radiation |
| Polyurethanes | Low-Medium | Low-High | Low-Medium | Medium-High | 10 | 147 | EtO |
| PVC (flexible) | Low | High | Low | High | 6-8 | 88-117 | Radiation |

*The maximum rated pressure is based on practical limitations and usefulness

Material of the balloon is an important factor. If the softening temperature (Tg) of a balloon's material is too low, the balloon may deform during use when exposed to steam. For example, the Tg of PET is 75° C. This means that after just one use, the PET balloon may deform and may not be useable for conducting additional ablation shots of a given PV or of other PVs in the patient. Therefore, it is desirable to use a material that has a Tg greater than 100° C. to be functional. In embodiments, there are two balloons, where each balloon has a different Tg value. In embodiments, the Tg value of each balloon is within a range of 60° C. to about 200° C. In some embodiments, the Tg is 80° C. In some embodiments, the Tg is 150° C. In some embodiments, the outer balloon is composed of Pellethane®. It is also desirable to use a material that has a sufficiently wide elasticity range at various operating temperatures. If the elasticity range is too low, the yield point is passed during operation and the balloon deforms such that the ablation zone may not be properly positioned during operation.

In embodiments, material of the inner balloon is non-compliant to semi-compliant, implying that the material eliminates any folds that may have been present during packaging, and conforms to atrial anatomy for better contact. A compliant balloon is likely to have a fixed volume at a fixed pressure. It is desirable that material of the inner balloon is more rigid than that of the outer balloon, so as to maintain a certain shape. Some of the semi-compliant balloon materials, for example PEBA families, face mechanical and thermal challenges when introduced to steam. Therefore, a preferred balloon material is a copolymer called Arnitel. Arnitel is also relatively semi-compliant but has higher softening and melt temperatures versus standard PEBA polymers. Materials such as Arnitel may be used to make the inner balloon, outer balloon, and shaft applications, in accordance with the embodiments of the present specification. An advantage of using it as a shaft material is that it is thermally bondable with inner balloons currently made using PET, thereby eliminating the need to use an adhesive bonding process.

Ablation catheter needs to be sheathed and unsheathed, particularly if the ablation catheter is only 1 fr or less than the guide sheath. In some embodiments, a hydrophilic coating on the ablation catheter is used to enable easy sheathing. Coating also enables efficient energy transfer to and protects the outer balloon surface from charring. In embodiments, the balloons are pleated in a specific direction, such as in the rightward direction, to allow for easy sheathing/re-sheathing.

In some embodiments, the guide sheath is braided and is of a higher durometer than the ablation catheter. Guide wires are typically positioned in the catheter or outer catheter sheath lining to help bend the sides. A distal opening of the guide sheath is positioned normal to the ostium (opening) of the pulmonary vein. In some embodiments, two guide sheaths are provided, where the two guide sheaths are of two different radii and of different deflection characteristics. In an embodiment, one pull wire for the first sheath creates a radius in a range of 0.1 inches to 0.75 inches. In an embodiment, a second pull wire to the second sheath creates a radius in a range of 0.5 inches to 10 inches. In some embodiments, catheter deflection is performed via a handle actuator. Each pull wire is attached to a knob or lever in the handle. A user would twist the knob or pull the lever to apply tension to the tip and deflect. The radius is determined by the catheter construction. In embodiments, each half of the catheter has a separate and unique construction, allowing for the two unique radii.

Figure 14B:
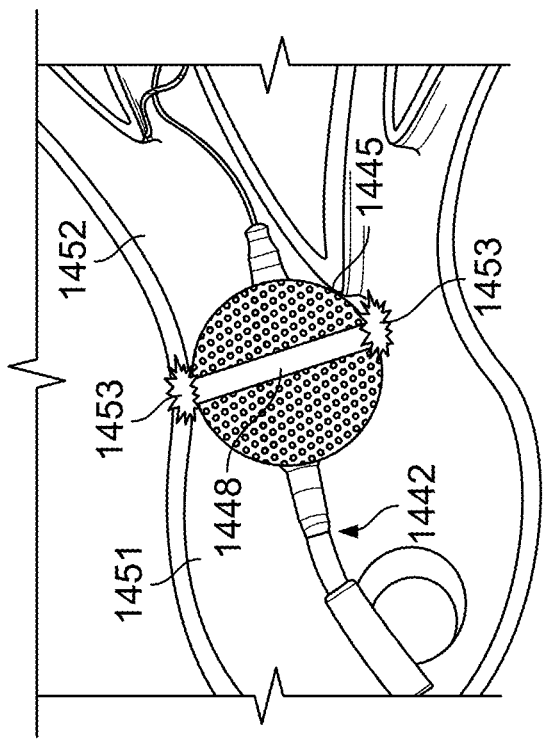
FIG. 14B illustrates cardiac ablation being performed by the cardiac ablation catheter of FIG. 14A.
Figure 14A:
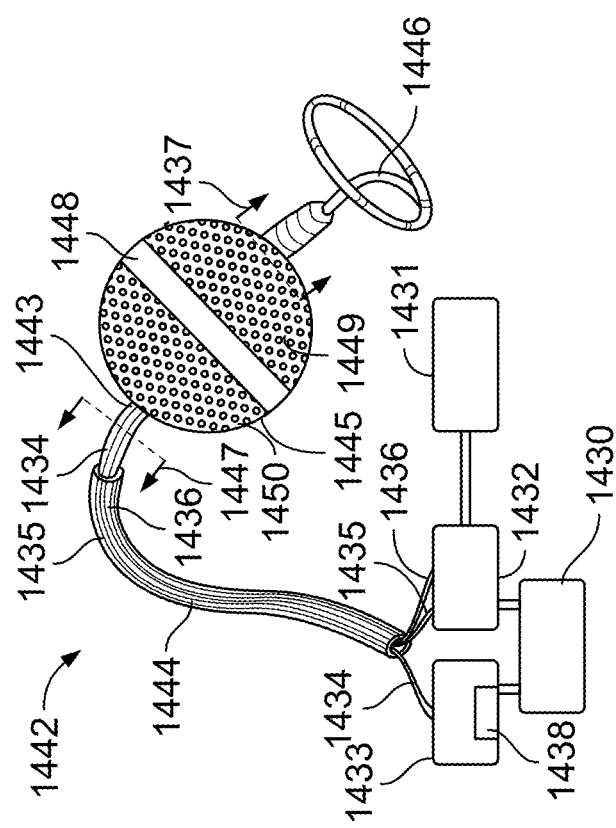
FIG. 14A illustrates a cardiac ablation catheter in accordance with one embodiment of the present specification.

FIG. 14A illustrates a cardiac ablation catheter 1442 in accordance with one embodiment of the present specification and FIG. 14B illustrates cardiac ablation being performed by the cardiac ablation catheter 1442 of FIG. 14A. The cardiac ablation catheter 1442 can be used to ablate cardiac tissue to treat an arrhythmia, such as atrial fibrillation. The catheter 1442 includes an elongate inner shaft 1443 covered by an outer shaft 1444. The inner shaft 1443 includes an inflatable balloon 1445 proximal its distal end. The inflatable balloon is in fluid communication with an air/vapor channel 1434 which extends through the inner shaft 1443 from the balloon 1445 to an air source, or first pump 1433, which is in data communication with, and controlled by, a controller 1430. The air source 1433 pulls air from the external environment through an optional filter 1438 to fill the balloon 1445. In an embodiment, the air source or first pump 1433 is reversible, thereby allowing air to be pumped into the balloon 1445 or out of the balloon 1445, as required and per instructions sent by the controller 1430. In another embodiment, $CO_2$ is used instead of air for inflation and deflation.

In some embodiments, an entire surface of the catheter 1442 is coated with heparin.

A mapping member 1446, which may be a radial extension, catheter, or any substrate comprising a plurality of sensors, detectors, or electrodes, is attached to the distal end of the inner shaft 1443 distal to the balloon 1445. The mapping member 1446 maps the area of cardiac tissue responsible for the arrhythmia. In some embodiments, the mapping member 1446 comprises an extension of the catheter and has a length of up to 75 mm. In some embodiments, the mapping member is pre-shaped in a loop shape perpendicular to the catheter body axis. In some embodiments, the mapping member 1446 is pre-shaped in a pig-tail shape to allow wall contact. In embodiments, the diameter of the pigtail or the loop is between 5 mm and 25 mm. In some embodiments, the mapping member 1446 comprises 1 to 8 electrodes configured to record signals from a pulmonary vein or pacing in a pulmonary vein.

The distal end of the outer shaft 1444 ends a distance proximal to the balloon 1445 such that a portion of the inner shaft 1443 between the balloon 1445 and outer shaft 1444 is exposed. Water 1447 can be pumped from a sterile water reservoir 1431, via a second pump 1432, through a first water lumen 1435 in the outer shaft 1444, where it exits proximal to the balloon 1445 for cooling a space proximal to the balloon 1445. Water 1437 can also be pumped from the sterile water reservoir 1431, via the second pump 1432, through a second water lumen 1436 in the inner shaft 1443, where it exits distal to the balloon 1445 and proximal to the mapping member 1446 for cooling a space distal to the balloon 1445. The first water lumen 1435 extends within the outer shaft 1444 from the second pump 1432 to the distal end of the outer shaft 1444. The second water lumen 1436 extends within the inner shaft 1443 from the second pump 1432 to the distal end of the inner shaft 1443. The controller 1430 is in data communication with, and controls, the second pump 1432, wherein the second pump 1432 is configured to pass water 1447, 1437 from the sterile water reservoir 1431 into the first water lumen 1435 and/or second water lumen 1436 of the outer shaft 1444 and inner shaft 1443, respectively. The balloon 1445 includes an ablation or hot zone 1448 proximate its equator and a first cold zone in its top hemisphere 1449, cooled by water 1437 pumped through the inner shaft 1443, and a second cold zone in its bottom hemisphere 1450, cooled by water 1447 pumped through the outer shaft 1444. The temperature of the ablation or hot zone 1448 is typically between 60-110° C. and the temperature of the cold zones 1449, 1450 is typically between 35-60° C., with the temperature of the cold zones 1449, 1450 decreasing as the cold zones 1449, 1450 extend away from the hot zone 1448. The equatorial hot zone 1448 remains heated by vapor used to heat the inside of the balloon 1445 and is distant enough from the water 1437, 1447 pumped through the inner shaft 1443 and outer shaft 1444 such that it does not become cooled.

Referring to FIG. 14B, the balloon 1445 of the catheter 1442 has been positioned in a heart 1451, proximate a pulmonary vein 1452. Heat supplied to the balloon 1445 by vapor is transferred from the hot zone 1448 to the target cardiac tissue 1453 to ablate the tissue 1453 and treat the arrhythmia. The hot zone 1448 is defined by the portion of the balloon contacting the target cardiac tissue 1453 where the water for cooling does not contact the balloon surface, while the cold zones 1449, 1450 are defined by the portion of the balloon not contacting the target cardiac tissue 1453, allowing for the water to contact and cool the balloon surface. In some embodiments, the two temperature zones can also be defined by constructing the balloon with two different materials with different thermal conductivity. In one embodiment, the hot zone is located more toward the distal hemisphere of the balloon facing a pulmonary vein (PV) ostium.

Figure 14C:
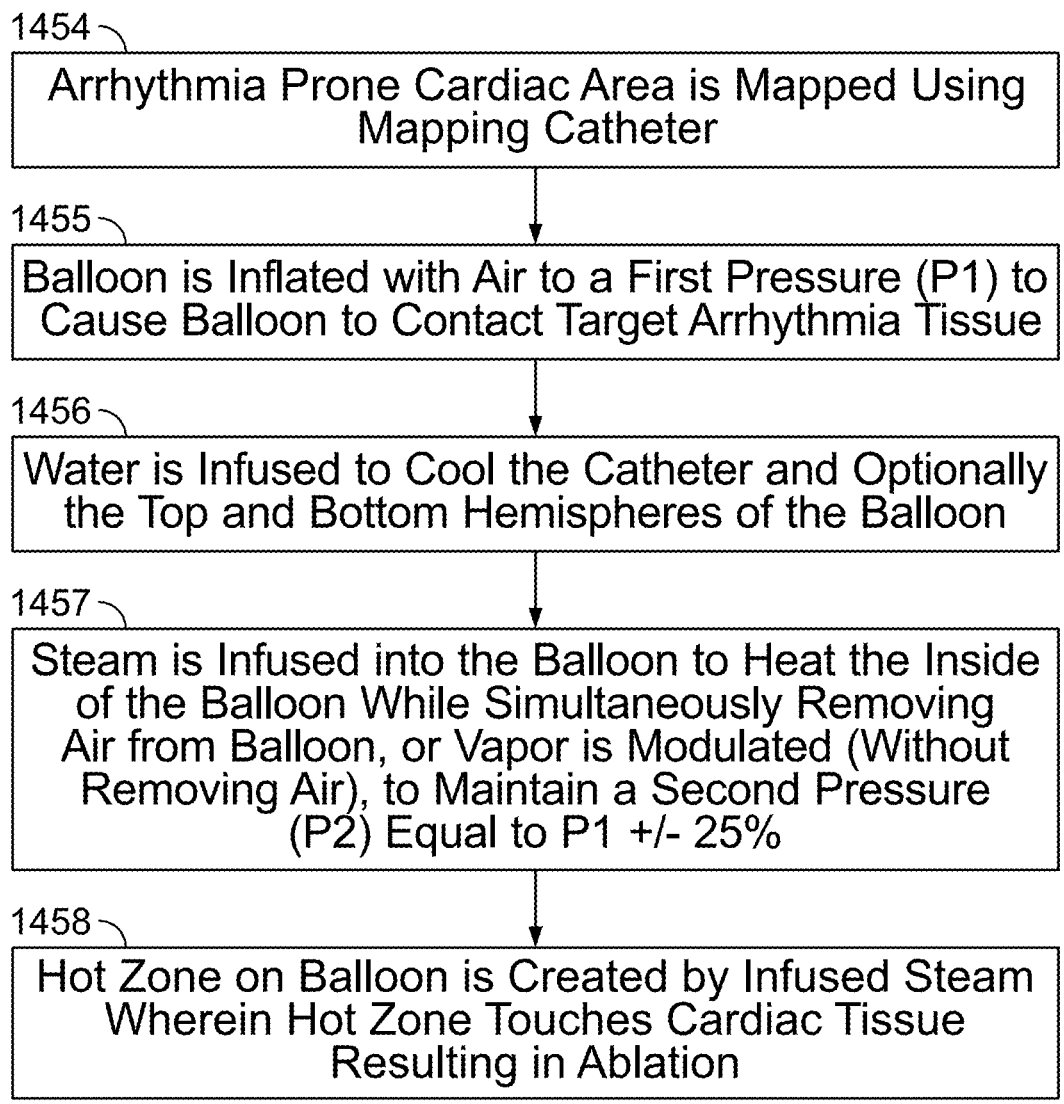
FIG. 14C is a flowchart illustrating the steps involved in one embodiment of a method of using the catheter of FIG. 14A to ablate cardiac tissue.

FIG. 14C is a flowchart illustrating the steps involved in one embodiment of a method of using the catheter of FIG. 14A to ablate cardiac tissue. At step 1454, an arrhythmia prone cardiac area is mapped using the mapping catheter. The balloon is inflated with air to a first pressure (P1) to cause the balloon to contact the target arrhythmia tissue at step 1455. At step 1456, water is infused to cool the catheter and optionally the top and bottom hemispheres of the balloon. In some embodiments, step 1456 occurs before, with or after step 1455. In some embodiments, blood assists in cooling the top and bottom hemispheres of the balloon. At step 1457, steam or vapor is infused into the balloon to heat the inside of the balloon while simultaneously removing air from the balloon to maintain a second pressure (P2) equal to P1+/−25%. The amount of vapor being delivered to the balloon may also be modulated (without removing air) to maintain the second pressure (P2) equal to P1+/−25%. A hot zone on the balloon is created by the infused steam wherein the hot zone touches the cardiac tissue resulting in ablation at step 1458.

Figure 14D:
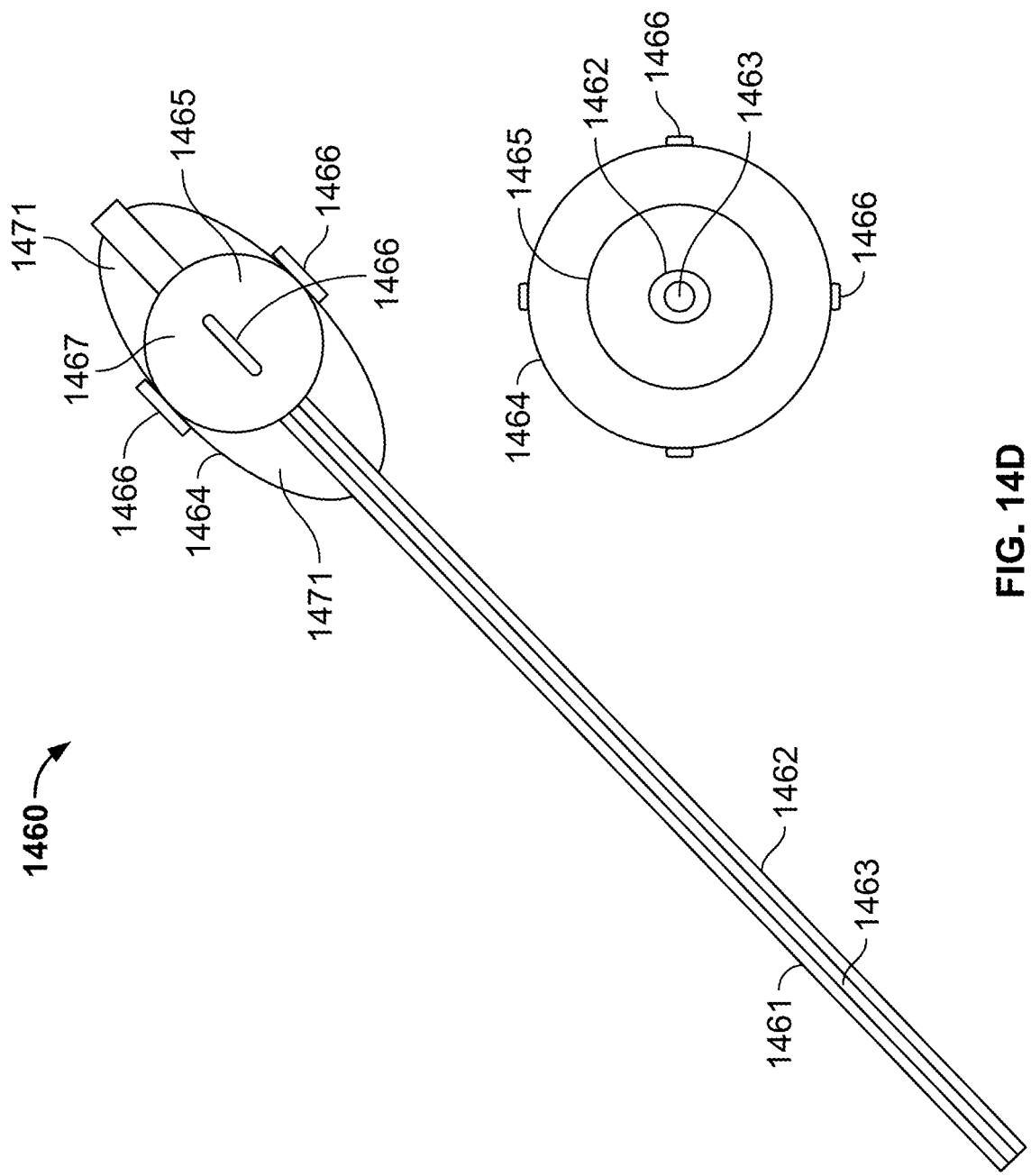
FIG. 14D illustrates a cardiac ablation catheter in accordance with another embodiment of the present specification.

FIG. 14D illustrates a cardiac ablation catheter 1460 in accordance with another embodiment of the present specification. The catheter 1460 includes an elongate body 1461, a proximal end, and a distal end with an air/water lumen 1462 and a vapor lumen 1463 supplied by ports at its proximal end. The air/water lumen 1462 is in fluid communication with a balloon 1464 attached to the distal end of the catheter 1460.

The balloon 1464 includes a plurality of optional mapping electrodes 1466 within or attached to the outer surface of its walls. In embodiments, the mapping electrodes 1466 are either glued metal electrodes or printed electrodes, within or attached to the outer surface of its walls in the middle of its length axis circularly configured to record cardiac signals to map areas of cardiac tissue responsible for an arrhythmia. In some embodiments, the mapping balloon 1464 includes up to 24 mapping electrodes.

The vapor lumen 1463 is in fluid communication with an ablation balloon 1465 attached to the distal end of the catheter 1460 and positioned within the balloon 1464. Once both balloons 1464, 1465 are inflated, a length of the balloon 1464 is greater than a length of the ablation balloon 1465 and a diameter of the ablation balloon 1465 approximates a diameter of the balloon 1464.

In some embodiments, an entire surface of the catheter 1460 is coated with heparin. In some embodiments, the ablation balloon 1465 is movable along a longitudinal axis of the balloons 1464, 1465 within and along an entire length of the balloon 1464, to better position the ablation balloon inside the balloon 1464, using a wire mechanism in a handle at the proximal end of the catheter 1460.

In embodiments, at least one dimension of the ablation balloon 1465 is different than the balloon 1466 by at least 10%. In some embodiments, the dimension is a length of the ablation balloon 1465. In embodiments, a shape of the ablation balloon 1465 is different from that of the balloon 1466. In embodiments, an intersection of the shapes of the ablation balloon 1465 and the balloon 1466 determine the shape and/or size of an ablation zone 1467.

During use, the balloon 1464 is inflated with water or air or $CO_2$ and the ablation balloon 1466 is inflated with vapor such that the ablation balloon 1465 comes into contact with the balloon 1464 and the balloon 1464 comes into contact with the target cardiac tissue proximate the equators of both balloons 1464, 1465. This creates a hot zone or ablation zone 1467 proximate the equator of the balloon 1464. Cold zones 1471 are located on the balloon 1464 where the inflated ablation balloon 1465 is not in contact with the inflated balloon 1464. Heat is transferred from inside the ablation balloon 1465 through the balloon 1464 and into the cardiac tissue to ablate the tissue and treat the arrhythmia.

FIG. 14E illustrates the balloon 1464 with optional mapping electrodes 1466 of the catheter 1460 of FIG. 14D. FIG. 14F illustrates a cross sectional view of a mid-shaft portion of the catheter 1460 of FIG. 14D. The catheter 1460 includes a compartmentalized outer wall 1468 which includes the air/water lumen 1462 and wires 1469 for the mapping electrodes. The catheter 1460 also includes the vapor lumen 1463 and, in one embodiment, a guidewire lumen 1470. FIG. 14G illustrates a cross sectional view of a distal tip portion of the catheter 1460 of FIG. 14D. The catheter 1460 includes a plurality of mapping electrodes 1466 built into its outer wall or, in an embodiment, into the wall of the mapping balloon, the vapor lumen 1463, and a guidewire lumen 1470.

Figure 14H:
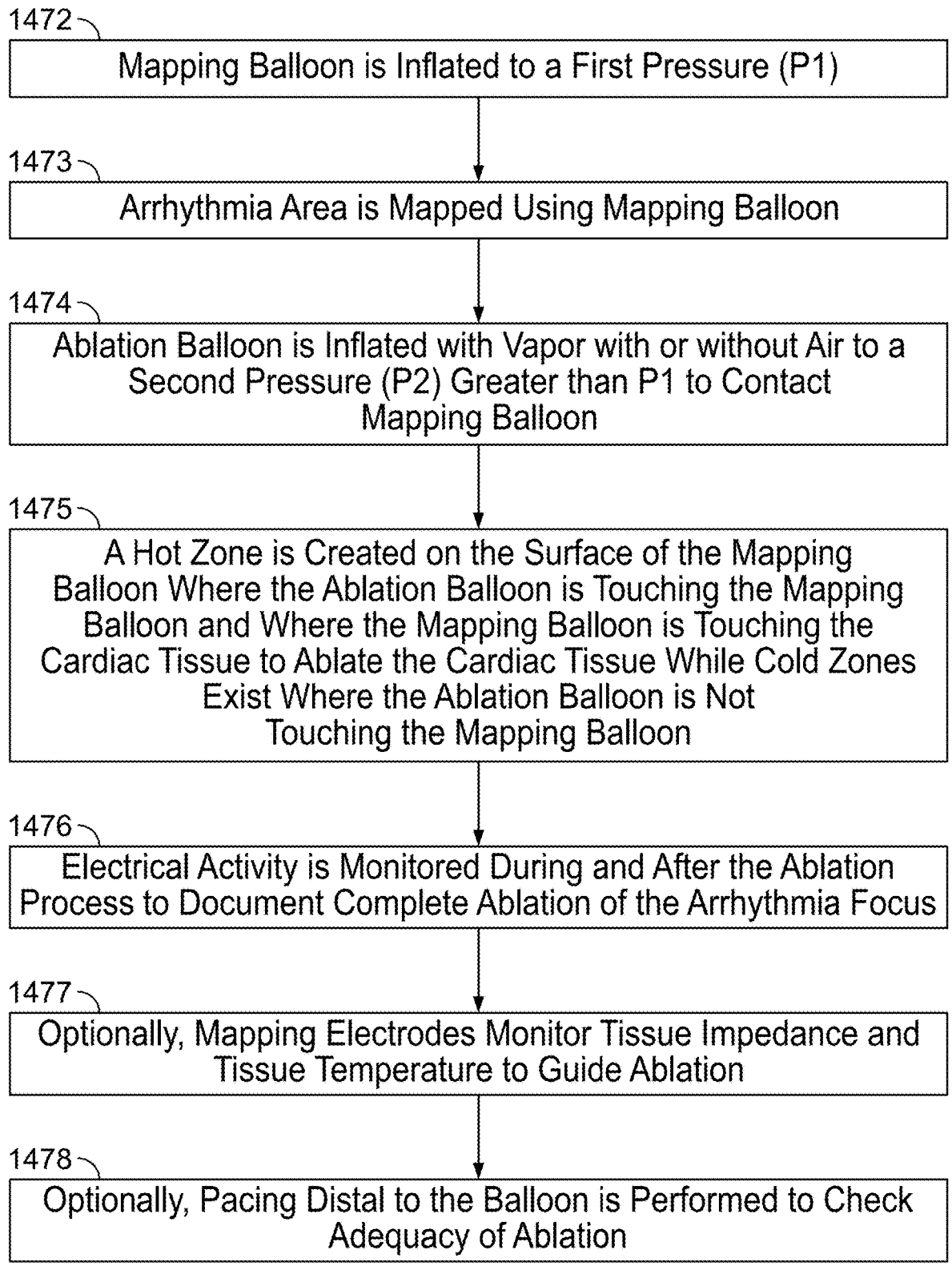
FIG. 14H is a flowchart illustrating the steps involved in one embodiment of a method of using the catheter of FIG. 14D to ablate cardiac tissue.

FIG. 14H is a flowchart illustrating the steps involved in one embodiment of a method of using the catheter of FIG. 14D to ablate cardiac tissue. At step 1472, the mapping balloon is inflated to a first pressure (P1). An arrhythmia area is mapped using the mapping balloon at step 1473. At step 1474, the ablation balloon is inflated with vapor with or without air or $CO_2$ to a second pressure (P2) greater than P1 to contact the mapping balloon. At step 1475, a hot zone is created on the surface of the mapping balloon where the ablation balloon is touching the mapping balloon and where the mapping balloon is touching the cardiac tissue to ablate the cardiac tissue while cold zones exist where the ablation balloon is not touching the mapping balloon. At step 1476, electrical activity is monitored during and after the ablation process to document complete ablation of the arrhythmia focus. Optionally, at step 1477, the mapping electrodes monitor tissue impedance and tissue temperature to guide the ablation. Optionally, at step 1478, pacing distal to the balloon is performed to check for adequacy of ablation. Pressure can be applied on the catheter shaft in order to deform the shape of the outer balloon by pressing it against the cardiac tissue, which in turn, changes a shape, a dimension or a surface area of the contact zone between the inner and outer balloon to in turn change a shape, a dimension or a surface area of the ablation zone.

Figure 14K:
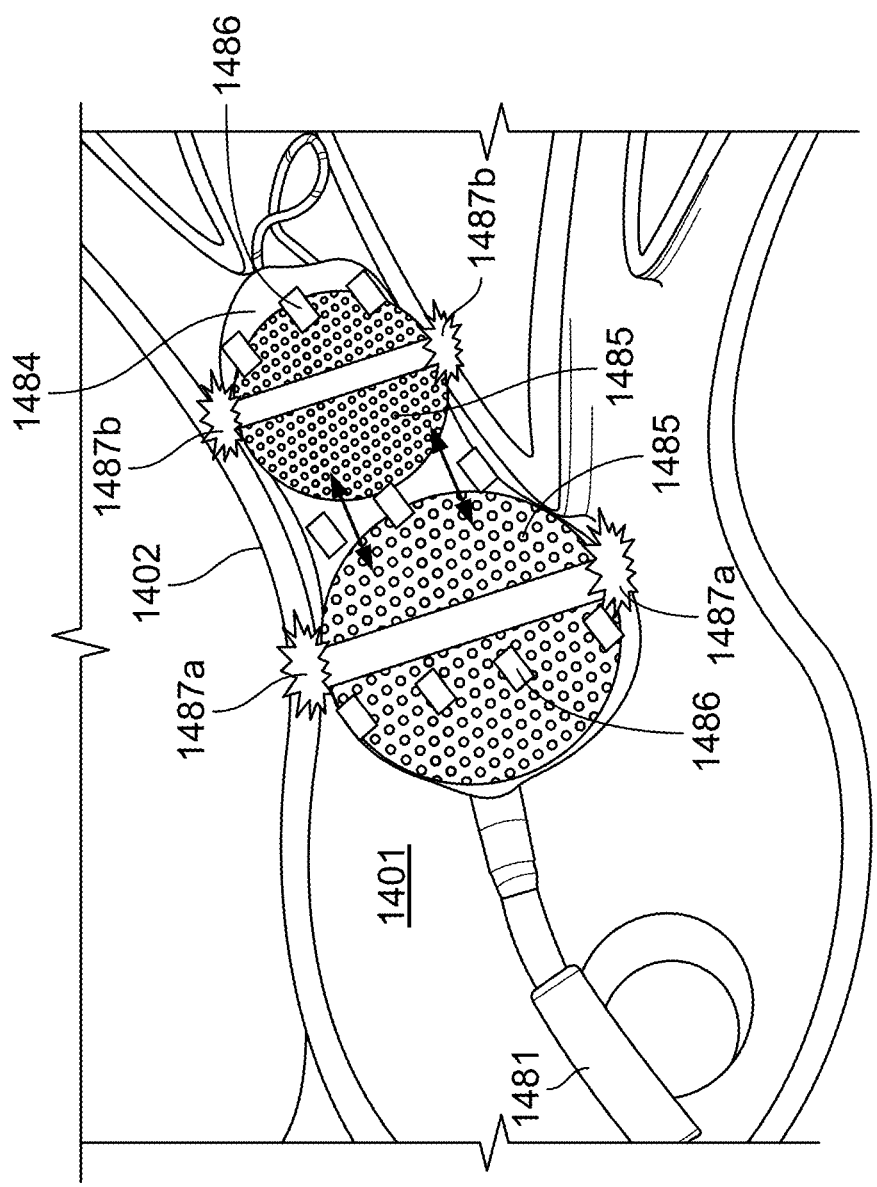
FIG. 14K illustrates cardiac ablation being performed by the cardiac ablation catheter of FIG. 14I.

FIG. 14I illustrates a cardiac ablation catheter 1480 in accordance with another embodiment of the present specification, FIG. 14J illustrates a cross-sectional view of a mid-portion of an elongate body 1481 of the catheter 1480 of FIG. 14I and FIG. 14K illustrates cardiac ablation being performed by the cardiac ablation catheter 1480 of FIG. 14I. Referring now to FIGS. 14I through 14K simultaneously, the catheter 1480 includes an elongate body 1481, a proximal end, and a distal end with an air/water lumen 1482 and a vapor lumen 1483 supplied by ports at its proximal end. The air/water lumen 1482 is in fluid communication with a balloon 1484 attached to the distal end of the catheter 1480. The air/water lumen 1482 optionally comprises a plurality of sub-channels or lumens (along the length of the elongate body 1481) to allow air/water to enter and exit the lumen 1482 at the proximal end of the catheter 1480.

The balloon 1484 includes a plurality of optional mapping electrodes 1486 within or attached to the outer surface of its walls. In embodiments, the mapping electrodes 1486 are either glued metal electrodes or printed electrodes, within or attached to the outer surface of its walls in the middle of its length axis circularly configured to record cardiac signals to map areas of cardiac tissue responsible for an arrhythmia. In some embodiments, the balloon 1484 includes up to 24 mapping electrodes.

The vapor lumen 1483 is in fluid communication with an ablation balloon 1485 attached to the distal end of the catheter 1480, positioned within the balloon 1484 and freely movable co-axially along a longitudinal axis within and along an entire length of the balloon 1484 to be positioned at a plurality of positions along a longitudinal axis 1488. In some embodiments, catheter 1480 includes a wire mechanism 1459 operable by a user at a handle of the catheter 1480 for moving the ablation balloon 1485 within the balloon 1484. In accordance with an exemplary embodiment, the catheter 1480 illustrates the ablation balloon 1485 being moved from a first position 1489*a* to a second position 1489*b* along the longitudinal axis 1488.

In some embodiments, an entire surface of the catheter 1480 is coated with heparin. In embodiments, at least one dimension of the ablation balloon 1485 is different than the balloon 1484 by at least 10%. In some embodiments, the dimension is a length of the ablation balloon 1485. In embodiments, a shape of the ablation balloon 1485 is different from that of the balloon 1484. In embodiments, an intersection of the shapes of the ablation balloon 1485 and the balloon 1484 determine the shape and/or size of an ablation zone 1487*a*. Once both balloons 1484, 1485 are inflated, a length (along the longitudinal axis 1488) of the balloon 1484 is greater than a length (along the longitudinal axis 1488) of the ablation balloon 1485 and a diameter of the ablation balloon 1485 approximates a diameter of the balloon 1484. During use, the balloon 1484 is inflated with $CO_2$ or air and the ablation balloon 1485 is inflated with vapor and placed at the first position 1489*a* (within the balloon 1484) such that the ablation balloon 1485 comes into contact with the balloon 1484 and the balloon 1484 comes into contact with the target cardiac tissue proximate the first position 1489*a* in a heart 1401 proximate a pulmonary vein 1402. This creates a hot zone or ablation zone 1487*a* proximate the first position 1489*a*. Heat is transferred from inside the ablation balloon 1485 through the balloon 1484 and into the cardiac tissue to ablate the tissue at the first position 1489*a*. The ablation balloon 1485 is thereafter moved to the second position 1489*b* (within the balloon 1484) such that the ablation balloon contacts the balloon 1484 and the balloon 1484 comes into contact with the target cardiac tissue proximate the second position 1489*b* within the pulmonary vein 1402. This creates a hot zone or ablation zone 1487*b* proximate the second position 1489*b*. Heat is now transferred from inside the ablation balloon 1485 through the balloon 1484 and into the cardiac tissue to ablate the tissue at the second position 1489*b*. Cold zones 1490 are located on the balloon 1484 where the inflated ablation balloon 1485 is not in contact with the inflated balloon 1484. It should be appreciated that the balloon 1484 and the ablation balloon 1485 may have to be inflated differentially at the first and second positions 1489*a*, 1489*b* in order to conform to the space (associated with the first and second positions 1489*a*, 1489*b*) within the pulmonary vein 1402.

In accordance with an aspect, the balloon 1484 is more flexible (compared to the ablation balloon 1485) and can free-form or conform to fit the shape of anatomical structure, such as the lumen of the pulmonary vein 1402, in order to create a contact sufficient for electrical contact between the electrodes 1486 and cardiac tissue. The ablation balloon 1485 is more firm and is meant to apply firm contact at the points (such as those corresponding to the first and second positions 1489a, 1489b) of its axial contact with the target tissue for ideal delivery of thermal energy to the target cardiac tissue.

Figure 14L:
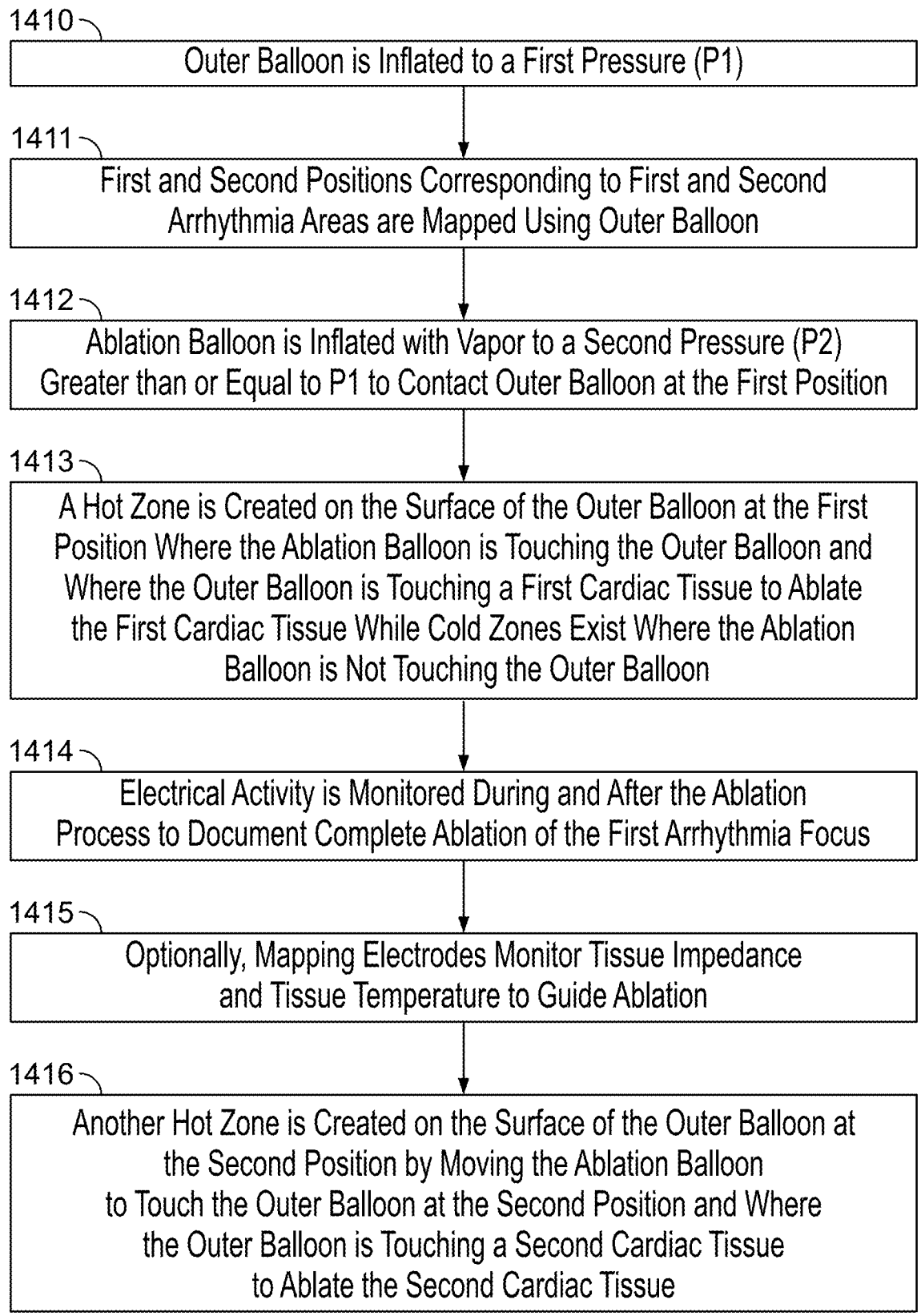
FIG. 14L is a flowchart illustrating the steps involved in one embodiment of a method of using the catheter of FIG. 14I to ablate cardiac tissue.

FIG. 14L is a flowchart illustrating the steps involved in one embodiment of a method of using the catheter of FIG. 14I to ablate cardiac tissue. At step 1410, the outer balloon with optional mapping electrodes is inflated to a first pressure (P1) using air or $CO_2$. The first and second positions corresponding to first and second arrhythmia areas are mapped using the outer balloon at step 1411. At step 1412, the ablation balloon is inflated with vapor to a second pressure (P2) greater than or equal to P1 to contact the outer balloon at the first position. In accordance with an embodiment, the air or $CO_2$ circulated into the outer balloon maintains a temperature of less than 60 degrees C. while maintaining the pressure in the outer balloon between 0.5× P1 and 1×P2. At step 1413, a hot zone is created on the surface of the outer balloon at the first position where the inner ablation balloon is touching the outer balloon and where the outer balloon is touching a first cardiac tissue to ablate the first cardiac tissue while cold zones exist where the inner ablation balloon is not touching the outer balloon. At step 1414, electrical activity is monitored during and after the ablation process to document complete ablation of the first arrhythmia focus. Optionally, at step 1415, the mapping electrodes monitor tissue impedance and tissue temperature to guide the ablation. Once ablation at the first position is completed, at step 1416, the inner ablation balloon is moved to create a hot zone on the surface of the outer balloon at the second position where the ablation balloon has been moved to touch the outer balloon and where the balloon touches a second cardiac tissue to ablate the second cardiac tissue. Steps 1414 and 1415 are repeated for the ablation process at the second position. It should be appreciated that in various embodiments, the ablation balloon can be moved to multiple positions and therefore create multiple hot zones on the surface of the outer balloon to ablate cardiac tissue corresponding to multiple positions. In embodiments, the mapping electrodes and the ablation zones are positioned on a distal surface of the outer balloon facing the cardiac tissue to be ablated.

Figure 14M:
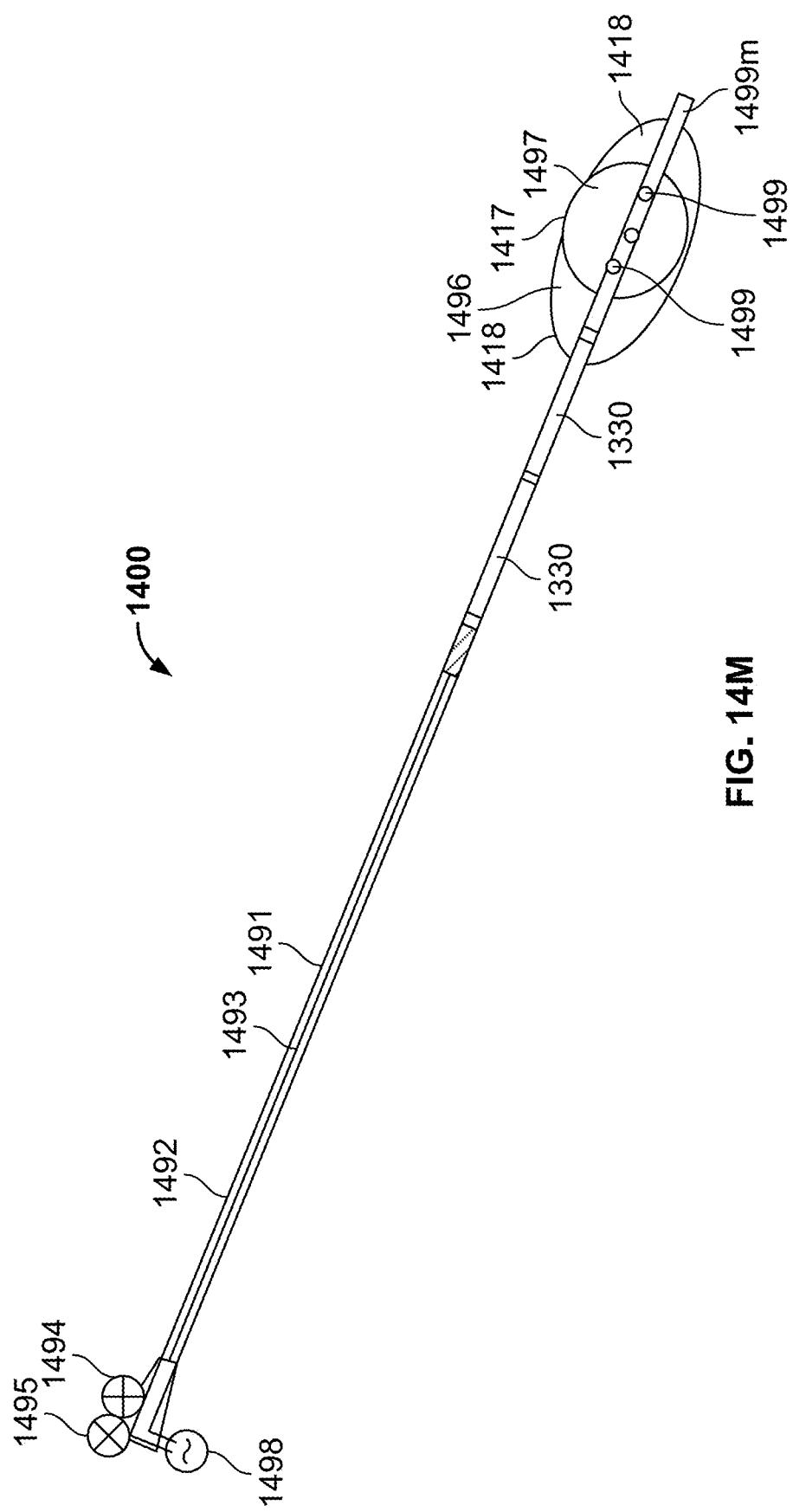
FIG. 14M illustrates a cardiac ablation catheter incorporating at least one flexible heating chamber of FIGS. 13A through 13D, in accordance with an embodiment of the present specification.

FIG. 14M illustrates a cardiac ablation catheter 1400 incorporating at least one flexible heating chamber 1330 of FIGS. 13A through 13D, in accordance with an embodiment of the present specification. The catheter 1400 includes an elongate body 1491 having a proximal end and a distal end with an air lumen 1492 and a water/vapor lumen 1493 that are in fluid communication with an air pump 1494 and water pump 1495 at a proximal end of the catheter 1400. The air lumen 1492 is in fluid communication with an outer balloon 1496 attached to the distal end of the catheter 1400.

The outer balloon 1496 may include a plurality of optional mapping electrodes within or attached to the outer surface of its walls. The mapping electrodes map the area of cardiac tissue responsible for an arrhythmia. In embodiments, the mapping electrodes are either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 1496 includes up to 24 mapping electrodes.

The water/vapor lumen 1493 is in fluid communication with an ablation balloon 1497 attached to the distal end of the catheter 1400 and positioned within the outer balloon 1496. A plurality of infusion ports 1499 are included in a portion of the distal end wherein the ablation balloon 1497 is attached.

In some embodiments, an entire surface of the catheter 1400 is coated with heparin. In some embodiments, the ablation balloon 1497 is movable along a longitudinal axis of the balloons 1496, 1497 within and along an entire length of the outer balloon 1496, to better position the inner ablation balloon inside the outer balloon, using a wire mechanism in a handle at the proximal end of the catheter 1400.

In embodiments, at least one dimension of the inner ablation balloon 1497 is different than the outer balloon 1496 by at least 10%. In some embodiments, the dimension is a length of the ablation balloon 1497. In embodiments, a shape of the ablation balloon 1497 is different from that of the outer balloon 1496. In embodiments, an intersection of the shapes of the ablation balloon 1497 and the outer balloon 1496 determine the shape and/or size of an ablation zone 1417.

In some embodiments, a mapping member 1499m, which may be a distal extension, catheter, or any substrate comprising a plurality of sensors, detectors, or electrodes, is attached to the distal end of the body 1491 distal to the outer balloon 1496. The mapping member 1499m maps the area of cardiac tissue responsible for the arrhythmia. In some embodiments, the mapping member 1499m has a length of up to 75 mm. In some embodiments, the mapping member 1499m is pre-shaped in a pig-tail shape to allow wall contact. In embodiments, the diameter of the pigtail is between 5 mm and 25 mm. In some embodiments, the mapping member 1499m comprises 1 to 8 electrodes configured to record signals from a pulmonary vein or pacing in a pulmonary vein. In some embodiments, the mapping member is a separate catheter that can be inserted or withdrawn through a lumen in the catheter 1400.

Once both balloons 1496, 1497 are inflated, a length of the outer balloon 1496 is greater than a length of the inner ablation balloon 1497 and a diameter of the ablation balloon 1497 approximates a diameter of the outer balloon 1496. The catheter 1400 also includes at least one flexible heating chamber 1330 (described with reference to FIGS. 13A through 13D) proximate to a proximal end of the mapping balloon 1496. In one embodiment, as shown in FIG. 14M, two heating chambers 1330 are arranged in series in the body 1491. An RF generator 1498 is coupled to a plurality of electrodes (such as, electrodes 1336, 1338 of FIG. 13B) included within the heating chamber 1330.

During use, the air pump 1494 supplies air or $CO_2$ or another cooling/insulating fluid via the air lumen 1492 causing the outer balloon 1496 to inflate, the water pump 1495 supplies water/saline to a proximal end of the heating chambers 1330 via water/vapor lumen 1493 while the RF generator 1498 supplies electrical current to the electrodes, causing them to heat up and vaporize water/saline flowing through the heating chambers 1330. The generated vapor exits through infusion ports 1499, thereby inflating the inner ablation balloon 1497 such that the ablation balloon 1497 comes into contact with the outer balloon 1496 and the outer balloon 1496 comes into contact with the target cardiac tissue proximate the equators of both balloons 1496, 1497. This creates a hot zone or ablation zone 1417 proximate the equator of the outer balloon 1496. Cold zones 1418 are located on the outer balloon 1496 where the inflated ablation balloon 1497 is not in contact with the inflated outer balloon 1496. Heat is transferred from inside the inner ablation balloon 1497 through the outer balloon 1496 at the hot zone 1417 and into the cardiac tissue to ablate the tissue and treat the arrhythmia. The flexible heating chambers 1330 impart improved flexibility and maneuverability to the catheter 1400, allowing a physician to better position the catheter 1400 when performing cardiac ablation procedures, such as ablating an arrhythmia focus in a heart of a patient.

Figure 14N:
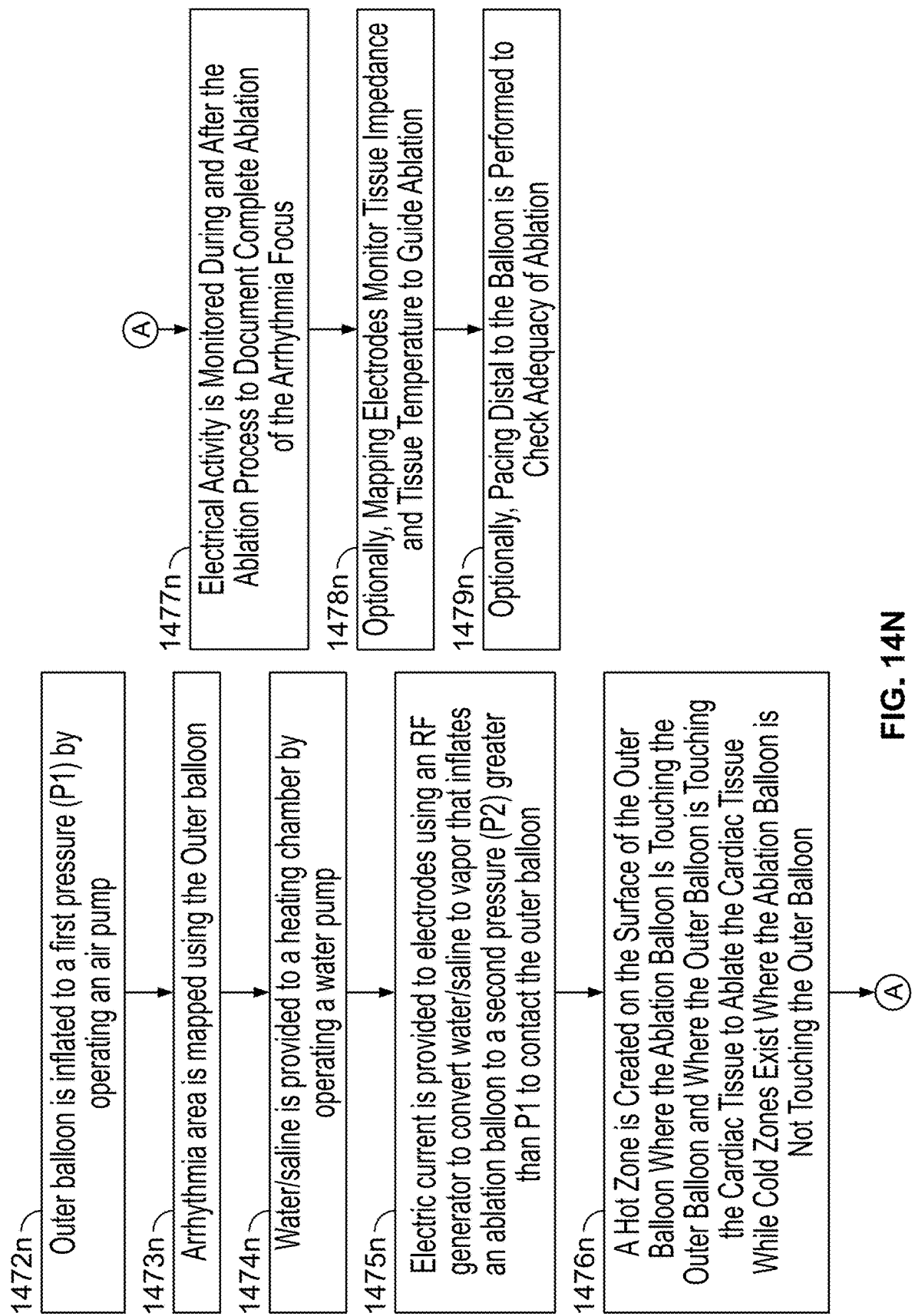
FIG. 14N is a flowchart illustrating the steps involved in one embodiment of a method of using the catheter of FIG. 14M to ablate cardiac tissue.

FIG. 14N is a flowchart illustrating the steps involved in one embodiment of a method of using the catheter 1400 of FIG. 14M to ablate cardiac tissue. At step 1472n, the outer balloon with optional mapping electrodes is inflated to a first pressure (P1) by operating an air pump. An arrhythmia area is optionally mapped using the outer balloon at step 1473n. At step 1474n, water/saline is provided to the at least one heating chamber by operating a water pump. At step 1475n, electric current is provided to electrodes of the heating chamber, using the RF generator, to convert water/saline to vapor that exits the infusion ports to inflate the ablation balloon to a second pressure (P2) greater than or equal to P1 thereby causing the inner ablation balloon to contact the outer balloon. At step 1476n, a hot zone is created on the anterior or distal surface of the outer balloon where the ablation balloon is touching the outer balloon and where the outer balloon is touching the cardiac tissue to ablate the cardiac tissue while cold zones exist where the ablation balloon is not touching the outer balloon. At step 1477n, electrical activity is optionally monitored during and after the ablation process to document complete ablation of the arrhythmia focus. Optionally, at step 1478n, mapping electrodes monitor tissue impedance and tissue temperature to guide the ablation. Optionally, at step 1479n, pacing distal to the balloon is performed to check for adequacy of ablation. The inner balloon can be optionally pre-inflated with $CO_2$ or air to a pressure less than or equal to P2 prior to insufflating it with vapor.

Figure 15:
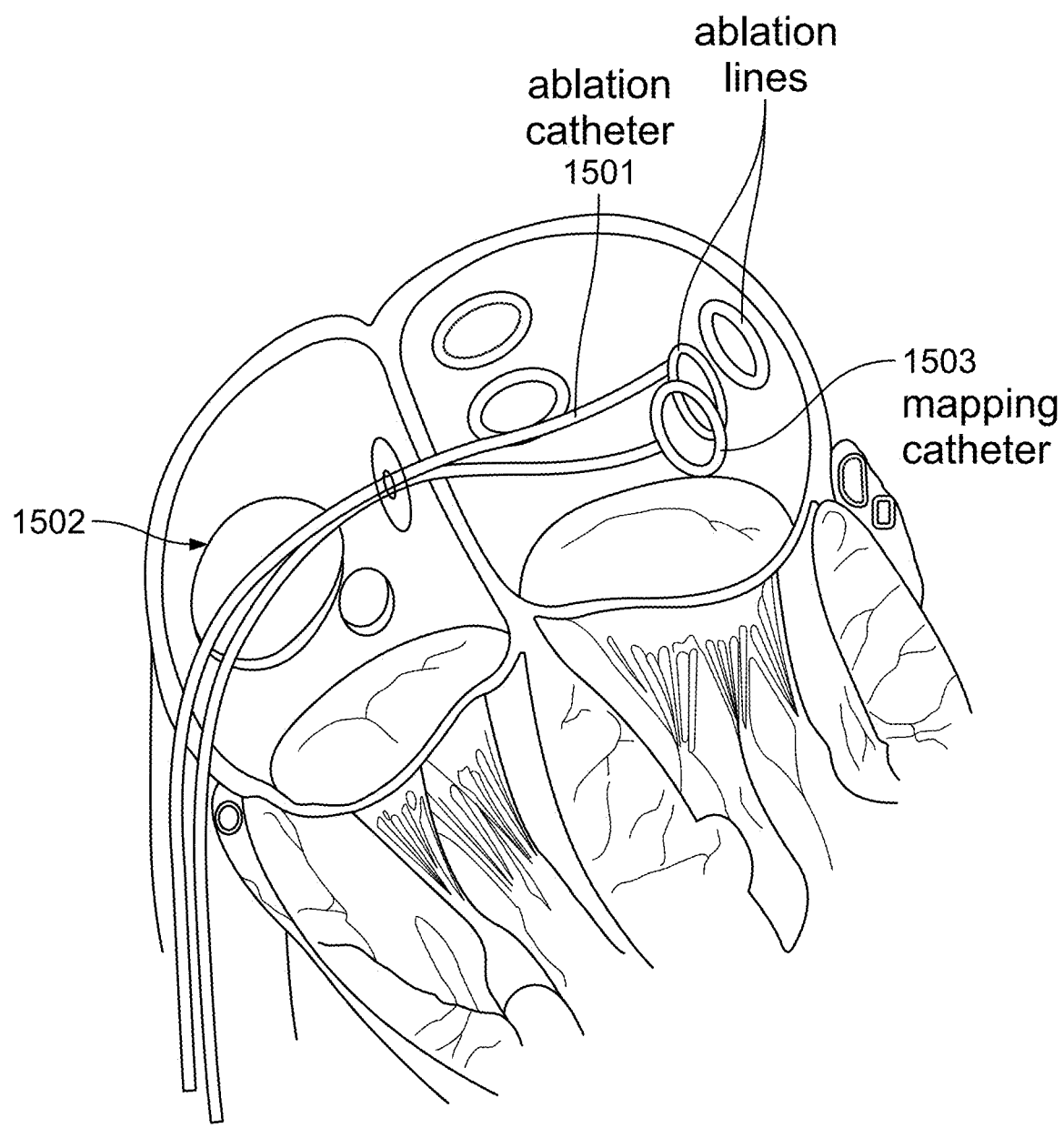
FIG. 15 illustrates a vapor ablation catheter introduced via a trans-septal approach into a left atrium of a heart in accordance with one embodiment of the present specification.

FIG. 15 illustrates a vapor ablation catheter 1501 introduced via a trans-septal approach into a left atrium of a heart 1502 in accordance with one embodiment of the present specification. In one embodiment, a flexible-tipped wire (not shown) is introduced through the lumen of the vapor ablation catheter 1501 and guided into the targeted pulmonary vein. A 20-50 mm vapor ablation balloon is located at the tip of the wire, which is then inflated in the chamber of the left atrium and guided over the wire to the antrum of the targeted pulmonary vein. A mapping catheter 1503 is also introduced at the site to guide the ablation.

Figure 16A:
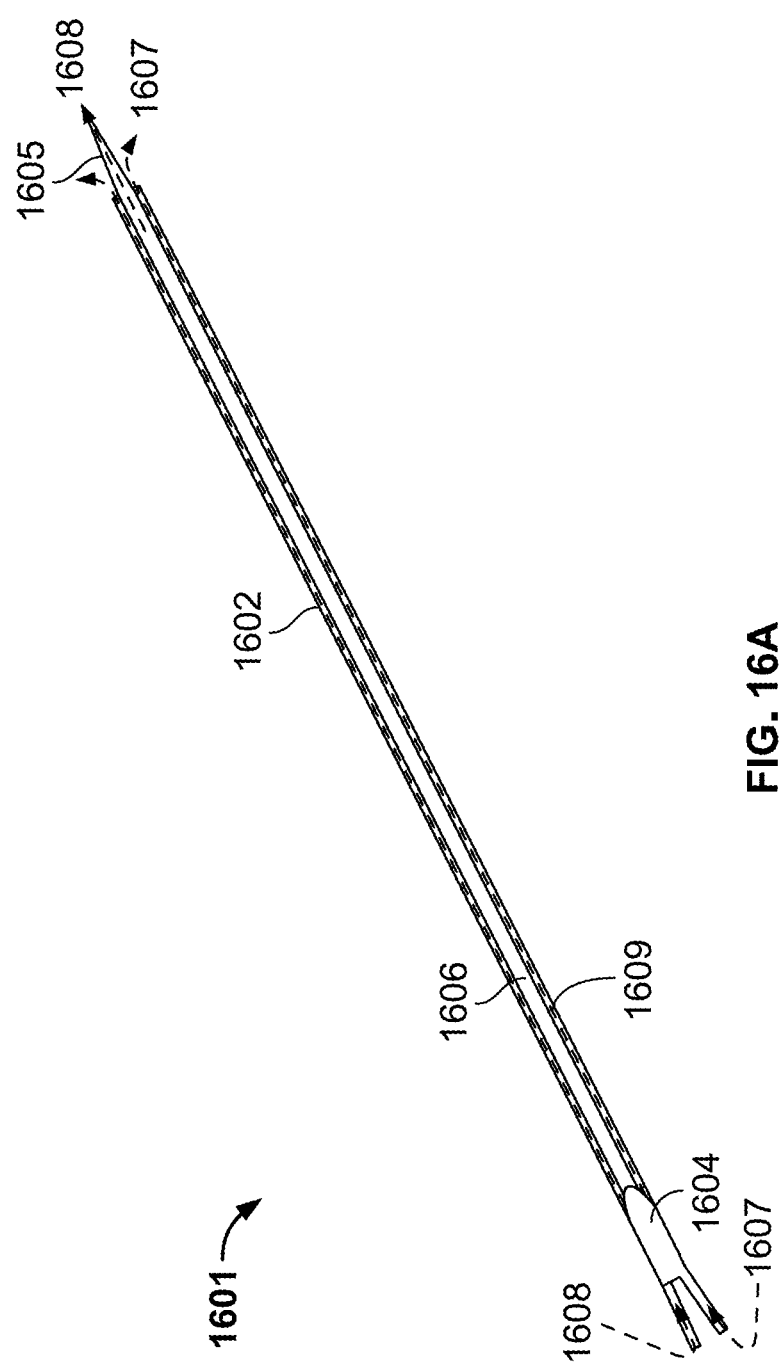
FIG. 16A illustrates a cardiac ablation catheter with a first distal attachment, in accordance with an embodiment.

FIG. 16A illustrates a cardiac ablation catheter 1601 in accordance with an embodiment of the present specification. The catheter includes a handle 1604. The catheter 1601 includes an elongate body 1602, a proximal end, and a distal end with an air, water or saline lumen 1609 and a vapor lumen 1606 supplied by ports at its proximal end. In some embodiments, air/water or preferably saline 1607 is circulated in the saline lumen 1609 to cool the body 1602 while vapor 1608 is being infused into the lumen 1606. The distal end of the body 1602 has a distal attachment, such as a retractable needle 1605 that is in fluid communication with the vapor lumen 1606. The retractable needle 1605 has at least one opening or infusion port at its distal end for allowing vapor 1608 to emanate therefrom to ablate target cardiac tissue, while the body 1602 is being cooled by the saline 1607 circulating in the saline lumen 1609. In various embodiments, the catheter 1601 includes a plurality of sensors, such as an electrical sensor, at the distal end of the catheter 1601, to monitor electrical activity during and after the ablation process and measure tissue impedance to document complete ablation of the target cardiac tissue, a pressure sensor to measure pressure in the vapor lumen 1606 and shut down vapor delivery once a predefined critical pressure is reached, and a temperature sensor to monitor tissue temperature to guide the ablation.

Figure 16B:
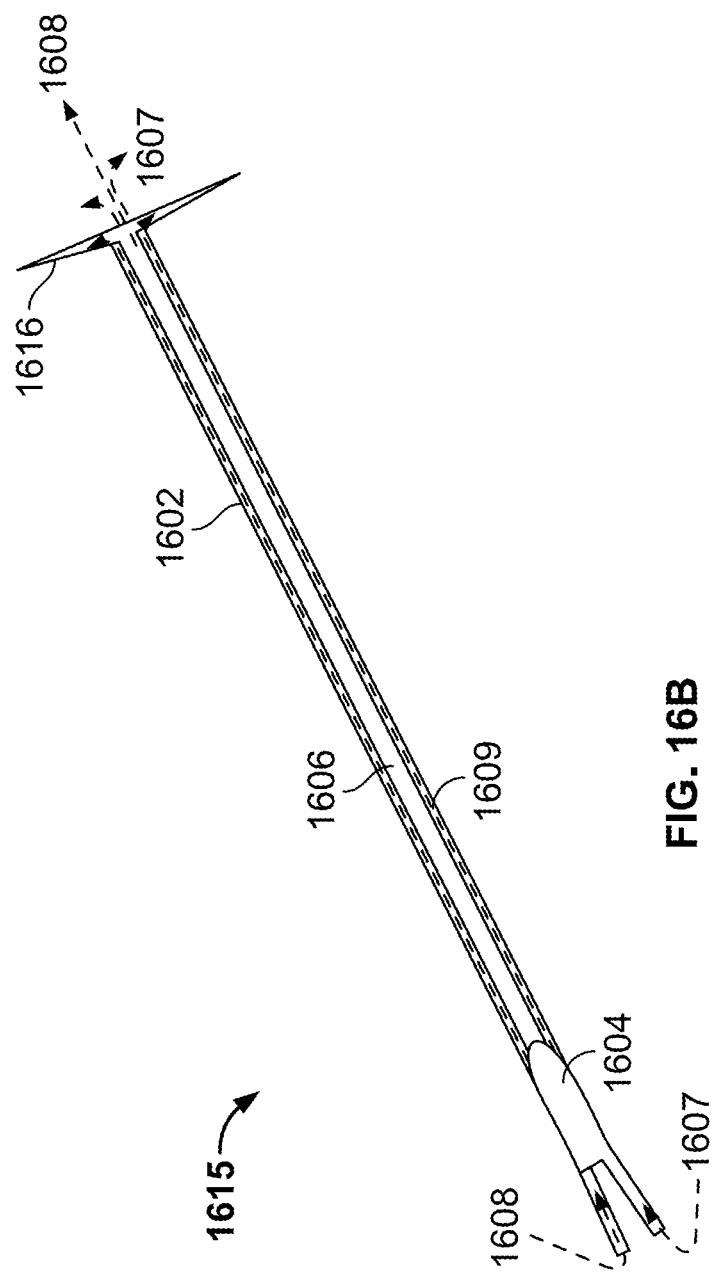
FIG. 16B illustrates a cardiac ablation catheter with a second distal attachment, in accordance with an embodiment.

It should be appreciated that the shape and size of the distal attachment is varied in various embodiments to adapt to a specific anatomy to be treated by ablation. For example, FIG. 16B illustrates another embodiment of a cardiac ablation catheter 1615 where the distal attachment is a retractable disc 1616 covered in a thermally insulated membrane and attached to the distal end of the elongate body 1602. The catheter includes a handle 1604. During use, vapor 1608 is delivered to the disc 1616 through the vapor lumen 1606 while saline 1607 is being circulated through the saline lumen 1609 to keep the elongate body 1602 and the outer surface of the disc 1616 cool. The vapor 1608 infuses out from at least one infusion port or opening at a distal surface of the retractable disc 1616 in order to ablate the target tissue. In various embodiments, the catheter 1615 includes a plurality of sensors, such as an electrical sensor, at the distal end of the catheter 1615, to monitor electrical activity during and after the ablation process and measure tissue impedance to document complete ablation of the target cardiac tissue, a pressure sensor to measure pressure in the vapor lumen 1606 and shut down vapor delivery once a predefined critical pressure is reached, and a temperature sensor to monitor tissue temperature to guide the ablation.

Figure 16C:
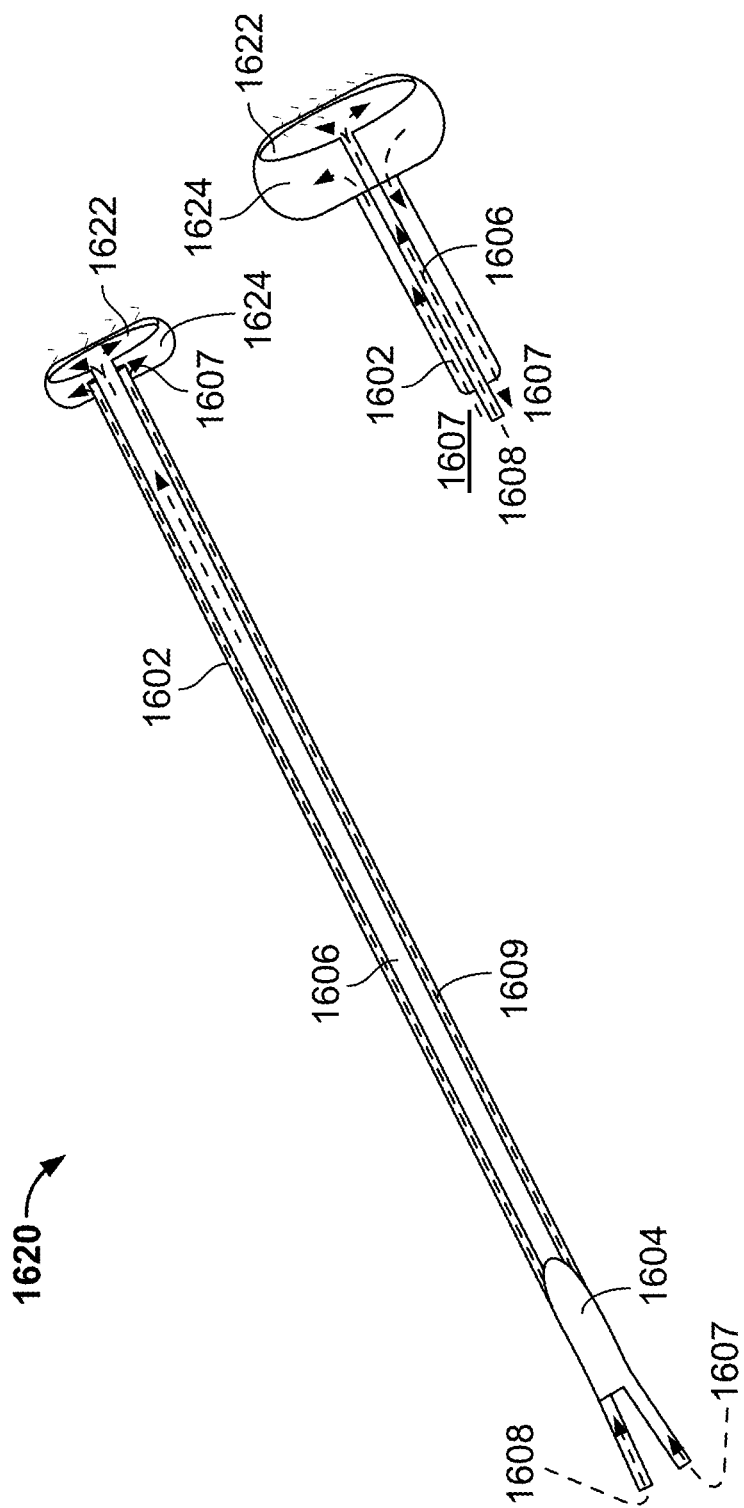
FIG. 16C illustrates a cardiac ablation catheter with a third distal attachment, in accordance with an embodiment.

In some embodiments, an entire surface of the catheter 1615 is coated with heparin. FIG. 16C illustrates yet another embodiment of a cardiac ablation catheter 1620 where the distal attachment comprises an inner balloon 1622 lying within an outer balloon 1624 at the distal end of the catheter 1620. The catheter includes a handle 1604. The outer balloon 1624 is in fluid communication with the air/$CO_2$ lumen 1609 while the inner balloon 1622 is in fluid communication with the saline/vapor lumen 1606. In some embodiments, an entire surface of the catheter 1620 is coated with heparin.

In embodiments, at least one dimension of the inner balloon 1622 is different than the outer balloon 1624 by at least 10%. In some embodiments, the dimension is a length of the inner balloon 1622. In embodiments, a shape of the inner balloon 1622 is different from that of the outer balloon 1624. In embodiments, an intersection of the shapes of the inner balloon 1622 and the outer balloon 1624 determine the shape and/or size of an ablation zone.

During use, the outer balloon 1624 is inflated with saline 1607 (or air/water alternatively) to enable the outer balloon 1624 to contact an area of ablation comprising target tissue to be ablated. Vapor 1608 is passed into the inner balloon 1622 to inflate the inner balloon 1622 to contact the outer balloon 1624 proximate the area of ablation. In various embodiments, the area of contact between the inner balloon 1622 and the external balloon 1624 is between 5% and 95% and lies at a distal end or tip of the outer balloon 1624.

In embodiments, the inner balloon 1622 is movable within the outer balloon 1624 and therefore contacts the outer balloon 1624 at different circumferential areas. In some embodiments, the inner balloon 1622 is movable along a longitudinal axis of the balloons 1622, 1624 within and along an entire length of the outer balloon 1624, to better position the inner balloon inside the outer balloon, using a wire mechanism in the handle 1604. A hot zone is created at the area of contact between the inner balloon 1622 and the outer balloon 1624, such that thermal energy from the inner balloon 1622 passes through the outer balloon 1624 to the area of ablation proximate the distal end or tip of the outer balloon 1624. The elongate body 1602 and portions of the outer balloon 1624, excluding the hot zone, remain cool owing to the circulating air or $CO_2$ or another cooling/insulating fluid 1607.

In various embodiments, the catheter 1620 includes a plurality of sensors, such as an electrical sensor, at the distal end of the catheter 1620, to measure tissue impedance for mapping the target tissue and monitor electrical activity during and after the ablation process to document complete ablation of the target tissue, a pressure sensor to measure pressure in the vapor lumen 1606 and shut down vapor delivery once a predefined critical pressure is reached, and a temperature sensor to monitor tissue temperature to guide the ablation.

In some embodiments, a mapping member, which may be a distal extension, catheter, or any substrate comprising a plurality of sensors, detectors, or electrodes, is attached to the distal end of the catheter distal to the outer balloon 1624. The mapping member maps the area of cardiac tissue responsible for the arrhythmia. In some embodiments, the mapping member has a length of up to 75 mm. In some embodiments, the mapping member is pre-shaped in a pig-tail shape to allow wall contact. In embodiments, the diameter of the pigtail is between 5 mm and 25 mm. In some embodiments, the mapping member comprises 1 to 8 electrodes configured to record signals from a pulmonary vein or pacing in a pulmonary vein. In some embodiments, the outer balloon 1624 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 1624 includes up to 24 mapping electrodes.

It should be noted that in various embodiments, saline, air, $CO_2$ or another cooling/insulating fluid 1607 enters the saline lumen 1609 at the proximal end of the catheter and exits from the proximal end of the catheter after circulating through the outer balloon 1624. In some embodiments, the cooling/insulating fluid 1607 enters and exits the saline lumen 1609 through the same opening. In other embodiments, the cooling/insulating fluid 1607 enters the saline lumen 1609 via first opening and exits the saline lumen through a second, separate opening different from the first opening.

Figure 17:
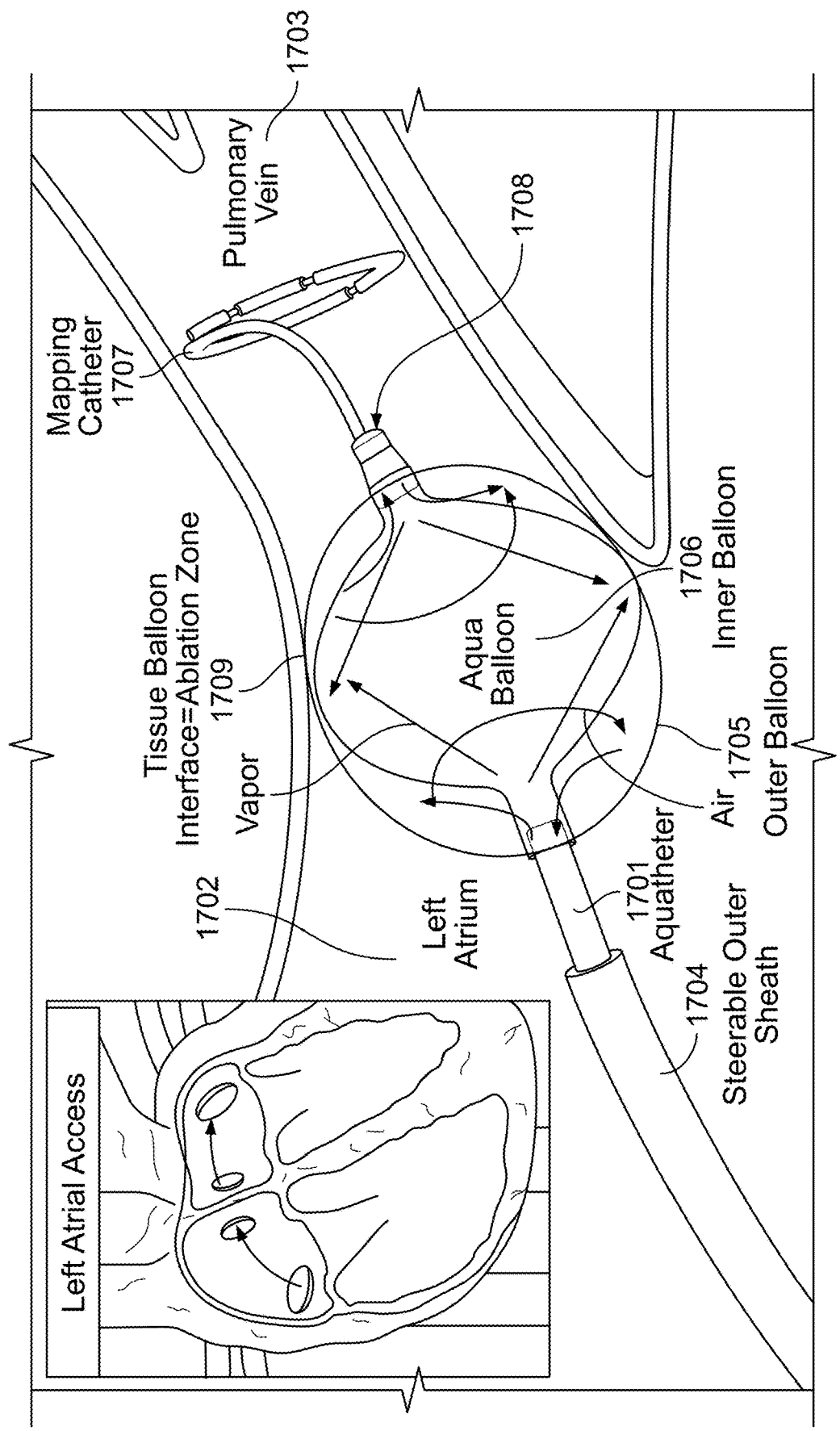
FIG. 17 illustrates one embodiment of a cardiac ablation catheter passing through a left atrium of a heart and into a pulmonary vein in accordance with one embodiment of the present specification.

FIG. 17 illustrates one embodiment of a cardiac ablation catheter 1701 passing through a left atrium 1702 of a heart and into a pulmonary vein 1703 in accordance with one embodiment of the present specification. In one embodiment, the catheter is encased in a steerable outer sheath 1704. At a distal end of the catheter is an outer balloon 1705 through which air or $CO_2$ circulates. Inside the outer balloon is an inner balloon 1706 filled with water vapor. It may be appreciated that the ablation zone 1709 here comprises the tissue-balloon interface. A mapping catheter 1707 is coupled to the balloon by means of a tip 1708.

In some embodiments, an entire surface of the catheter 1701 is coated with heparin.

In some embodiments, the inner balloon 1706 is movable along a longitudinal axis of the balloons 1705, 1706 within and along an entire length of the outer balloon 1705, to better position the inner balloon inside the outer balloon, using a wire mechanism in a handle at the proximal end of the catheter 1701. In some embodiments, pressure is applied to the outer balloon using a steerable outer sheath to press the outer balloon against the cardiac tissue to be ablated, changing a size, a shape or a dimension of the intersection between the two balloons, in turn changing a size, a shape or a dimension of the ablation zone.

In embodiments, at least one dimension of the inner balloon 1706 is different than the outer balloon 1705 by at least 10%. In some embodiments, the dimension is a length of the inner balloon 1706. In embodiments, a shape of the inner balloon 1706 is different from that of the outer balloon 1705. In embodiments, an intersection of the shapes of the inner balloon 1706 and the outer balloon 1705 determine the shape and/or size of an ablation zone.

In some embodiments, a mapping member, which may be a distal extension, catheter, or any substrate comprising a plurality of sensors, detectors, or electrodes, is attached to the distal end of the catheter 1701 distal to the outer balloon 1705. The mapping member maps the area of cardiac tissue responsible for the arrhythmia. In some embodiments, the mapping member has a length of up to 50 mm. In some embodiments, the mapping member is pre-shaped in a pig-tail shape to allow wall contact. In embodiments, the diameter of the pigtail is between 5 mm and 25 mm. In some embodiments, the mapping member comprises 1 to 8 electrodes configured to record signals from a pulmonary vein or pacing in a pulmonary vein.

In some embodiments, the outer balloon 1705 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 1705 includes up to 24 mapping electrodes.

Figure 18A:
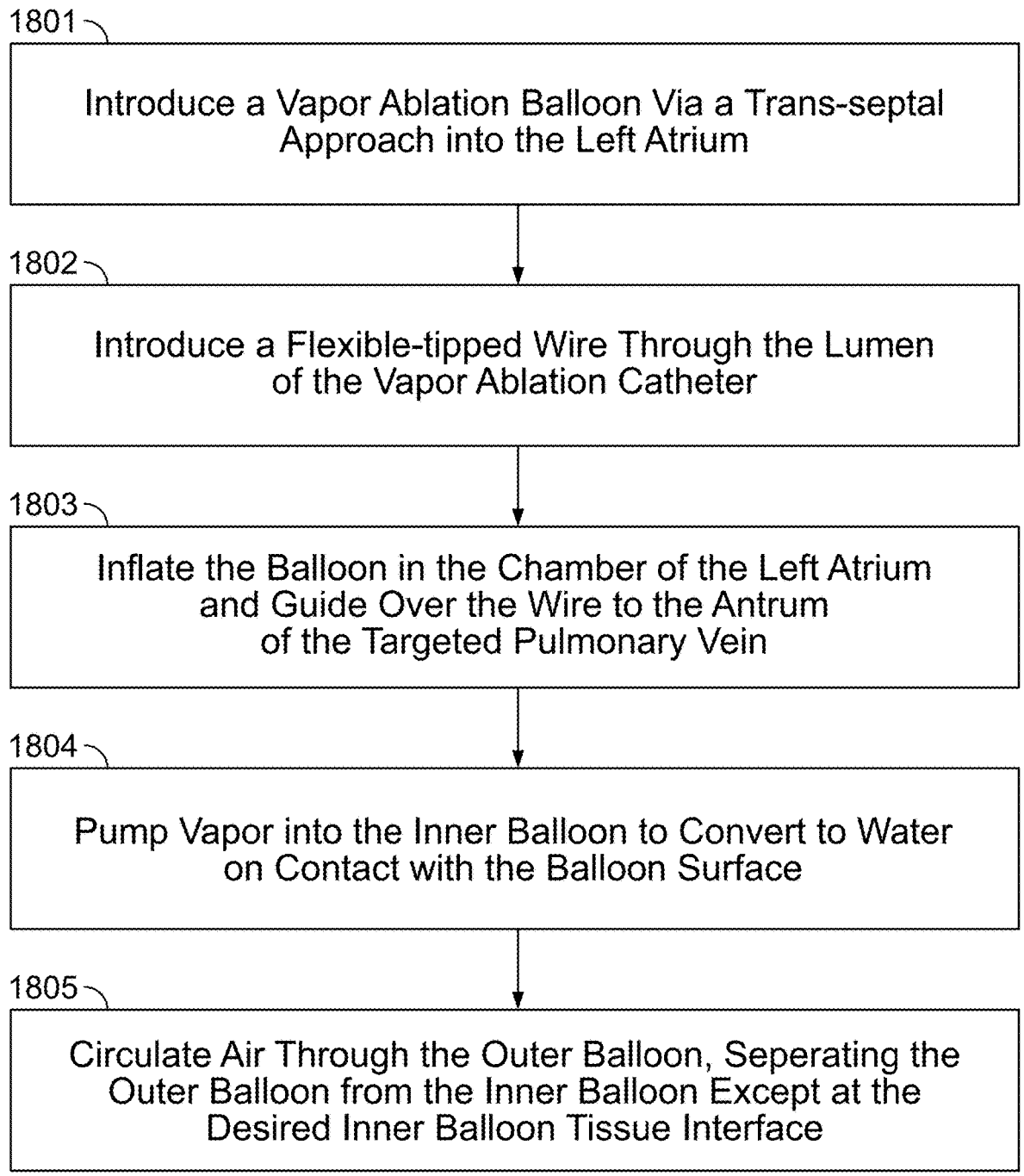
FIG. 18A is a flowchart listing the steps involved in one embodiment of a method of cardiac ablation.

FIG. 18A is a flowchart listing the steps involved in one embodiment of a method of cardiac ablation. The ablation device used is similar to that described with reference to FIG. 17. At step 1801, a 10-50 mm vapor ablation balloon is introduced via a trans-septal approach into the left atrium. Next, in step 1802, a flexible-tipped wire is introduced through the lumen of the vapor ablation catheter and guided into the targeted pulmonary vein. The outer balloon is then inflated in the chamber of the left atrium and guided over the wire to the antrum of the targeted pulmonary vein in 1803. Next, in 1804, vapor in a range of 99 to 115° C. is pumped into the inner balloon and converted to water on contact with the balloon surface due to the temperature change at the balloon/tissue interface. This conversion of vapor to water is an exothermic reaction that delivers heat to the tissue, resulting in the balloon/tissue interface becoming extremely hot, for example, between 60 and 115° C. The extremely hot temperature at the balloon/tissue interface creates an irreversible injury to the pulmonary vein/atrial tissue, thereby ablating the tissue. Air or $CO_2$ or a cooling/insulating fluid is circulated through the outer balloon, separating the outer balloon from the inner balloon except at the desired inner/outer balloon tissue interface, insulating the rest of the surface of the inner balloon from contacting the surrounding tissue or blood in 1805.

Figure 18B:
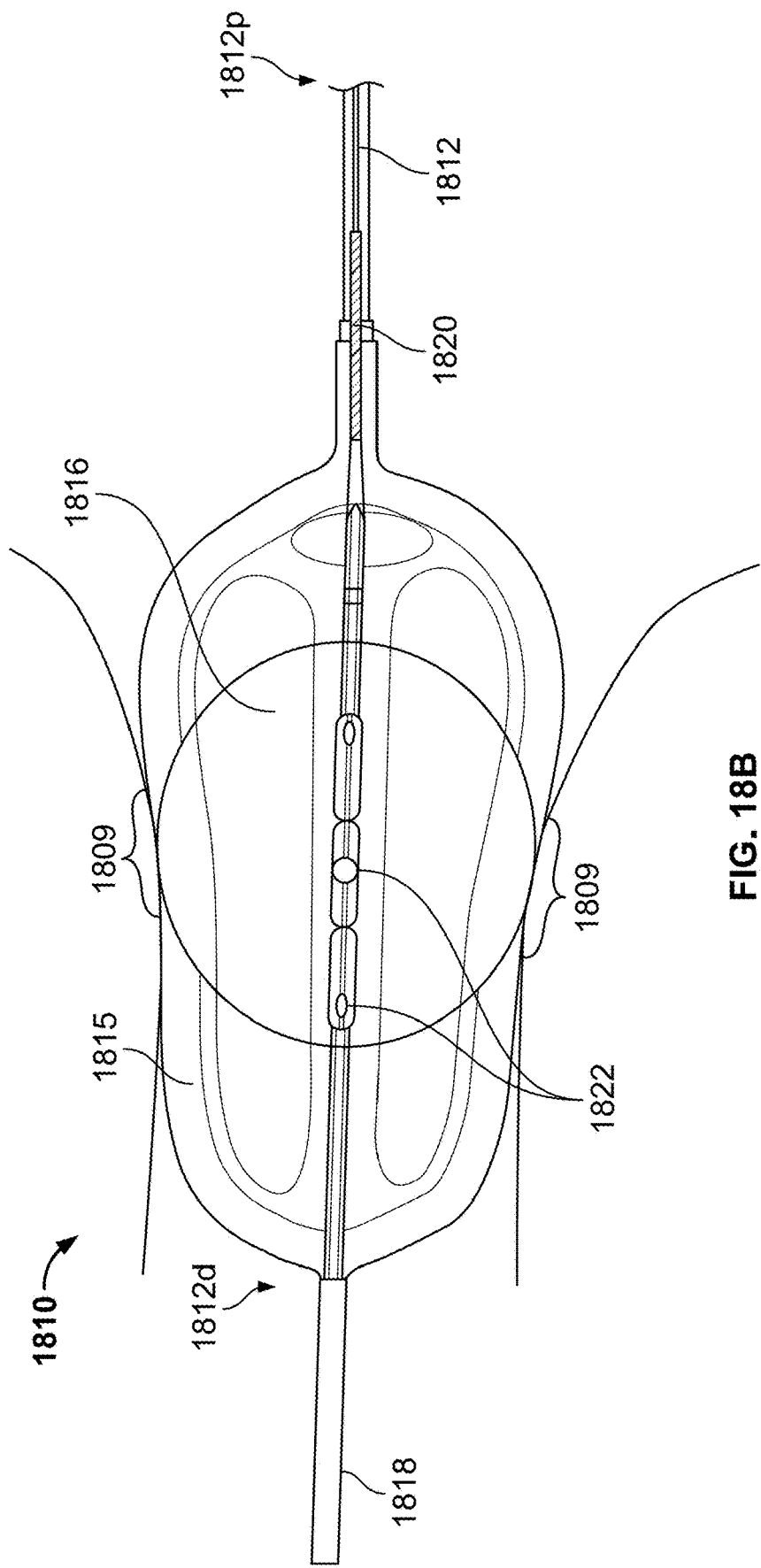
FIG. 18B illustrates a perspective view of a dual balloon cardiac ablation catheter, in accordance with an embodiment of the present specification.
Figure 18C:
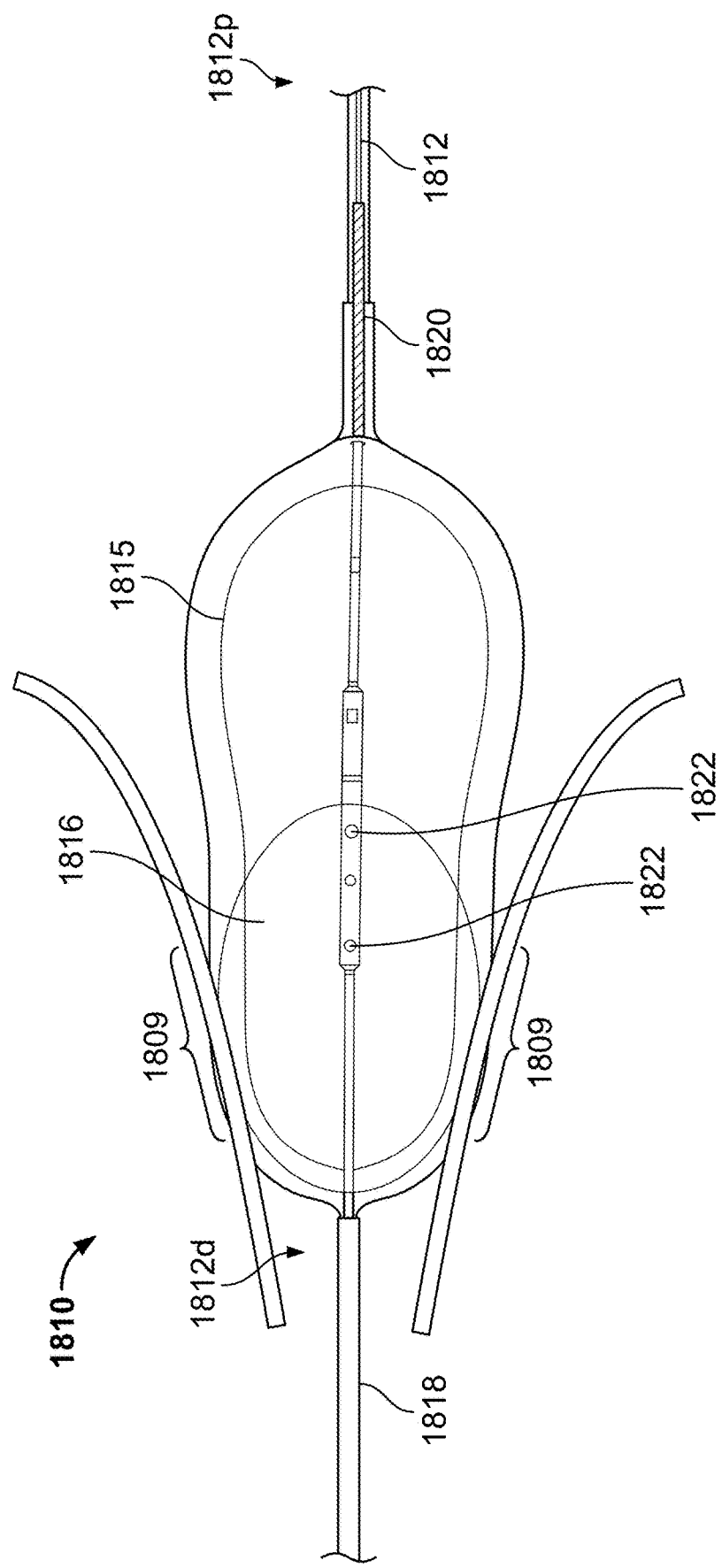
FIG. 18C illustrates another perspective view of the catheter of FIG. 18B, in accordance with an embodiment of the present specification.

FIGS. 18B and 18C illustrate a dual balloon cardiac ablation catheter 1810 in accordance with an embodiment of the present specification. The cardiac ablation catheter 1810 can be used to ablate cardiac tissue to treat an arrhythmia, such as atrial fibrillation. The catheter 1810 includes an elongate body 1812, a proximal end 1812*p*, and a distal end 1812*d* with at least one air lumen and a vapor lumen supplied by ports at its proximal end. The at least one air lumen is in fluid communication with an inflatable outer balloon 1815 attached to the distal end of the catheter 1810. The at least one air lumen extends from the outer balloon 1815 to an air pump which is in data communication with, and controlled by, a controller. The air pump pulls air (cooling fluid) from the external environment through an optional filter to fill the outer balloon 1815. In an embodiment, the air pump is reversible, thereby allowing air to be pumped into the balloon 1815 or out of the balloon 1815, as required and per instructions sent by the controller. In another embodiment, the body 1812 comprises a first lumen in fluid communication with the outer balloon 1815 and configured to carry air to the outer balloon 1815 and a second lumen also in fluid communication with the outer balloon 1815 and configured to carry air away from the outer balloon 1815. In one embodiment $CO_2$ or another cooling/insulating fluid can be used instead of air, The vapor lumen is in fluid communication with an inflatable inner balloon 1816 attached to the distal end of the catheter 1810 and positioned within the outer balloon 1815. The vapor lumen extends from the inner balloon 1816 to a water/vapor pump which is also in data communication with, and controlled by, the controller. Water is pumped from a sterile water reservoir via the water/vapor pump through the water/vapor lumen. In some embodiments, the inner balloon 1816 is movable along a longitudinal axis of the balloons 1815, 1816 within and along an entire length of the outer balloon 1815, to better position the inner balloon inside the outer balloon, using a wire mechanism in a handle at the proximal end of the catheter 1810. For example, FIG. 18C illustrates the inner balloon 1816 moved to lie proximate a distal end of the outer balloon 1815.

In some embodiments, at least one flexible heating chamber 1820 (such as those described with reference to FIGS. 13A through 13D) is positioned in-line within the vapor lumen of the elongate body 1812 proximate and proximal to the balloons 1815, 1816. It should be appreciated that, in various embodiments, the catheter 1810 does not include a heating chamber within the vapor lumen and that any heating chamber of the present specification may be used with the catheter 1810 to generate vapor for ablation. During operation, the at least one flexible heating chamber 1820, or any other heating chamber of the present specification, converts water flowing from the proximal end into vapor that exits through a plurality of ports 1822, positioned on a portion of the body 1812 lying within the inner balloon 1816, thereby inflating the inner balloon 1816.

In embodiments, at least one dimension of the inner balloon 1816 is different than the outer balloon 1815 by at least 10%. In some embodiments, the dimension is a length of the inner balloon 1816. In some embodiments, once both balloons 1815, 1816 are inflated, a length of the outer balloon 1815 is greater than a length of the inner balloon 1816 and a diameter of the inner balloon 1816 approximates a diameter of the outer balloon 1815. In various embodiments, the outer and inner balloons 1815, 1816 have any one of a spherical, conical, elliptical, square or stepped shape when inflated. In embodiments, a shape of the inner balloon 1816 is different from that of the outer balloon 1815. In embodiments, an intersection of the shapes of the inner balloon 1816 and the outer balloon 1815 determine the shape and/or size of an ablation zone 1809, defined as an area of contact of the two balloons 1815, 1816.

In some embodiments, a mapping member 1818, which may be a distal extension, catheter, or any substrate comprising a plurality of sensors, detectors, or electrodes, is attached to the distal end of the body 1812 distal to the outer balloon 1815. The mapping member 1818 maps the area of cardiac tissue responsible for the arrhythmia. In some embodiments, the mapping member 1818 has a length of up to 50 mm. In some embodiments, the mapping member 1818 is pre-shaped in a pig-tail shape to allow wall contact. In embodiments, the diameter of the pigtail is between 5 mm and 25 mm. In some embodiments, the mapping member 1818 comprises 1 to 8 electrodes configured to record signals from a pulmonary vein or pacing in a pulmonary vein.

In some embodiments, the outer balloon 1815 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 1815 includes up to 24 mapping electrodes. In embodiments, the mapping electrodes measure cardiac electrical activity to assess at least one therapeutic endpoint.

In some embodiments, an entire surface of the catheter 1810, including the balloons 1815, 1816, mapping electrodes and the mapping member 1818, is coated with heparin.

Figure 18D:
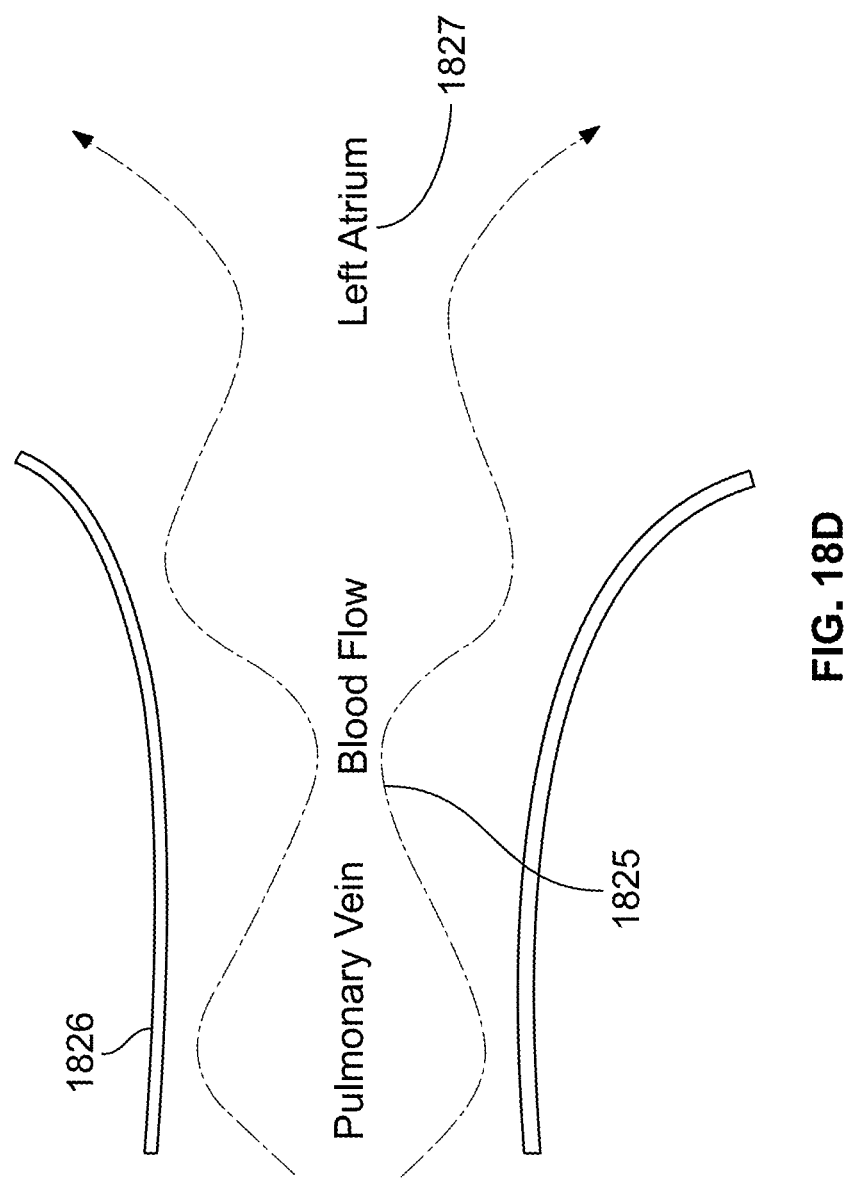
FIG. 18D illustrates blood flow to a left atrium via a pulmonary vein of a heart, in accordance with an embodiment of the present specification.
Figure 18E:
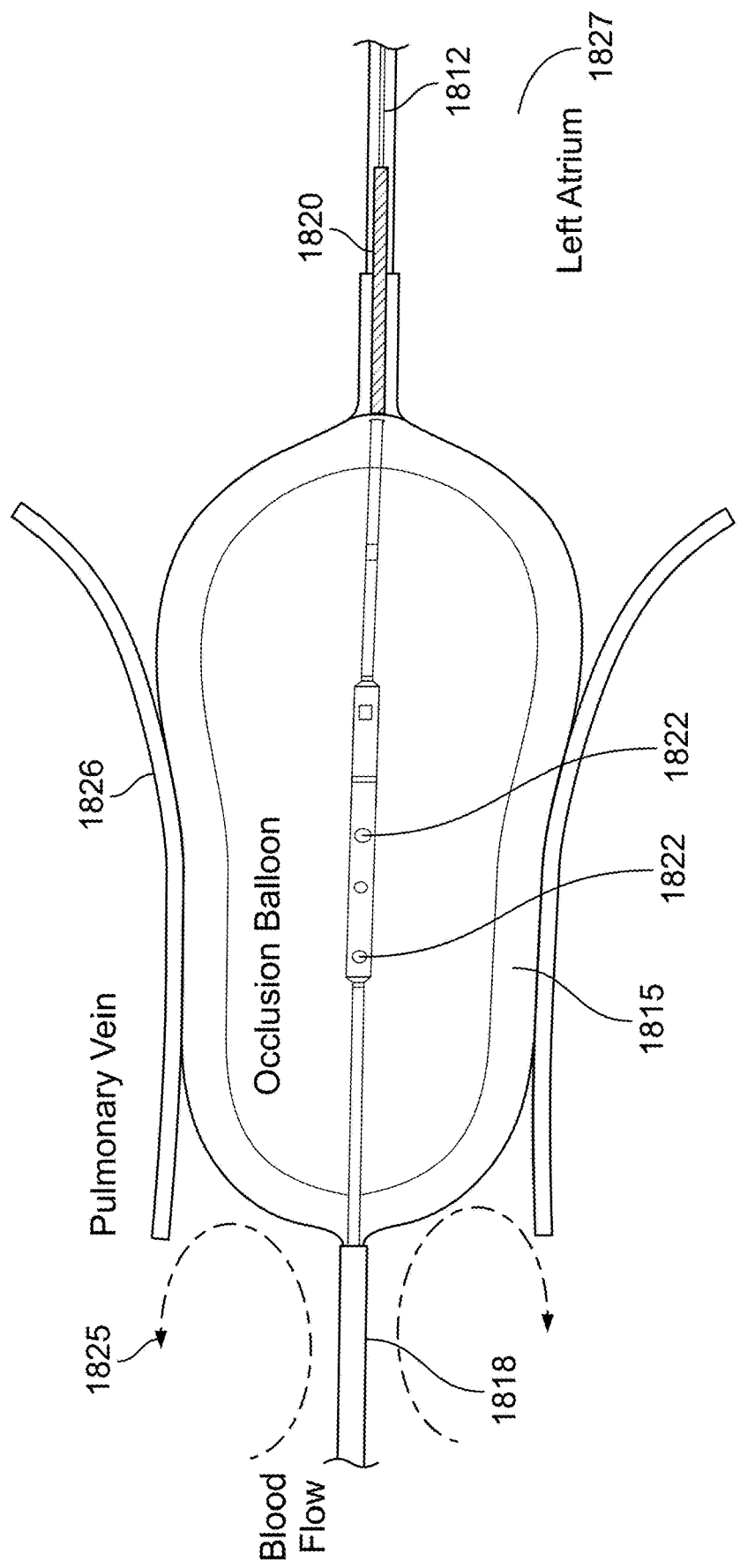
FIG. 18E illustrates the catheter of FIG. 18B positioned in a pulmonary vein with an outer balloon inflated to occlude blood flow, in accordance with an embodiment of the present specification.

FIG. 18D illustrates blood flow 1825 to a left atrium 1827 through a pulmonary vein 1826. During operation, the cardiac ablation catheter 1810 is introduced, through a trans-septal puncture, into a left atrium 1827 of a heart and the outer balloon is advanced to a pulmonary vein 1826. Next, as shown in FIG. 18E, the outer balloon 1815 is inflated with air to occlude the blood flow 1825 from the pulmonary vein 1826 to the left atrium 1827. In some embodiments, occlusion of the blood flow 1825 is confirmed with a dye study.

Figure 18F:
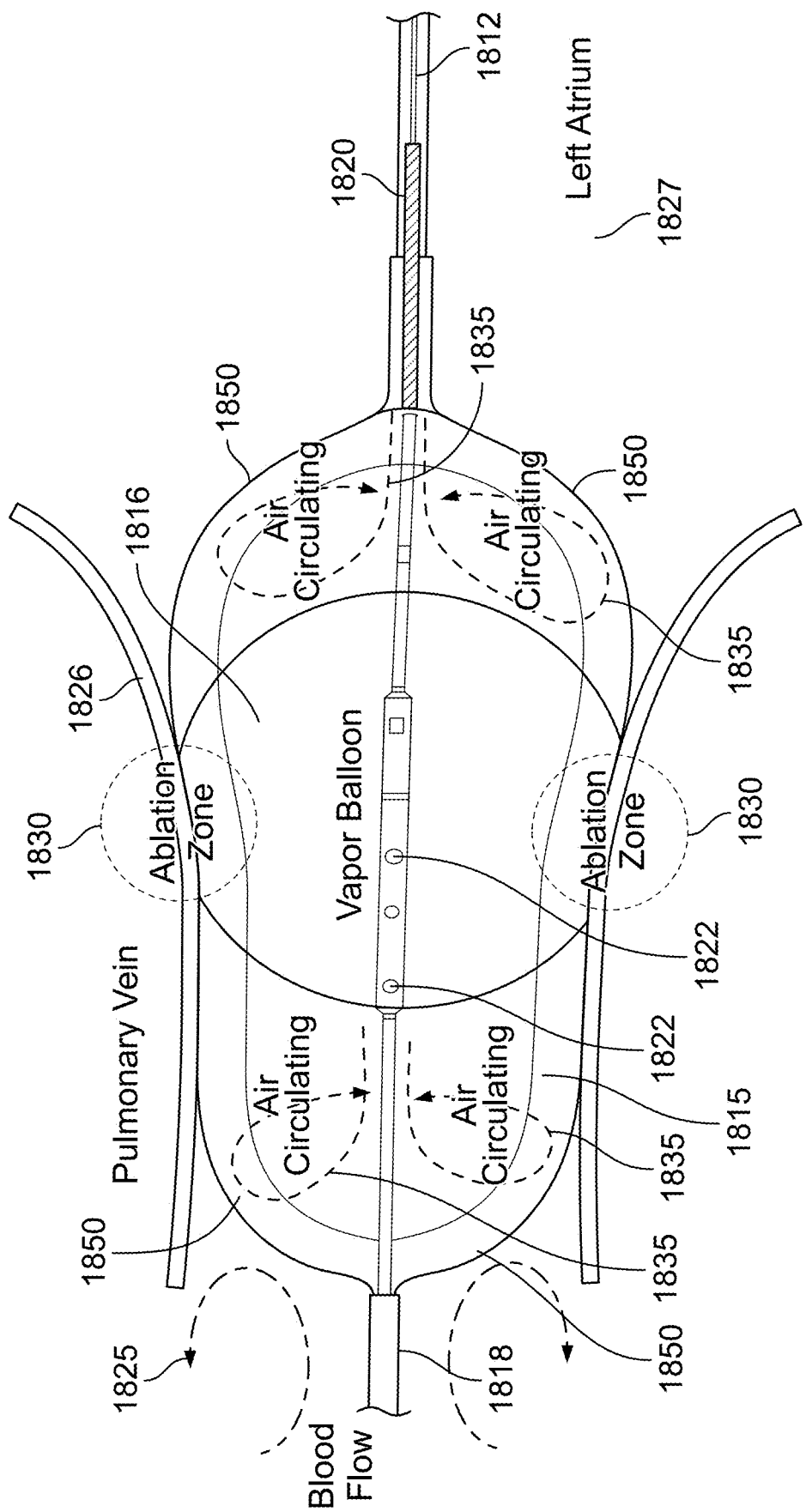
FIG. 18F illustrates a perspective view of the catheter of FIG. 18B performing ablation of cardiac tissue, in accordance with an embodiment of the present specification.
Figure 18G:
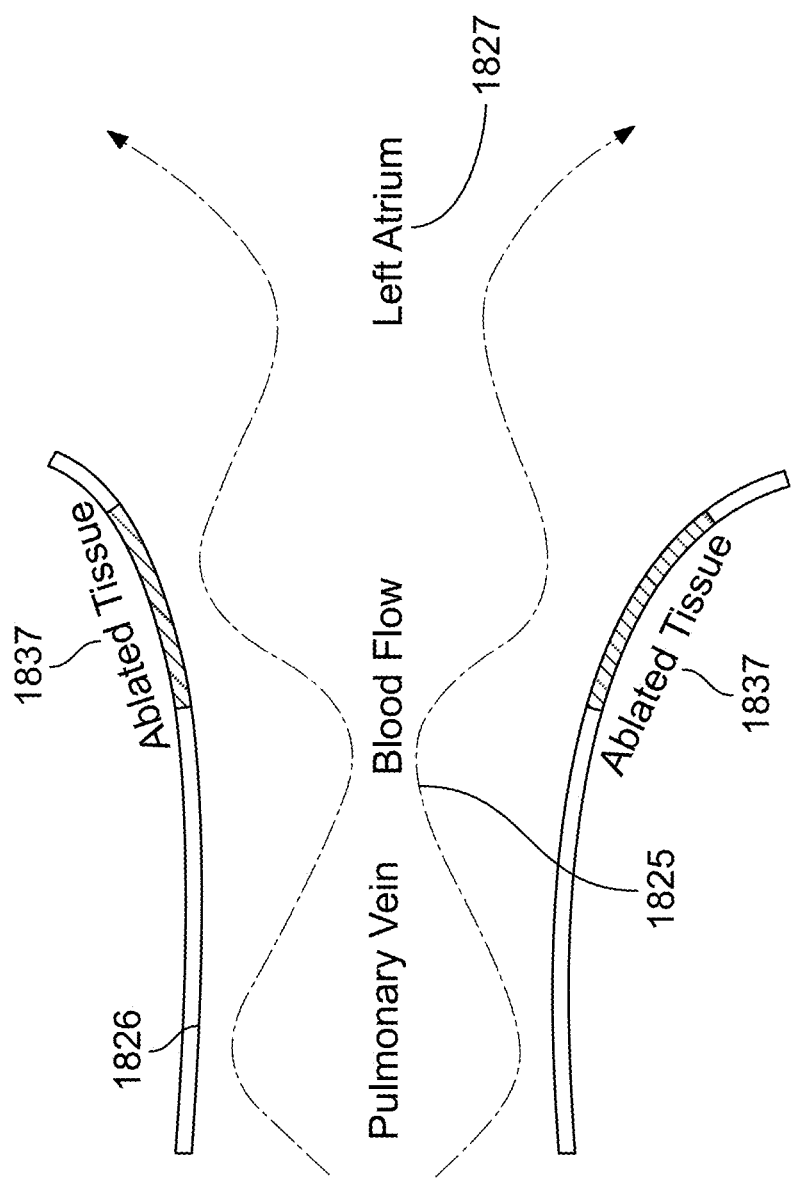
FIG. 18G illustrates the pulmonary vein of FIG. 18D with ablated cardiac tissue, in accordance with an embodiment of the present specification.
Figure 18H:
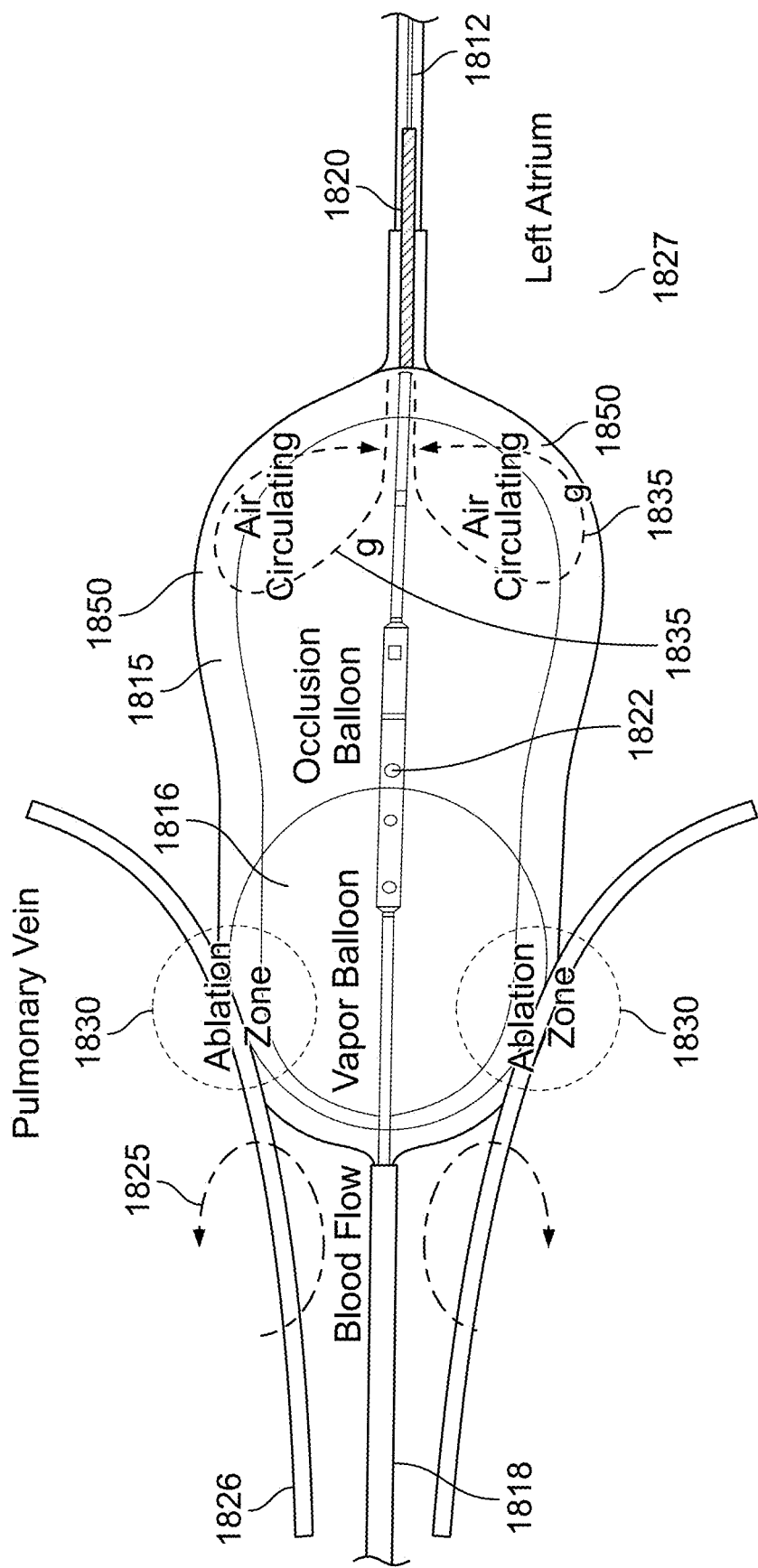
FIG. 18H illustrates another perspective view of the catheter of FIG. 18B performing ablation of cardiac tissue, in accordance with an embodiment of the present specification.

Thereafter, as shown in FIGS. 18F and 18H, the inner balloon 1816 is inflated with vapor such that the inner balloon 1816 comes into contact with desired portions or areas of the outer balloon 1815 and the outer balloon 1815 comes into contact with a hot zone/area or ablation zone/area 1830 comprising target cardiac tissue. The occluded blood flow 1825 is also shown in FIGS. 18F and 18H. In some embodiments, as shown in FIG. 18F, the hot zone 1830 is formed proximate the equators of both balloons 1815, 1816. In some embodiments, as shown in FIG. 18H, the hot zone 1830 is formed proximate a distal end of the outer balloon 1815. Cold zones or areas 1850 are located on the outer balloon 1815 where the inflated inner balloon 1816 is not in contact with the inflated outer balloon 1815. Consequently, thermal energy is transferred from inside the inner balloon 1816 through the outer balloon 1815 at the ablation zone 1830 and into the cardiac tissue to ablate the tissue and treat the arrhythmia.

The non-contact areas or cold zones 1850, between the inner and outer balloon, are filled with air or $CO_2$ 1835 which acts as an insulator. In some embodiments, the distal and proximal cold zones 1850 are linked through a channel to equilibrate the pressure. In one embodiment, the channel is a lumen in the catheter or integrated into an outside surface of the inner balloon, thereby fluidly connecting the distal cold zone 1850 and proximal cold zone 1850. Optionally, the air or $CO_2$ 1835 in the outer balloon 1815 is circulated out the catheter 1810 to actively cool the outer balloon 1815 or move the heated air in the outer balloon 1815 out through the catheter 1810, preventing inadvertent injury to the cardiac tissue in proximity to the non-contact surface of the outer balloon 1815. The thermal energy is delivered for a desired duration following which the outer balloon 1815 is deflated and the inner balloon 1816 self deflates due to condensation of vapor. The catheter 1810 is removed and, as shown in FIG. 18G, a circumferential ablation 1837 is created in the pulmonary vein 1826 (or the left atrium 1827, if needed, in some embodiments) to treat an atrial arrhythmia. Optionally, the pulmonary vein 1826

(or the left atrium 1827, if needed, in some embodiments) is paced with a pacing catheter to confirm completeness of the circumferential ablation.

In some embodiments, the outer balloon 1815 includes a thermocouple in a predetermined area to detect contact of the inner balloon 1816 with the outer balloon 1815. In some embodiments, the outer balloon 1815 includes a thermocouple in a predetermined area to monitor delivery of thermal energy to the target cardiac tissue. In some embodiments, the outer balloon 1815 includes a thermocouple outside a predetermined area of the outer balloon 1815 to measure the temperature in the outer balloon 1815 and keep the temperature away from the predetermined area (hot zone) at less than 60 degrees Celsius. In some embodiments, the inner balloon 1816 includes a pressure sensor to measure pressure inside the inner balloon 1816. In some embodiments, the inner balloon comprises a temperature sensor to monitor proper steam production. In various embodiments, the inner and outer balloons are connected to a pressure valve to maintain a constant pressure within the inner and the outer balloon.

Figure 18I:
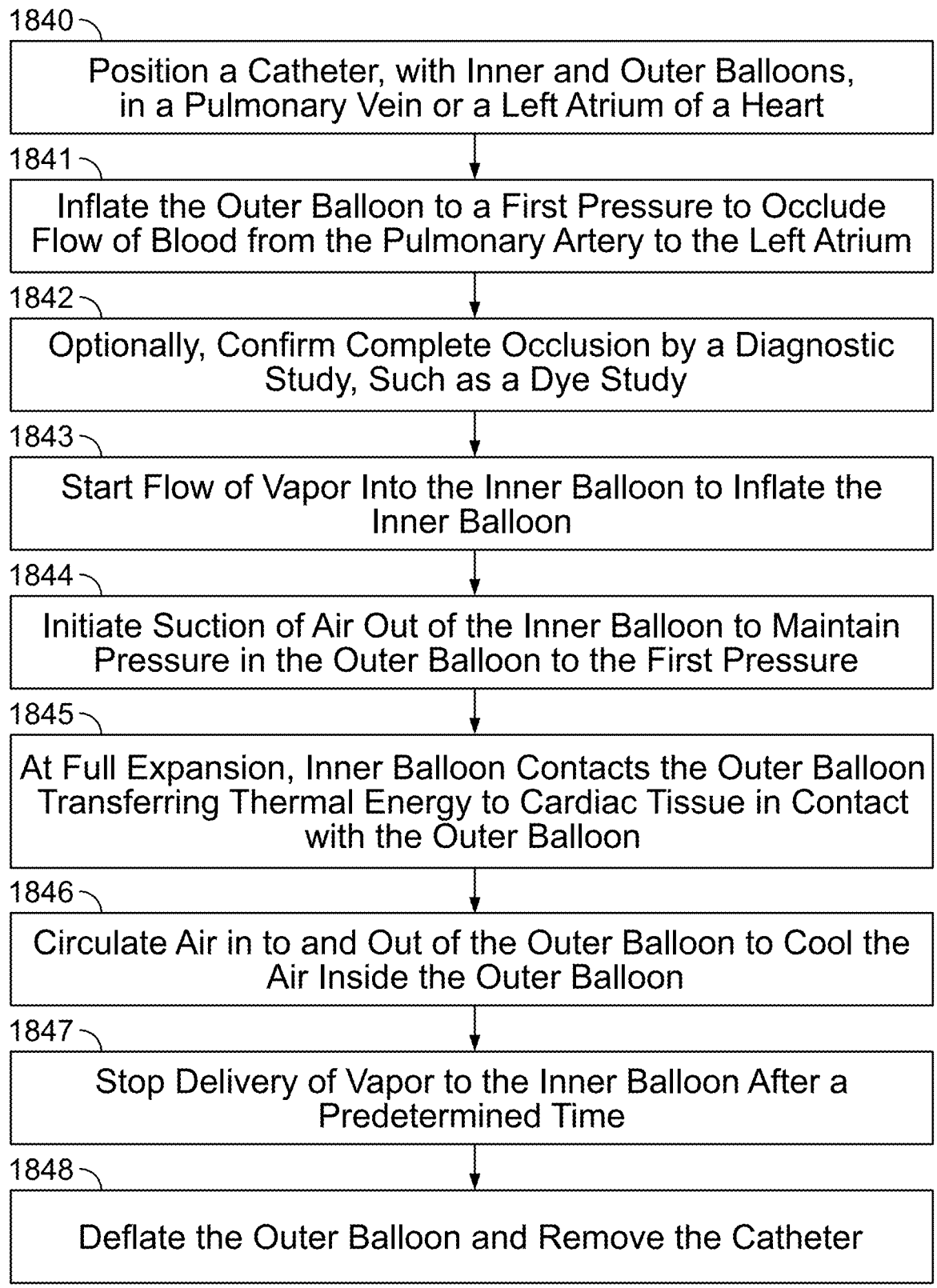
FIG. 18I is a flowchart illustrating a plurality of steps of a method of ablating cardiac tissue, to treat an arrhythmia, using the catheter of FIG. 18B, in accordance with an embodiment of the present specification.

FIG. 18I is a flowchart illustrating a plurality of steps of a method of ablating cardiac tissue, to treat an arrhythmia, using a cardiac ablation catheter, in accordance with embodiments of the present specification. At step 1840, the catheter and the balloons are positioned in a pulmonary vein or the left atrium of a patient's heart. At step 1841, the outer balloon is inflated to a first pressure (P1) to occlude flow of blood from the pulmonary vein to the left atrium, wherein the pressure is greater than a mean pulmonary vein pressure and less than 5 atm. Optionally, at step 1842, completeness of the occlusion of blood flow is confirmed using diagnostic study such as, but not limited to, dye study. At step 1843, flow of vapor is started into the inner balloon which in turn inflates the inner balloon and raises the temperature inside the inner balloon to greater than 100 degrees Celsius. Optionally, a pressure sensor measures the pressure inside the inner balloon. Optionally, the inner balloon is connected to a pressure valve with a predetermined pressure rating to maintain a constant maximum pressure within the inner balloon. Optionally, in some embodiments, the inner balloon can be moved inside the outer balloon along a length of the catheter to better position the inner balloon inside the outer balloon. At step 1844, inflation of the inner balloon and/or heating of the air in the outer balloon will result in a rise in the pressure in the outer balloon and therefore suction of air is initiated out of the inner balloon to maintain the pressure P1 of the outer balloon. In some embodiments, the outer balloon is connected to a pressure valve with a predetermined pressure rating to maintain a constant maximum pressure within the outer balloon.

At step 1845, the inner balloon, at full expansion, contacts with a predetermined area (also referred to as a hot zone or an ablation zone) of the outer balloon, transmitting thermal energy from inside of the inner balloon through the outer balloon into the surrounding cardiac tissue which is in contact with the predetermined area of the outer balloon, to cause thermal injury to the cardiac tissue in a circumferential pattern. Optionally, at least one electrode on an outer surface of the outer balloon contacts a cardiac tissue to measure cardiac electrical activity to assess one of a plurality of therapeutic endpoints. Optionally, a thermocouple, positioned in a predetermined area of the outer balloon, is used to detect contact of the inner balloon with the outer balloon. Optionally, a thermocouple, positioned in a predetermined area of the outer balloon, is used to monitor delivery of thermal energy to the cardiac tissue.

Optionally, at step 1846, air or $CO_2$ is circulated into and out of the outer balloon to cool the air inside the outer balloon to maintain a temperature of a portion of the outer balloon below 60 degrees Celsius. Optionally, a thermocouple, positioned at a predetermined area of the outer balloon, is used to measure the temperature in the outer balloon and keep the temperature away from the predetermined area below 60 degrees Celsius.

At step 1847, delivery of vapor to the inner balloon is stopped after a predetermined time, allowing the internal balloon to deflate, thereby removing the contact area between the inner balloon and the outer balloon and stopping the delivery of thermal energy from the inside of the inner balloon through the outer balloon into the surrounding cardiac tissue. Optionally, additional suction is applied to the inner balloon to further deflate the balloon. Deflation of the inner balloon will result in a decrease in pressure in the outer balloon which may in turn break the seal between the outer balloon and the pulmonary vein, allowing for the blood to start flowing across the ablated cardiac tissue, further cooling the cardiac tissue. Automated pressure control of the fluid in the outer balloon in connection with a fluid in a pump at the controller level may counteract this deflation.

At step 1848, the outer balloon is deflated by suctioning out air and the catheter is removed after the ablation is complete or the therapeutic objective is met. In some embodiments, the inner balloon self deflates, following deflation of the outer balloon, due to condensation of vapor. Optionally, the pulmonary vein is electrically paced, prior to removing the catheter at step 1848, to check whether a therapeutic objective has been met.

FIG. 19A illustrates a side cross section view of one embodiment of a cardiac ablation catheter 1902, where the distal attachment comprises an inner balloon 1904 lying within an outer balloon 1903 at the distal end of the catheter 1902. Cooling fluid is circulated through the outer balloon 1903, while the inner balloon 1904 is inflated with steam or water vapor. In one embodiment, the outer balloon 1903 is made up of a harder material, such as PET, while the inner balloon 1904 is made up of a more flexible material, such as latex. At the proximal end 1902b of the catheter 1902 is a handle 1907, having channels or lumens 1908 extending there through for carrying steam and cooling water.

In some embodiments, an entire surface of the catheter 1902 is coated with heparin. In some embodiments, the inner balloon 1904 is movable along a longitudinal axis of the balloons 1903, 1904 within and along an entire length of the outer balloon 1903, to better position the inner balloon inside the outer balloon, using a wire mechanism in the handle 1907 at the proximal end of the catheter 1902.

In embodiments, at least one dimension of the inner balloon 1904 is different than the outer balloon 1903 by at least 10%. In some embodiments, the dimension is a length of the inner balloon 1904. In embodiments, a shape of the inner balloon 1904 is different from that of the outer balloon 1903. In embodiments, an intersection of the shapes of the inner balloon 1904 and the outer balloon 1903 determine the shape and/or size of an ablation zone 1909.

In some embodiments, a mapping member 1952, which may be a distal extension, catheter, or any substrate comprising a plurality of sensors, detectors, or electrodes, is attached to the distal end of the catheter 1902 distal to the outer balloon 1903. The mapping member 1952 maps the area of cardiac tissue responsible for the arrhythmia. In some embodiments, the mapping member 1952 has a length of up to 75 mm. In some embodiments, the mapping member 1952 is pre-shaped in a pig-tail shape to allow wall contact. In embodiments, the diameter of the pigtail is between 5 mm and 25 mm. In some embodiments, the mapping member 1952 comprises 1 to 8 electrodes configured to record signals from a pulmonary vein or pacing in a pulmonary vein. In another embodiment, the mapping member 1952 comprises up to 64 electrodes.

In some embodiments, the outer balloon 1903 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 1903 includes up to 24 mapping electrodes. In other embodiments, the outer balloon 1903 includes up to 64 mapping electrodes.

During operation, water vapor/steam at a temperature of around 100~125 degrees C. is input from a luer connector 1910 and carried via the catheter 1902 to the inner balloon 1904. This allows the inner balloon 1904 to inflate and contact the outer balloon 1903 proximate the area of ablation. The ablation zone or hot zone 1909 is created at the area of contact between the inner balloon 1904 and the external balloon 1903, such that thermal energy from the inner balloon 1904 passes through the outer balloon 1903 to the area of ablation. The elongate body and portions of the outer balloon 1903, excluding the hot zone 1909, remain cool owing to the circulating water. In some embodiments, saline is input from a luer connector 1910 and carried via the catheter 1902 to an inline heating member 1999 at the distal end of the catheter proximate the outer balloon which generates water vapor/steam at a temperature of around 100~125 degrees C. that is then delivered to the inner balloon 1904.

As noted above, channels are provided in the catheter 1902 for carrying cooling or insulating fluid and steam. Cooling or insulating fluid enters the catheter 1902 from a tube 1911 at the proximal end of the catheter and exits from another tube 1912 at the proximal end of the catheter after circulating through the outer balloon 1903. Luer connectors 1913 are provided to enable cooling fluid to be supplied to and exit from the tubes 1911 and 1912, respectively. In one embodiment, the luer connector 1910 at the inlet of water vapor is a pressure resistant luer lock. In one embodiment the cooling fluid is water. In another embodiment, the cooling fluid is air or $CO_2$. In one embodiment the temperature of the cooling fluid is between 0 degree Celsius and 40 degree Celsius. In another embodiment, the cooling fluid is at room temperature.

In one embodiment, the length of the catheter 1902 between its distal end 1902a and proximal end 1902b is about 1800 mm, with a margin of ±500 mm. In one embodiment, the outer balloon 1902 is substantially cylindrical in shape, with tapering ends, while the inner balloon 1904 is substantially spherical in shape. In another embodiment, the outer balloon is pear shaped. In one embodiment, the total length of the outer balloon 1903 between its two ends is about 83 mm, while the length of the cylindrical portion is about 60 mm, with a margin of ±25 mm, and its width is about 24 mm with a margin of ±15 mm. In one embodiment, the diameter of the inner balloon 1904 is about 25 mm with a margin of ±15 mm. In another embodiment, the length of the outer balloon is 45 mm, with a margin of ±25 mm.

FIG. 19B illustrates a detailed inside view of the catheter 1902 with various lumens. Referring to FIG. 19B, the central lumen 1901 is used to carry steam into the inner balloon 1904. The first outer lumen 1914 is used to carry cooling fluid from the tube 1911 into the outer balloon 1903, and the second outer lumen 1915 of the catheter is used to carry cooling fluid coming back from the outer balloon and is exit through the tube 1912. All the lumens are encased in another tube or handle 1905 for reinforcement.

Figure 19C:
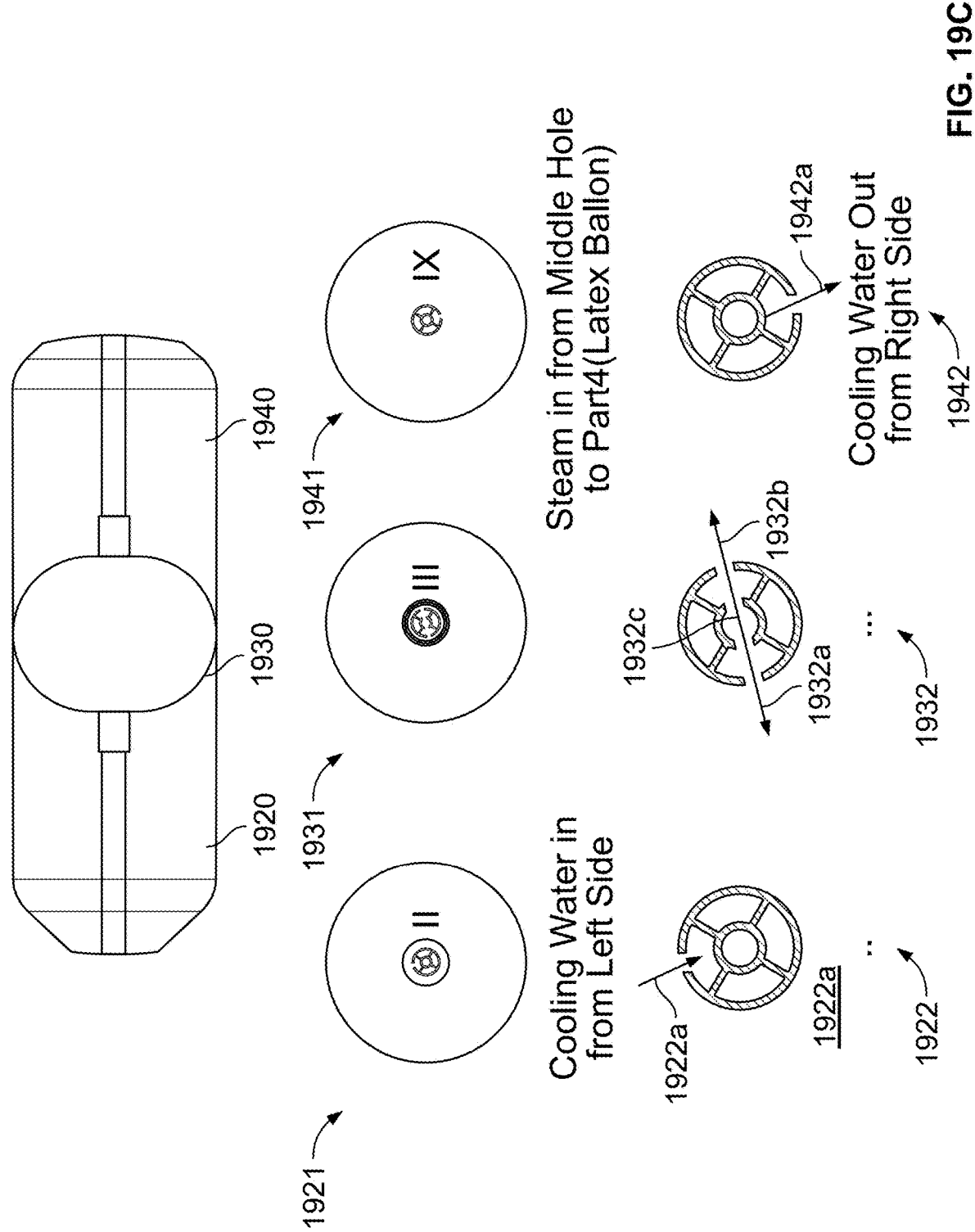
FIG. 19C illustrates the flow mechanism for a catheter, as it passes through the inner balloon and the outer balloon, in accordance with one embodiment.

In one embodiment, the channels or lumens of the catheter 1902, shown in FIG. 19B are designed with openings at appropriate places, to ensure correct flow of fluids—steam into the inner balloon and cooling fluid in and out of the outer balloon. FIG. 19C illustrates the flow mechanism for catheter 1902, as it passes through the inner balloon 1904 and the outer balloon 1903. Referring to FIG. 19C, the cross sectional views of the catheter lumens at locations 1920, 1930 and 1940, are illustrated as 1921, 1931 and 1941. Details of the cross section views can be seen in 1922, 1932 and 1942. As can be seen in 1922, there is an opening 1922a in the tube to allow cooling fluid into the channel from the outer balloon. This cooling fluid is carried by the lumen to the exit (vial tube 1912 in FIG. 19B). As can be seen in 1942, there is an opening 1942a in the tube to allow cooling fluid out of the channel into the outer balloon. This cooling fluid is supplied by tube 1911 (shown in FIG. 19B) and carried by the channel to the outer balloon. In 1932, two openings 1932a and 1932b can be seen in the channel, through which steam is supplied from the central lumen 1932c to the inner balloon. In some embodiments, the cooling fluid is air, $CO_2$ or water.

Figure 20A:
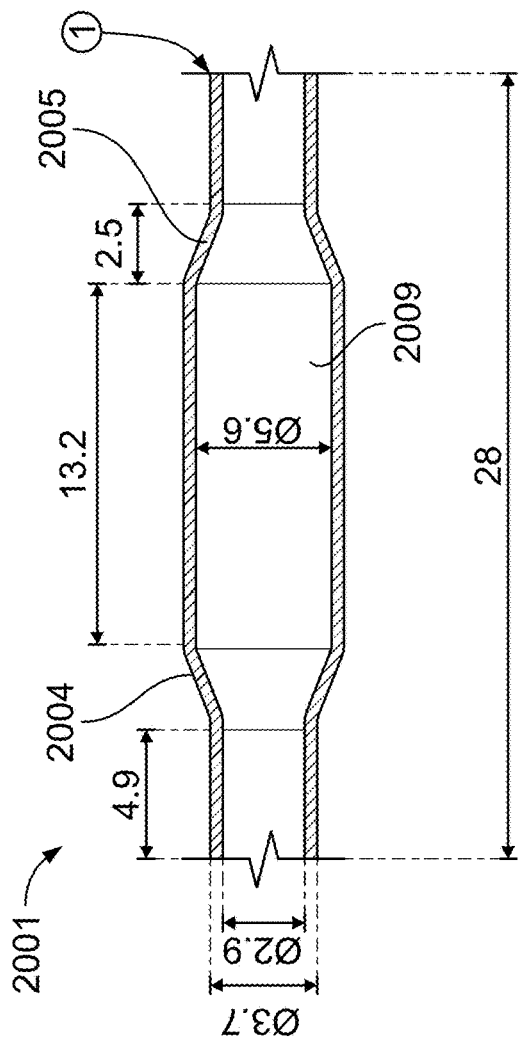
FIG. 20A illustrates a side cross section view and a perspective view of the inner balloon, when the balloon is in unexpanded state, according to one embodiment.
Figure 20A:
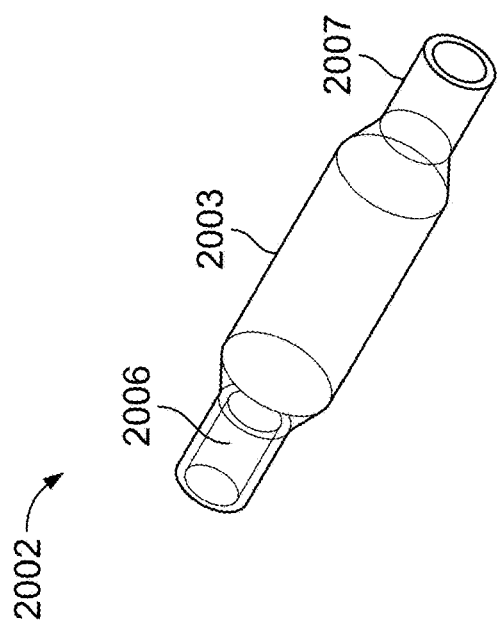

FIG. 20A illustrates a side cross section 2001 and a perspective view 2002 of the inner balloon (shown as 1904 in FIGS. 19A, 19B and 19C), when the balloon is in an unexpanded state, that is, it is not inflated with steam. Referring to FIG. 20A, in one embodiment, the balloon 2003 in unexpanded form has a substantially cylindrical shape, and is tapered at both the ends 2004 and 2005. The ends extend into tube like structures 2006 and 2007, which help in keeping the catheter in place when it is passed through the balloon, as shown in FIG. 19A. In one embodiment, the total length of the balloon in the unexpanded state is about 28 mm with a margin of ±15 mm, while the length of the cylindrical portion 2009 is about 13.2 mm with a margin of ±10 mm. The length of each tubular segment 2006, 2007 is about 4.9 mm, while the length of the tapered portions 2004, 2005 is 2.5 mm on each side. In one embodiment, the inner diameter of each tubular segment is about 2.9 mm, while the outer diameter is 3.7 mm. The width of the widest portion of the balloon 2009 is about 5.6 mm with a margin of ±2.5 mm.

Figure 20B:
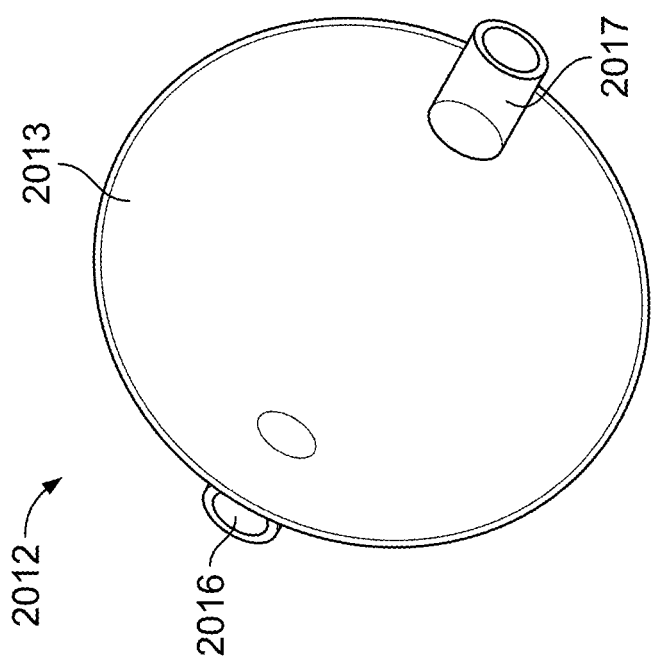
FIG. 20B illustrates a side cross section view and a perspective view of the inner balloon, when the balloon is in expanded state, according to one embodiment.
Figure 20B:
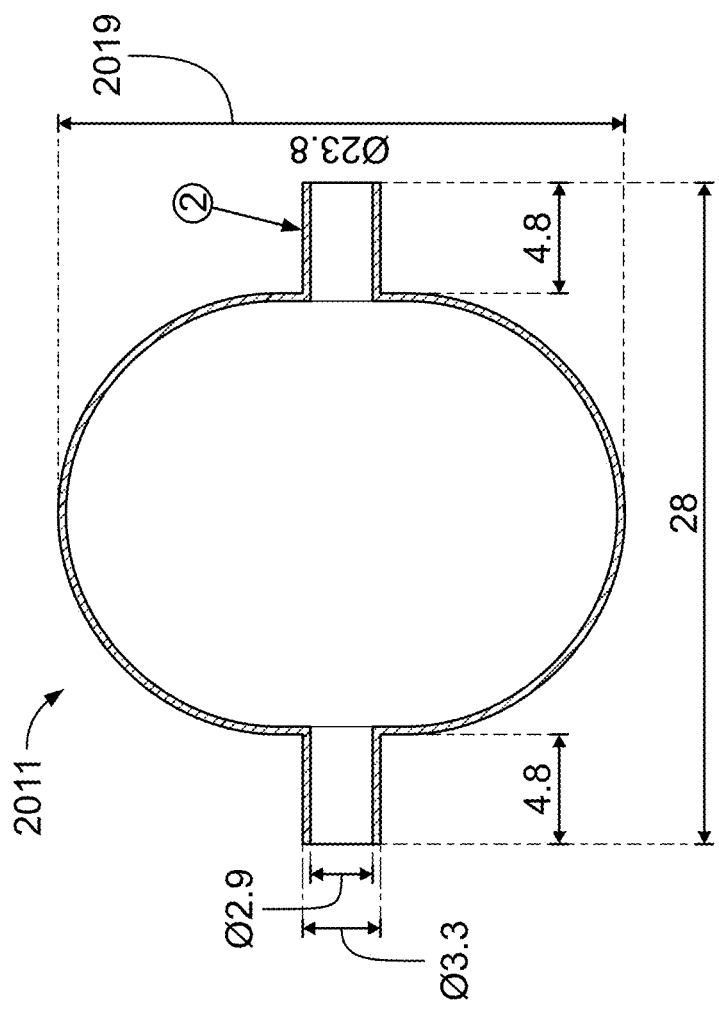

FIG. 20B illustrates a side cross section 2011 and a perspective view 2012 of the inner balloon (shown as 1904 in FIGS. 19A, 19B and 19C), when the balloon is in an expanded state, that is, it is inflated with steam. Referring to FIG. 20B, in one embodiment, the balloon 2013 in expanded form has a shape of an elongated spheroid. Tube like structures 2016 and 2017 extend from two opposite sides in the balloon, which help in keeping the catheter in place when it is passed through the balloon, as shown in FIG. 19A. In one embodiment, the total length of the balloon in expanded state, including the tubular segments 2016, 2017 is about 28 mm with a margin of ±15 mm, while the length of each individual tube segment is about 4.8 mm with a margin of ±2.0 mm. In one embodiment, the inner diameter of each tubular segment is about 2.9 mm, while the outer diameter is 3.3 mm with a margin of ±2.0 mm, when the balloon 2013 is in expanded state. In one embodiment, the length of the major axis 2019 of the elongated spheroid shaped balloon is about 23.8 mm with a margin of ±15 mm, when the balloon is inflated.

Figure 21A:
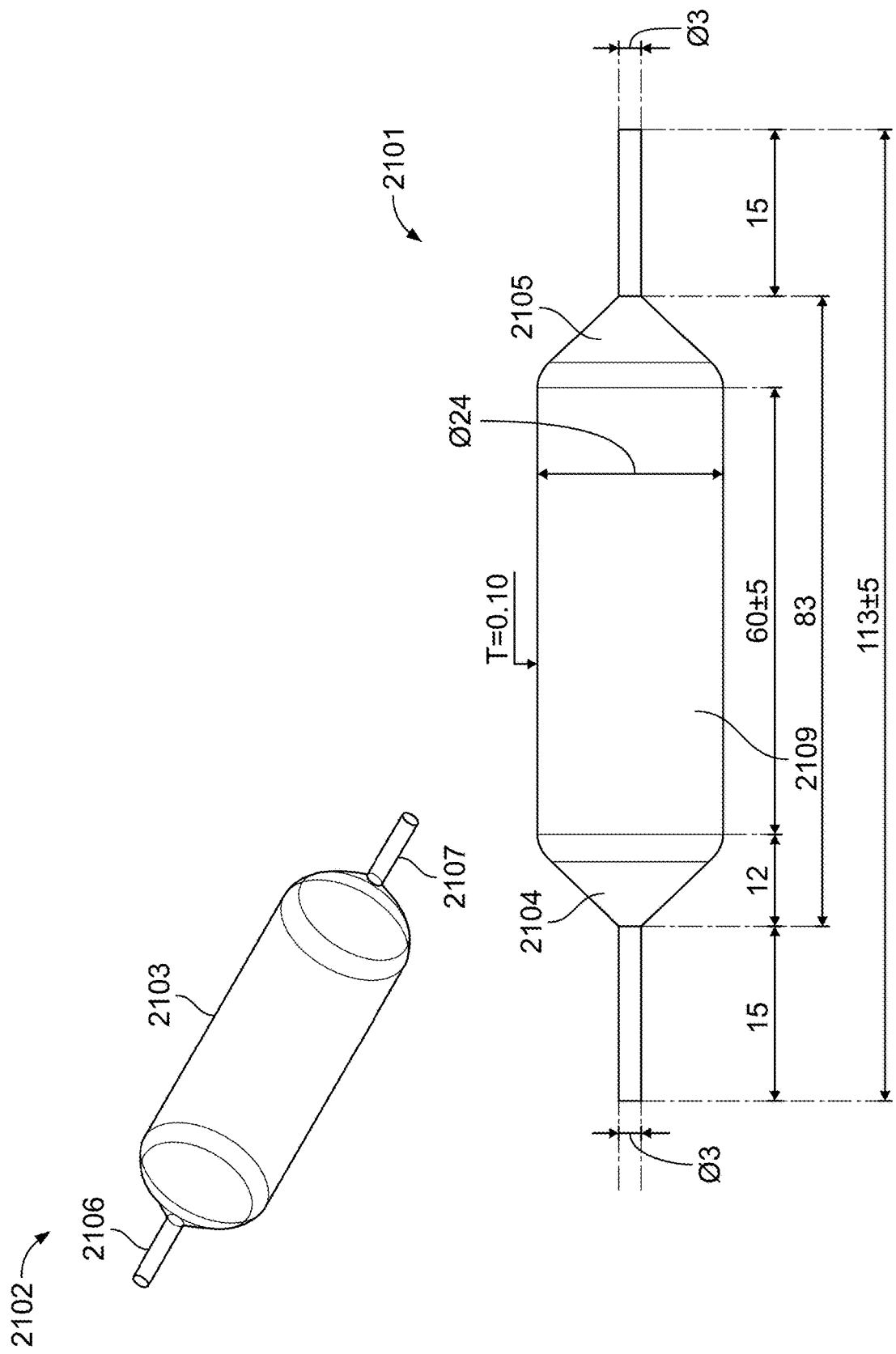
FIG. 21A illustrates a side cross section view and a perspective view of the outer balloon, in accordance with one embodiment.

FIG. 21A illustrates a side cross section 2101 and a perspective view 2102 of the outer balloon (shown as 1903 in FIG. 19A) in an expanded state. Referring to FIG. 21A, in one embodiment, the balloon 2103 has a substantially cylindrical shape, and is substantially tapered or conical at both the ends 2104 and 2105. The ends extend into tube like structures or necks 2106 and 2107, which help in keeping the catheter in place when it is passed through the outer balloon, as shown in FIG. 19A. In one embodiment, the total length of the balloon including the tubular necks or structures 2106, 2107 is about 113±35 mm, while the length of the cylindrical portion 2109 is about 60±25 mm. The length of each tubular segment 2106, 2107 is about 15 mm with a margin of ±15 mm, while the length of the tapered portions 2104, 2105 is 12 mm on each side with a margin of ±10 mm. In one embodiment, the diameter of each tubular segment is about 3 mm. The width of the cylindrical portion of the balloon 2109 is about 24 mm with a margin of ±15 mm, while the thickness of the material of the balloon is about 0.10 mm.

Figure 21B:
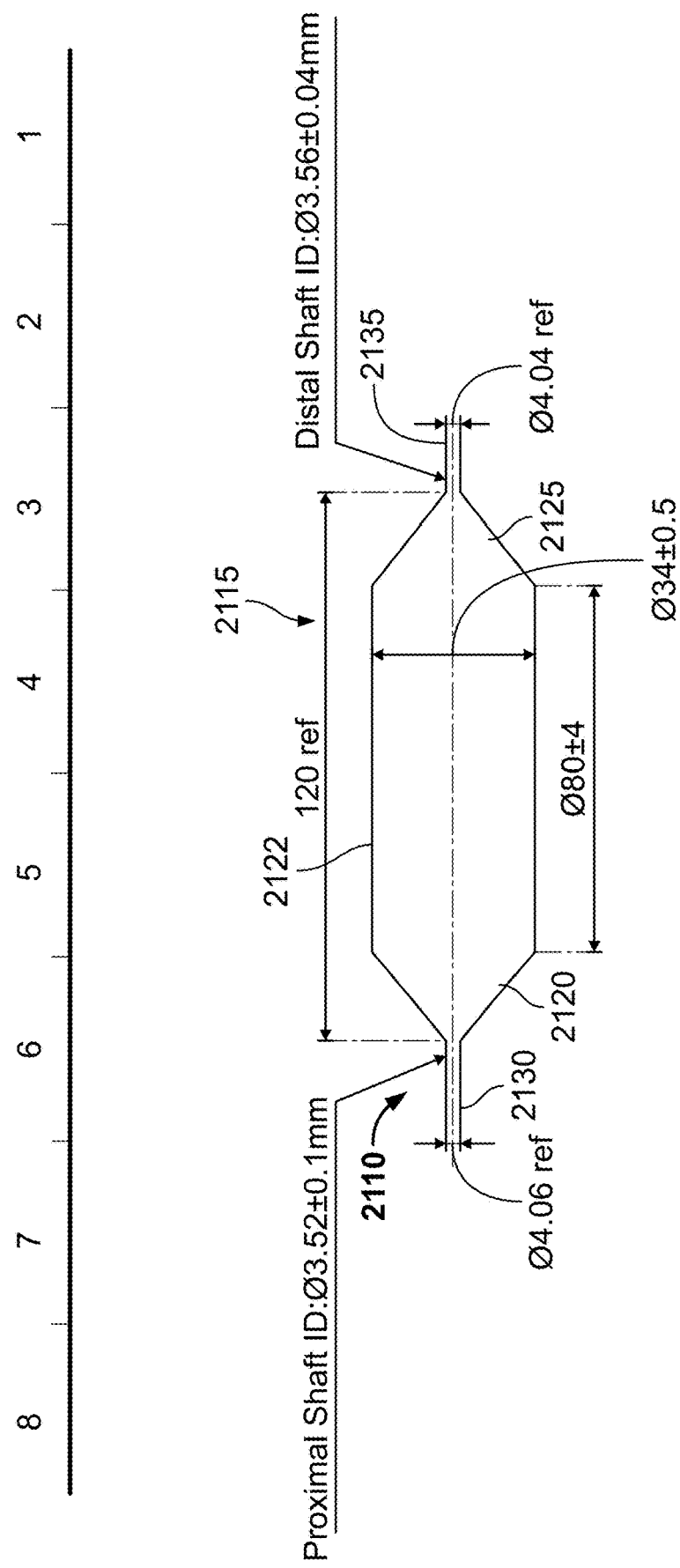
FIG. 21B illustrates a side cross section view of the outer balloon, in accordance with another embodiment.

FIG. 21B illustrates a side cross section view 2110 of the outer balloon (shown as 1903 in FIG. 19A) in an expanded state, in accordance with another embodiment of the present specification. The balloon 2115 has a substantially cylindrical shape, and is substantially tapered or conical at both the ends 2120 and 2125. The ends extend into tube like structures or necks 2130 and 2135, which help in keeping the catheter in place when it is passed through the outer balloon, as shown in FIG. 19A. In one embodiment, the total length of the balloon including the tapered or conical ends 2120, 2125 is about 120 mm, while the length of the cylindrical portion 2122 is about 80±4 mm. In one embodiment, the inner diameter of each tubular segment is about 3.52±0.1 mm and the outer diameter of each tubular segment is about 4.06 mm. The width of the cylindrical portion of the balloon 2115 is about 34 mm with a margin of ± or −0.5 mm.

Figure 22:
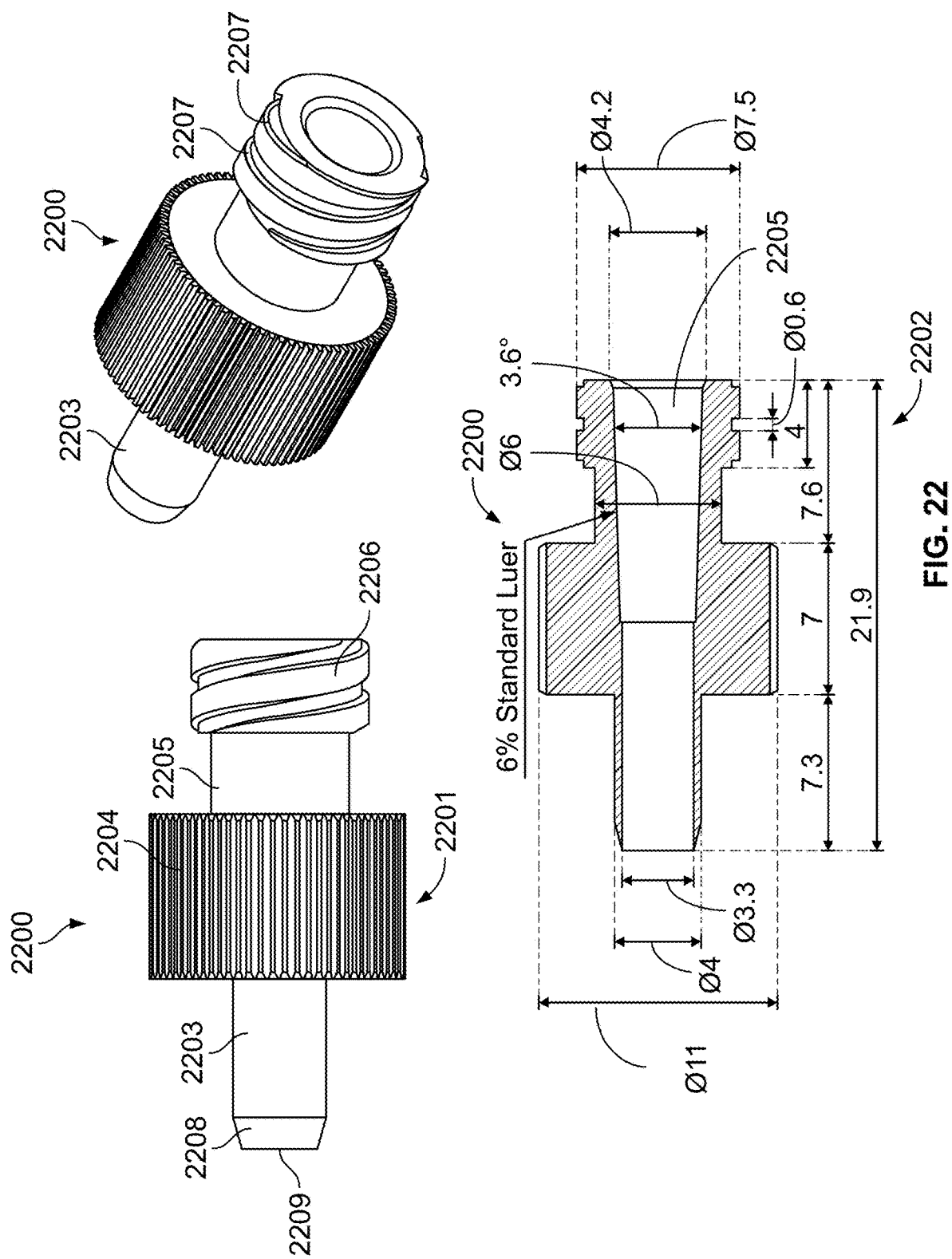
FIG. 22 illustrates a side view, a side cross section view, and a perspective view of a pressure resistant luer lock positioned at the proximal end of the catheter, in accordance with one embodiment of the present specification.

FIG. 22 illustrates a side view 2201, side cross section 2202, and perspective view 2203 of a pressure resistant luer lock 2200 positioned at the proximal end of the catheter, shown as 1910 in FIG. 19A. Referring to FIG. 22, in one embodiment, the luer lock 2203 comprises a grip 2204 in the center for handling the lock 2203, a male connector 2203 at its distal end 2209, and a female connector 2206 at its proximal end 2210. The male connector 2203 includes a tapered end 2208 and is configured to attach securely to the proximal end of handle 1907 in FIG. 19A to form a luer lock for the steam inlet in the catheter. The female connector 2206 includes an opening 2211 for receiving a tube of a steam source and grooves 2207 for securing said steam source tube. The grip 2204 is used for handling the lock 2200 when attaching the lock to a steam source. In one embodiment, the total length of the lock 2200 is about 21.9 mm. At the female connector 2206, the outer diameter is about 7.5 mm, while the inner diameter is about 4.2 mm. The width of the female connector 2206 is about 4 mm, in one embodiment. In one embodiment, grooves 2207 are etched on the female connector 2206, which have a uniform width of about 0.6 mm. The diameter of the male connector 2203 just before it tapers is about 4 mm, while the diameter is reduced to 3.3 mm at the distal end 2209. In one embodiment, the lock 2200 has a 6% standard taper.

In one embodiment, the grip 2204 of the luer lock 2200 has a width of about 7 mm and a diameter of about 11 mm.

Figure 23A:
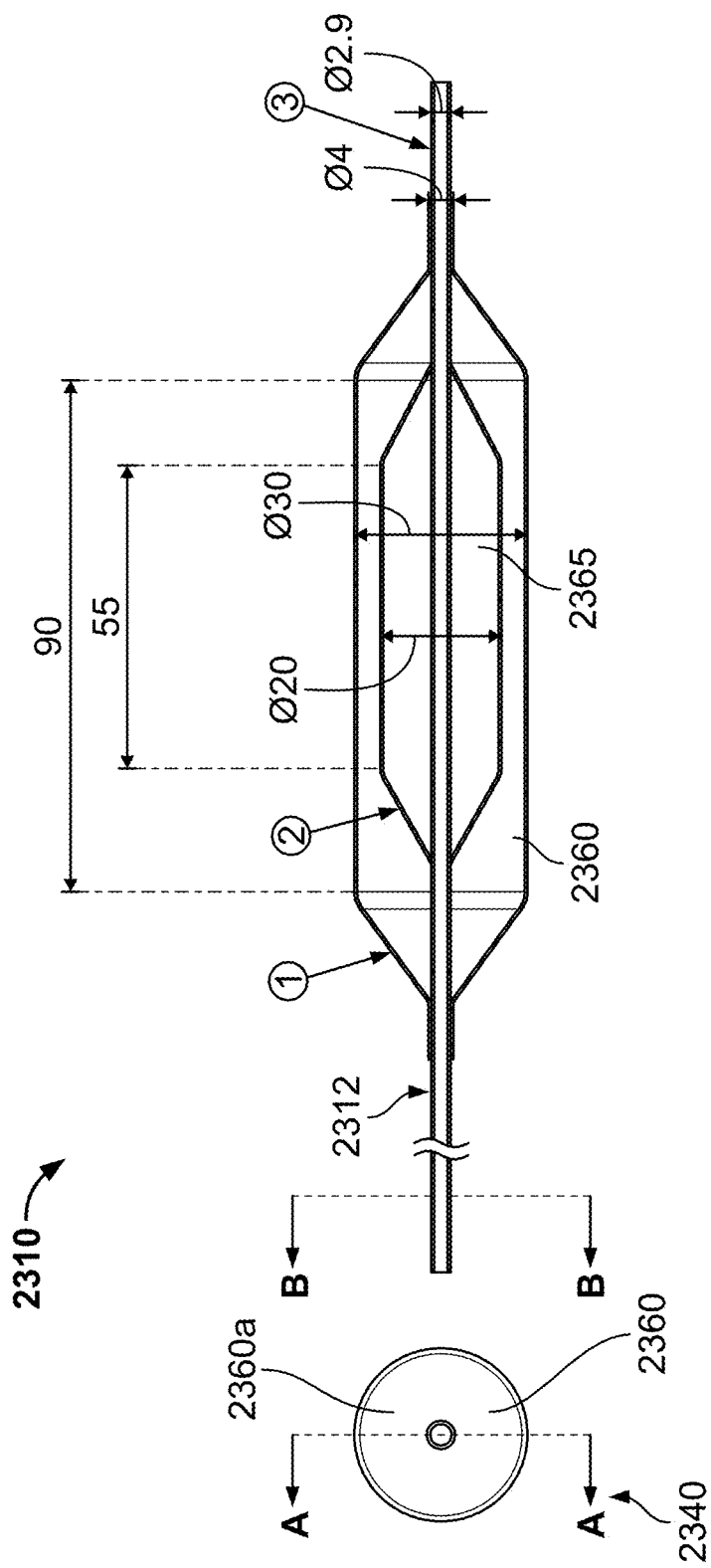
FIG. 23A illustrates a longitudinal cross section view and a transverse perspective view of a dual balloon cardiac ablation catheter, in accordance with some embodiments of the present specification.
Figure 23C:
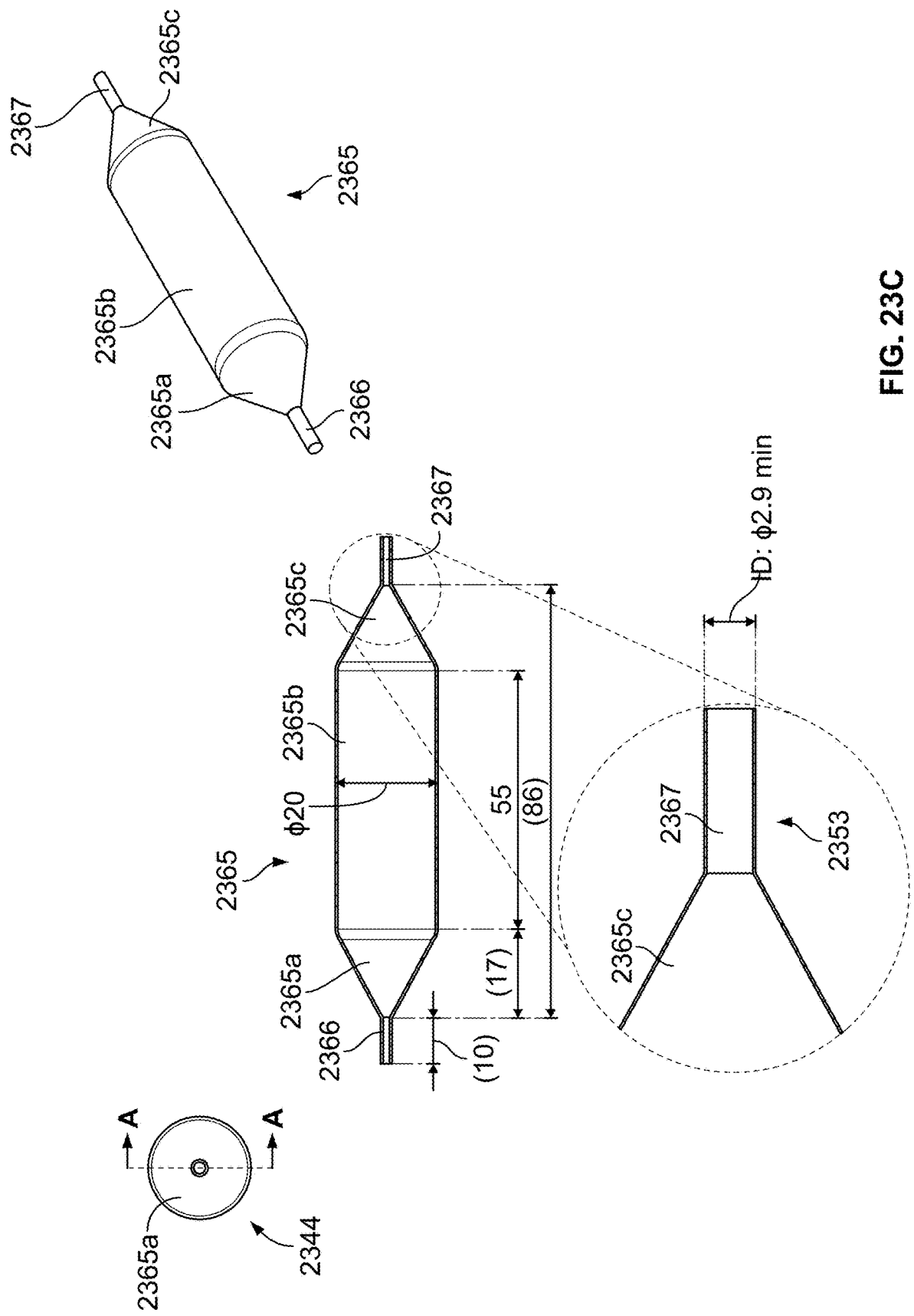
FIG. 23C illustrates a plurality of views of an inner balloon of the catheter of FIG. 23A, in accordance with some embodiments of the present specification.
Figure 23D:
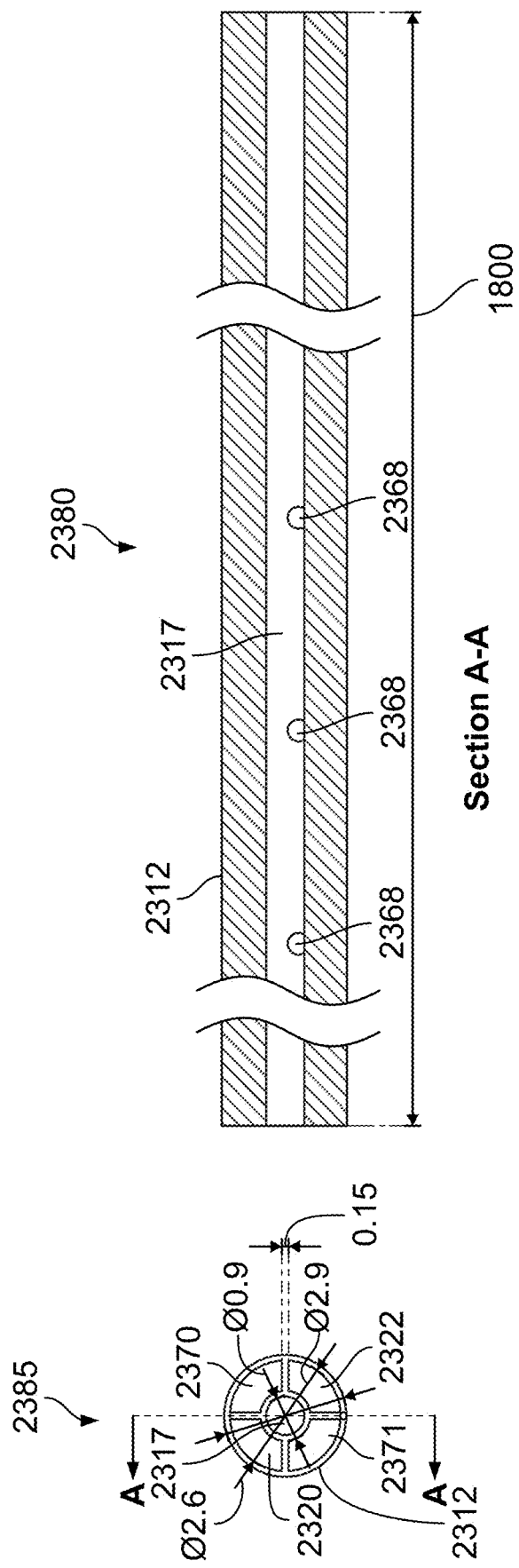
FIG. 23D illustrates longitudinal and transverse cross-sectional views of an elongate body of the catheter of FIG. 23A, in accordance with some embodiments of the present specification.

FIG. 23A illustrates a longitudinal cross section view and a transverse perspective view of a dual balloon cardiac ablation catheter 2310, FIGS. 23B and 23C illustrate various views of outer and inner balloons, respectively, of the catheter 2310, and FIG. 23D illustrates longitudinal and transverse cross-sectional views of an elongate body 2312 of the catheter 2310, in accordance with some embodiments of the present specification. Referring to FIGS. 23A through 23D simultaneously, unless otherwise mentioned specifically, the elongate body 2312 has a proximal end, a distal end and a plurality of lumens.

Referring now to FIG. 23A along with longitudinal and transverse cross-section views 2380, 2385 of FIG. 23D, in one embodiment, the elongate body 2312 includes a first cooling fluid infusion lumen 2320 and a second cooling fluid suction lumen 2322 (positioned diametrically opposite with respect to the first cooling fluid infusion lumen 2320, in some embodiments) that are in fluid communication with an inflatable outer balloon 2360 attached to the distal end of the catheter 2310. In embodiments, the cooling fluid is water, air or carbon-dioxide. During operation, the cooling fluid enters the first cooling fluid infusion lumen 2320 from the proximal end of the catheter and exits through the second cooling fluid suction lumen 2322 from the proximal end of the catheter after circulating through the outer balloon 2360. The cooling fluid is circulated through the catheter 2310 and the outer balloon 2360 using a cooling fluid pump which is in data communication with, and controlled by, a controller.

In an embodiment, the elongate body 2312 also includes a central water/vapor lumen 2317 that is in fluid communication, via a plurality of vapor infusion ports 2368, with an inflatable inner balloon 2365 attached to the distal end of the catheter 2310 and positioned within the outer balloon 2360. In some embodiments, the plurality of vapor infusion ports 2368 are located along a portion of the water/vapor lumen 2317 that lies within the inner balloon 2365. The elongate body 2312 also includes third and fourth lumens 2370, 2371 (positioned diametrically opposite with respect to each other).

In some embodiments, the elongate body 2312 has a length of 1800 mm, an outer diameter of 2.9 mm and an inner diameter of 2.6 mm. In some embodiments, a thickness of a material (such as, but not limited to, PET) of the elongate body 2312 is 0.15 mm. In some embodiments, the central water/vapor lumen 2317 has an inner diameter of 0.9 mm.

In some embodiments, at least one flexible heating chamber (such as those described with reference to FIGS. 19A through 19D), comprising a plurality of electrodes, is positioned in-line within the central water/vapor lumen 2317. In some embodiments, the at least one flexible heating chamber is positioned in-line within the central water/vapor lumen such that the plurality of electrodes are at least partially inside the inner balloon 2365. During operation, a water/vapor pump which is also in data communication with, and controlled by, the controller pumps water from a sterile water reservoir through the water/vapor lumen 2317 to enter a proximal end of the at least one flexible heating chamber. The at least one flexible heating chamber coverts water into vapor that exits through at least one vapor infusion port 2368 to inflate the inner balloon 2365 and contact the outer balloon 2360 proximate an area of ablation. An ablation zone or hot zone is created at the area of contact between the inner balloon 2365 and the outer balloon 2360, such that thermal energy from the inner balloon 2365 passes through the outer balloon 2360 to the area of ablation. The elongate body 2312 and portions of the outer balloon 2360, excluding the hot zone, remain cool owing to the circulating cooling fluid.

Referring to FIG. 23B, in an embodiment, the outer balloon 2360 has a compound shape (when in fully expanded state) comprising of a substantially cylindrical portion 2360b having substantially tapering or conical proximal and distal ends 2360a, 2360c (shown in side perspective views 2340, 2342 of the outer balloon 2360 in FIGS. 23A, 23B respectively). The ends extend into tube like structures 2361 and 2362, which help in keeping the catheter in place when it is passed through the balloon. In an embodiment, the outer balloon 2360 has a length of 130 mm between the substantially tapering or conical proximal and distal ends 2360a, 2360c, the substantially cylindrical portion 2360b has a length of 90 mm and an outer diameter of 30 mm, and each of the tube like structures 2361, 2362 has a length of 10 mm and an internal diameter of 4 mm (also shown in an enlarged view 2352 of one of the tube like structures). In one embodiment, the outer balloon 2360 is made up of a harder material relative to the inner balloon, such as PET, that has a thickness of 0.1 mm.

Referring to FIG. 23C, in an embodiment, the inner balloon 2365 has a compound shape (when in fully inflated state) comprising of a substantially cylindrical portion 2365b having substantially tapering or conical proximal and distal ends 2365a, 2365c (also shown in a side perspective view 2344 of the inner balloon 2365). The ends extend into tube like structures 2366 and 2367, which help in keeping the catheter in place when it is passed through the balloon. In an embodiment, the inner balloon 2365 has a length of 86 mm between the substantially tapering or conical proximal and distal ends 2365a, 2365c, each of the substantially tapering or conical proximal and distal ends 2365a, 2365c has a length of 17 mm, the substantially cylindrical portion 2365b has a length of 55 mm and an outer diameter of 20 mm, and each of the tube like structures 2366, 2367 has a length of 10 mm and an internal diameter of 2.9 mm (shown in an enlarged view 2353 of one of the tube like structures). In one embodiment, the inner balloon 2365 is made up of a more flexible material relative to the outer balloon, such as latex.

In some embodiments, the inner balloon 2365 is movable along a portion of the elongate body 2312 within the outer balloon 2360 to better position the inner balloon within the outer balloon and ensure proper contact of the inner balloon with the outer balloon, using a wire mechanism in a handle at the proximal end of the catheter 2310.

In some embodiments, a mapping member, which may be a distal extension, catheter, or any substrate comprising a plurality of sensors, detectors, or electrodes, is attached to the distal end of the body 2312 distal to the outer balloon 2360. The mapping member maps the area of cardiac tissue responsible for the arrhythmia. In some embodiments, the mapping member has a length of up to 75 mm. In some embodiments, the mapping member is pre-shaped in a pig-tail shape or a lasso-loop shape to allow wall contact. In embodiments, the diameter of the pigtail is between 5 mm and 25 mm. In some embodiments, the mapping member comprises 1 to 8 electrodes configured to record signals from a pulmonary vein or pacing in a pulmonary vein.

In some embodiments, the outer balloon 2360 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 2360 includes up to 24 mapping electrodes. In embodiments, the mapping electrodes measure cardiac electrical activity to assess at least one therapeutic endpoint.

In some embodiments, an entire surface of the catheter 2310, including the balloons 2360, 2365, mapping electrodes and the mapping member, is coated with heparin.

Figure 24A:
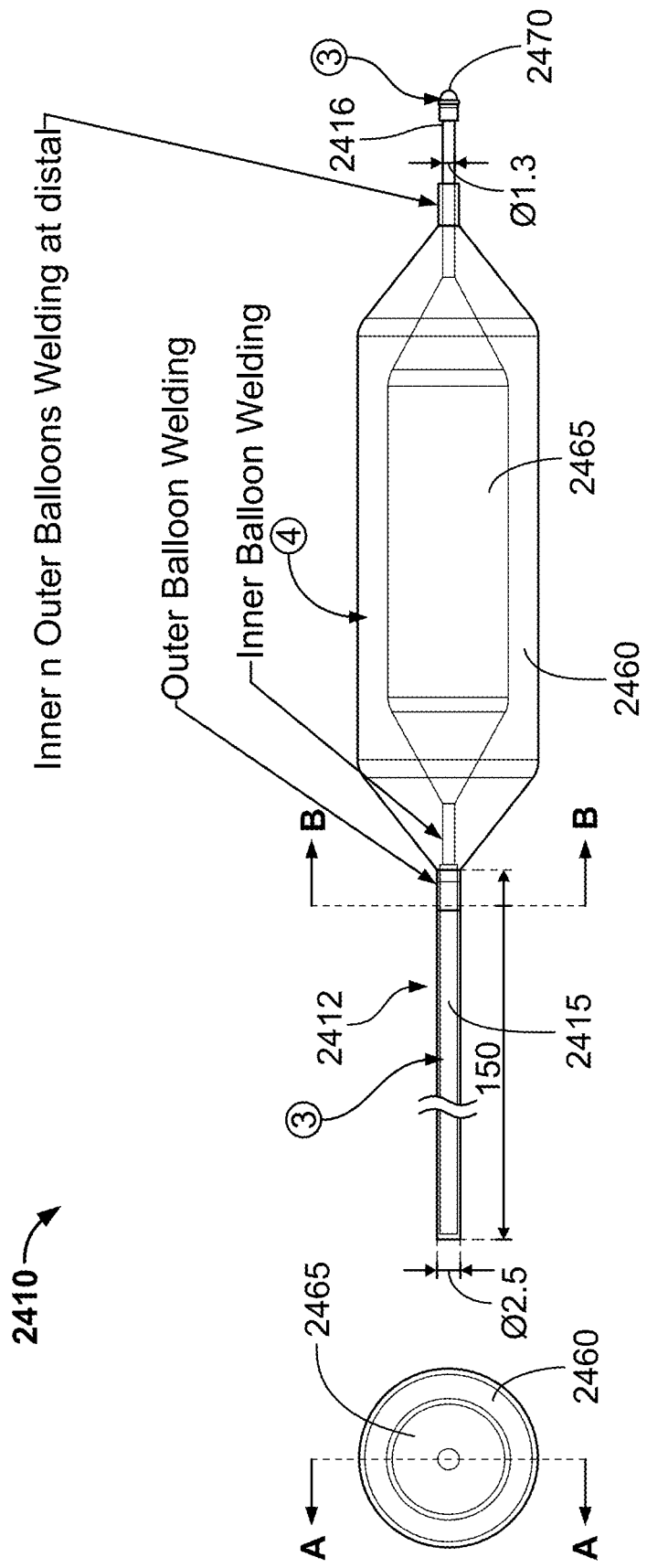
FIG. 24A illustrates longitudinal and transverse perspective views of a dual balloon cardiac ablation catheter, in accordance with some embodiments of the present specification.
Figure 24B:
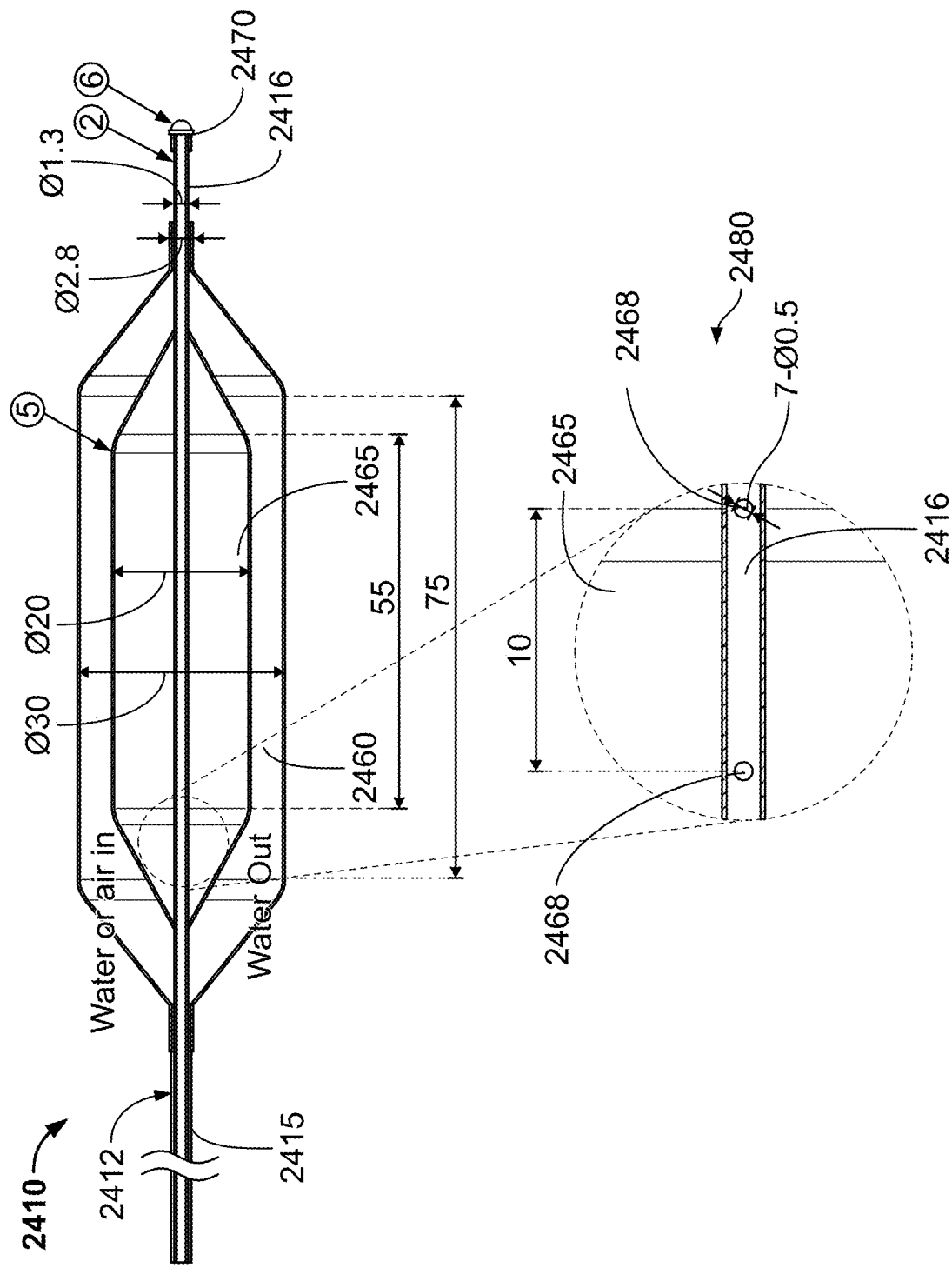
FIG. 24B illustrates a longitudinal cross-sectional view along with an enlarged view of a portion of the catheter of FIG. 24A, in accordance with some embodiments of the present specification.
Figure 24C:
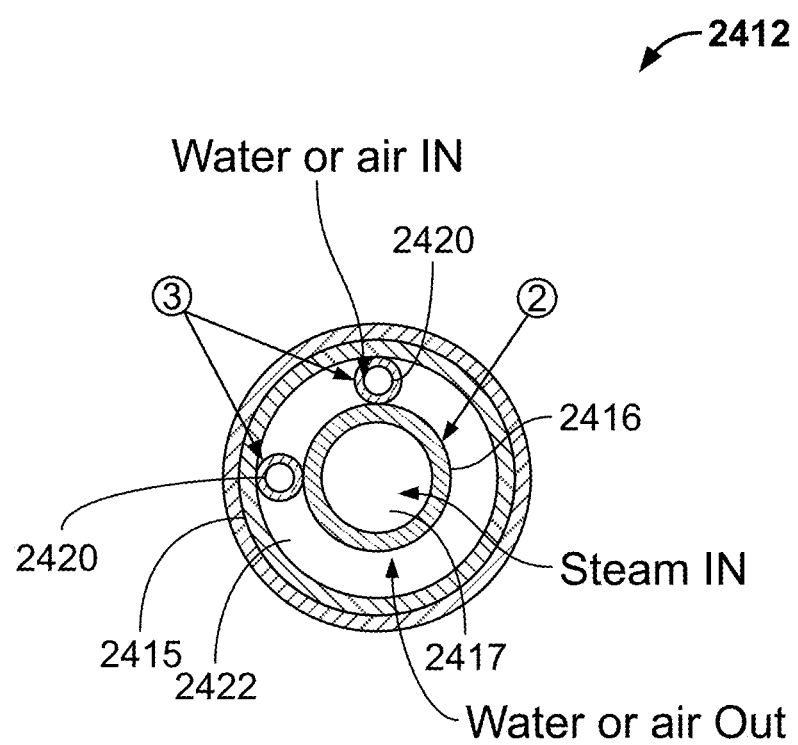
FIG. 24C illustrates a transverse cross-sectional view of an elongate body of the catheter of FIG. 24A, in accordance with some embodiments of the present specification.

FIG. 24A illustrates longitudinal and transverse perspective views of a dual balloon cardiac ablation catheter 2410, FIG. 24B illustrates a longitudinal cross-sectional view along with an enlarged view of a portion of the catheter 2410 and FIG. 24C illustrates a transverse cross-sectional view of an elongate body 2412 of the catheter, in accordance with some embodiments of the present specification. Referring to FIGS. 24A, 24B and 24C simultaneously, unless otherwise mentioned specifically, the elongate body 2412 has a proximal end, a distal end and a plurality of lumens.

In one embodiment, the elongate body 2412 includes an outer catheter 2415 having a lumen and an inner catheter 2416 having a water/vapor lumen 2417. The inner catheter 2416 is positioned within the lumen of the outer catheter 2415 so as to form a ring-like cooling fluid suction lumen 2422 between the two catheters 2415, 2416. The two catheters 2415, 2416 are coaxial, in accordance with an embodiment. The ring-like cooling fluid suction lumen 2422 accommodates first and second cooling fluid infusion tubes 2420.

The first and second cooling fluid infusion tubes 2420 and the ring-like cooling fluid suction lumen 2422 are in fluid communication with an inflatable outer balloon 2460 attached to the distal end of the catheter 2410. In embodiments, distal ends of the outer catheter 2415 and of the first and second cooling fluid infusion tubes 2420 lie or terminate at a proximal end of the outer balloon 2460 whereas a distal end of the inner catheter 2416 projects beyond a distal end of the outer balloon 2460. In embodiments, the cooling fluid is water, air or carbon-dioxide. During operation, the cooling fluid enters the first and second cooling fluid infusion tubes 2420 from the proximal end of the catheter and exits through the ring-like cooling fluid suction lumen 2422 from the proximal end of the catheter after circulating through the outer balloon 2460. The cooling fluid is circulated through the catheter 2410 and the outer balloon 2460 using a cooling fluid pump which is in data communication with, and controlled by, a controller.

The water/vapor lumen 2417 is in fluid communication, via a plurality of vapor infusion ports 2468, with an inflatable inner balloon 2465 attached to the distal end of the catheter 2410 and positioned within the outer balloon 2460. In some embodiments, the plurality of vapor infusion ports 2468 are located along a portion of the inner catheter 2416 lying within the inner balloon 2465.

Figure 24D:
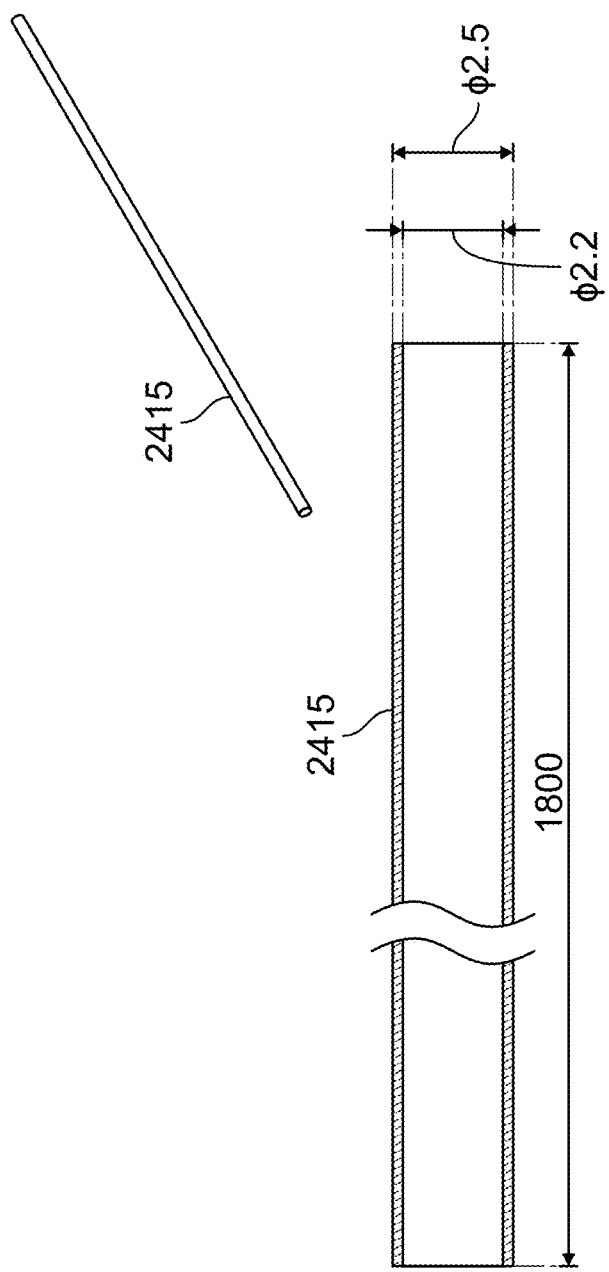
FIG. 24D illustrates transverse and longitudinal cross-sectional views of an outer catheter of the catheter of FIG. 24A, in accordance with some embodiments of the present specification.
Figure 24D:
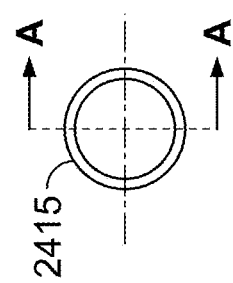
Figure 24E:
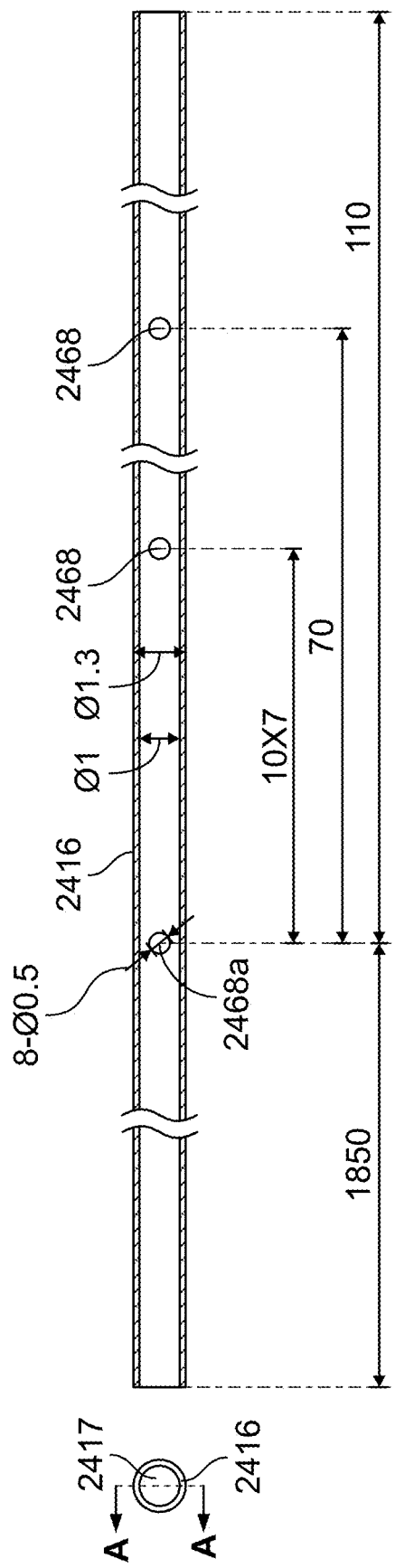
FIG. 24E illustrates transverse and longitudinal cross-sectional views of an inner catheter of the catheter of FIG. 24A, in accordance with some embodiments of the present specification.
Figure 24F:
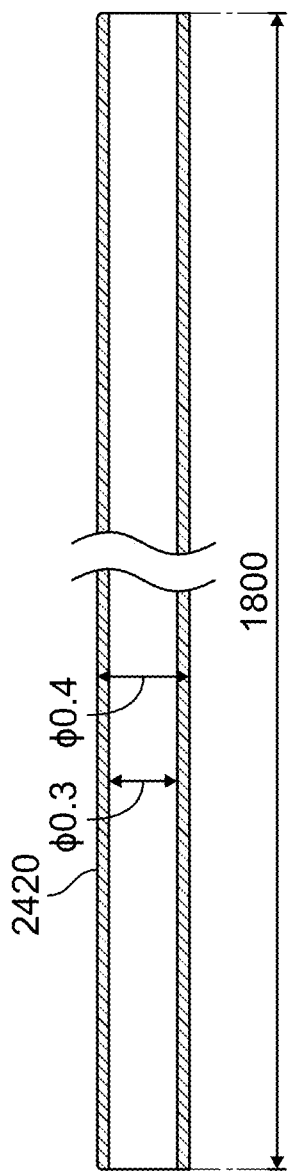
FIG. 24F illustrates transverse and longitudinal cross-sectional views of a cooling tube of the catheter of FIG. 24A, in accordance with some embodiments of the present specification.
Figure 24F:
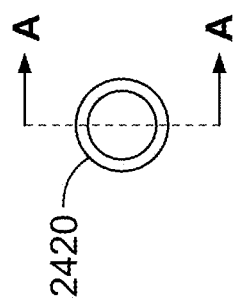

As shown in transverse cross-sectional, longitudinal cross-sectional and perspective views of FIG. 24D, in some embodiments, the outer catheter 2415 has a length of 1800 mm, an inner diameter of 2.2 mm and an outer diameter of 2.5 mm. As shown in transverse and longitudinal cross-sectional views of FIG. 24E, the inner catheter 2416 has a length of 1960 mm, an inner diameter of 1 mm and an outer diameter of 1.3 mm. In some embodiments, seven vapor infusion ports 2468 are located on the inner catheter 2416 (and in communication with the water/vapor lumen 2417) wherein each port 2468 has a diameter of 0.5 mm. In some embodiments, a proximal port 2468a is located at a distance of 1850 mm from a proximal end of the inner catheter 2416 and at a distance of 110 mm from a distal end of the inner catheter 2416. In some embodiments, as also shown in an enlarged view 2480 of FIG. 24B, the plurality of vapor infusion ports 2468 are spaced by a distance of 10 mm from each other. As shown in transverse and longitudinal cross-sectional views of FIG. 24F, in some embodiments, each of the first and second cooling fluid infusion tubes 2420 has a length of 1800 mm, an inner diameter of 0.3 mm and an outer diameter of 0.4 mm.

In some embodiments, at least one flexible heating chamber (such as those described with reference to FIGS. 19A through 19D), comprising a plurality of electrodes, is positioned in-line within the central water/vapor lumen 2417. In some embodiments, the at least one flexible heating chamber is positioned in-line within the central water/vapor lumen 2417 such that the plurality of electrodes are at least partially inside the inner balloon 2465. During operation, a water/vapor pump which is also in data communication with, and controlled by, the controller pumps water from a sterile water reservoir through the water/vapor lumen 2417 to enter a proximal end of the at least one flexible heating chamber. The at least one flexible heating chamber coverts water into vapor that exits through the plurality of vapor infusion ports 2468 to inflate the inner balloon 2465 and contact the outer balloon 2460 proximate an area of ablation. An ablation zone or hot zone is created at the area of contact between the inner balloon 2465 and the outer balloon 2460, such that thermal energy from the inner balloon 2465 passes through the outer balloon 2460 to the area of ablation. The elongate body 2412 and portions of the outer balloon 2460, excluding the hot zone, remain cool owing to the circulating cooling fluid.

Figure 24G:
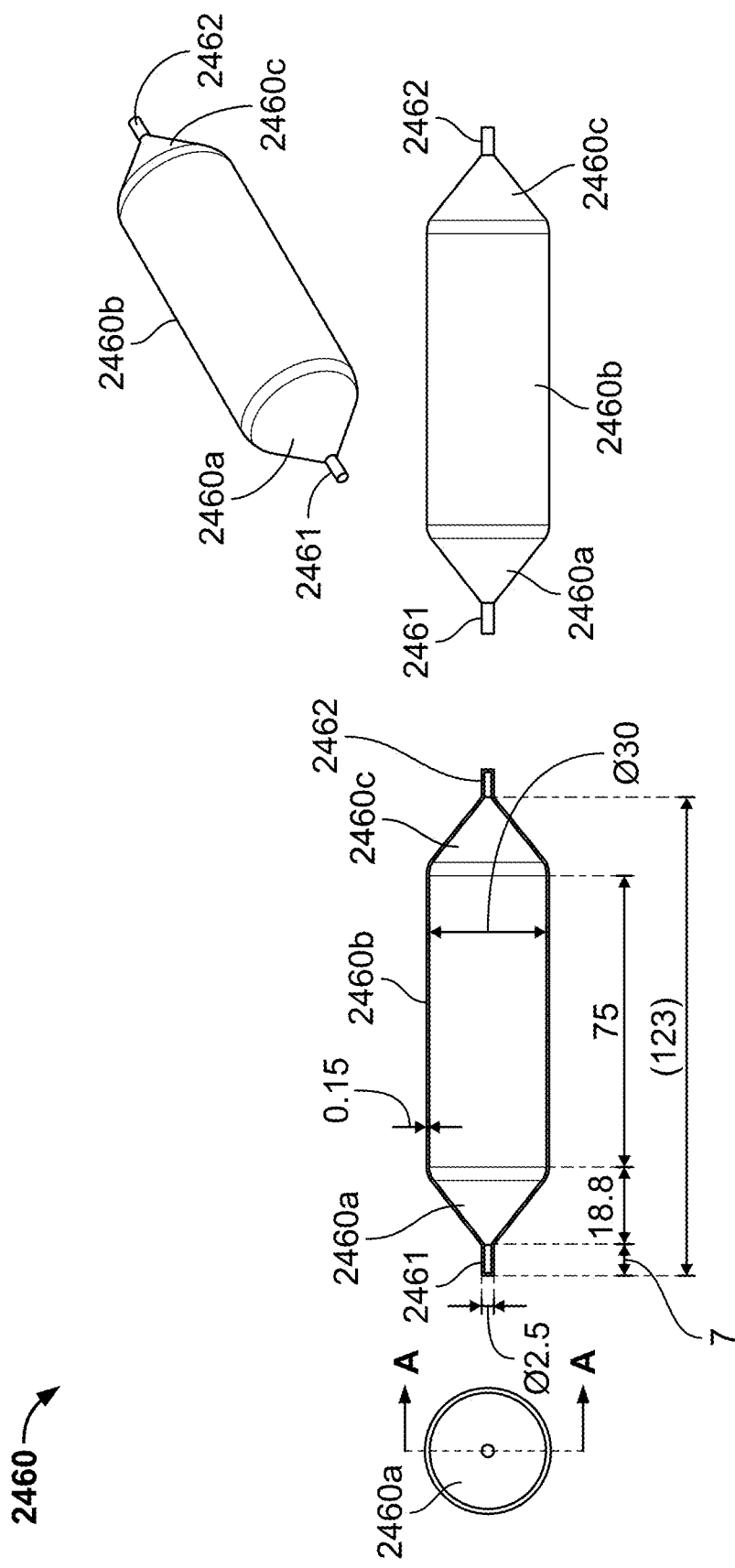
FIG. 24G illustrates transverse and various perspective views of an outer balloon of the catheter of FIG. 24A, in accordance with some embodiments of the present specification.

Referring to a transverse view and various perspective views of FIG. 24G, in an embodiment, the outer balloon 2460 has a compound shape (when in fully expanded state) comprising of a substantially cylindrical portion 2460b having substantially tapering or conical proximal and distal ends 2460a, 2460c. The ends extend into tube like structures 2461 and 2462, which help in keeping the catheter in place when it is passed through the balloon. In an embodiment, the outer balloon 2460 has a length of 123 mm between the tube like structures 2461 and 2462, the substantially cylindrical portion 2460b has a length of 75 mm and an outer diameter of 30 mm, each of the tube like structures 2461, 2462 has a length of 7 mm and an internal diameter of 2.5 mm, and each of the substantially tapering or conical ends 2460a, 2460c has a length of 18.8 mm. In one embodiment, the outer balloon 2460 is made up of a harder material relative to the inner balloon, such as PET, that has a thickness of 0.15 mm.

Figure 24H:
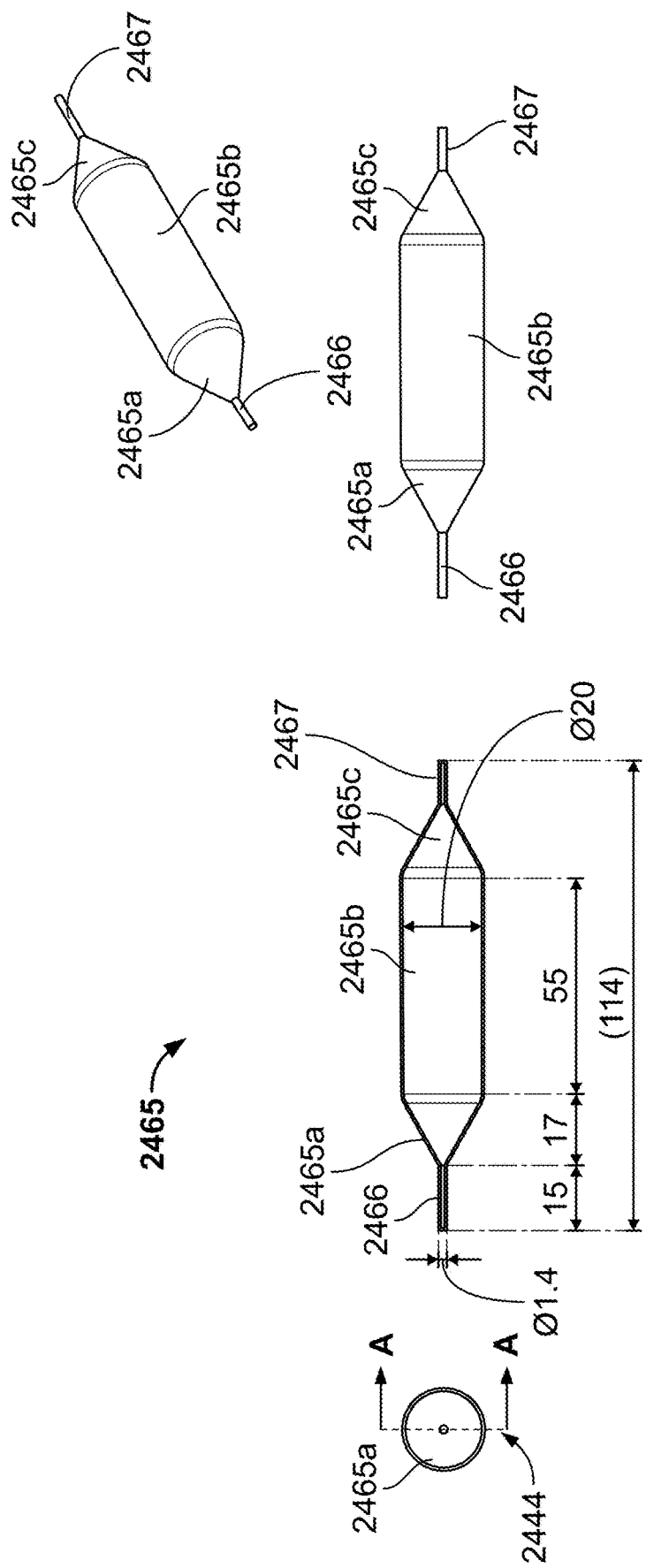
FIG. 24H illustrates transverse and various perspective views of an inner balloon of the catheter of FIG. 24A, in accordance with some embodiments of the present specification.

Referring to FIG. 24H, in an embodiment, the inner balloon 2465 has a compound shape (when in fully inflated state) comprising of a substantially cylindrical portion 2465b having substantially tapering or conical proximal and distal ends 2465a, 2465c (also shown in a side perspective view 2444 of the inner balloon 2465). The ends extend into tube like structures 2466 and 2467, which help in keeping the catheter in place when it is passed through the balloon. In an embodiment, the inner balloon 2465 has a length of 114 mm between the tube like structures 2466 and 2467, the substantially cylindrical portion 2465b has a length of 55 mm and a diameter of 20 mm, each of the tube like structures 2466, 2467 has a length of 15 mm and a diameter of 1.4 mm, and each of the substantially tapering or conical ends 2465a, 2465c has a length of 17 mm. In one embodiment, the inner balloon 2465 is made up of a more flexible material relative to the outer balloon, such as latex.

In some embodiments, the inner balloon 2465 is movable along a portion of the inner catheter 2416 within the outer balloon 2460 to better position the inner balloon within the outer balloon and ensure proper contact of the inner balloon with the outer balloon, using a wire mechanism in a handle at the proximal end of the catheter 2410.

Figure 24I:
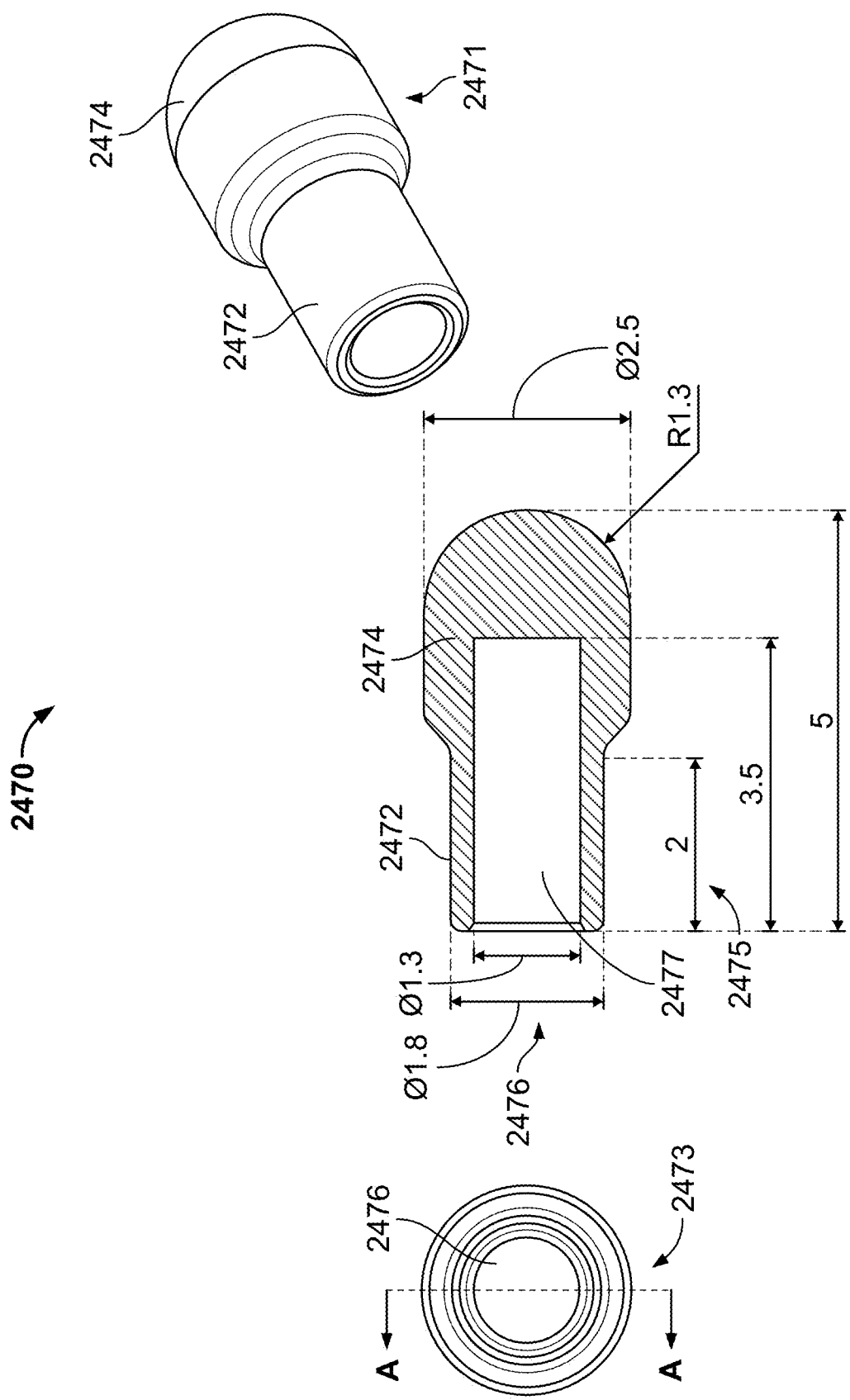
FIG. 24I illustrates an angular perspective view, a side perspective view and a longitudinal cross-sectional view of a bulbous or olive tip, in accordance with an embodiment of the present specification.

In an embodiment, the distal end of the elongate body 2412 has a bulbous tip 2470 which may have an oval or olive-shaped tip (olive-tip) to make the distal end relatively atraumatic to tissues when the catheter 2410 is introduced into a body lumen. FIG. 24I illustrates an angular perspective view 2471, a side perspective view 2473 and a longitudinal cross-sectional view 2475 of the bulbous or olive tip 2470, in accordance with an embodiment of the present specification. The tip 2470 has a proximal substantially cylindrical portion 2472 that leads to a substantially oval or olive distal portion 2474. The cylindrical portion 2472 has an opening 2476, at a proximal end, leading to a cylindrical pathway 2477 that accommodates a portion of the distal end of the catheter 2410 (that is, the distal end of the inner catheter 2416) when the tip 2470 is mounted on the distal end of the catheter 2410.

In an embodiment, a total length of the oval or olive tip 2470 is 5 mm. In an embodiment, the proximal substantially cylindrical portion 2472 has an outer diameter of 1.8 mm and a length of 2 mm. In an embodiment, the opening 2476 has a diameter of 1.3 mm and the cylindrical pathway 2477 has a length of 3.5 mm. In an embodiment, the substantially oval or olive distal portion 2474 has a width of 2.5 mm and a radius of 1.3 mm.

In some embodiments, a mapping member, which may be a distal extension, catheter, or any substrate comprising a plurality of sensors, detectors, or electrodes, is attached to the distal end of the body 2412 distal to the outer balloon 2460. The mapping member maps the area of cardiac tissue responsible for the arrhythmia. In some embodiments, the mapping member has a length of up to 75 mm. In some embodiments, the mapping member is pre-shaped in a pig-tail shape or a lasso-loop shape to allow wall contact. In embodiments, the diameter of the pigtail is between 5 mm and 25 mm. In some embodiments, the mapping member comprises 1 to 8 electrodes configured to record signals from a pulmonary vein or pacing in a pulmonary vein.

In some embodiments, the outer balloon 2460 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 2460 includes up to 24 mapping electrodes. In embodiments, the mapping electrodes measure cardiac electrical activity to assess at least one therapeutic endpoint.

In some embodiments, an entire surface of the catheter 2410, including the balloons 2460, 2465, oval or olive tip 2470, mapping electrodes and the mapping member, is coated with heparin.

Figure 25A:
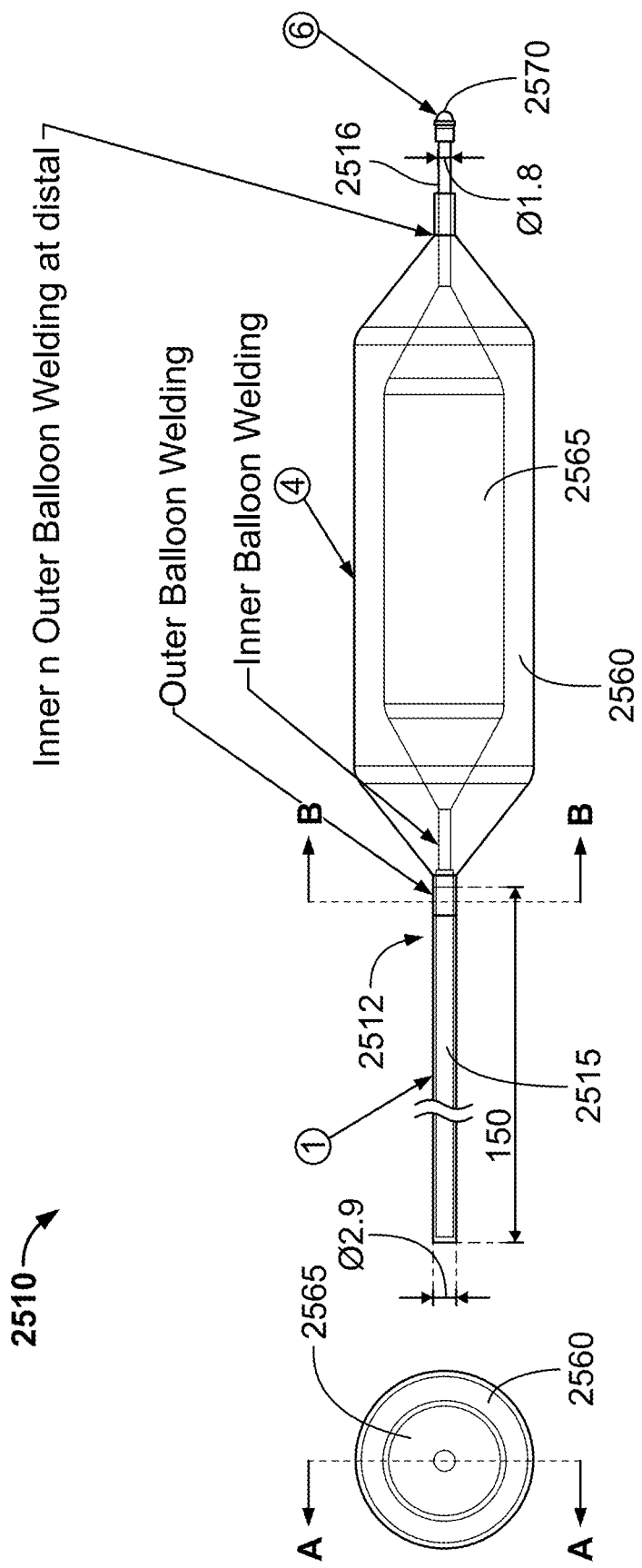
FIG. 25A illustrates longitudinal and transverse perspective views of a dual balloon cardiac ablation catheter, in accordance with some embodiments of the present specification.
Figure 25B:
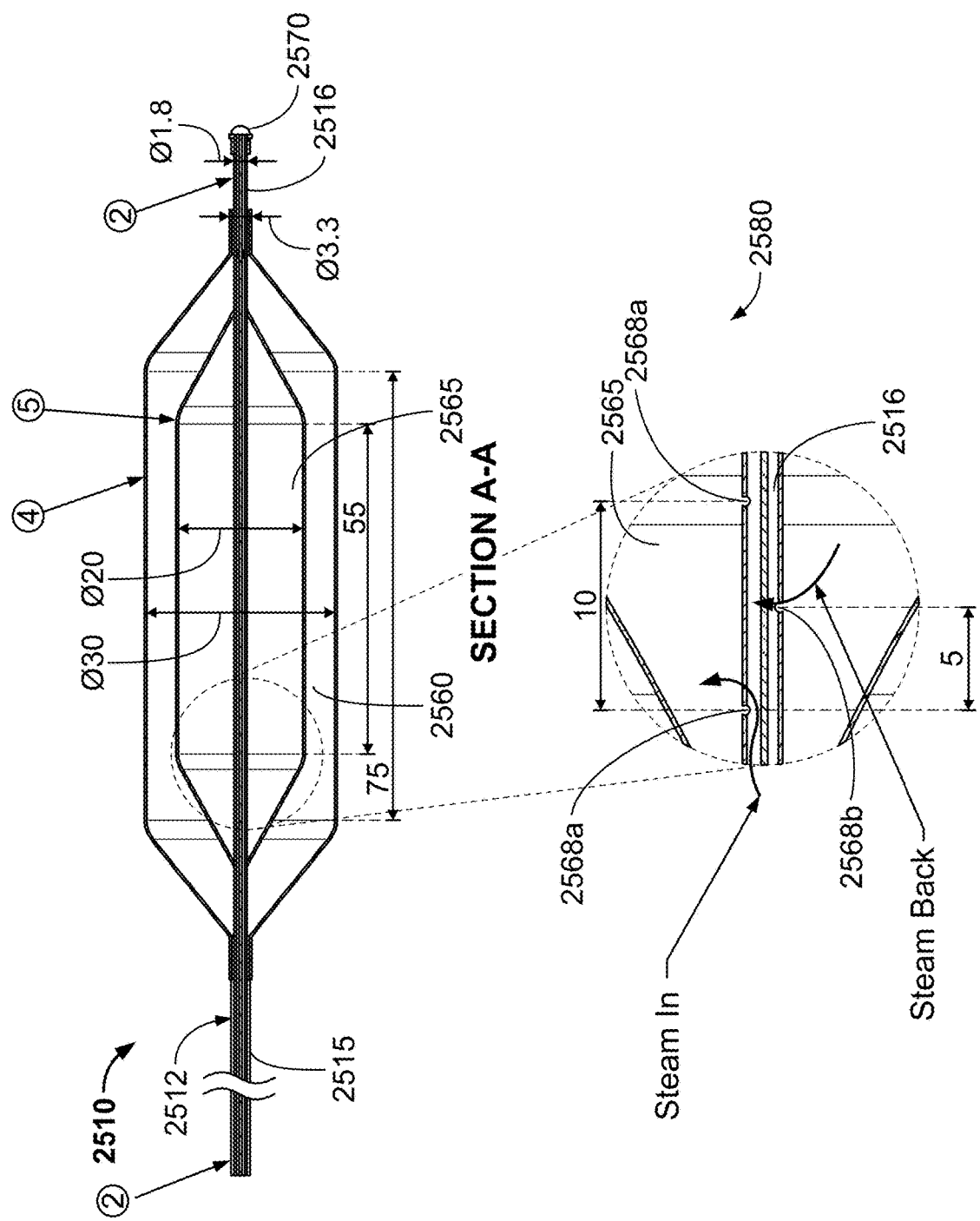
FIG. 25B illustrates a longitudinal cross-sectional view along with an enlarged view of a portion of the catheter of FIG. 25A, in accordance with some embodiments of the present specification.
Figure 25C:
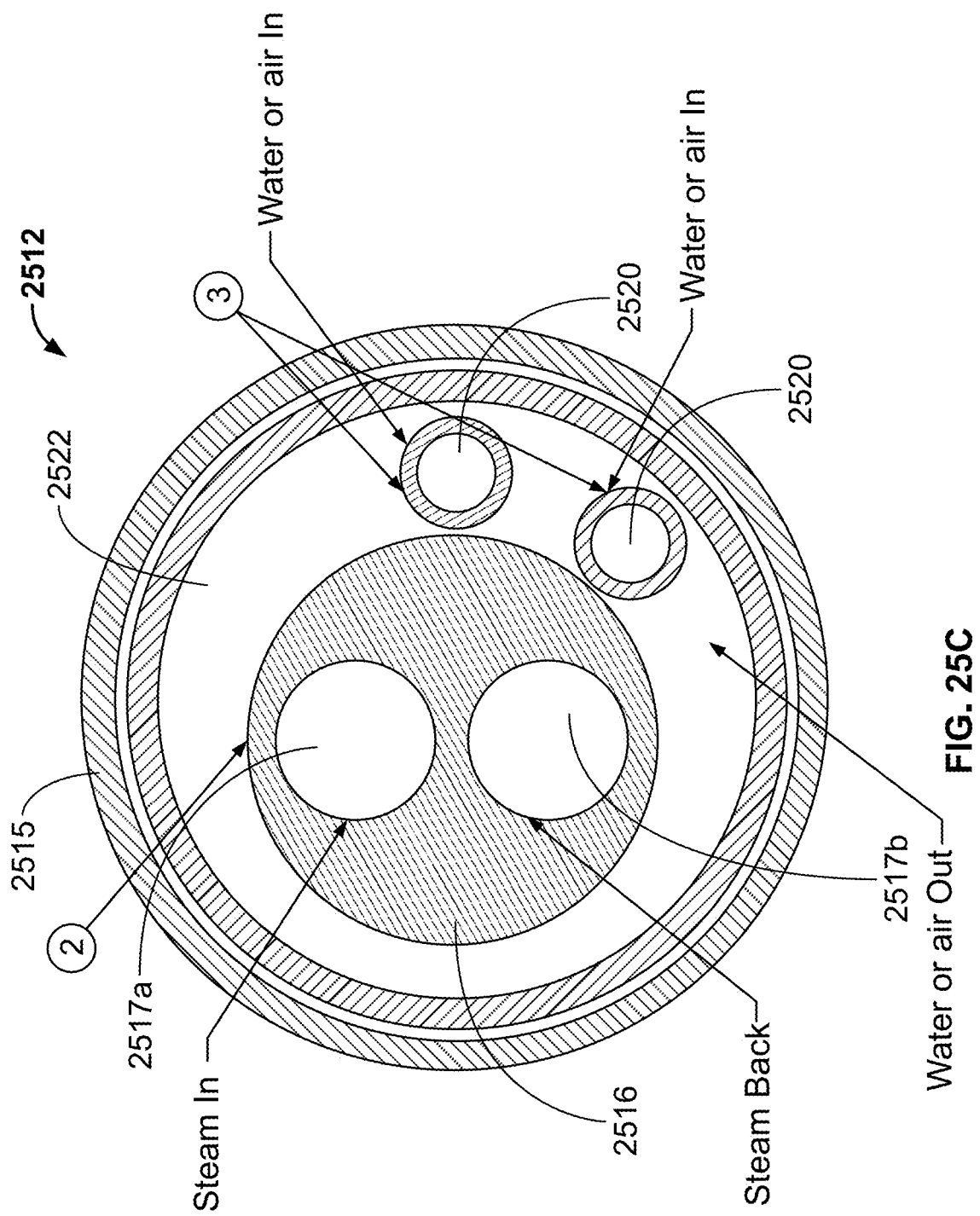
FIG. 25C illustrates a transverse cross-sectional view of an elongate body of the catheter of FIG. 25A, in accordance with some embodiments of the present specification.

FIG. 25A illustrates longitudinal and transverse perspective views of a dual balloon cardiac ablation catheter 2510, FIG. 25B illustrates a longitudinal cross-sectional view along with an enlarged view of a portion of the catheter 2510 and FIG. 25C illustrates a transverse cross-sectional view of an elongate body 2512 of the catheter, in accordance with some embodiments of the present specification. Referring to FIGS. 25A, 25B and 25C simultaneously, unless otherwise mentioned specifically, the elongate body 2512 has a proximal end, a distal end and a plurality of lumens.

In one embodiment, the elongate body 2512 includes an outer catheter 2515 having a lumen and an inner catheter 2516 having a first water/vapor infusion lumen 2517a and a second vapor suction lumen 2517b. In some embodiments, the first and second vapor lumens 2517a, 2517b are diametrically opposite to each other. The inner catheter 2516 is positioned within the lumen of the outer catheter 2515 so as to form a cooling fluid suction pathway 2522 between the two catheters 2515, 2516. The cooling fluid suction pathway 2522 accommodates first and second cooling fluid infusion tubes 2520.

The first and second cooling fluid infusion tubes 2520 and the cooling fluid suction pathway 2522 are in fluid communication with an inflatable outer balloon 2560 attached to the distal end of the catheter 2510. In embodiments, distal ends of the outer catheter 2515 and of the first and second cooling fluid infusion tubes 2520 lie or terminate at a proximal end of the outer balloon 2560 whereas a distal end of the inner catheter 2516 projects beyond a distal end of the outer balloon 2560. In embodiments, the cooling fluid is water, air or carbon-dioxide. During operation, the cooling fluid enters the first and second cooling fluid infusion tubes 2520 from the proximal end of the catheter 2510 and exits through the cooling fluid suction pathway 2522 from the proximal end of the catheter 2510 after circulating through the outer balloon 2560. The cooling fluid is circulated through the catheter 2510 and the outer balloon 2560 using a cooling fluid pump which is in data communication with, and controlled by, a controller.

The first water/vapor infusion lumen 2517a is in fluid communication, via a plurality of vapor infusion ports 2568a, with an inflatable inner balloon 2565 attached to the distal end of the catheter 2510 and positioned within the outer balloon 2560. The second vapor suction lumen 2517b is also in fluid communication with the inflatable inner balloon 2565 via a plurality of vapor suction ports 2568b. In some embodiment, suction of the vapor suction ports 2568b is controlled by a pressure sensor controlled external pump or by a self-opening pressure valve. In some embodiments, the plurality of vapor infusion and suction ports 2568a, 2568b are located along a portion of the inner catheter 2516 lying within the inner balloon 2565.

Figure 25E:
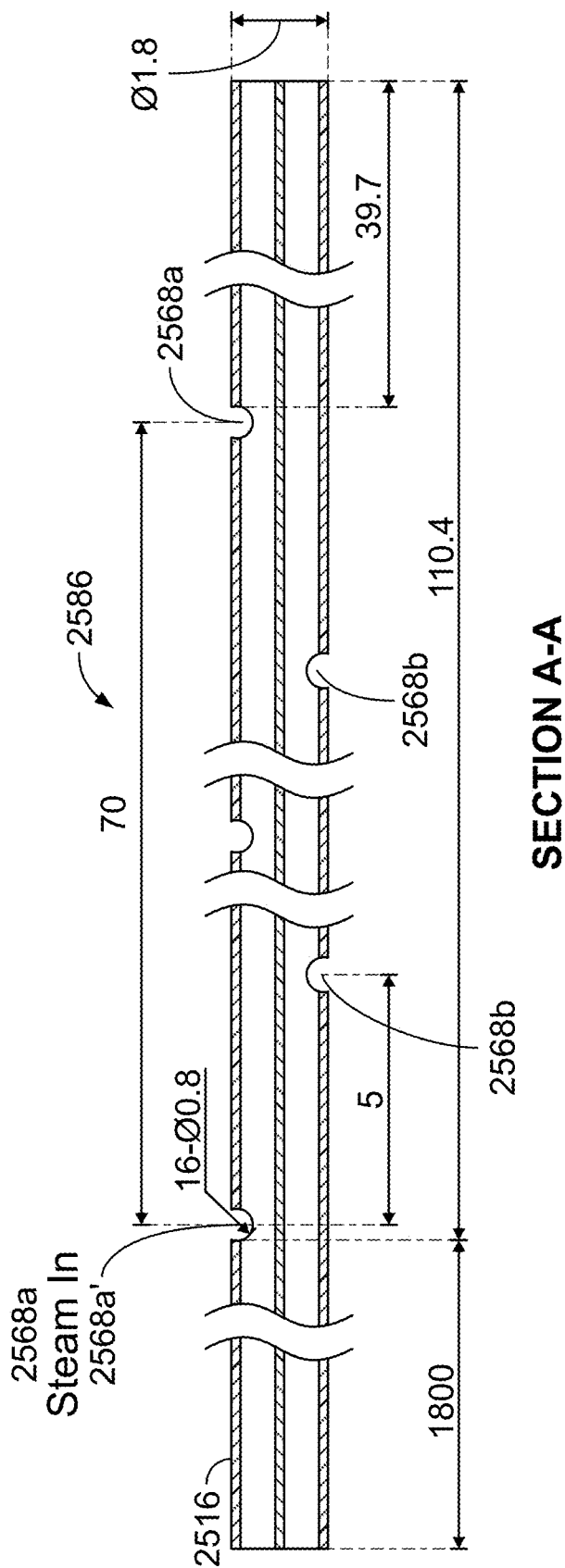
FIG. 25E illustrates transverse and longitudinal cross-sectional views of an inner catheter of the catheter of FIG. 25A, in accordance with some embodiments of the present specification.
Figure 25E:
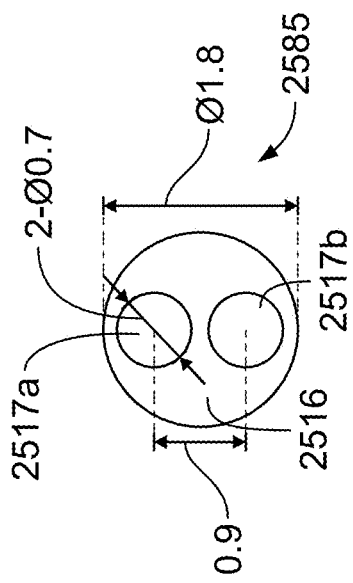

As shown in transverse cross-sectional, longitudinal cross-sectional and perspective views of FIG. 25D, in some embodiments, the outer catheter 2515 has a length of 1800 mm, an inner diameter of 2.6 mm and an outer diameter of 2.9 mm. In some embodiments, as shown in a transverse cross-sectional view 2585 of FIG. 25E, the inner catheter 2516 has an outer diameter of 1.8 mm, the centers of the first and second vapor lumens 2517a, 2517b are separated by a distance of 0.9 mm and the internal diameter of each of the first and second vapor lumens 2517a, 2517b is 0.7 mm. In some embodiments, as shown in the longitudinal cross-sectional view 2586 of FIG. 25E, the inner catheter 2516 has a length of 1910.4 mm.

In some embodiments, seven vapor infusion ports 2568a are located on the inner catheter 2516 along the first water/vapor infusion lumen 2517a wherein each port 2568a has a diameter of 0.8 mm. In some embodiments, a proximal port 2568a' is located at a distance of 1800 mm from a proximal end of the inner catheter 2516 and at a distance of 110.4 mm from a distal end of the inner catheter 2516. In some embodiments, as also shown in an enlarged view 2580 of FIG. 25B, the plurality of vapor infusion ports 2568a are spaced by a distance of 10 mm from each other. In some embodiments, six vapor suction ports 2568b are located on the inner catheter 2516 along the second vapor suction lumen 2517b wherein each port 2568b has a diameter of 0.8 mm. In some embodiments, as also shown in an enlarged view 2580 of FIG. 25B, the plurality of vapor infusion ports 2568a are spaced by a distance of 10 mm from each other and the plurality of vapor suction ports 2568b are also spaced by a distance of 10 mm from each other. Also, in some embodiments, each of the vapor suction ports 2568b is located at a distance of 5 mm from an immediately preceding and an immediately successive vapor infusion port 2568a.

Figure 25F:
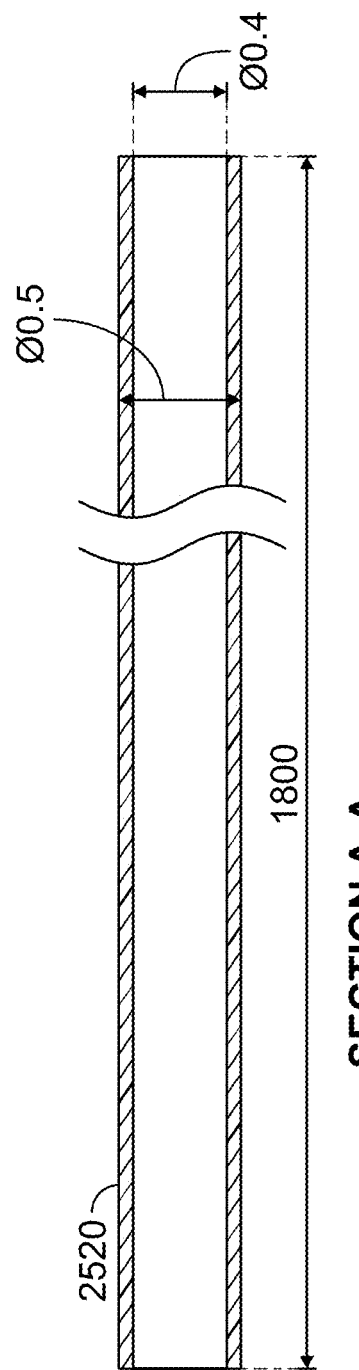
FIG. 25F illustrates transverse and longitudinal cross-sectional views of a cooling tube of the catheter of FIG. 25A, in accordance with some embodiments of the present specification.
Figure 25F:
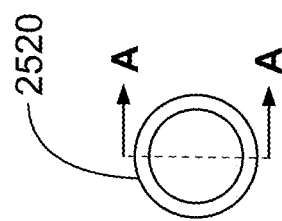

As shown in transverse and longitudinal cross-sectional views of FIG. 25F, in some embodiments, each of the first and second cooling fluid infusion tubes 2520 has a length of 1800 mm, an inner diameter of 0.4 mm and an outer diameter of 0.5 mm.

In some embodiments, at least one flexible heating chamber (such as those described with reference to FIGS. 19A through 19D), comprising a plurality of electrodes, is positioned in-line within the first water/vapor infusion lumen 2517a. In some embodiments, the at least one flexible heating chamber is positioned in-line within the first water/vapor infusion lumen 2517a such that the plurality of electrodes are at least partially inside the inner balloon 2565. During operation, a water/vapor pump which is also in data communication with, and controlled by, the controller pumps water from a sterile water reservoir through the water/vapor lumen 2517a to enter a proximal end of the at least one flexible heating chamber. The at least one flexible heating chamber coverts water into vapor that exits through the plurality of vapor infusion ports 2568a to inflate the inner balloon 2565 and contact the outer balloon 2560 proximate an area of ablation. An ablation zone or hot zone is created at the area of contact between the inner balloon 2565 and the outer balloon 2560, such that thermal energy from the inner balloon 2565 passes through the outer balloon 2560 to the area of ablation. The elongate body 2512 and portions of the outer balloon 2560, excluding the hot zone, remain cool owing to the circulating cooling fluid. For deflation, vapor is suctioned out of the inner balloon 2565 through the plurality of vapor suction ports 2568b and via the second vapor suction lumen 2517b.

Figure 25G:
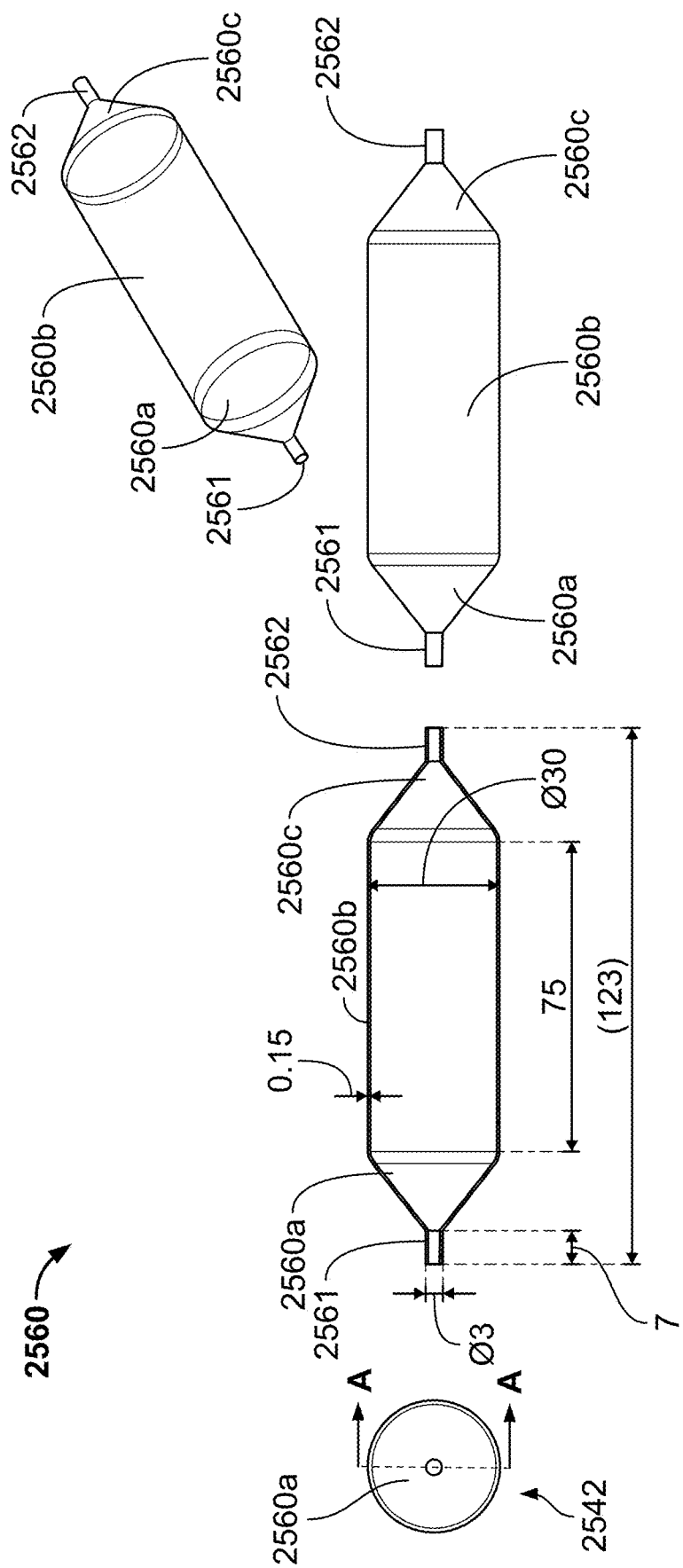
FIG. 25G illustrates transverse and various perspective views of an outer balloon of the catheter of FIG. 25A, in accordance with some embodiments of the present specification.

Referring to side and various perspective views of FIG. 25G, in an embodiment, the outer balloon 2560 has a compound shape (when in fully expanded state) comprising of a substantially cylindrical portion 2560b having substantially tapering or conical proximal and distal ends 2560a, 2560c (shown in side perspective view 2542 of the outer balloon 2560 in FIG. 25G). The ends extend into tube like structures 2561 and 2562, which help in keeping the catheter in place when it is passed through the balloon. In an embodiment, the outer balloon 2560 has a length of 123 mm between the tube like structures 2561 and 2562, the substantially cylindrical portion 2560b has a length of 75 mm and an outer diameter of 30 mm, each of the tube like structures 2561, 2562 has a length of 7 mm and an internal diameter of 3 mm, and each of the substantially tapering or conical ends 2560a, 2560c has a length of 7 mm. In one embodiment, the outer balloon 2560 is made up of a harder material relative to the inner balloon, such as PET, that has a thickness of 0.15 mm.

Figure 25H:
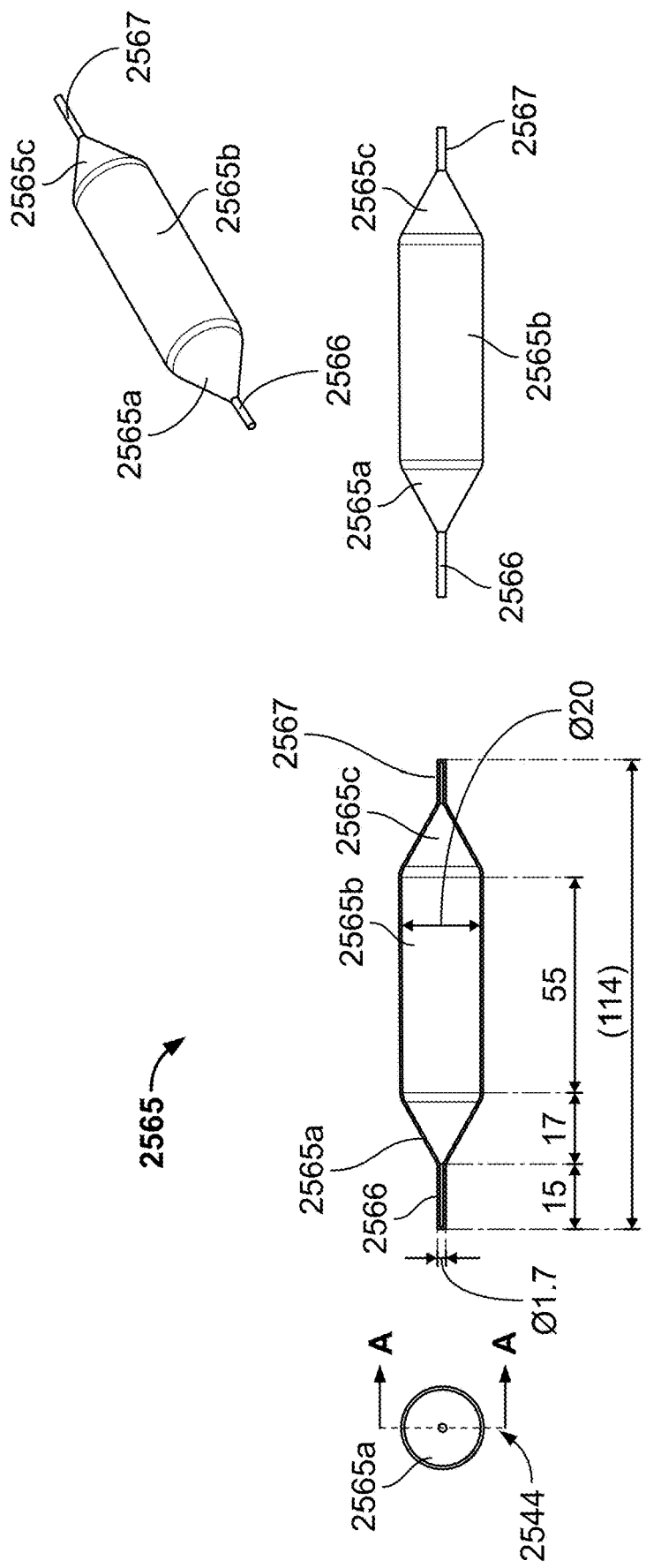
FIG. 25H illustrates transverse and various perspective views of an inner balloon of the catheter of FIG. 25A, in accordance with some embodiments of the present specification.

Referring to side and various perspective views of FIG. 25H, in an embodiment, the inner balloon 2565 has a compound shape (when in fully inflated state) comprising of a substantially cylindrical portion 2565b having substantially tapering or conical proximal and distal ends 2565a, 2565c (also shown in a side perspective view 2544 of the inner balloon 2565). The ends extend into tube like structures 2566 and 2567, which help in keeping the catheter in place when it is passed through the balloon. In an embodiment, the inner balloon 2565 has a length of 114 mm between the tube like structures 2566 and 2567, the substantially cylindrical portion 2565b has a length of 55 mm and a diameter of 20 mm, each of the tube like structures 2566, 2567 has a length of 15 mm and a diameter of 1.7 mm, and each of the substantially tapering or conical ends 2565a, 2565c has a length of 17 mm. In one embodiment, the inner balloon 2565 is made up of a more flexible material relative to the outer balloon, such as latex.

In some embodiments, the inner balloon 2565 is movable along a portion of the inner catheter 2516 within the outer balloon 2560 to better position the inner balloon within the outer balloon and ensure proper contact of the inner balloon with the outer balloon, using a wire mechanism in a handle at the proximal end of the catheter 2510.

Figure 25I:
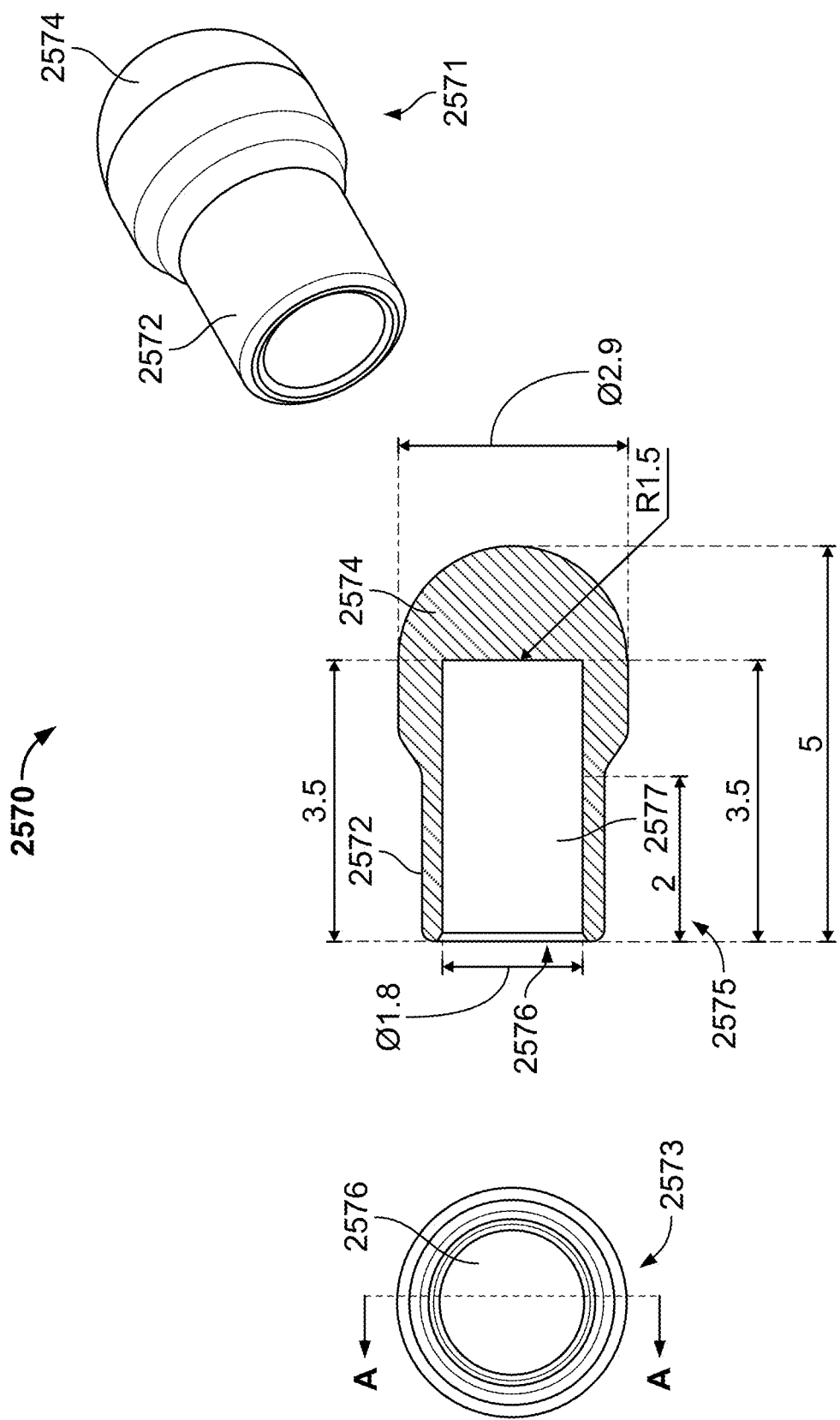
FIG. 25I illustrates an angular perspective view, a side perspective view and a longitudinal cross-sectional view of a bulbous or olive tip, in accordance with an embodiment of the present specification.

In an embodiment, the distal end of the elongate body 2512 has a bulbous tip 2570 which may have an oval or olive-shaped tip (olive-tip) to make the distal end relatively atraumatic to tissues when the catheter 2510 is introduced into a body lumen. FIG. 25I illustrates a perspective view 2571, a side perspective view 2573 and a longitudinal cross-sectional view 2575 of the bulbous or olive tip 2570, in accordance with an embodiment of the present specification. The tip 2570 has a proximal substantially cylindrical portion 2572 that leads to a substantially oval or olive distal portion 2574. The cylindrical portion 2572 has an opening 2576, at a proximal end, leading to a cylindrical pathway 2577 that accommodates a portion of the distal end of the catheter 2510 (that is, the distal end of the inner catheter 2516) when the tip 2570 is mounted on the distal end of the catheter 2510.

In an embodiment, a total length of the oval or olive tip 2570 is 5 mm. In an embodiment, the proximal substantially cylindrical portion 2572 has a length of 2 mm. In an embodiment, the opening 2576 has a diameter of 1.8 mm and the cylindrical pathway 2577 has a length of 3.5 mm. In an embodiment, the substantially oval or olive distal portion 2574 has a width of 2.9 mm and a radius of 1.5 mm.

In some embodiments, a mapping member, which may be a distal extension, catheter, or any substrate comprising a plurality of sensors, detectors, or electrodes, is attached to the distal end of the body 2512 distal to the outer balloon 2560. The mapping member maps the area of cardiac tissue responsible for the arrhythmia. In some embodiments, the mapping member has a length of up to 75 mm. In some embodiments, the mapping member is pre-shaped in a pig-tail shape or lasso-loop shape to allow wall contact. In embodiments, the diameter of the pigtail is between 5 mm and 25 mm. In some embodiments, the mapping member comprises 1 to 8 electrodes configured to record signals from a pulmonary vein or pacing in a pulmonary vein.

In some embodiments, the outer balloon 2560 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 2560 includes up to 24 mapping electrodes. In embodiments, the mapping electrodes measure cardiac electrical activity to assess at least one therapeutic endpoint. In one embodiment, eight equally spaced mapping electrodes are positioned in a circle encompassing the outer balloon 2560, forming a loop with a diameter of 20 mm.

In some embodiments, an entire surface of the catheter 2510, including the balloons 2560, 2565, oval or olive tip 2570, mapping electrodes and the mapping member, is coated with heparin.

Figure 25J:
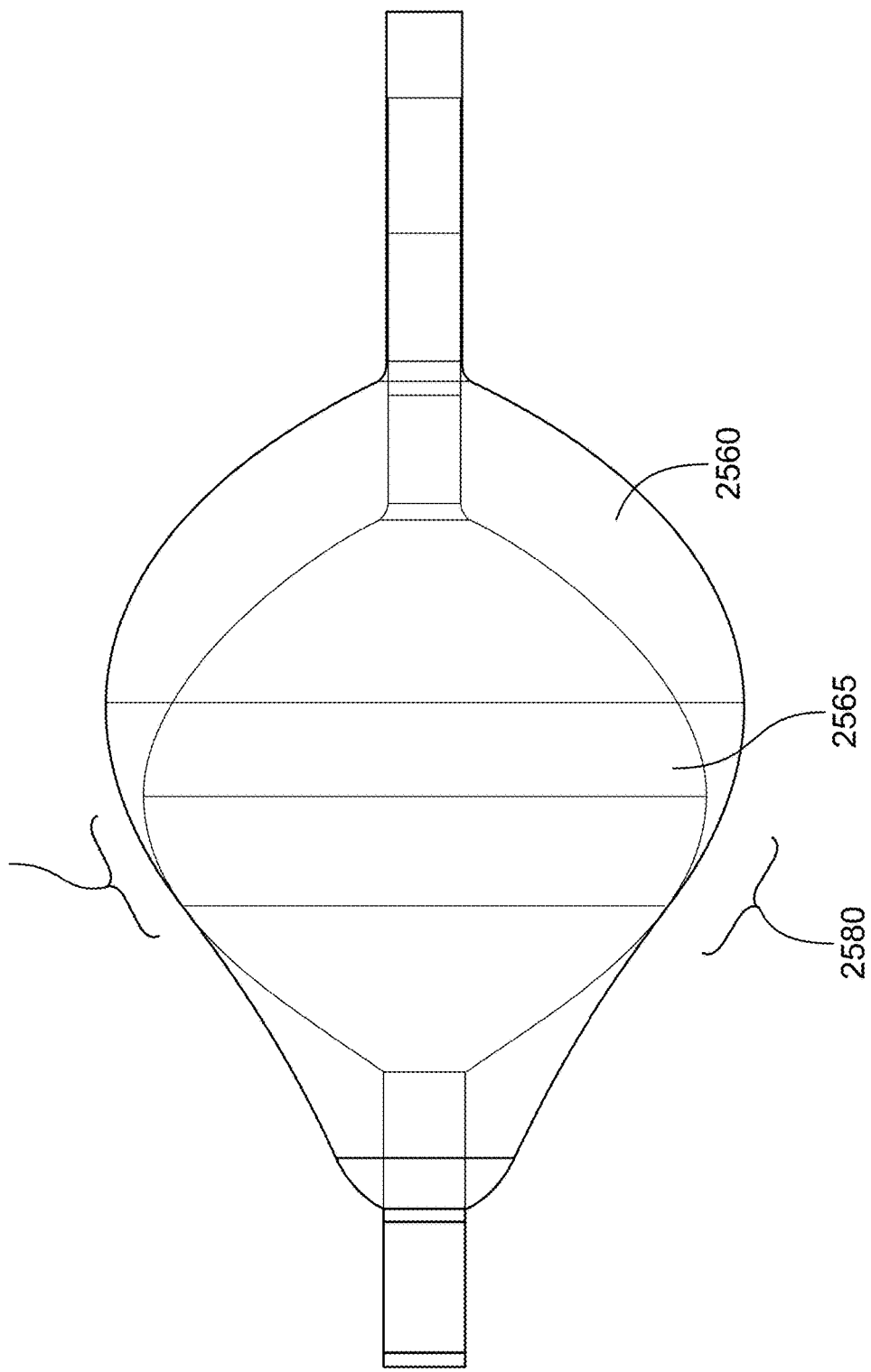
FIG. 25J illustrates when the inner balloon is inflated with vapor such that inner balloon comes into contact with desired portions or areas of the outer balloon, and the outer balloon comes into contact with a hot zone/area or ablation zone/area comprising target cardiac tissue, in accordance with some embodiments of the present specification.

Creation of a distinct ablation zone the size of which is preferably variable depending on the anatomy of the patient is one of the objectives of embodiments of the present specification. Another objective is the creation of a "transition" or "insulation" zone proximal and distal to the ablation zone. FIG. 25J illustrates when the inner balloon 2565 is inflated with vapor such that inner balloon 2565 comes into contact with desired portions or areas of the outer balloon 2560 to form a hot zone/area or ablation zone/area 2580 which is used to ablate the target cardiac tissue. Since the outer balloon 2560 configuration changes based on how it is pressed into the patient's pulmonary vein, the precise ablation zone 2580 configuration also changes, thereby molding itself to the patient's pulmonary vein and pulmonary vein ostial anatomy. More specifically, in accordance with the embodiments of the present specification, the outer balloon 2560 deforms to optimally contact the pulmonary vein and, based on that deformation, the inner balloon 2565 primarily contacts the outer balloon 2560 at the point of deformation, which is the location of the desired ablation. This is because, ablation with steam requires confining the heating to a specific anatomical area so that the heat does not go to adjacent structures or to blood causing complications. This concept creates a dynamic ablation zone which custom fits to individual patient's anatomy. FIGS. 25K and 25L illustrate exemplary double balloon embodiments with insulation regions identified as ablation zone 2580 defined by areas of contact 2580a and 2580b. The ablation zone 2580 may have circumferences corresponding to the anatomical size and shape of the patient's pulmonary vein. The ablation zone may vary based on the patient's anatomy. The non-contact areas or cold zones, between the inner 2565 and outer balloon 2560, are filled with air which act as insulation zones 2582a on the proximal side and 2582b on the distal side of the outer balloon 2560. In some embodiments, the insulation zone extends around the circumference of the area between inner 2565 and outer 2560 balloons for a width of about 0.1 mm. Further, in embodiments, the insulation zones 2582a and 2582b extend over a length of 1 mm to 20 mm. In some embodiments, the ablation zone 2580 covers an area of the outer balloon surface ranging from 1% to 99%, where the insulation zone correspondingly reduces from 99% to 1%. In some embodiments, the ablation zone 2580 covers an area of the outer balloon surface ranging from 5% to 95%, where the insulation zone correspondingly reduces from 95% to 5%.

The ablation zone 2580, defined by the area of contact of the inflated inner balloon 2565 with the outer balloon 2560 and therefore, the area of outer balloon 2560 contacting the patient's tissue, is an area where the blood cannot flow. In some embodiments, the ablation zone 2580 spreads within a width of 1 mm to 20 mm. The temperature of outer surface of the insulation zones 2582a and 2582b is less than the temperature of the ablation zone 2580. In accordance with the various embodiments of the present specification, a variable ablation zone 2580 is achieved, and is surrounded by an insulating zone 2582a and 2582b. The variable ablation zone 2580 provides for a better cross section fit within different patients' anatomies. The variable ablation zone 2580 also results in a variable insulation zone 2582a and 2582b. The variability is a result of the two balloons 2560 and 2565 having variable shape, size and durometer. As a result, the inner balloon 2565 is less compliant and keeps a relatively rigid shape while the outer balloon is more compliant and shapes to a patient's atrial and pulmonary vein anatomy. The interaction between the cardiac tissue, the compliant and easily deformed outer balloon and semi-compliant and rigid inner balloon results in a dynamic/variable ablation zone. Accordingly, the inner balloon has a degree of compliance that is less than the outer balloon's degree of compliance.

Optionally, the inner balloon 2565 'floats' within the outer balloon and axial force may be applied by a user through a guide sheath, further deforming the outer balloon and pushing the inner balloon 2565 in any orientation and creating the ablation zone 2580 where tissue contact is made by the outer balloon and the inner balloon intersection. Width of the ablation zone 2580 could be increased by increasing axial force transmitted via the guide sheath to the outer and the inner balloons. Additionally, the inner balloon can float relative to the outer balloon and guide sheath pressure can be used to move the inner balloon relative to the outer balloon.

FIG. 25L also illustrates a coated portion 2584 over inner balloon 2565 that acts as insulation within the insulation zones 2582a and 2582b, in accordance with an embodiment of the present specification. In some embodiments inner portions of the outer balloon 2560 are coated to provide insulation, instead of outer portion of the inner balloon 2565. In embodiments, the coating is a ceramic coating, such as for example parylene; or a gel coating. The coating is provided in areas that are likely to be the insulation zones 2582a and 2582b, and is absent from the ablation zone 2580.

In some embodiments, a membrane thickness of either or both inner 2565 and outer 2560 balloons is variable along its circumferential length along its longitudinal axis. FIG. 25M illustrates an exemplary embodiment of a double balloon configuration where the outer balloon 2563 has a thicker membrane 2584, 2587 along insulation zones 2583a and 2583b, and is relatively thinner along the ablation zone 2581 where heat transfer is required, so as to create a relative degree of insulation.

Figure 25N:
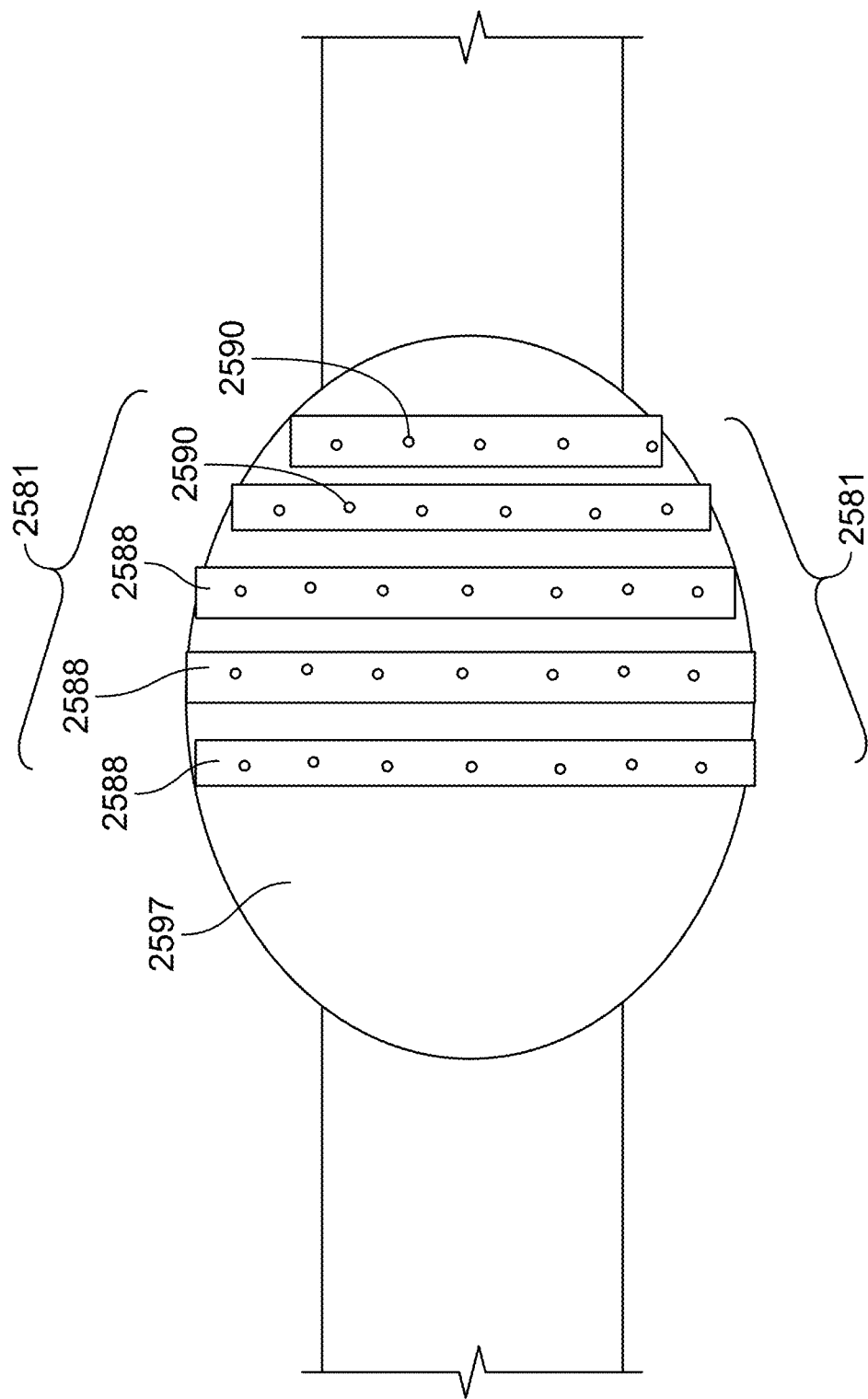
FIG. 25N illustrates a double balloon embodiment with at least one of the two balloons comprising multiple discrete channels going around its circumference, in accordance with the present specification.

FIG. 25N illustrates double balloon embodiment with at least one of the two balloons 2560' comprising multiple discrete channels 2588 extending around its circumference, in accordance with the present specification. Balloon 2560' is either inner balloon such as balloon 2565 or outer balloon such as balloon 2560. Each channel 2588 is connected to a lumen through which the steam passes. In some embodiments, the channels 2588 are connected through a valve to the lumens. Once balloon 2560' is positioned in the right location, radiopaque markers 2590 are used around its surface to determine which channel 2588 is in best contact with a target surface for ablation. Once the optimum channel is identified, an appropriate valve may be opened to the identified channel and steam is sent through that channel, thereby ablating the target surface.

In alternative embodiments, insulation, such as insulation zone 2582a and 2582b is created by various means. In one method, an air gap is provided by adhering a patched membrane or foam, or any other material, to the outer surface of the inner balloon 2565 or the inner surface of the outer balloon 2560. In another embodiment, insulation is facilitated with the use of insulated pockets over a surface of the inner balloon 2565.

Figure 25O:
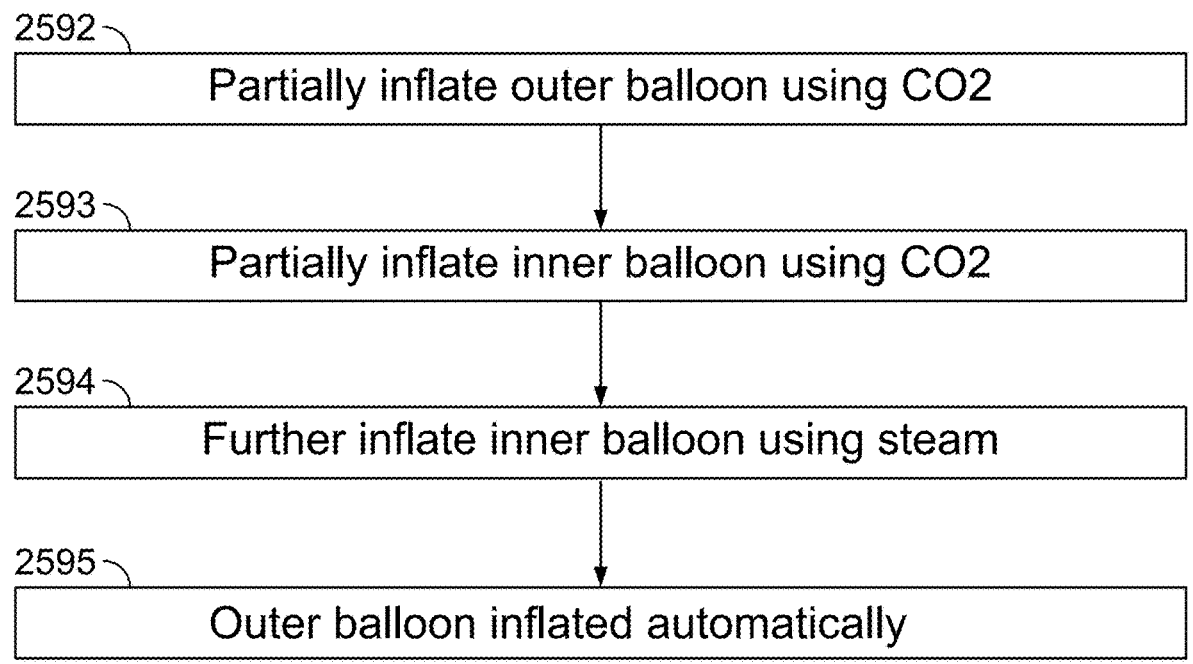
FIG. 25O is a flow chart illustrating an exemplary protocol for inflating a double balloon ablation device, in accordance with some embodiments of the present specification.

FIG. 25O is a flow chart illustrating an exemplary protocol for inflating a double balloon ablation device, in accordance with some embodiments of the present specification. First at 2592, an outer balloon, such as balloon 2560, is partially inflated using a little amount of Carbon dioxide ($CO_2$). In an embodiment, the outer balloon is inflated to a volume of approximately 30 cubic centimeter (cc) with $CO_2$. Then, at 2593, an inner balloon, such as balloon 2565, is partially inflated using $CO_2$, which is a part of its priming function. At 2594, the inner balloon is further inflated using steam. In some embodiments, creating the steam uses up to 15 cc of saline. Inflating the inner balloon with steam automatically inflates the outer balloon at 2595. As the outer balloon inflates, it serves to push blood out of the way proximally and distally from an ablation zone. In some embodiments, the outer balloon surface inflates to a diameter in a range of 20 mm to 100 mm.

Pressure is regulated in the inflated balloons using pressure valves in the outflow channel connected to the inner balloon and the outflow channel connected to the outer balloon. In embodiments, the pressure is maintained between 0 psi and 50 psi in both the outer and the inner balloons. In some embodiments, a check valve (self-opening valve) is in the outflow channel coming from the outer balloon and set at a Pound-force per Square Inch (psi) value in a range of 0 to 5 psi. In some embodiments, another check valve (self-opening valve) is in the outflow channel coming from the inner balloon and set at a psi value in a range of 0.5 to 10. In some embodiments, the outer balloon valve opens between a pressure of 0 to 1.0 psi. In some embodiments, the inner balloon pressure is released above 2.0 to 3.0 psi. The ratio of volume maintained for the inner balloon and the outer balloon is dynamic, and is controlled by controlling the pressure in the balloons. In some embodiments, the outer balloon is inflated first to a maximum volume, the inner balloon is "primed", and then steam is created. The outer balloon volume does not change as steam is created, due to the pressure valve control, while the inner balloon volume increases to 100% of its volume, which, in some embodiments, equals approximately 40% of the volume of the outer balloon. The check valves serve to automatically control pressure in the balloons. In some embodiments, the pressure in the inner balloon is same as or greater than the pressure in the outer balloon. Therefore, the pressure remains within its pre-defined range, otherwise the check valve opens. In alternative embodiments, an active pressure management system, such as suction, is used to regulate the pressure.

In order to achieve optimal heat tolerance, inflation, and compliance, it is important to use an appropriate material for manufacturing the outer and inner balloons. If the softening temperature (Tg) of a balloon's material is too low, the balloon may deform during use when exposed to steam. For example, the Tg of PET is 75° C. This means that after just one use, the PET balloon may deform and may not be useable for conducting additional ablation shots of a given PV or of other PVs in the patient. Therefore, it is desirable to use a material that has a Tg greater than 100° C. to be functional. In embodiments, there are two balloons, where each balloon has a different Tg value. In embodiments, the Tg value of each balloon is within a range of 60° C. to about 200° C. In some embodiments, the Tg is 80° C. In some embodiments, the Tg is 150° C.

It is also desirable to use a material that has a sufficiently wide elasticity range at various operating temperatures. If the elasticity range is too low, the yield point is passed during operation and the balloon deforms such that the ablation zone may not be properly positioned during operation. In embodiments, thermo-plastic copolyester material such as those provided by Arnitel, may be used, which has a Tg of about 150° C.

In embodiments, material of the inner balloon is semi-compliant, implying that the material eliminates any folds that may have been present during packaging, and conforms to atrial anatomy for better contact. A compliant balloon is likely to have a fixed volume at a fixed pressure. It is desirable that material of the inner balloon is more rigid than that of the outer balloon, so as to maintain a certain shape and is not easily deformed by pressing against cardiac tissue. Some of the semi-compliant balloon materials, for example PEBA families, face mechanical and thermal challenges when introduced to steam. Therefore, one possible balloon material is a copolymer called Arnitel. Arnitel is also relatively semi-compliant but has higher softening and melt temperatures versus standard PEBA polymers. Materials such as Arnitel may be used to make the inner balloon and shaft applications, in accordance with the embodiments of the present specification. An advantage of using it as a shaft material is that it is thermally bondable with inner balloons currently made using PET, thereby eliminating the need to use an adhesive bonding process.

Figure 26A:
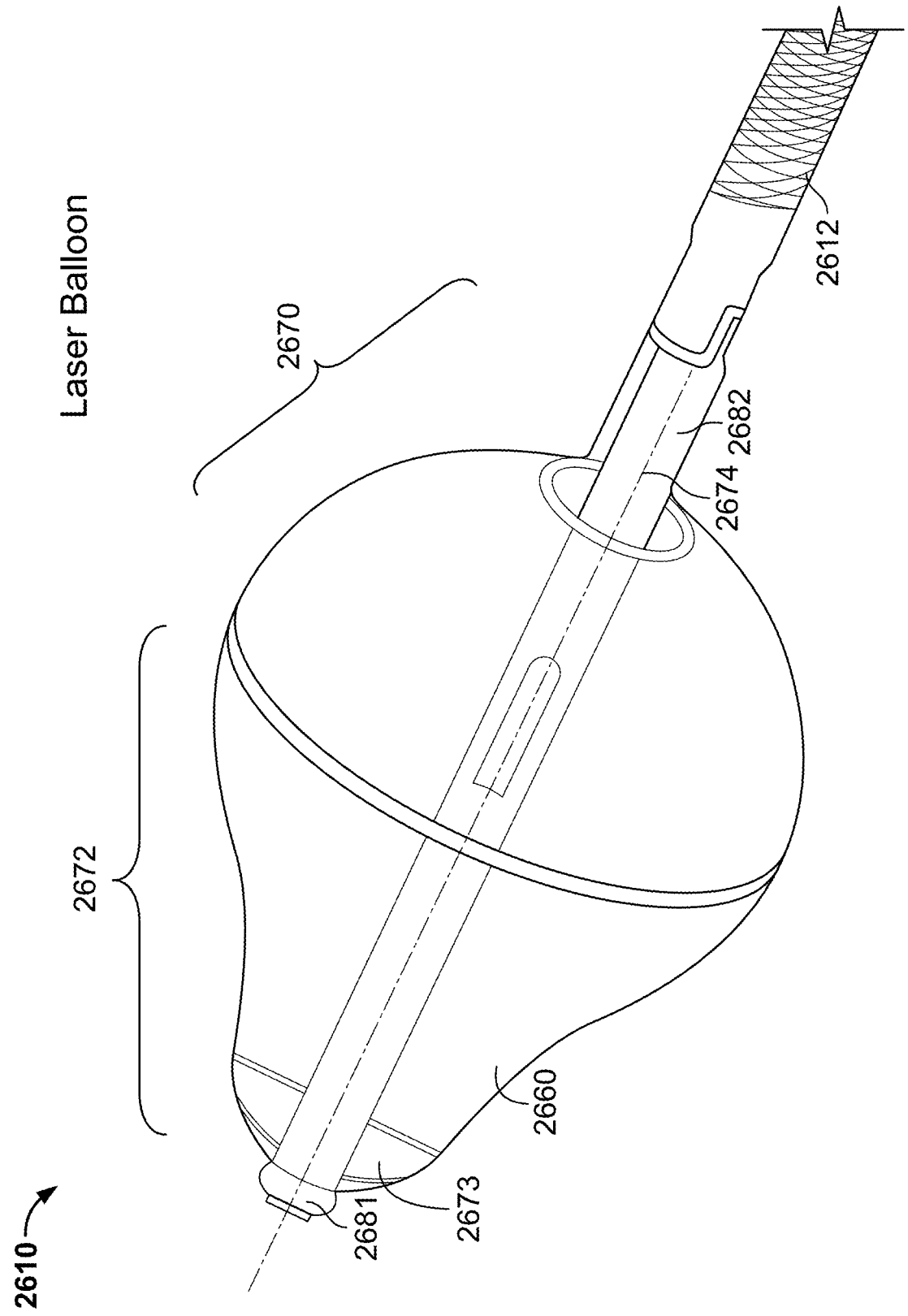
FIG. 26A illustrates a substantially pear shaped outer balloon of a dual balloon cardiac ablation catheter, in accordance with some embodiments of the present specification.
Figure 26B:
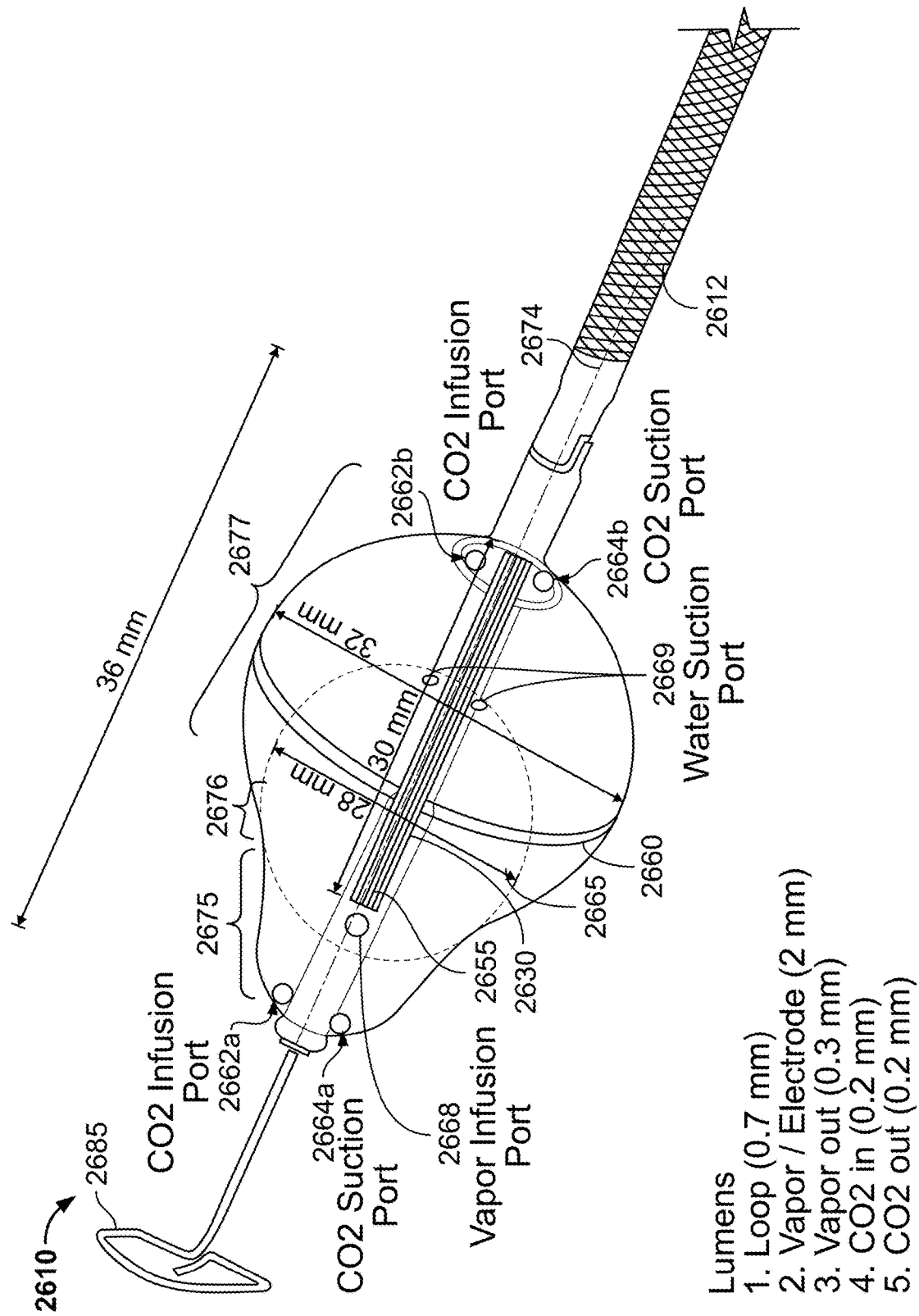
FIG. 26B illustrates a perspective view of a dual balloon cardiac ablation catheter having a substantially pear shaped outer balloon and a substantially spherical inner balloon, in accordance with some embodiments of the present specification.
Figure 26C:
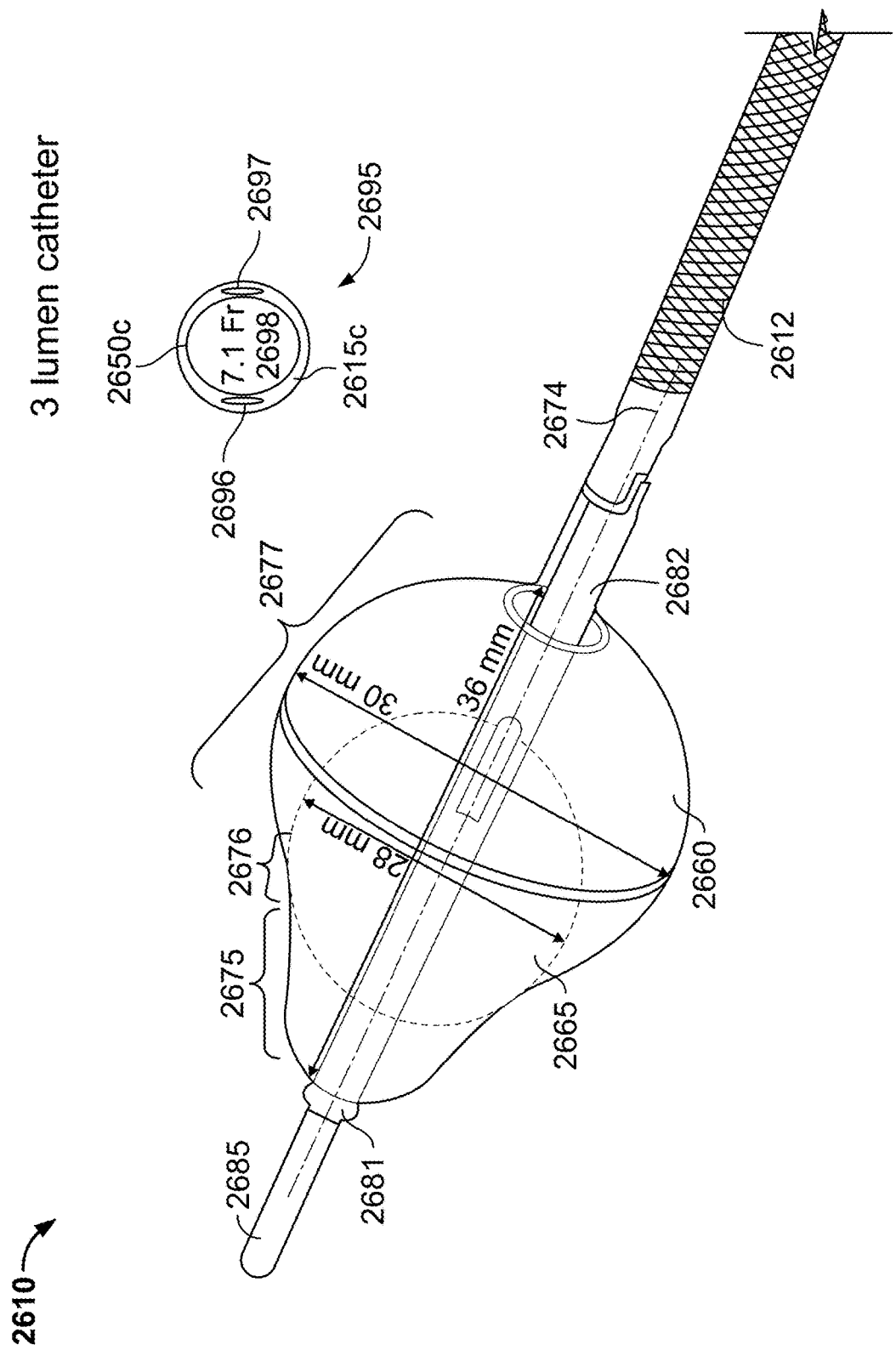
FIG. 26C illustrates another perspective view of the catheter of FIG. 26B, in accordance with some embodiments of the present specification.
Figure 26D:
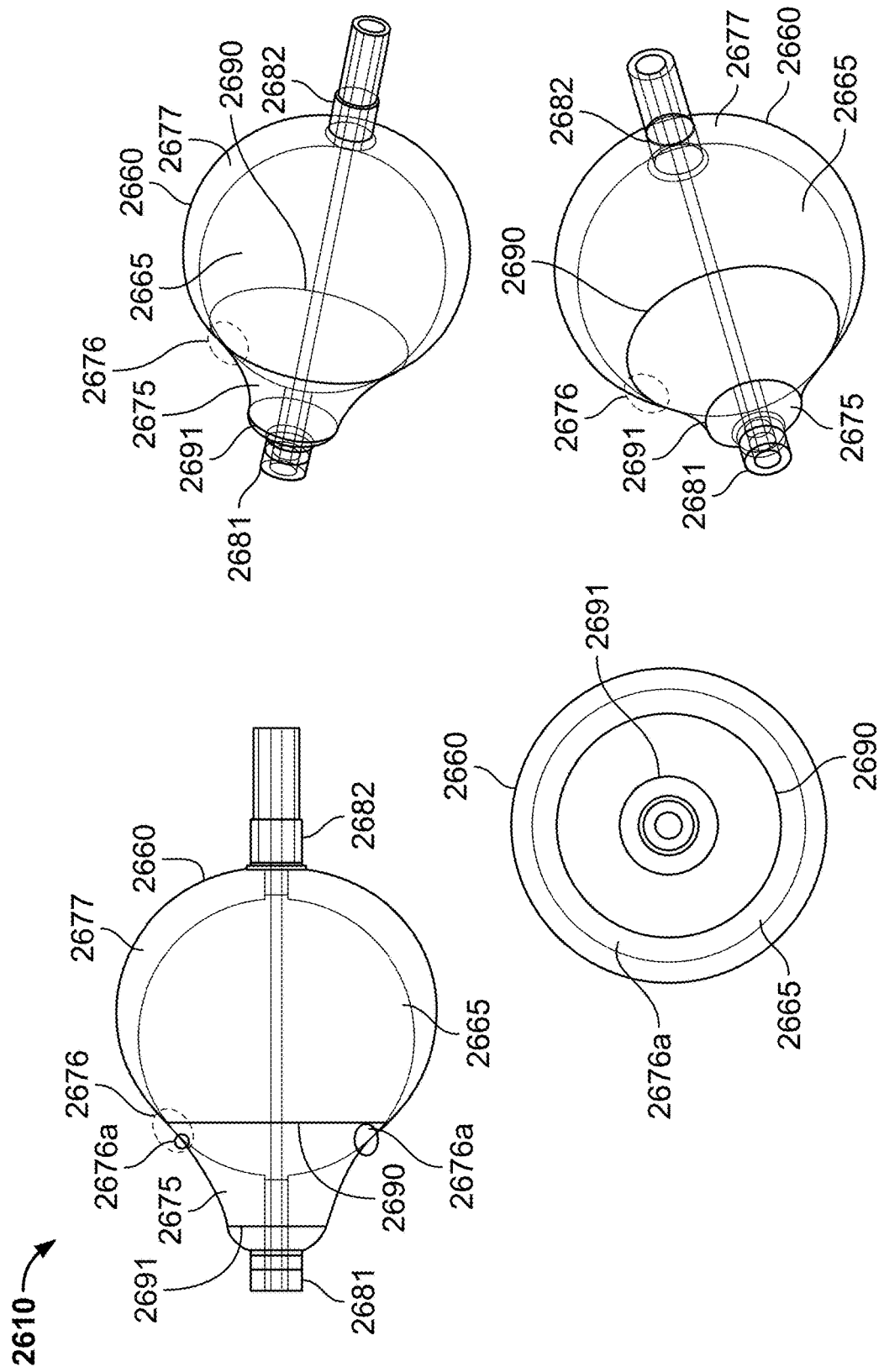
FIG. 26D illustrates a plurality of perspective views of the catheter of FIG. 26B, in accordance with some embodiments of the present specification.
Figure 26E:
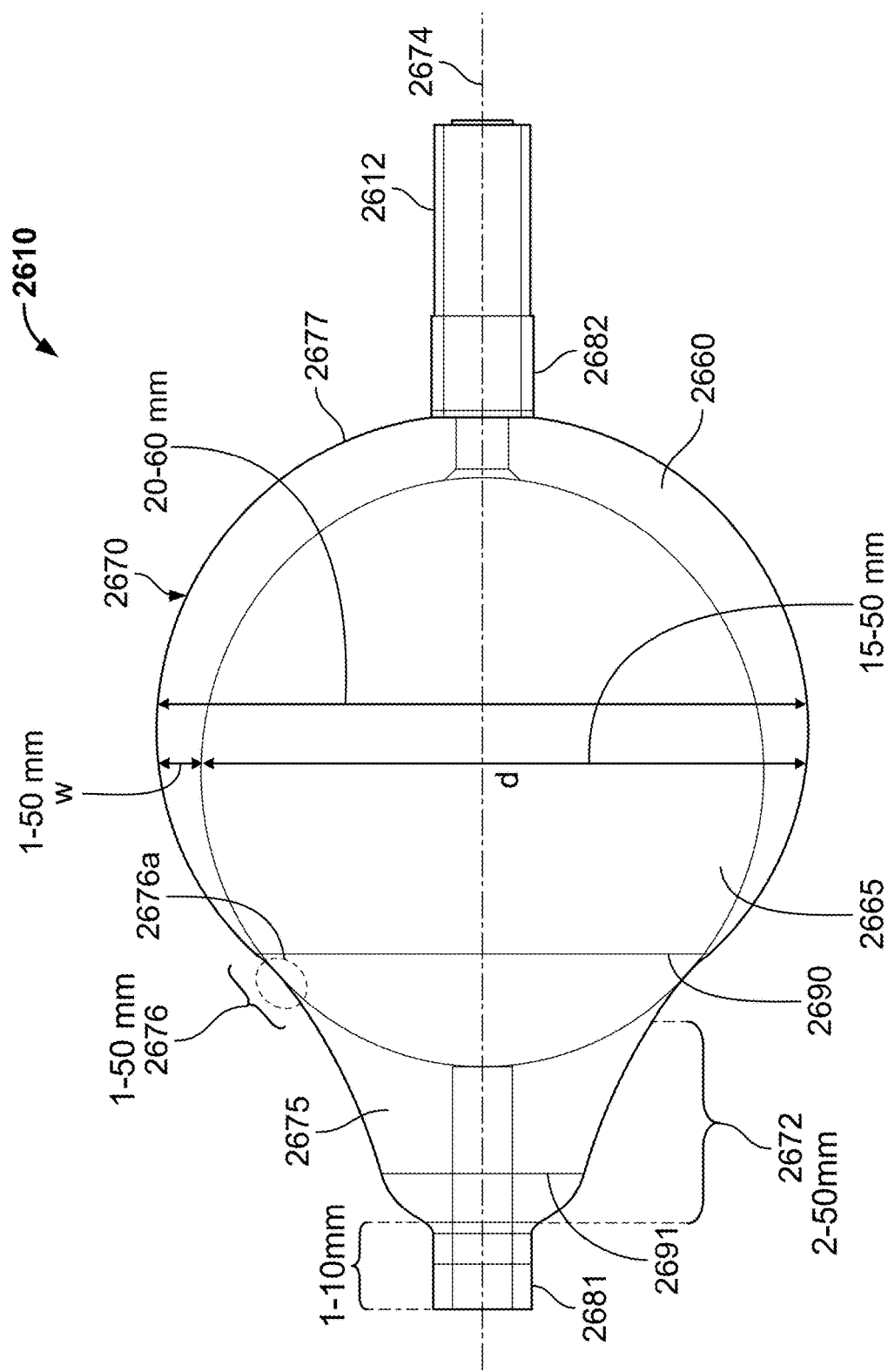
FIG. 26E illustrates another perspective view of the catheter of FIG. 26B, in accordance with some embodiments of the present specification.
Figure 26F:
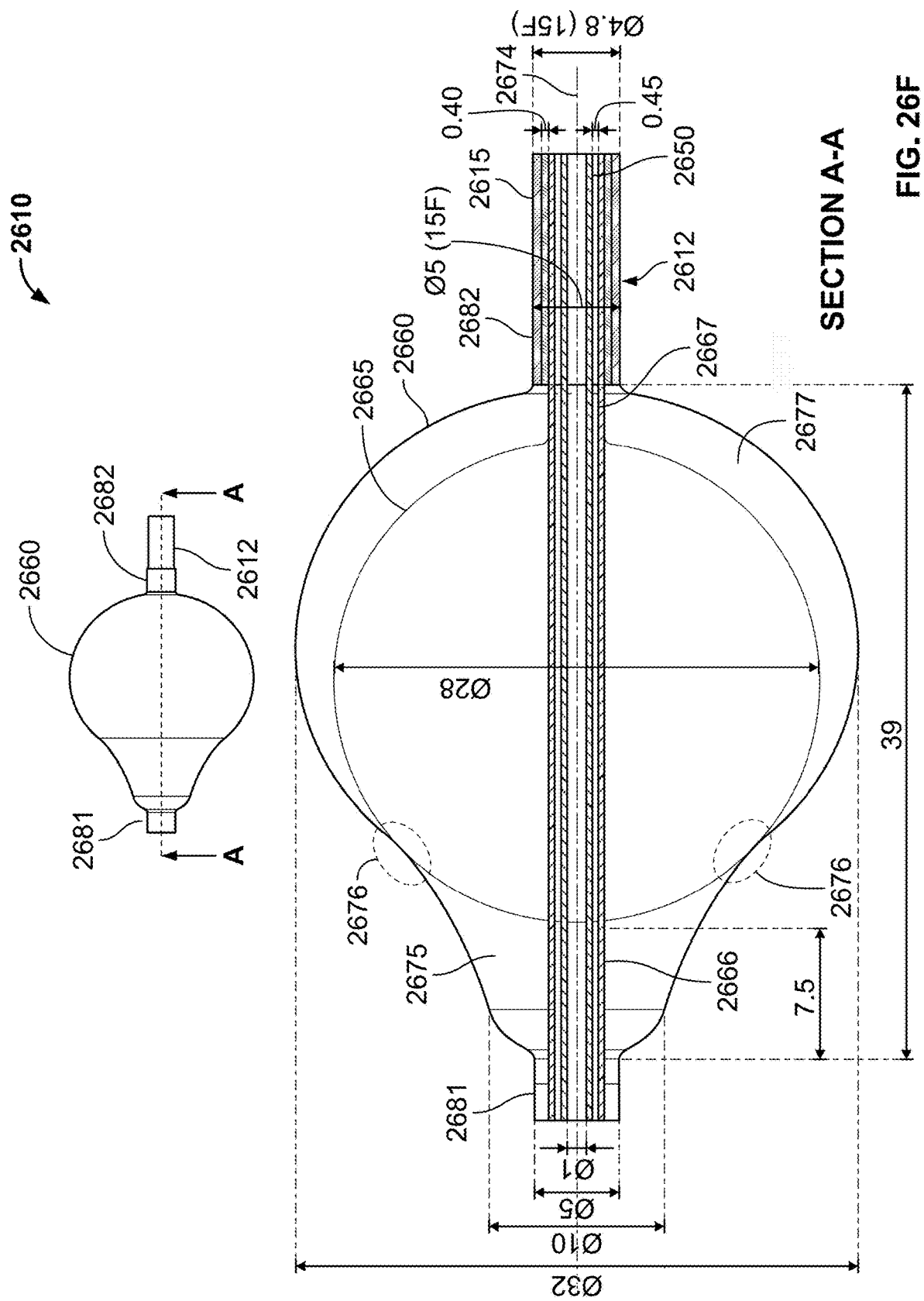
FIG. 26F illustrates a longitudinal cross-sectional view of the catheter of FIG. 26B, in accordance with some embodiments of the present specification.
Figure 26G:
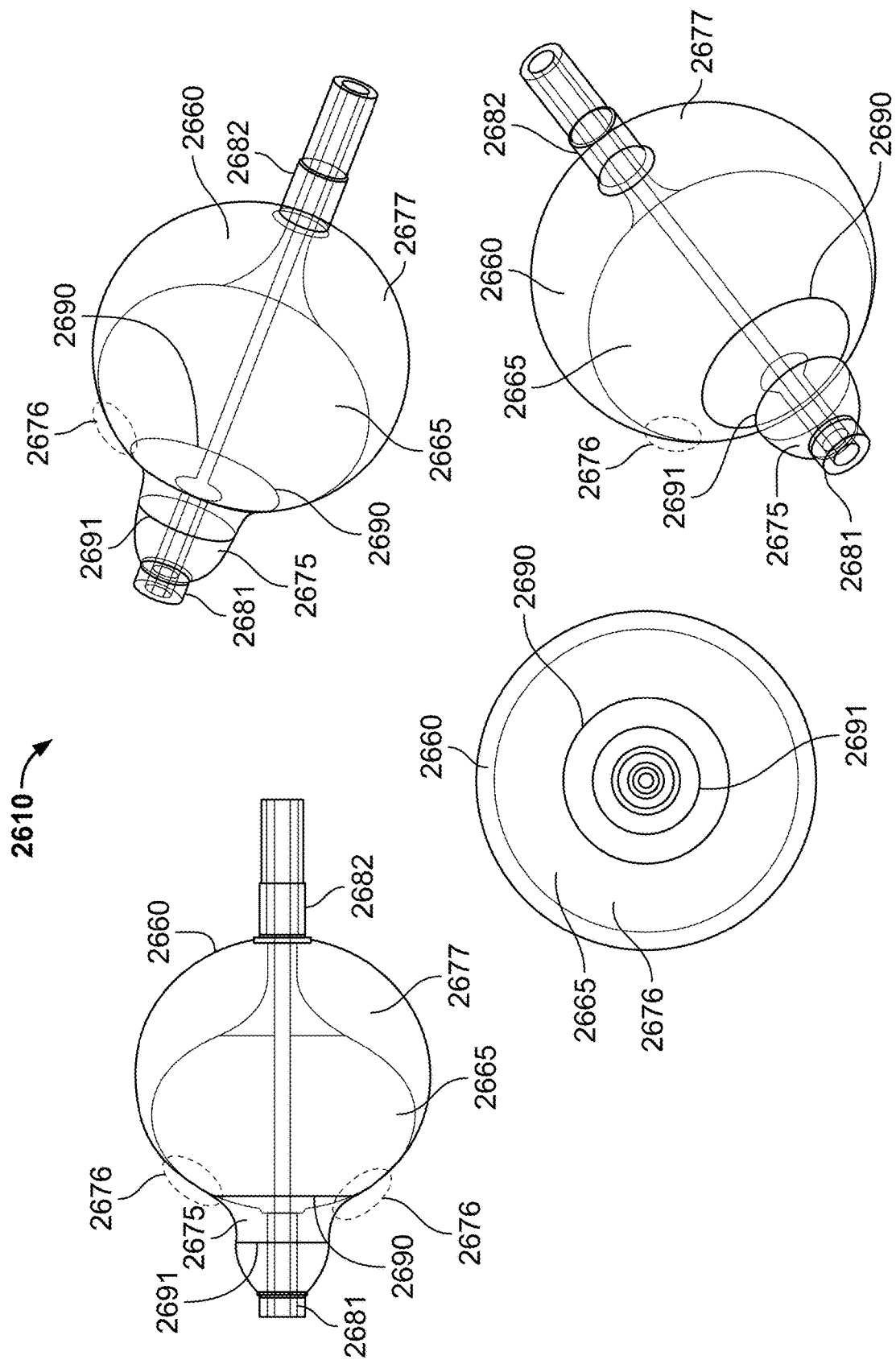
FIG. 26G illustrates a plurality of perspective views of the catheter of FIG. 26B wherein the inner balloon is substantially ovoid in shape, in accordance with some embodiments of the present specification.
Figure 26H:
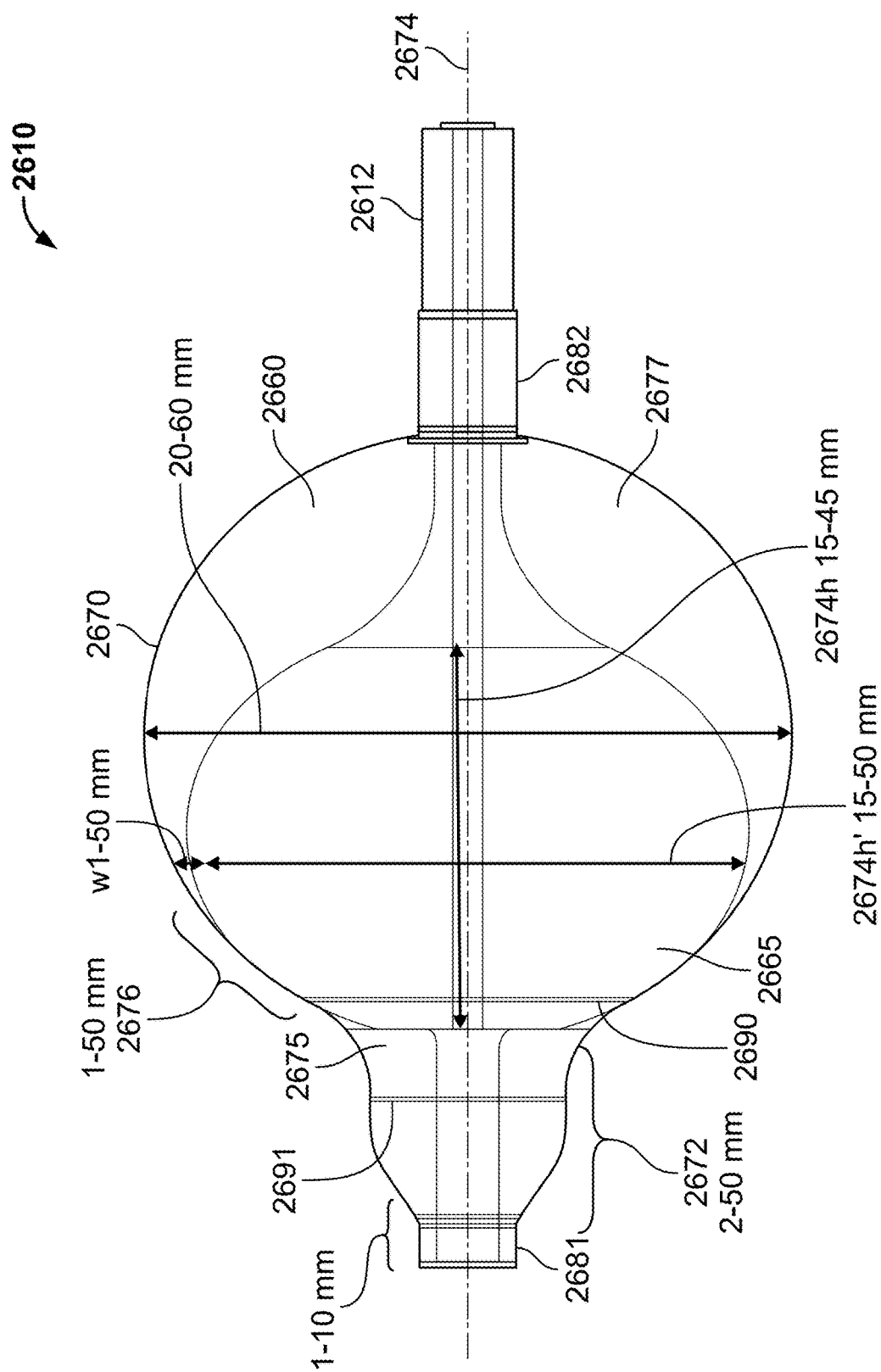
FIG. 26H illustrates another perspective view of the catheter of FIG. 26B wherein the inner balloon is substantially ovoid in shape, in accordance with some embodiments of the present specification.
Figure 26I:
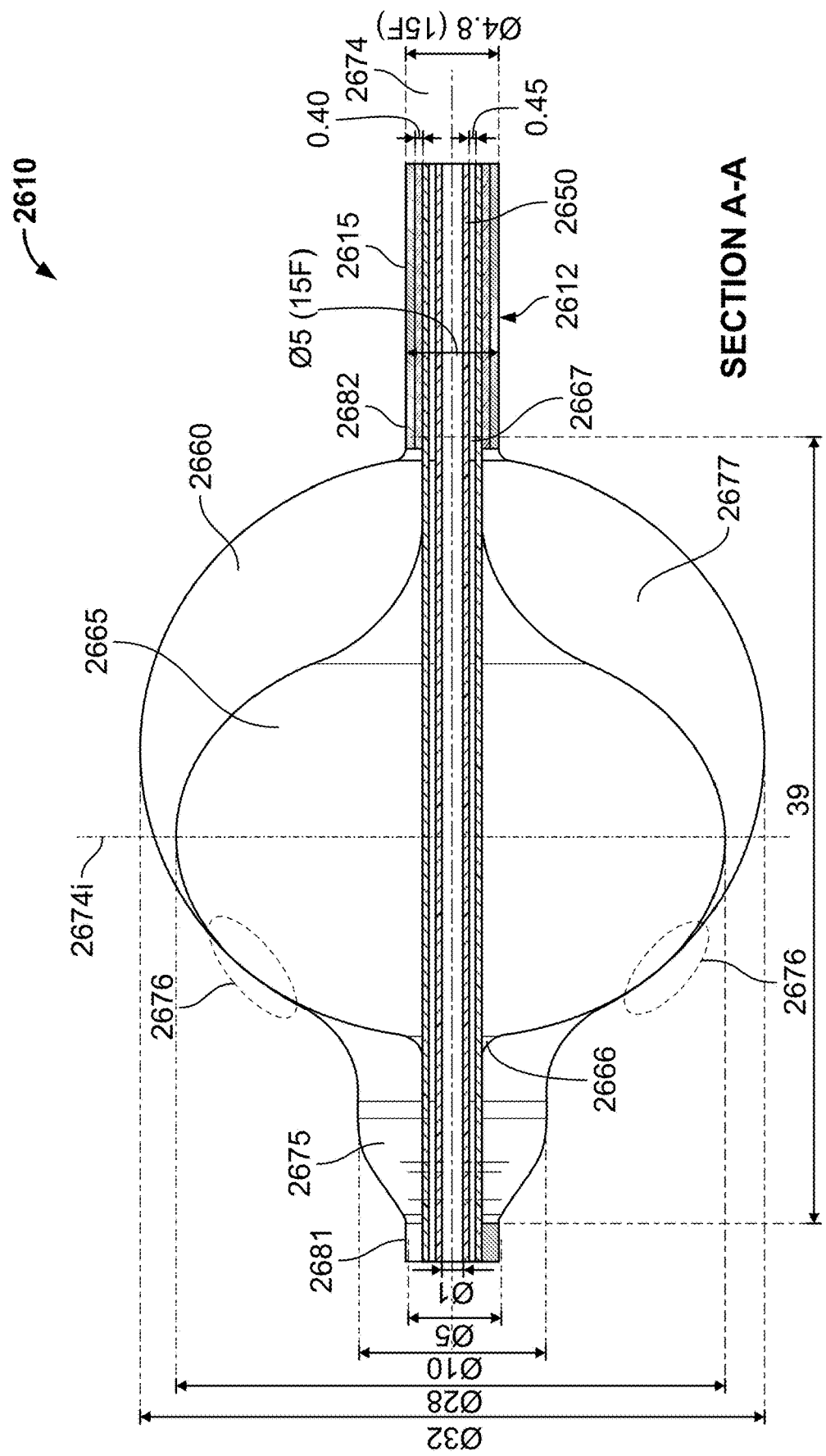
FIG. 26I illustrates a longitudinal cross-sectional view of the catheter of FIG. 26B wherein the inner balloon is substantially ovoid in shape, in accordance with some embodiments of the present specification.
Figure 26K:
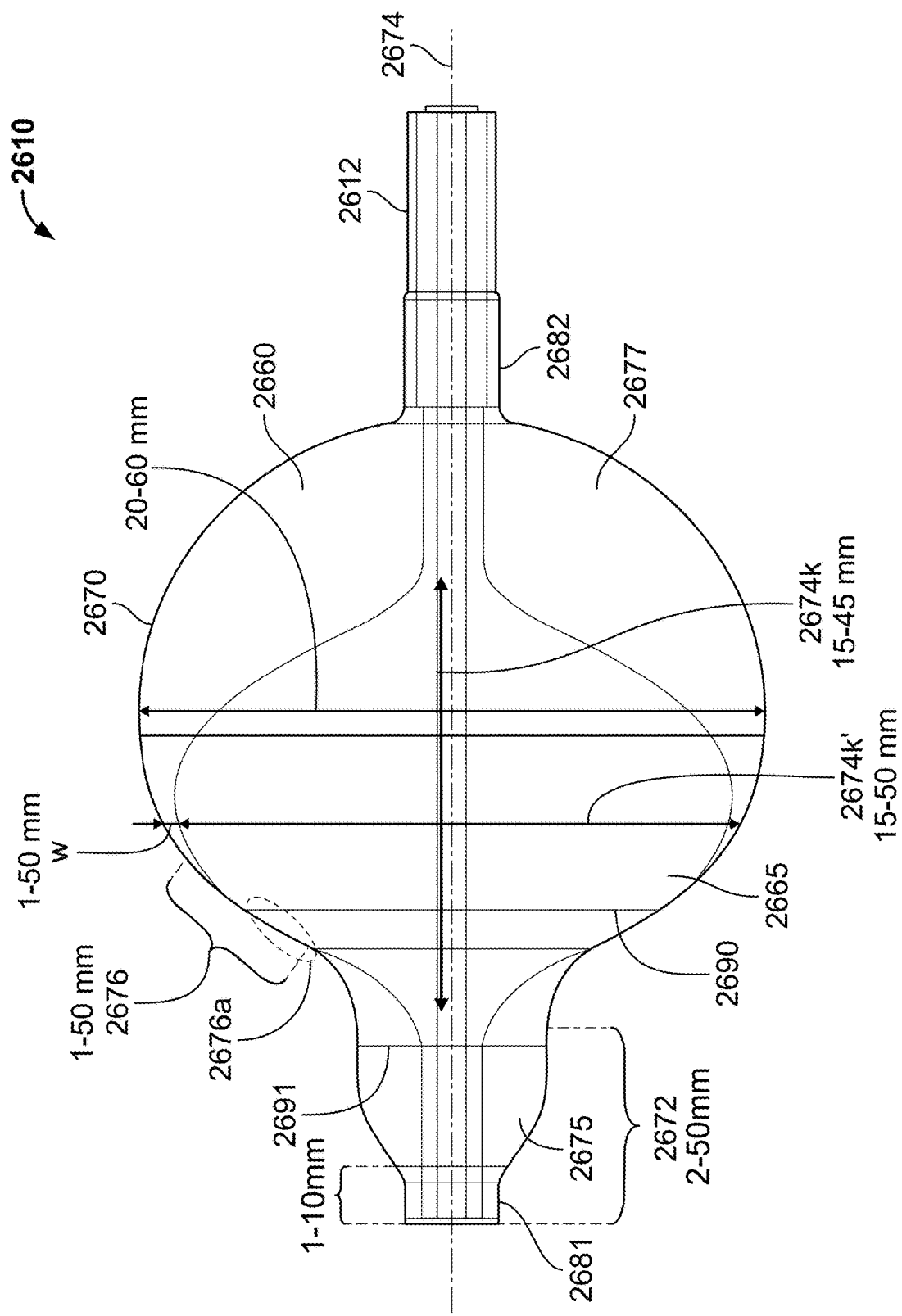
FIG. 26K illustrates another perspective view of the catheter of FIG. 26B wherein the inner balloon is substantially conical in shape, in accordance with some embodiments of the present specification.
Figure 26L:
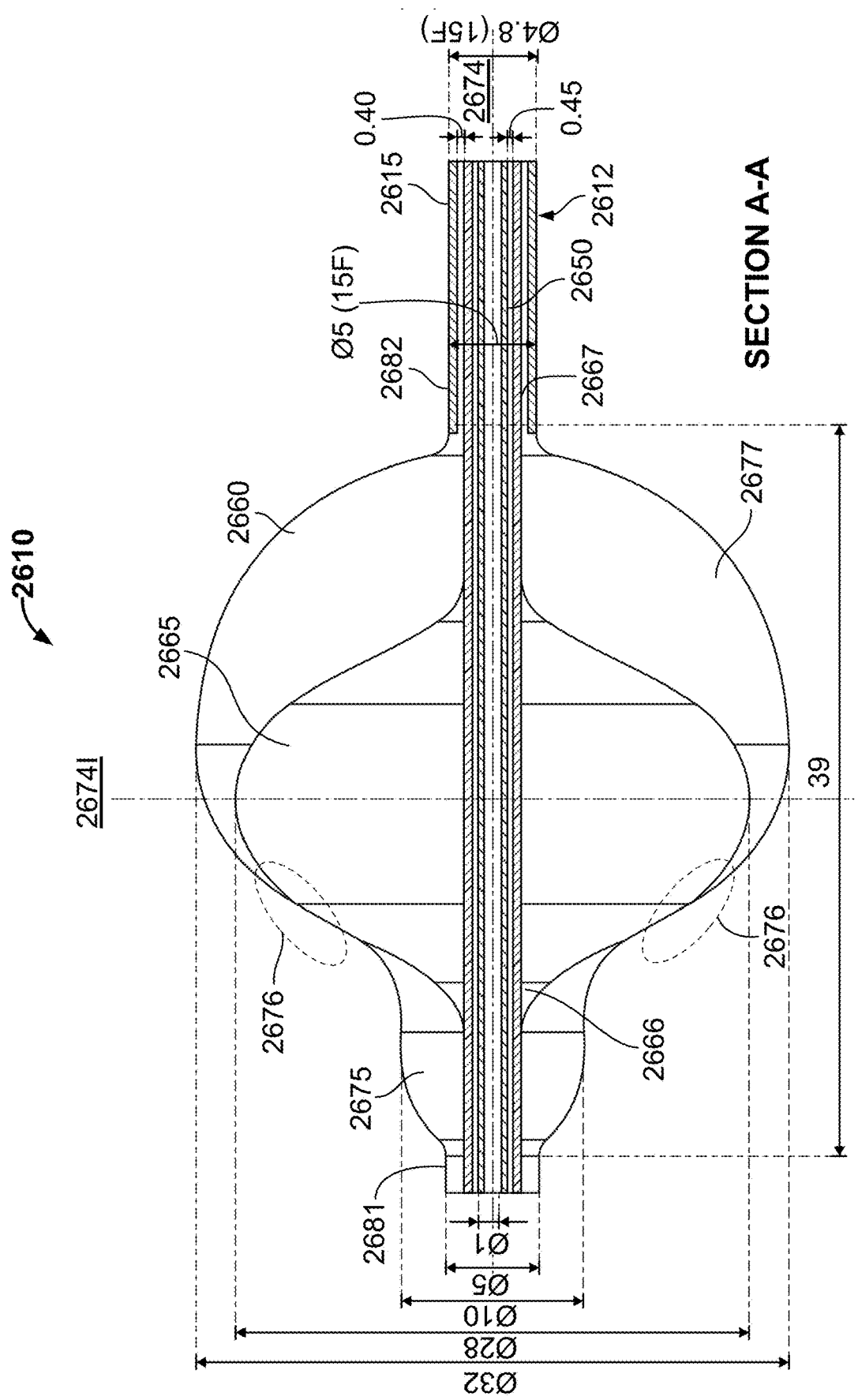
FIG. 26L illustrates a longitudinal cross-sectional view of the catheter of FIG. 26B wherein the inner balloon is substantially conical in shape, in accordance with some embodiments of the present specification.
Figure 26O:
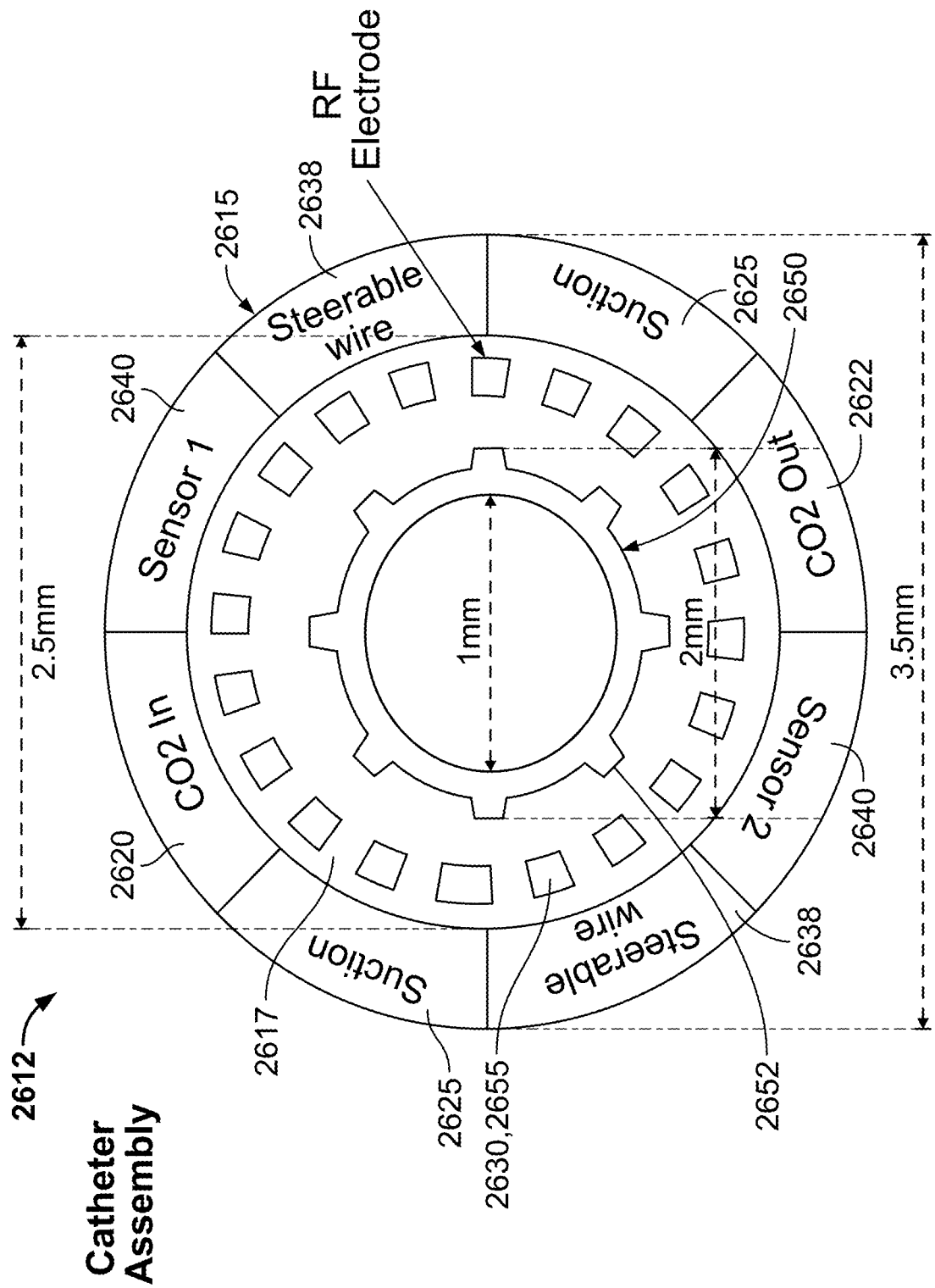
FIG. 26O illustrates another transverse cross-sectional view of the elongate body of the catheter of FIG. 26B, in accordance with some embodiments of the present specification.
Figure 26P:
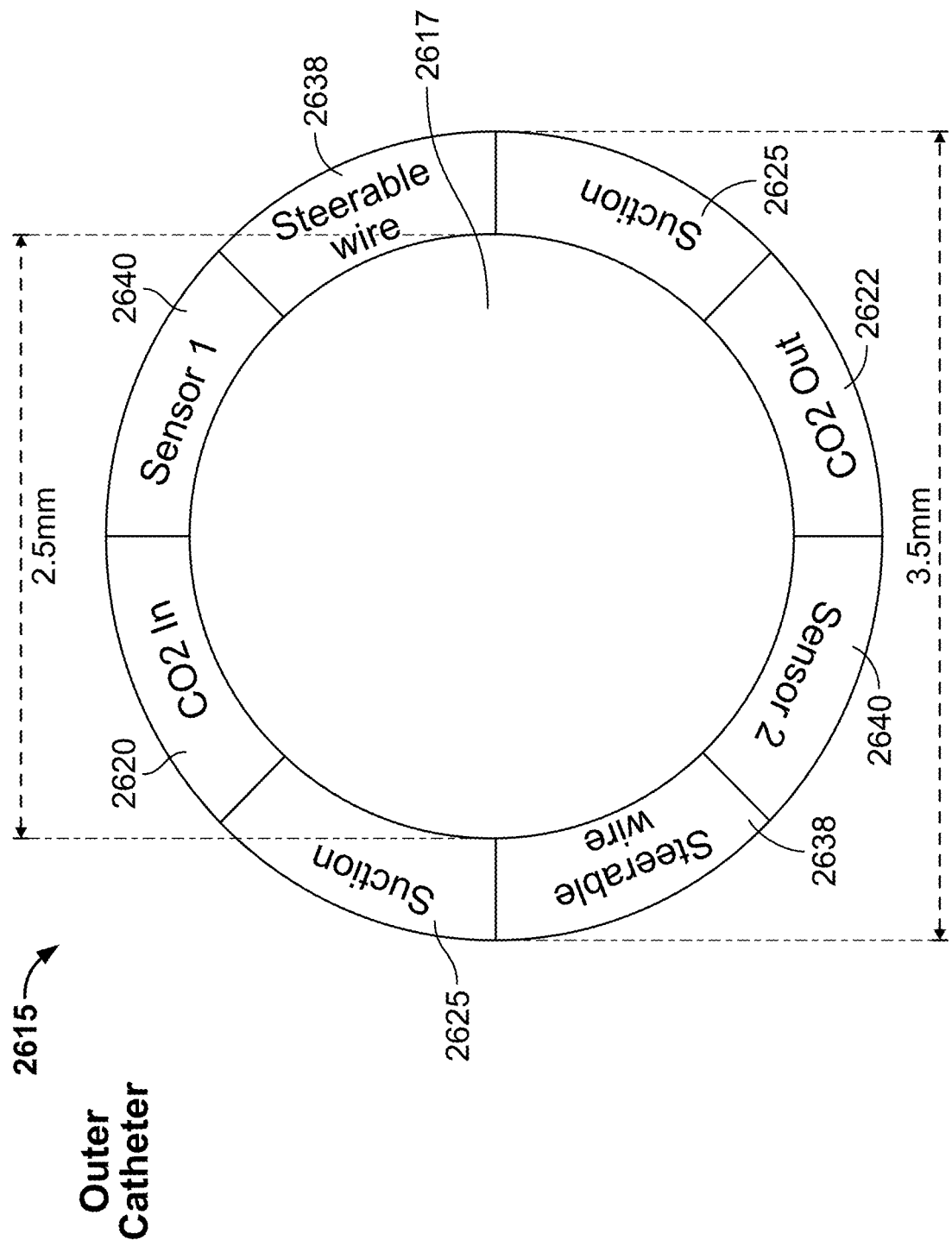
FIG. 26P illustrates a transverse cross-sectional view of an outer catheter of the catheter of FIG. 26B, in accordance with some embodiments of the present specification.

FIGS. 26A, 26B, 26C, 26D, 26E, 26G, 26H, 26J and 26K illustrate perspective views of a dual balloon cardiac ablation catheter 2610, FIGS. 26F, 26I, 26L and 26M illustrate longitudinal cross-sectional views of the catheter 2610, FIGS. 26N and 26O illustrates transverse cross-sectional views of an elongate body 2612 of the catheter 2610 while FIGS. 26P and 26Q illustrates transverse cross-sectional views of outer and inner catheters, respectively, of the elongate body 2612, in accordance with some embodiments of the present specification. In some embodiments, the cardiac ablation catheters 2610 can be used to ablate cardiac tissue to treat an arrhythmia, such as atrial fibrillation.

Referring now to FIGS. 26A through 26Q, the elongate body 2612 has a proximal end, a distal end, an outer catheter 2615 and an optional inner catheter or lumen 2650. One preferred embodiment does not have an inner catheter 2650 and only comprises an outer catheter 2615 with the associated lumens, as described. A handle is disposed at the proximal end of the body 2612. In some embodiments, the outer and inner catheters or lumen 2615, 2650 are coaxial. In alternate embodiments, the outer and inner catheters or lumens 2615, 2650 are eccentric.

In an embodiment, the outer catheter 2615 (FIGS. 26N, 26O, 26P) includes a central vapor lumen 2617, which may be circular or elliptical, and a plurality of additional lumens located circumferentially, wherein each of the additional lumens is fluidically isolated from the central vapor lumen 2617 and from each other along the length of the catheter. In embodiments, each of the lumens has a diameter within a range of 25% to 300% of each of the other lumen diameters. The plurality of circumferentially positioned lumens include a cooling fluid infusion lumen 2620, a cooling fluid suction lumen 2622 (positioned diametrically opposite with respect to the infusion lumen 2620, in some embodiments), two fluid suction lumens 2625 (positioned diametrically opposite with respect to each other, in some embodiments), two lumens 2638 (positioned diametrically opposite with respect to each other, in some embodiments) to allow at least one steerable wire to be introduced there-through to enable bi-directional steerability, and two sensor lumens 2640 (positioned diametrically opposite with respect to each other, in some embodiments) to allow one or more electrical leads from the handle to connect to sensors such as, but not limited to, thermocouples and pressure transducers. In various embodiments, the cooling fluid includes air, water or carbon-dioxide.

In an embodiment, the inner catheter or lumen 2650 (FIGS. 26N, 26O, 26Q) comprises a hollow core positioned coaxially within the vapor lumen 2617 of the outer catheter 2615. The inner catheter or lumen 2650 extends from a proximal end to a distal end of the catheter and in configured to pass a guide wire or sensing pacing wire and to inject a flush, coolant, or contrast. In some embodiments, the inner catheter is a solid core structure 2650 and does not function as an actual catheter. In other embodiments, there is no inner catheter 2650 and there is only the outer catheter 2615 with the lumens as shown. At least one flexible heating chamber 2630 (such as those described with reference to FIGS. 19A through 19D), positioned in-line within the central water/vapor lumen 2617, comprises a plurality of electrodes 2655 disposed between the outer catheter 2615 and the inner catheter 2650. Electrical leads connect the electrodes 2655 to a plug in the handle. In some embodiments, the inner catheter 2650 includes a plurality of circumferential protrusions or fins 2652 (FIGS. 26O and 26Q) to provide channels for saline flow between the outer surface of catheter 2650 and the electrode 2655.

In embodiments, the two cooling fluid lumens 2620, 2622 are in fluid communication with an inflatable outer balloon 2660 attached to the distal end of the catheter 2610. The two cooling fluid lumens 2620, 2622 extend from the outer balloon 2660 to a cooling fluid pump which is in data communication with, and controlled by, a controller. In some embodiments, the cooling fluid lumens 2620, 2622 are pressure controlled or integrated in the cooling fluid pump and function as a coupled, regulated fluid circuit. During operation, the cooling fluid pump pushes the cooling fluid into the infusion lumen 2620 (through an optional filter) to exit via first and second infusion ports 2662a, 2662b, shown in FIG. 26B, thereby inflating the outer balloon 2660. In an embodiment, the cooling fluid pump is reversible, thereby allowing the cooling fluid to be pumped out of the balloon 2660 via first and second suction ports 2664a, 2664b through the cooling fluid suction lumen 2622, as required and per instructions sent by the controller. The first and second infusion ports 2662a, 2662b are respectively located at distal and proximal ends of the other balloon 2660. The first and second suction ports 2664a, 2664b are respectively located at distal and proximal ends of the other balloon 2660. In some embodiments, the first and second infusion ports 2662a, 2662b have diameters of 0.2 mm. In some embodiments, the first and second suction ports 2664a, 2664b have diameters of 0.2 mm.

The vapor lumen 2617 is in fluid communication with an inflatable inner balloon 2665 attached to the distal end of the catheter 2610 and positioned within the outer balloon 2660. The vapor lumen 2617 extends from the inner balloon 2665 to a water/vapor pump which is also in data communication with, and controlled by, the controller. A proximal end of the vapor lumen 2617, at the handle, has a luer lock connection to a sterile water/saline reservoir. Optionally, a Y-adapter is included to allow a guidewire/mapping catheter to pass through, while injecting saline into the vapor lumen to convert to steam when it passes across the electrode at the distal tip. Water/saline is pumped from the sterile water/saline reservoir via the water/vapor pump through the water/vapor lumen 2617 to enter a proximal end of the at least one flexible heating chamber 2630 (shown in FIG. 26B). The at least one flexible heating chamber 2630 converts water into vapor that exits through at least one vapor infusion port 2668, positioned on a portion of the body 2612 lying within the inner balloon 2665, to inflate the inner balloon 2665. In some embodiments, the flexible heating chamber 2630 is attached to the inner balloon 2665. In some embodiments, the inner balloon 2665 is configured to inflate only within a predefined location within the outer balloon 2660. In some embodiments, the outer balloon 2660 includes retaining structures to ensure the inner balloon 2665 inflates within the predefined location. In some embodiments, the inner balloon 2665 is configured to withstand an operating temperature of at least 125° C. In some embodiments, the inner balloon 2665 is configured to have a burst pressure rating of at least 5 atm at the rated temperature. In some embodiments, the inner balloon 2665 is configured to withstand at least 50 cycles of 0-180 second ablation treatments conducted using at least a 30 watt power level. In some embodiments, the outer balloon 2660 is configured to withstand an operating temperature of at least 110° C.

In some embodiments, as visible in FIG. 26B, the at least one vapor infusion port 2668 is positioned proximate a distal end of the inner balloon 2665. In some embodiments, the at least one vapor infusion port 2668 has a diameter of 2.0 mm. At least two water suction ports 2669 are positioned on the portion of the body 2612 lying within the inner balloon 2665. In some embodiment, the at least two water suction ports 2669 are positioned proximate a proximal end of the inner balloon 2665. When the inner balloon 2665 is filled with vapor, some of the vapor converts or condenses into water on contact with the balloon surface. This water (condensed vapor) is suctioned out of the inner balloon 2665 through the at least two water suction ports 2669 that are in fluid communication with the two water suction lumens 2625, respectively.

In some embodiments, as shown in FIGS. 26N, 26O and 26P, the outer catheter 2615 has an outer diameter of 3.5 mm and an inner diameter of 2 to 2.5 mm (that is, the inner diameter of the central vapor lumen 2617 is 2 to 2.5 mm). In some embodiments, as shown in FIGS. 26F, 26I and 26L, the outer catheter 2615 has an outer diameter of 4.8 mm. In some embodiments, a maximum outer diameter of an outer catheter is 7.4 mm.

In some embodiments, as shown in FIGS. 26F, 26I, 26L, 26H, 26I and 26K, the inner catheter 2650 has an outer diameter, including the plurality of electrodes fins 2652, of 2 mm. In embodiments where the inner catheter 2650 is hollow, the inner catheter 2650 has an internal diameter of −1 mm+/−0.5 mm. It should be appreciated, however, that the inner catheter 2650 is optional and a preferred embodiment comprises solely a single catheter (the outer catheter 2615) with a central elliptical lumen and a plurality of additional lumens located circumferentially around the central lumen, wherein each of the plurality of additional lumens are fluidically isolated from the central elliptical lumen along the length of the catheter.

FIG. 26C illustrates a cross-sectional view 2695 showing a three lumen flow mechanism of the catheter 2610, in accordance with an alternate embodiment of the present specification. The cross-sectional view 2695 shows a catheter 2615c with a coaxial inner lumen 2650c having a size range of 2 to 9 French. The catheter 2615c has a water/vapor first lumen 2696 in fluid communication with the inner balloon 2665 to suction saline or water or vapor from the inner balloon 2665 and a fluid infusion and/or suction second lumen 2697 in fluid communication with the outer balloon 2660. The catheter has a third lumen 2698 which includes an in-line flexible heating element to convert water, introduced from a proximal end, into steam that enters the inner balloon 2665 via at least one vapor infusion port.

Referring now to FIGS. 26A through 26L, in some embodiments, the inflatable outer balloon 2660 is pear shaped (when inflated or expanded) that may be approximately defined by a proximal half-spherical first portion 2670 transitioning into a distal conical second portion 2672 that tapers into a substantially rounded or spherical distal end 2673. Stated differently, the outer balloon, when inflated, has a length, an axis that extends along the length and through the center of the outer balloon, and a distance from the axis to an outer surface of the outer balloon. That distance changes along the outer balloon length and may be defined by four distinct distances, D1, D2, D3, and D4, extending from the distal end of the axis to an outer surface of the outer balloon (D1) and moving sequentially proximally up the axis.

Figure 26R:
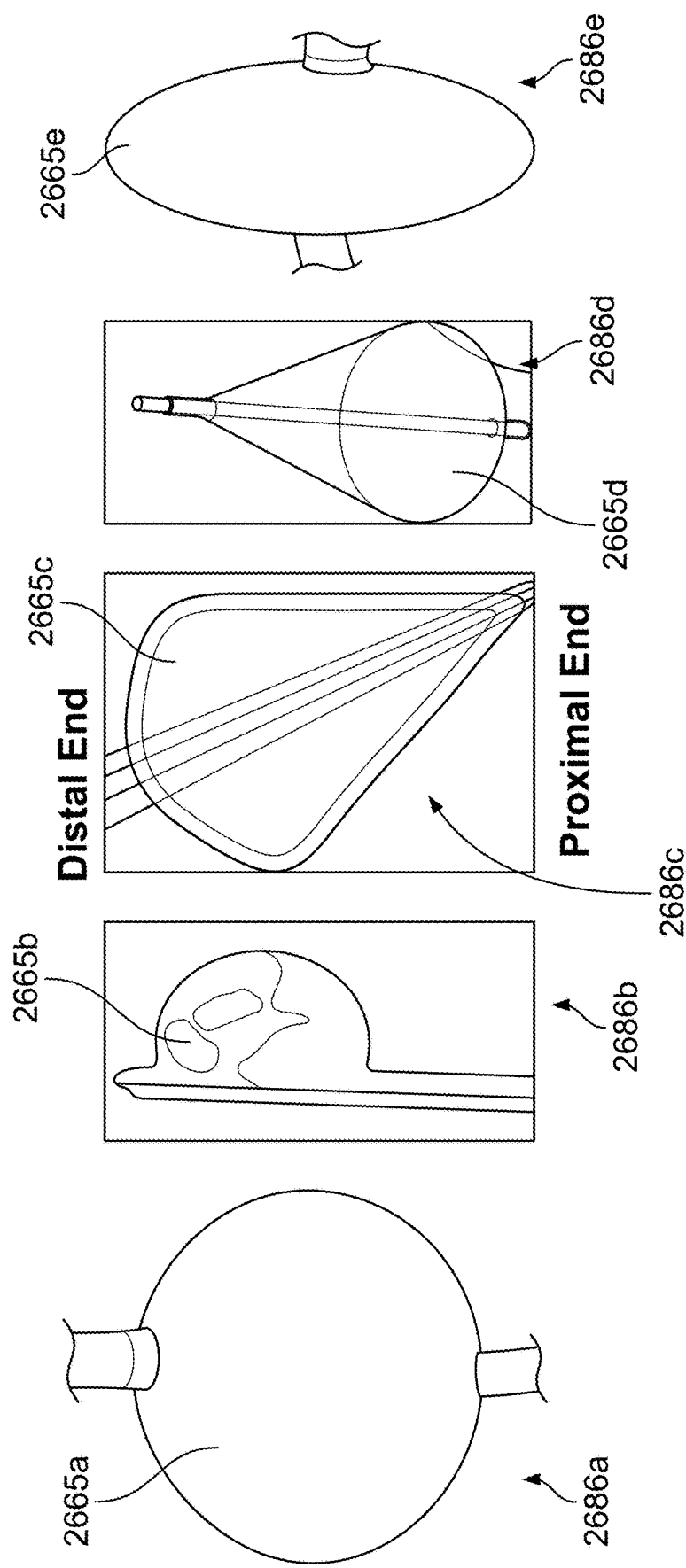
FIG. 26R illustrates a plurality of exemplary shapes of the inner balloon of the catheter of FIG. 26B, in accordance with some embodiments of the present specification.
Figure 26S:
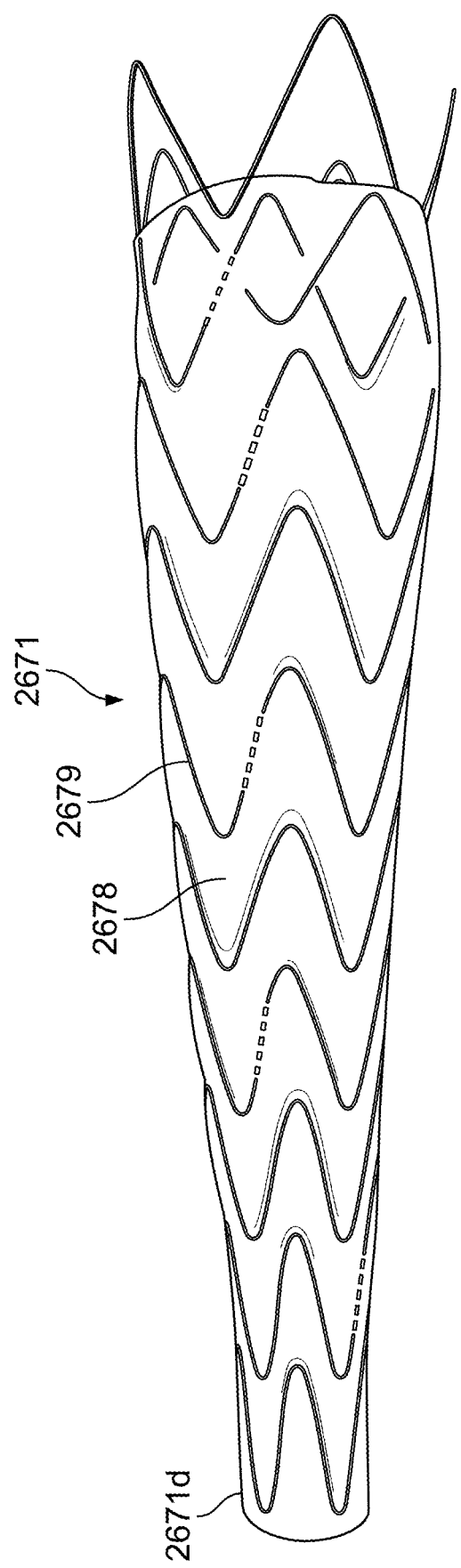
FIG. 26S illustrates an outer expandable member to be used in place of an outer balloon, in accordance with some embodiments of the present specification.
Figure 26T:
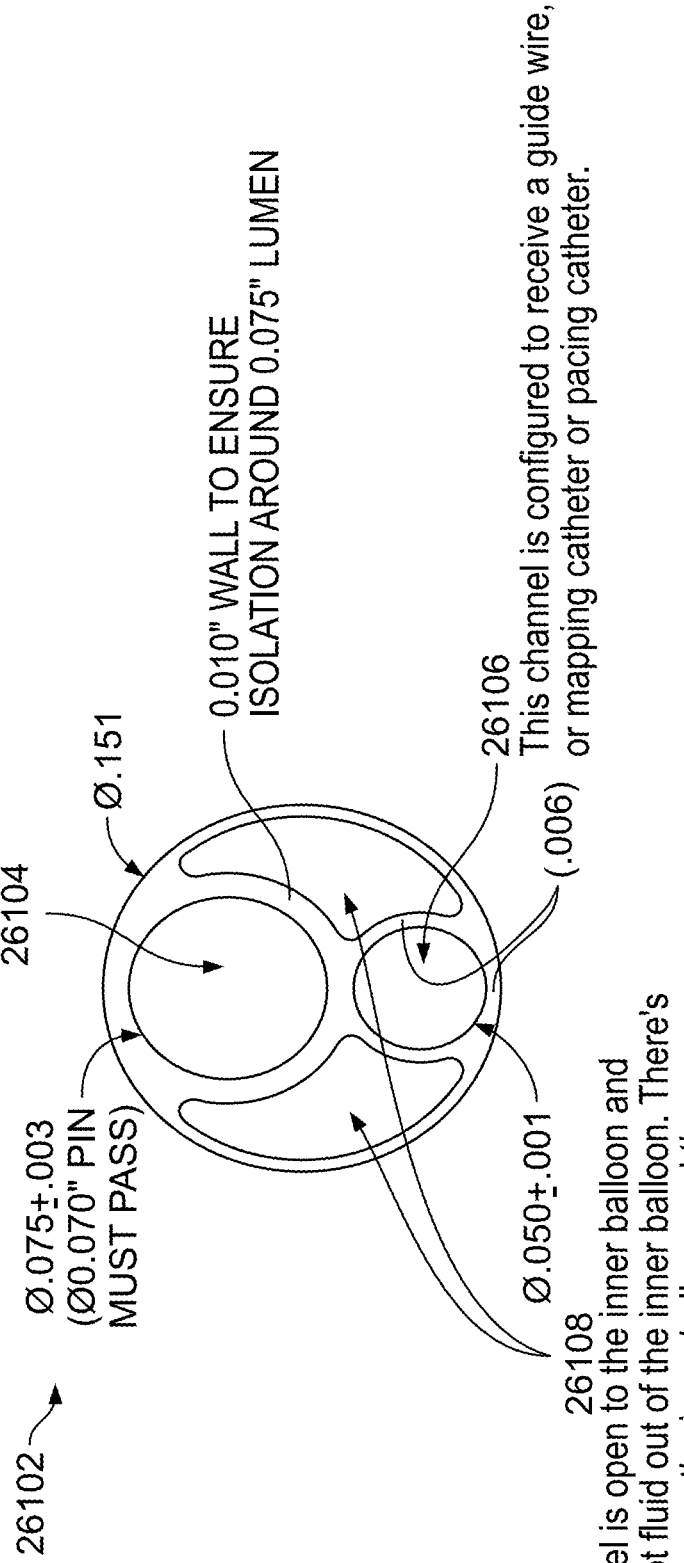
FIG. 26T illustrates a cross sectional view of another embodiment of an ablation catheter, in accordance with the present specification.
Figure 26U:
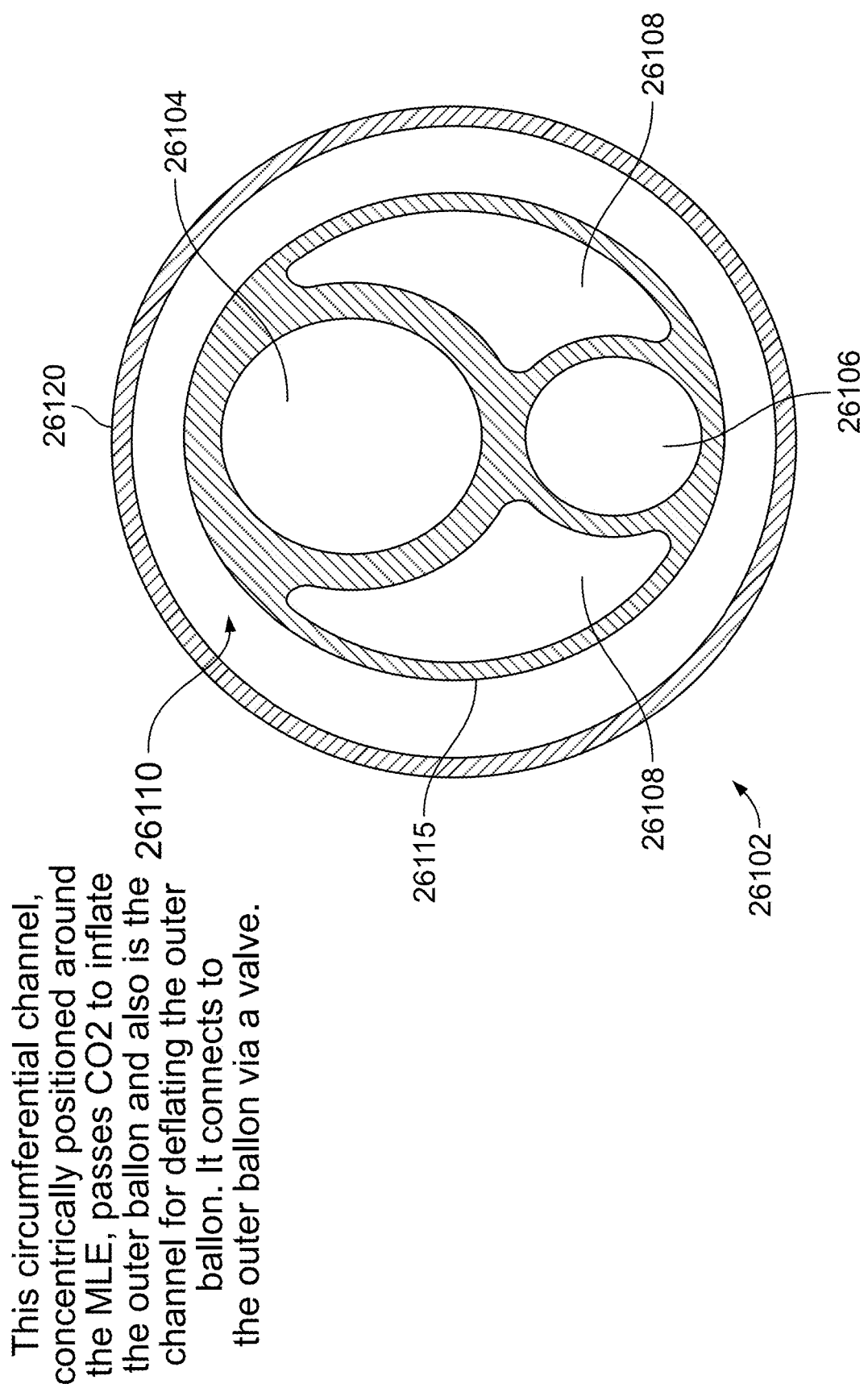
FIG. 26U illustrates a concentrically positioned channel between an outer circumference of ablation catheter of FIG. 26T, and an outer shaft, in accordance with some embodiments of the present specification.
Figure 26V:
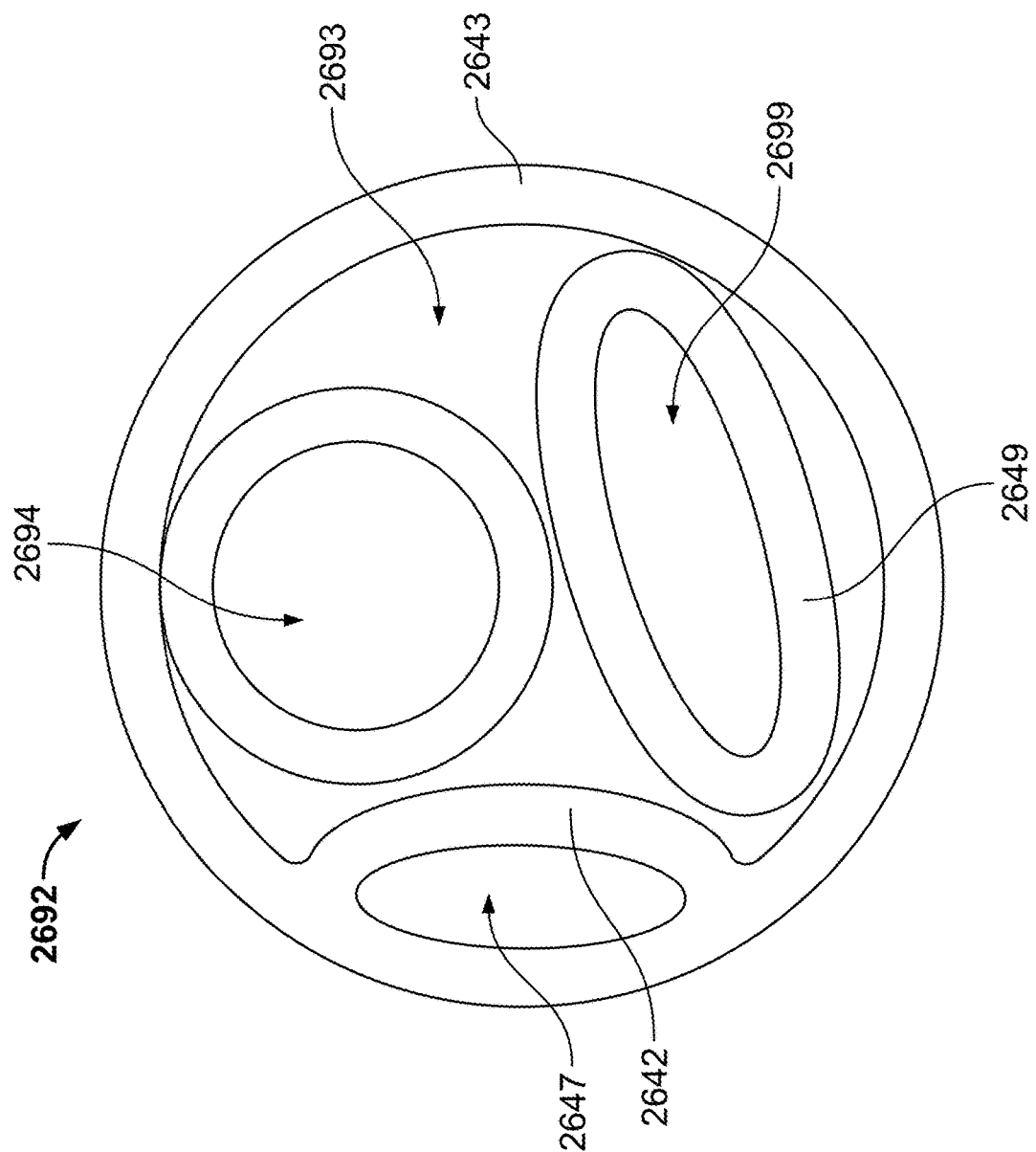
FIG. 26V illustrates a cross sectional view of another embodiment of an ablation catheter, in accordance with the present specification.
Figure 26W:
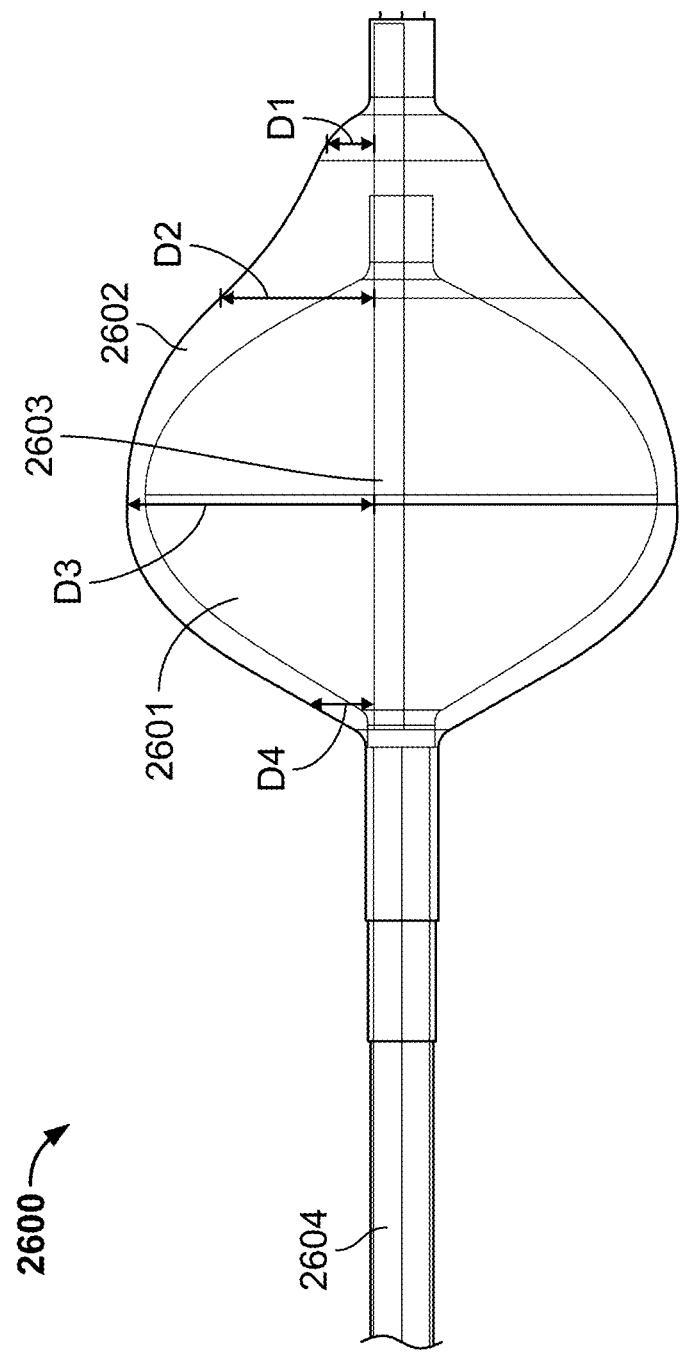
FIG. 26W illustrates a distal end of an ablation catheter depicting an inner balloon positioned within an outer balloon, in accordance with some embodiments of the present specification.

Specifically, referring to FIG. 26W, starting from the distal end of the outer balloon, the distance D1, located at a point that is between 0 mm and 4 mm (preferably 0 mm) from the distal point of attachment of the outer balloon to the catheter, is in a range of 1 mm to 20 mm. Moving proximally, the distance D2, located at a point that is between 7 mm and 14 mm (preferably 10 mm) from the distal point of attachment of the outer balloon to the catheter, is in a range of 15 mm to 30 mm. Moving proximally, the distance D3, located at a point that is between 25 mm and 35 mm (preferably 30 mm) from the distal point of attachment of the outer balloon to the catheter, is in a range of 20 mm to 50 mm. Moving proximally, the distance D4, located at a point that is between 30 mm and 45 mm (preferably 33 mm) from the distal point of attachment of the outer balloon to the catheter, is in a range of 1 mm to 20 mm. Accordingly, D1 and D4 are preferably less than D3 or D2 and D3 is preferably greater than each of D1, D2, and D4.

In another embodiment, the maximum distance from the central axis of the outer balloon to the outer surface of the outer balloon (e.g. D3) is less than a length of the outer balloon, measured from a proximal point of attachment of the outer balloon to the catheter to a distal point of attachment of the outer balloon to the catheter. In another embodiment, the distances from the central axis to the outer surface of the outer balloon increases from a first minimum to a first maximum as one proceeds distally down the outer balloon length. After reaching the first maximum, the distance decreases to a second minimum, where the second minimum is greater than the first minimum. The distance from the first maximum to second minimum ranges from 2 mm to 35 mm. After reaching the second minimum, the distance decreases again to a third minimum, where the second minimum is greater than the third minimum. The distance from the second minimum to the third minimum ranges from 2 mm to 25 mm.

In embodiments, the pear shape of the inflatable outer balloon 2660 is symmetrical about a longitudinal axis 2674. In embodiments, proximal and distal ends of the outer balloon 2660 extend into tube-like structures or necks 2681, 2682 which help in keeping the catheter 2610 in place when it is passed through the balloon. In an alternate embodiment, the outer balloon 2660 has a short cylindrical shape configured to position or lodge into a pulmonary vein.

In some embodiments, as shown in FIGS. 26B through 26F, the inner balloon 2665 is spherical in shape. In some embodiments, as shown in FIGS. 26G, 26H and 26I, the inner balloon 2665 has a substantially ovoid shape. In some embodiments, as shown in FIGS. 26J, 26K and 26L, the inner balloon 2665 has a substantially conical shape. In various embodiments, proximal and distal ends of the inner balloon 2665 extend into tube-like structures or necks 2666, 2667 which help in keeping the catheter 2610 in place when it is passed through the balloon. In some embodiments, the space within the inner balloon 2665 is divided into a plurality of compartments wherein each of the compartments can be independently inflated with vapor.

In other embodiments, the inflatable inner balloon 2665 has a shape such as, but not limited to, disc, elliptical, a rectangular prism, and a triangular prism. FIG. 26R illustrates a plurality of exemplary shapes of the inner balloon 2665, in accordance with some embodiments of the present specification. A first view 2686a shows a substantially spherical shaped inner balloon 2665a, a second view 2686b shows a half spherical shaped inner balloon 2665*b*, a third view 2686*c* shows a cone shaped inner balloon 2665*c* such that the apex of the cone lies at a proximal end while the base of the cone lies at a distal end, a fourth view 2686*d* shows another cone shaped inner balloon 2665*d* such that the apex of the cone lies at the distal end while the base of the cone lies at the proximal end, and a fifth view 2686*e* shows an elliptical shaped inner balloon 2665*e*. In other embodiments, half balloons may be derived from any of the full shaped balloons illustrated in views 2686*a*, 2686*c*, 2686*d* and 2686*e*. In embodiments, quarter or ¼ balloons may be derived from any of the shaped balloons illustrated in views 2686*a*, 2686*c*, 2686*d* and 2686*e*.

As shown in FIGS. 26B through 26L, in accordance with an aspect of the present specification, when the outer and inner balloons 2660, 2665 are fully inflated, the pear shaped outer balloon 2660 is characterized by three area, regions or zones—a) a distal first zone 2675 that is a cooler zone (since the outer and inner balloons 2660, 2665 do not contact in this zone) and is sized and shaped to lodge in a pulmonary vein, b) a middle second zone 2676 (also referred to as a hot zone or ablation zone) where the outer balloon 2660 contacts the vapor filled inner balloon 2665 thereby creating a hot zone or ablation zone, and c) a proximal third zone 2677 that is positioned in a left atrium to provide for a cooler surface (since the outer and inner balloons 2660, 2665 do not contact in this zone) so as to not scald the atrium. In various embodiments, the hot zone or ablation zone shape is dependent on the shapes of the inner and outer balloons and, in some embodiments, is shaped like the external surface of an outer perimeter of a torus or donut, wherein the area of the external surface, and therefore of the ablation zone, is dependent on the physiology of the patient.

In some embodiments, the inner balloon 2665 is a ring-tube that is positioned inside the outer balloon 2660 towards the hot or ablation zone 2676. In some embodiments, the inner balloon 2665 has a shape of a doughnut or tube, such that an outer rim, at an equator, of the inner balloon 2665 is attached to an inner side, at an equator, of the outer balloon 2660.

In some embodiments, as shown in FIG. 26B, when fully expanded the proximal half-spherical first portion 2670 of the outer balloon 2660 has a diameter of 32 mm while a length of the outer balloon 2660 is 36 mm along the longitudinal axis 2674. In some embodiments, a diameter of the inner balloon 2665 is 28 mm, when fully expanded.

In some embodiments, as shown in FIG. 26C, when fully expanded the proximal half-spherical first portion 2670 of the outer balloon 2660 has a diameter of 30 mm while a length of the outer balloon 2660 is 36 mm along the longitudinal axis 2674. In some embodiments, a diameter of the inner balloon 2665 is 28 mm, when fully expanded.

In some embodiments, as shown in FIGS. 26E, 26H and 26K, when fully expanded the proximal half-spherical first portion 2670 has a diameter ranging from 20 mm to 60 mm, the distal conical second portion 2672 has a length (along the longitudinal axis 2674) ranging from 2 mm to 50 mm while a length of each of the necks 2681, 2682 ranges from 1 mm to 10 mm.

In some embodiments, as shown in FIG. 26E, when fully expanded, the inner balloon 2665 assumes a spherical shape having a diameter 'd' ranging from 15 mm to 50 mm. In some embodiments, the contact or ablation zone 2676 has a width ranging from 1 mm to 50 mm. In some embodiments, a gap or width 'w' between the outer and inner balloons 2660, 2665, along the diameter 'd' of the inner balloon 2665, in the non-ablation zone, ranges from 0.1 mm to 50 mm.

In some embodiments, as shown in FIG. 26H, when fully expanded, the inner balloon 2665 assumes an ovoid shape having a horizontal axis 2674*h* along the longitudinal axis 2674 and a vertical axis 2674*h*' substantially perpendicular to the longitudinal axis 2674. In some embodiments, a first length along the horizontal axis 2674*h* ranges from 15 mm to 45 mm and a second length along the vertical axis 2674*h*' ranges from 15 mm to 50 mm. In some embodiments, the contact or ablation zone 2676 has a width ranging from 1 mm to 50 mm. In some embodiments, a gap or width 'w' between the outer and inner balloons 2660, 2665, along the vertical axis 2674*h*', in the non-ablation zone, ranges from 0.1 mm to 50 mm.

In some embodiments, as shown in FIG. 26K, when fully expanded, the inner balloon 2665 assumes a conical shape having a horizontal axis 2674*k* along the longitudinal axis 2674 and a vertical axis 2674*k*' substantially perpendicular to the longitudinal axis 2674. In some embodiments, a first length along the horizontal axis 2674*k* ranges from 15 mm to 45 mm and a second length along the vertical axis 2674*k*' ranges from 15 mm to 50 mm. In some embodiments, the contact or ablation zone 2676 has a width ranging from 1 mm to 50 mm. In some embodiments, a gap or width 'w' between the outer and inner balloons 2660, 2665, along the vertical axis 2674*k*', in the non-ablation zone, ranges from 0.1 mm to 50 mm.

In some embodiments, as shown in FIGS. 26D, 26E, 26J, and 26K, the inner balloon 2665 contacts the outer balloon 2660, at the contact or ablation zone 2676, more anteriorly than posteriorly. In other words, the area of contact between the inner balloon and outer balloon is positioned such that more than 50% of said area of contact is located within a proximal end of the outer balloon, wherein the distal or posterior end is defined as the portion of the outer balloon that is halfway, or more (more distal), along the length of the outer balloon when the outer balloon is inflated and the proximal end or anterior end is defined as the portion of the outer balloon that is halfway, or less (more proximal), along the length of the outer balloon when the outer balloon is inflated.

In some embodiments, the contact or ablation zone 2676 on anterior surface 2676*a* of the outer balloon 2660 is at least 10% more than on posterior surface or end of the outer balloon 2660. In some embodiments, the contact or ablation zone 2676 ranges from 10% to 95% of the anterior surface 2676*a* of the outer balloon 2660. In some embodiments, the contact or ablation zone 2676 is greater than 25% of the circumference of the outer balloon 2660. In some embodiments, the contact or ablation zone 2676 ranges from 10% to 50% of the surface area of the outer balloon 2660.

In some embodiments, as shown in FIGS. 26D, 26E, 26J, 26H, 26J and 26K a first circumferential marker 2690 on the outer balloon 2660 is indicative of the contact or ablation zone 2676. In some embodiments, as shown in FIG. 26D, a second circumferential marker 2691, on the outer balloon 2660, is marked proximate the distal end of the outer balloon 2660. In various embodiments, the circumferential markers are radiopaque to provide radiographic visualization of the balloons to ensure proper placement during ablation procedures.

In some embodiments, as shown in FIGS. 26F, 26I and 26L, when fully expanded the proximal half-spherical first portion 2670 of the outer balloon 2660 has a diameter of 26 mm while a length of the outer balloon 2660 is 39 mm along the longitudinal axis 2674. A length of the conical second portion 2672 is 7.5 mm along the longitudinal axis 2674 while a width of the conical second portion 2672 towards its distal end is 10 mm. In some embodiments, diameter of each of the necks 2681, 2682 is 5 mm. In some embodiments, the outer catheter 2615 has an outer diameter of 4.8 mm while the inner catheter or lumen 2650 has an inner diameter of 1 mm.

In some embodiments, as shown in FIG. 26F, a diameter of the inner balloon 2665 is 28 mm when fully expanded, wherein the balloon 2665 is spherical. In some embodiments, as shown in FIG. 26I, a diameter (along a vertical axis 2674i) of the inner balloon 2665 is 28 mm when fully expanded, wherein the balloon 2665 is ovoid shaped. In some embodiments, as shown in FIG. 26L, a diameter (along a vertical axis 2674l) of the inner balloon 2665 is 28 mm when fully expanded, wherein the balloon 2665 is conical shaped.

In some embodiments, the outer balloon 2660 is more compliant than the inner balloon 2665. In some embodiments, the outer balloon has a radial expansion in a range of 10% to 25% at 1 atm pressure. In embodiments, the inner balloon 2665 is semi-compliant, and may have less than 10% radial expansion at 1 atm. In some embodiments, the inner balloon 2665 is coated or compounded with a hydrophilic coating or with barium, gold, platinum, or other radio-opaque material for radiographic visualization. In other embodiments, the outer surfaces of the balloons are dotted with silver or gold paint dots for radiographic visualization. In some embodiments, up to 25 dots are painted on each balloon.

In some embodiments, the at least one flexible heating chamber 2630 is positioned in-line within the central water/vapor lumen 2617 such that the plurality of electrodes 2655 are at least partially inside the inner balloon 2665. In one embodiment, as shown in FIG. 26B, the flexible heating chamber 2630 is positioned such that a distal end of the chamber 2630 lies at a distance of 30 mm, within the inner balloon 2665, from a proximal end of the outer balloon 2660.

In some embodiments, the inner balloon 2665 is movable along the longitudinal axis 2674 within and along a portion of a length of the outer balloon 2660, to better position the inner balloon inside the outer balloon and ensure proper contact of the inner balloon with the outer balloon, using a wire mechanism in a handle at the proximal end of the catheter 2610.

In some embodiments, as shown in FIG. 26M, proximal and distal constraining elements 2680a, 2680b are positioned inside the outer balloon 2660 such that the inner balloon 2665 is constrained to inflate or expand between the proximal and distal constraining elements 2680a, 2680b. In embodiments, the proximal and distal constraining elements 2680a, 2680b are desirable when the inner balloon 2665 is semi-compliant or compliant. In accordance with aspects of the present specification, the proximal and distal constraining elements 2680a, 2680b control or modify a shape of the expanding inner balloon 2665 so as to preferably allow contact of the inner balloon 2665 with the outer balloon 2660 at the predefined target middle or ablation zone 2676. The proximal element 2680a ensures that the inner balloon 2665 does not move proximally away from the desired middle or ablation zone 2676 during operation. In embodiments, the proximal and distal constraining elements 2680a, 2680b are permeable to allow cooling fluid, such as air or carbon-dioxide, to flow into the outer balloon 2660 to fully inflate it but mechanically constrain an expansion or inflation of the inner balloon 2665 such that the inner balloon 2665 just fills the space between the proximal and distal constraining elements 2680a, 2680b. In some embodiments, the proximal and distal constraining elements 2680a, 2680b are meshes or nets. In some embodiments, the outer balloon 2660 is compartmentalized using strips or webbing of the same material as the outer catheter 2615.

In accordance with an aspect of the present specification, during ablation, the outer balloon 2660 is maintained at a pressure and is never under vacuum. In some embodiments, the outer balloon 2660 is under a first pressure while the inner balloon 2665 is under a second pressure. In some embodiments, the first pressure is equal to or less than the second pressure. In some embodiments, a pressurization difference between the outer and inner balloons 2660, 2665 is less than 20 psi. In some embodiments, there is a minimum desired volume difference between the outer and inner balloons 2660, 2665. In some embodiments, the outer balloon 2660 has a volume, during operation, that is at least 10% greater than a volume of the inner balloon 2665. In some embodiments, the volume difference of at least 10% is distributed between the first and third zones 2675, 2677. In some embodiments, the outer balloon 2660 has a volume, during operation, that is at least 5% greater than a volume of the inner balloon 2665. In some embodiments, the volume difference of at least 5% is distributed between the first and third zones 2675, 2677.

In some embodiments, a mapping member 2685, which may be a distal extension, catheter, or any substrate comprising a plurality of sensors, detectors, or electrodes, is attached to the distal end of the body 2612 distal to the outer balloon 2660. The mapping member 2685 maps the area of cardiac tissue responsible for the arrhythmia. In some embodiments, the mapping member 2685 has a length of up to 75 mm. In some embodiments, the mapping member 2685 is pre-shaped in a pig-tail shape to allow wall contact. In embodiments, the diameter of the pigtail is between 5 mm and 35 mm. In some embodiments, the mapping member 2685 comprises 1 to 32 electrodes configured to record signals from a pulmonary vein or pacing in a pulmonary vein. In some embodiments, the catheter body further includes a lumen for advancing a mapping member. In some embodiments, the lumen for advancing a mapping member has a diameter in a range of 0.5-1.5 mm. In some embodiments, the lumen for advancing a mapping member has a diameter of 1.0 mm.

In some embodiments, the outer balloon 2660 includes a plurality of mapping electrodes, either glued metal electrodes or printed electrodes, within or attached to the outer surface of its walls in the middle of its length axis circularly configured to record cardiac signals to map areas of cardiac tissue responsible for an arrhythmia. In some embodiments, the outer balloon 2660 includes up to 24 mapping electrodes. In embodiments, the mapping electrodes measure cardiac electrical activity to assess at least one therapeutic endpoint.

In some embodiments, an entire surface of the catheter 2610, including the balloons 2660, 2665, mapping electrodes and the mapping member 2685, is coated with heparin or a hydrophilic coating.

During operation, the cardiac ablation catheter 2610 is introduced, through a trans-septal puncture, into a left atrium and the outer balloon is advanced to a pulmonary vein of a heart. Next, the outer balloon 2660 is inflated with a cooling/insulating fluid, such as air or carbon-dioxide, to occlude blood flow from a pulmonary vein to the left atrium. In some embodiments, occlusion of the blood flow is confirmed with a dye study. Thereafter, the inner balloon 2665 is inflated with vapor such that the inner balloon 2665 comes into contact with desired portions or areas (that is, the middle hot zone 2676) of the outer balloon 2660 and the outer balloon 2660 remains contact with an ablation zone comprising target cardiac tissue. Cold zones or areas 2675, 2677 are located on the outer balloon 2660 where the inflated inner balloon 2665 is not in contact with the inflated outer balloon 2660. Consequently, thermal energy is transferred from inside the inner balloon 2665 through the outer balloon 2660 at the middle hot zone 2676 (the ablation zone) and into the cardiac tissue to ablate the tissue and treat the arrhythmia.

The non-contact areas or cold zones 2675, 2677, between the inner and outer balloons, are filled with the cooling/insulating fluid which acts as an insulator. The thermal energy is delivered for a desired duration following which the inner balloon 2665 self deflates due to condensation of vapor and the outer balloon 2660 is deflated. The catheter 2610 is removed and a circumferential ablation is created in the pulmonary vein (or the left atrium, if needed, in some embodiments) to treat an atrial arrhythmia. Optionally the pulmonary vein (or the left atrium, if needed, in some embodiments) is paced to confirm completeness of the circumferential ablation.

In some embodiments, the outer balloon 2660 includes a thermocouple in a predetermined area to detect contact of the inner balloon 2665 with the outer balloon 2660. In some embodiments, the outer balloon 2660 includes a thermocouple in a predetermined area to monitor delivery of thermal energy to the target cardiac tissue. In some embodiments, the outer balloon 2660 includes a thermocouple outside a predetermined area of the outer balloon 2660 to measure the temperature in the outer balloon 2660 and control the temperature outside the predetermined area to remain at less than 60 degrees Celsius, and ideally at less than 54 degrees Celsius. In some embodiments, the inner balloon 2665 includes a pressure sensor to measure pressure inside the inner balloon 2665. In some embodiments, the thermocouples and/or the pressure sensor are introduced through the two sensor lumens 2640.

FIG. 26S illustrates an outer expandable member 2671 to be used in place of an outer balloon, in accordance with some embodiments of the present specification. In some embodiments, the catheters of the present specification include an outer expandable member 2671, rather than an outer balloon, and the inner balloon is positioned within the outer expandable member 2671. In some embodiments, the outer expandable member 2671 has a conical shape with an elongate body that tapers toward its distal end 2671d. The outer expandable member 2671 is comprised of a flexible material 2678 and includes a shape memory wire 2679 extending along its body. In some embodiments, the flexible material 2678 comprises silicone. In some embodiments, the shape memory wire 2679 comprises Nitinol. In some embodiments, the outer expandable member 2671 is compressed for delivery, similarly to a deflated outer balloon, and the catheter is advanced to a left atrium of a patient. The distal end 2671d is positioned in a pulmonary vein of the patient. The shape memory wire 2679 changes to its post deployment shape upon delivery, for example, in response to body temperature of the patient, resulting in the expansion of the outer expandable member 2671 to its deployed shape as seen in FIG. 26S. In comparison to the double balloon catheter embodiments of the present specification, the outer expandable member 2671 expands passively due to its shape memory properties, rather than being actively expanded via gas or liquid insufflation, as with the outer balloon. After the outer expandable member 2671 has changed to its post deployment shape, the inner balloon is inflated with ablative agent, for example, steam, and comes into contact with a portion of the outer expandable member 2671 at a hot zone. Thermal energy is transferred from this hot zone to the cardiac tissue in contact therewith for ablation. In some embodiments, portions of the outer expandable member 2671 distal and proximal to the hot zone are in contact with the cardiac tissue. These portions function to both prevent blood from contacting the hot zone surface and becoming coagulated and also as an outer insulator to cardiac tissue proximal and distal to the hot zone.

FIG. 26T illustrates a cross sectional view of another embodiment of an ablation catheter 26102, in accordance with the present specification. In an embodiments, catheter 26102 is manufactured using a copolymer such as Arnitel or Pebax. In embodiments, the catheter 26102 is a multi-lumen extrusion (MLE) catheter comprising a channel 26104, a channel, 26106, and at least two diametrically opposite channels 26108. In some embodiments, diameter of ablation catheter 26102 is in a range of 2 mm to 10 mm. Channels 26104, 26106, and 26108 lie at the center of the ablation catheter 26102. Channel 26104 is used to position an electrode and to pass saline through it. Channel 26014 is open to the inner balloon, such as inner balloon 2665. Channel 26104 is circular and is configured to allow an electrode pin of at least 0.07 mm to pass through it, therefore, the channel 26104 is configured to be of a diameter in a range of 0.072 to 0.078 mm. A wall that is approximately 0.010 mm separates channel 26104 from the other channels 26106 and 26108. The circular shape of channel 12104 enables optimal fit for the electrode with no spaces around the periphery of the electrode. If there were spaces, saline would pass behind the electrode and not get heated. In some embodiments, inner circumference of channel 26104 is coated with a hydrophilic coating to attract fluid. In some embodiments, channel 26104 eliminates at a point distal to the output of channel 26104 into the inner balloon, thereby providing additional space for folded/pleated balloon material. This further allows a decrease in the ablation catheter size and to steer better because of reduced stiffness.

Channel 26106 is configured to receive at least one of a guide wire, mapping catheter, and pacing catheter. Further, channels 26108 are open to the inner balloon and receive hot fluid out of the inner balloon. In embodiments, a valve between the inner balloon and channels 26108 ensures that hot fluid only flows out when either the pressure in the balloon exceeds a threshold, or when the valve is opened to evacuate the inner balloon.

FIG. 26U illustrates a concentrically positioned channel 26110 between an outer circumference of ablation catheter 26102 and an outer shaft, in accordance with some embodiments of the present specification. In embodiments, channel 26110 is used to pass $CO_2$ to inflate as well as deflate an outer balloon, such as outer balloon 2660. In embodiments, channel 26110 is connected to the outer balloon through a valve.

FIG. 26V illustrates a cross sectional view of another embodiment of an ablation catheter 2692, in accordance with the present specification. The catheter 2692 includes a plurality of separate lumens for balloon insufflation, guide wire advancement, for housing an electrode/steam generation (steam in), and for vapor out. In an embodiment, the catheter 2692 includes a first lumen 2693 configured to allow vapor to be released or suctioned from the catheter 2692 after ablation. The first lumen 2693 is positioned within the catheter, bounded by the catheter wall 2643. A first elongate, tubular member 2644 is positioned within the first lumen 2693 and includes a second lumen 2694 configured to receive a push/pull guide wire. In some embodiments, the first elongate, tubular member 2644 has a circular cross-section. A second tubular, elongate member 2649 is also positioned within the first lumen 2693 and includes a third lumen 2699 configured to house an electrode and receive a first fluid to be converted to vapor (steam in) and inflate an inner balloon. In some embodiments, $CO_2$ may first be delivered to the third lumen 2699 to partially inflate the inner balloon. In some embodiments, the second, elongate tubular member 2699 has an oval cross-section. An elongate portion 2642 of the catheter wall 2643 extends inward, into the first lumen 2693, along the entire length of the catheter, creating a fourth lumen 2647 configured to receive a second fluid for inflating an outer balloon and releasing or suctioning the second fluid for deflating the outer balloon.

FIG. 26W illustrates a distal end of an ablation catheter 2600 depicting an inner balloon 2601 positioned within an outer balloon 2602, in accordance with some embodiments of the present specification. An elongate tubular member 2603 extends within a lumen of the catheter body 2604 and is configured to receive a push/pull guide wire.

Figure 26X:
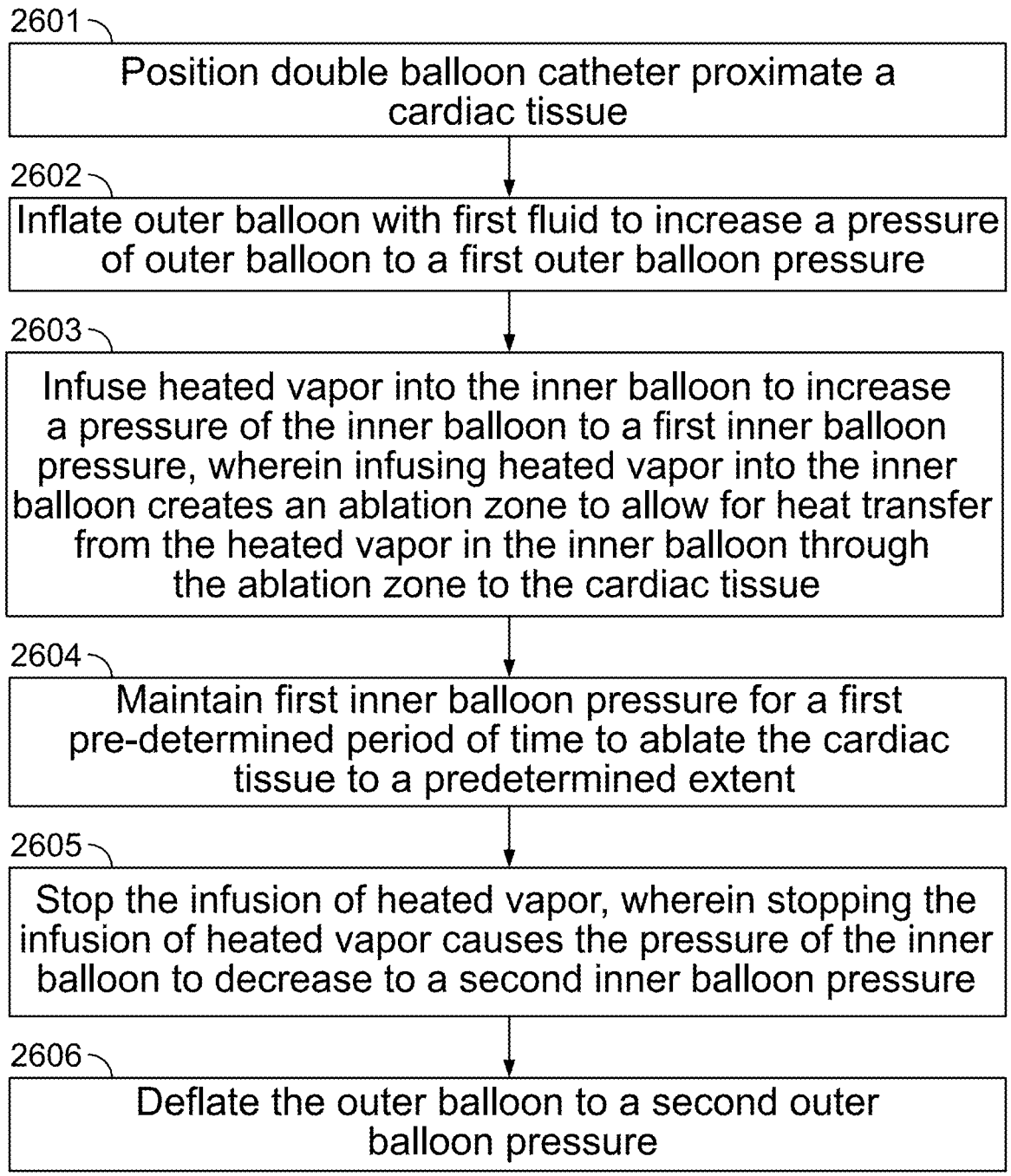
FIG. 26X is a flowchart listing the steps in a method of ablating cardiac tissue, in accordance with some embodiments of the present specification.

FIG. 26X is a flowchart listing the steps in a method of ablating cardiac tissue, in accordance with some embodiments of the present specification. At step 2601, a catheter is positioned proximate a cardiac tissue of a patient. In embodiments, the catheter comprises an elongate body having a lumen, a proximal end and a distal end and an outer balloon and an inner balloon positioned at the distal end such that the inner balloon is positioned within the outer balloon. In various embodiments, the cardiac tissue is a pulmonary vein, a portion of a pulmonary vein, a pulmonary vein ostium, an atrium, tissue proximate to a pulmonary vein antrum, or a left atrial appendage. In some embodiments, the method further comprises documenting a degree of pulmonary vein occlusion achieved by inflating the outer balloon. At step 2602, the outer balloon is inflated with a first fluid to increase a pressure of the outer balloon to a first outer balloon pressure. In some embodiments, the first fluid is air or $CO_2$. In some embodiments, the first outer balloon pressure is between 0.01 atm and 5 atm and preferably between 0.1 atm and 5 atm or any range or increment therein.

At step 2603, heated vapor in infused into the inner balloon to increase a pressure of the inner balloon to a first inner balloon pressure, wherein infusing heated vapor into the inner balloon creates an ablation zone and wherein a surface area of the ablation zone is defined by a portion of the inner balloon contacting a portion of the outer balloon to thereby allow for heat transfer from the heated vapor in the inner balloon through the ablation zone to the cardiac tissue. In some embodiments, the heated vapor comprises steam and a temperature of the heated vapor is at least 100° C. In some embodiments, the method further comprises inflating the inner balloon with a second fluid prior to infusing the heated vapor into the inner balloon. In embodiments, the second fluid is air or $CO_2$. The first inner balloon pressure is maintained for a first pre-determined period of time to ablate the cardiac tissue to a predetermined extent at step 2604. In some embodiments, the first pre-determined period of time is between 1 second and 5 minutes. In some embodiments, the first outer balloon pressure is maintained for the first pre-determined period of time. At step 2605, the infusion of heated vapor is stopped, wherein stopping the infusion of heated vapor causes the pressure of the inner balloon to decrease to a second inner balloon pressure. At step 2606, the outer balloon is deflated to a second outer balloon pressure.

In some embodiments, the surface area of the ablation zone is a function of a surface area of tissue positioned at a junction between the patient's pulmonary vein and the patient's left atrium. In some embodiments, the method further comprises removing a fluid created by a condensation of the heated vapor in the inner balloon, wherein the removal of the fluid decreases the pressure of the inner balloon to a third inner balloon pressure that is less than or equal to the first inner balloon pressure. In some embodiment, the catheter comprises a plurality of electrodes positioned proximate the distal end of the catheter and the heated vapor is generated by directing saline through the lumen and over the plurality of electrodes. In some embodiments, the method further comprises documenting a degree of removing an occlusion of the pulmonary vein after deflating the outer balloon.

In some embodiments, the method further comprises placing a guide wire or pacing catheter into a heart of the patient and placing the catheter over the guide wire or pacing catheter. In embodiments, the method further comprises sensing or stimulating a pulmonary vein using the guide wire or pacing catheter to determine a degree of pulmonary vein isolation. In some embodiments, a distal tip of the catheter is configured to deflect from a linear configuration to a curved configuration, wherein the curved configuration is defined by the distal tip being adapted to turn up to 150 degrees through a radius ranging from 0.5 to 2.5 inches.

In some embodiments, the inflated outer balloon is in contact with a portion of an ostium of a pulmonary vein and occludes at least a portion of the pulmonary vein 2 mm to 15 mm distal to the pulmonary vein ostium. In some embodiments, the ablation zone has a width of 2 mm to 15 mm and has a curved length at least partially defined by an extent of contact between the inflated outer balloon and a surface of the cardiac tissue. In some embodiments, a distance between an outer surface of the inflated outer balloon and an outer surface of the uninflated inner balloon is in a range of 1 mm to 25 mm.

In some embodiments, the method further comprises using at least one of fluoroscopy, three dimensional mapping, or an endoscopic procedure to determine an extent of contact of between at least two of the inner balloon, the outer balloon, and the cardiac tissue.

In some embodiments, the catheter further comprises at least one sensor. In embodiments, the sensor is configured to monitor contact of the inner balloon with the outer balloon or configured to monitor a temperature or pressure of the outer balloon or a temperature or pressure of the inner balloon.

In some embodiments, the further comprises introducing the catheter through a venous puncture in a femoral vein of the patient and advancing the catheter into a left atrium of the patient and into a pulmonary vein or left atrial appendage through a trans-septal puncture.

In some embodiments, the ablation zone is positioned away from a source of production of the heated vapor no further than 100 mm. In some embodiments, the ablation zone is only created when a pressure opposing a surface of the outer balloon is greater than 0.1 psi.

In some embodiments, the method further comprises repeating steps to ablate cardiac tissue for a second pre-determined period of time, wherein the second pre-determined period of time is equal to 50% to 250% of the first pre-determined period of time.

In some embodiments, ablation is performed to treat atrial fibrillation or ablate a left atrial appendage in the patient.

In some embodiments, upon being inflated, the outer balloon has a pear-shaped configuration, wherein the pear-shaped configuration comprises a proximal body that narrows into a tapered distal end.

In some embodiments, upon being inflated, a shape of the outer balloon is defined by a curve of a surface of the outer balloon that is further defined by a plane intersecting an entire length of the catheter, wherein the curve is characterized by a first point, a second point, and a third point sequentially positioned, and extending along the length of the catheter, between a proximal point and a distal point, wherein a first slope between the proximal point and first point has a first value, a second slope between the first point and second point has a second value, a third slope between the second point and the third point has a third value, a fourth slope between the third point and distal point has a fourth value, and wherein an absolute value of the first value is greater than an absolute value of the second value, an absolute value of the third value or an absolute value of the fourth value, the absolute value of the second value is greater than the absolute value of the third value, and the absolute value of the fourth value is greater than the absolute value of the third value; and wherein, when inflated, the inner balloon has the shape of an oblate spheroid where the minor axis, or short axis, coincides with the longitudinal axis of the catheter and the major axis, or long axis, is perpendicular to the catheter.

In some embodiments, upon being inflated, a shape of the outer balloon may be defined by a first distance from a central axis of the outer balloon to a first proximal point on an outer surface of the outer balloon, a second distance from the central axis to a second proximal point on the outer surface of the outer balloon, a third distance from the central axis to a third point on the outer surface of the outer balloon, a fourth distance from the central axis to a first distal point on the outer surface of the outer balloon, and a fifth distance from the central axis to a second distal point on the outer surface of the outer balloon, wherein each of the first proximal point, the second proximal point, the third point, the first distal point, and the second distal point are sequentially positioned along a length of the central axis starting from a proximal position and extending distally, wherein the second distance is greater than the first distance, the third distance, and the fifth distance and wherein the fourth distance is greater than the first distance, the second distance, the third distance, and the fifth distance.

In some embodiments, upon the inner balloon and outer balloon being inflated, the ablation zone has a width and curved length defined by an extent of contact between the outer balloon and a portion of the cardiac tissue.

Figure 26Y:
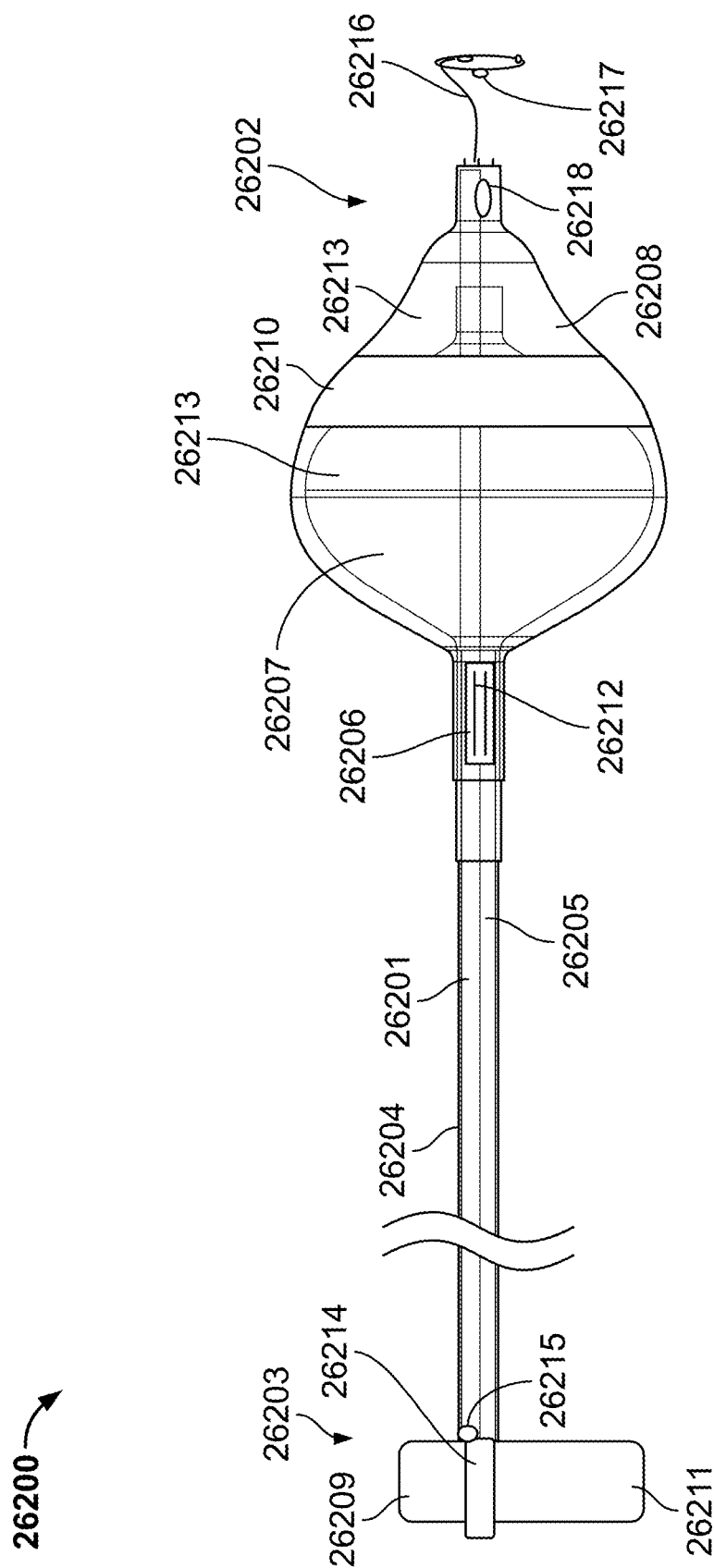
FIG. 26Y illustrates an system for ablating cardiac tissue in accordance with embodiments of the present specification.

FIG. 26Y illustrates an system 26200 for ablating cardiac tissue in accordance with embodiments of the present specification. The system comprises 26200: a catheter 26201 adapted to be positioned proximate a cardiac tissue of a patient, wherein the catheter comprises: a distal end 26202; a proximal end 26203; a first lumen 26204; a second lumen 26205 comprising a heating element 26206; an inner balloon 26207 positioned at the distal end 26202 of the catheter 26201 and in fluid communication with the second lumen 26204; and an outer balloon 26208 positioned at the distal end 26204 of the catheter 26201 and enclosing the inner balloon 26207, wherein the outer balloon 26208 is in fluid communication with a first fluid source 26209 via the first lumen 26204 and wherein, upon inflation of the outer balloon 26208 with a first fluid and inflation of the inner balloon 26207 with a heated vapor, an ablation zone 26210 is formed at a contact area of the inner balloon 26207 with the outer balloon 26208; and a controller 26211, wherein the controller 26211 comprises programmatic instructions that, when executed, cause: the first fluid to be infused into the outer balloon 26208; and a second fluid to be directed through the second lumen and placed in contact with the heating element to form the heated vapor.

In some embodiments, the outer balloon 26208 is not fixedly attached to the inner balloon 26207 in said contact area. In some embodiments, a contour of a surface area of the ablation zone 26210 is a function of, and dependent on, a portion of the pulmonary vein of the patient. In some embodiments, the ablation zone 26210 is defined by a surface area and a size of the surface area ranges from 5% to 95% of a surface area of at least one of the inner balloon 26207 or outer balloon 26208. In some embodiments, the ablation zone 26210 has a width in a range of 1 mm to 20 mm. In some embodiments, the first fluid is air or $CO_2$. In some embodiments, the second fluid is saline or carbonated saline, the heated vapor is steam, and the heated vapor has a temperature of at least 100° C. In some embodiments, the heating element 26206 is flexible and comprises a plurality of electrodes 26212 positioned within the second lumen 26205 and configured to receive an electrical current activated by the controller. In some embodiments, each of the plurality of electrodes 26212 comprises at least one edge adapted to be exposed to fluid present in the second lumen. In some embodiments, the heating element 26206 is defined by a distal end and the distal end is positioned at a distance in a range of 0 mm to 80 mm from a proximal end of the outer balloon 26208. In some embodiments, the system 26200 further comprising one or more insulation zones 26213, wherein each of the one or more insulation zones 26213 is defined by a surface area of the outer balloon 26208 that is proximal or distal to the ablation zone 26210 and wherein each of the one or more insulation zones 26213 has an average temperature that is less than an average temperature of the ablation zone 26210. In some embodiments, each of the one or more insulation zones 26213 has a width of at least 0.1 mm and extends along a curved length in a range of 1 mm to the entire circumference of the outer balloon, or any increment therein.

In some embodiments, the inner balloon 26207 is configured to be movable along a horizontal longitudinal axis within the outer balloon 26208 and the catheter 26201 further comprises a mechanism 26214 configured to move the inner balloon 26207 within the outer balloon 26208.

In some embodiments, the controller 26211 further comprises programmatic instructions that, when executed, cause the outer balloon 26208 to be inflated to a first pressure and maintained at the first pressure during ablation. In some embodiments, the controller 26211 further comprises programmatic instructions that, when executed, cause the inner balloon 26207 to be inflated to a second pressure during ablation, wherein the first pressure is equal to or less than the second pressure. In some embodiments, the first pressure is between 0.01 atm and 5 atm and preferably between 0.1 atm and 5 atm or any range or increment therein.

In some embodiments, the system 26200 further comprises one or more pressure valves 26215 in fluid communication with the first lumen 26204, wherein each of the one or more pressure valves 26215 is configured to control a movement of fluid into, or out of, the outer balloon 26208 based upon a predetermined pressure level.

In some embodiments, the controller 26200 further comprises programmatic instructions that, when executed, cause the ablation zone 26210 to be maintained for a period of time between 1 second and 5 minutes.

In some embodiments, the system further comprises a mapping member 26216 positioned at the distal end 26202 of the catheter 26201 and configured to map an area of cardiac tissue responsible for a cardiac arrhythmia, wherein the mapping member 26216 comprises a plurality of sensors, detectors, or electrodes 26217. In some embodiments, the mapping member 26216 comprises a range of 1 to 64 electrodes configured to record signals form the pulmonary vein or pacing in the pulmonary vein.

In some embodiments, the system further comprises at least one sensor 26218, wherein the at least one sensor 26218 is positioned at the distal end 26202 of the catheter 26201 or at the proximal end 26203 of the catheter 26201. In some embodiments, the sensor 26218 comprises a temperature sensor configured to monitor a delivery of thermal energy to the cardiac tissue. In some embodiments, the sensor 26218 comprises a pressure sensor configured to measure a pressure inside the inner balloon.

In some embodiments, the outer balloon 26208 is defined by a pear shape and configured to be positioned in the pulmonary vein of the patient to occlude the pulmonary vein.

In some embodiments, when inflated, the outer balloon 26208 has an axis that extends along a length of the outer balloon 26208 and through the center of the outer balloon 26208 and a distance from the axis to an outer surface of the outer balloon changes along said length.

In some embodiments, upon being inflated, a shape of the outer balloon 26208 is defined by a curve of a surface of the outer balloon 26208 that is further defined by a plane intersecting an entire length of the catheter 26201, wherein the curve is characterized by a first point, a second point, and a third point sequentially positioned, and extending along the length of the catheter 26201, between a proximal point and a distal point, wherein a first slope between the proximal point and first point has a first value, a second slope between the first point and second point has a second value, a third slope between the second point and the third point has a third value, a fourth slope between the third point and distal point has a fourth value, and wherein an absolute value of the first value is greater than an absolute value of the second value, an absolute value of the third value or an absolute value of the fourth value, the absolute value of the second value is greater than the absolute value of the third value, and the absolute value of the fourth value is greater than the absolute value of the third value; and wherein, when inflated, the inner balloon has the shape of an oblate spheroid where the minor axis, or short axis, coincides with the longitudinal axis of the catheter 26201 and the major axis, or long axis, is perpendicular to the catheter 26201.

In some embodiments, upon being inflated, a shape of the outer balloon 26208 may be defined by a first distance from a central axis of the outer balloon 26208 to a first proximal point on an outer surface of the outer balloon 26208, a second distance from the central axis to a second proximal point on the outer surface of the outer balloon 26208, a third distance from the central axis to a third point on the outer surface of the outer balloon 26208, a fourth distance from the central axis to a first distal point on the outer surface of the outer balloon 26208, and a fifth distance from the central axis to a second distal point on the outer surface of the outer balloon 26208, wherein each of the first proximal point, the second proximal point, the third point, the first distal point, and the second distal point are sequentially positioned along a length of the central axis starting from a proximal position and extending distally, wherein the second distance is greater than the first distance, the third distance, and the fifth distance and wherein the fourth distance is greater than the first distance, the second distance, the third distance, and the fifth distance.

In some embodiments, the inner balloon 26207 has a spherical, ovoid, conical, disc, elliptical, rectangular prism, or triangular prism shape.

In some embodiments, when inflated, the outer balloon 26208 is characterized by at least one first radial length extending from a central point on an axis extending longitudinally along the catheter 26201 and through the outer balloon 26208 to a point on a surface of the outer balloon 26208, wherein, when inflated, the inner balloon 26207, is characterized by at least one second radial length extending from a central point on an axis extending longitudinally along the catheter 26201 and through the inner balloon 26207 to a point on a surface of the inner balloon 26207, and wherein the at least one first radial length is different than the at least one second radial length. In some embodiments, the at least one first radial length is greater than the at least one second radial length by any amount or by at least 10%.

In some embodiments, upon the inner balloon 26207 and outer balloon 26208 being inflated, the ablation zone 26210 has a width and curved length defined by an extent of contact between the outer balloon 26208 and the cardiac tissue.

Figure 27:
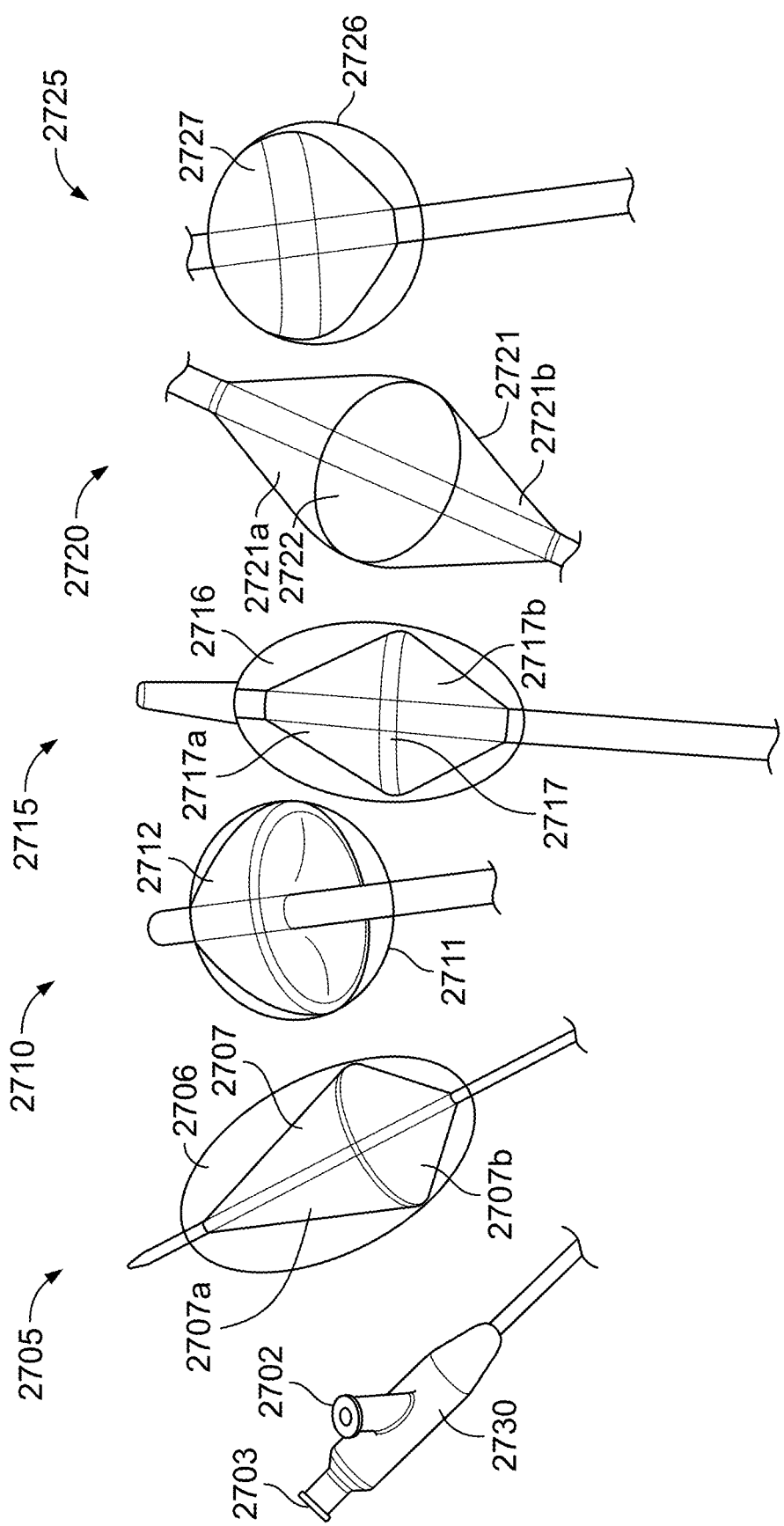
FIG. 27 shows a first plurality of double balloon configurations, in accordance with some embodiments of the present specification.

FIG. 27 shows a plurality of double balloon configurations, in accordance with some embodiments of the present specification. FIG. 27 shows first, second, third, fourth and fifth double balloon catheters 2705, 2710, 2715, 2720 and 2725. The first catheter 2705 illustrates a substantially elliptical outer balloon 2706 attached to a distal tip of the catheter 2705. A twin-conical inner balloon 2707 is attached to the distal tip of the catheter 2705 within the outer balloon 2706. In accordance with an embodiment, the twin-conical inner balloon 2707 comprises first and second conical portions 2707a, 2707b coupled at their bases. In an embodiment, a height of the first conical portion 2707a is greater than a height of the second conical portion 2707b.

The third catheter 2715 also illustrates a substantially elliptical outer balloon 2716 attached to a distal tip of the catheter 2715. A twin-frustum inner balloon 2717 is attached to the distal tip of the catheter 2715 within the outer balloon 2716. In accordance with an embodiment, the twin-frustum inner balloon 2717 comprises first and second frustum (or truncated cone) portions 2717a, 2717b coupled at their bases. In an embodiment, a height of the first frustum portion 2707a is greater than a height of the second frustum portion 2707b.

The second catheter 2710 illustrates a substantially spherical outer balloon 2711 attached to a distal tip of the catheter 2710. A conical inner balloon 2712 is attached to the distal tip of the catheter 2710 within the outer balloon 2711. In accordance with an embodiment, an apex or vertex of the conical inner balloon 2712 lies towards a distal end of the outer balloon 2711 while a base of the conical inner balloon 2712 lies towards a proximal end of the outer balloon 2711.

The fifth catheter 2725 also illustrates a substantially spherical outer balloon 2726 attached to a distal tip of the catheter 2725. A conical inner balloon 2727 is attached to the distal tip of the catheter 2725 within the outer balloon 2726. In accordance with an embodiment and in contrast to the second catheter 2710, an apex or vertex of the conical inner balloon 2727 lies towards a proximal end of the outer balloon 2726 while a base of the conical inner balloon 2727 lies towards a proximal end of the outer balloon 2726.

The fourth catheter 2720 illustrates a substantially twin-conical outer balloon 2721 attached to a distal tip of the catheter 2720. In accordance with an embodiment, the twin-conical outer balloon 2721 comprises first and second conical portions 2721a, 2721b coupled at their bases. In an embodiment, a height of the first conical portion 2721a is substantially equal to a height of the second conical portion 2721b. A substantially elliptical inner balloon 2722 is attached to the distal tip of the catheter 2720 within the outer balloon 2721. For each of the catheters 2705, 2710, 2715, 2720 and 2725, a volume of the inner balloon is less than a volume of the outer balloon. In some embodiments, the volume of the outer balloon is at least 10% greater than the volume of the inner balloon, when both balloons are fully inflated. In various embodiments, a surface area of contact between the inner and outer balloons, in fully inflated state, is less than 90% Each of the first, second, third, fourth and fifth double balloon catheters 2705, 2710, 2715, 2720 and 2725 have a handle attached to their respective proximal ends. FIG. 27 shows an exemplary handle 2730 including a first inlet port 2702 through which a cooling fluid such as, for example, air or carbon-dioxide, is pumped to inflate an outer balloon and a second inlet port 2703 through which an ablative agent such as, for example, vapor is pumped to inflate an inner balloon. In various embodiments, the handle 2730 is configured to be operated by a single operator.

Figure 28:
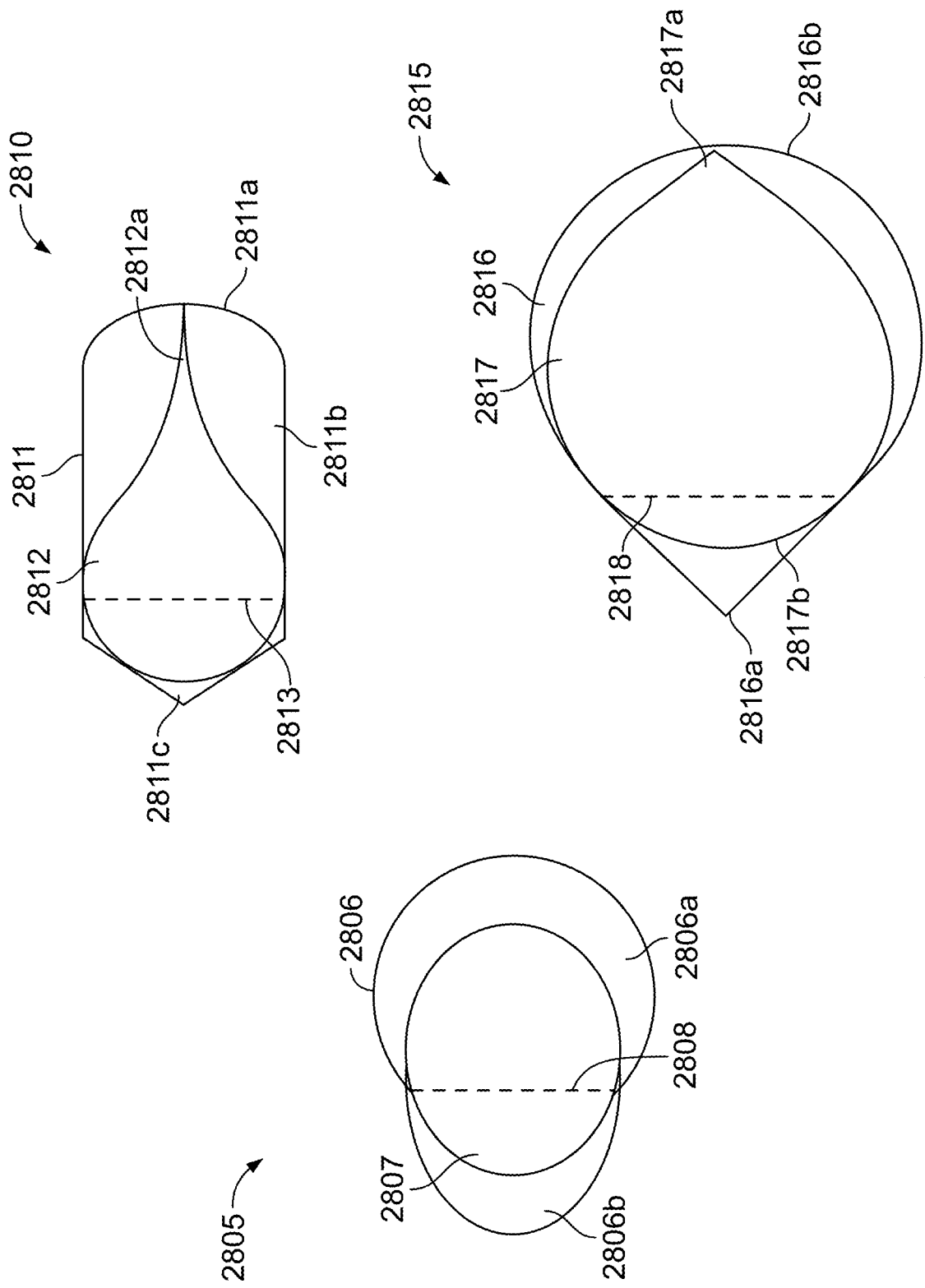
Figure 28:
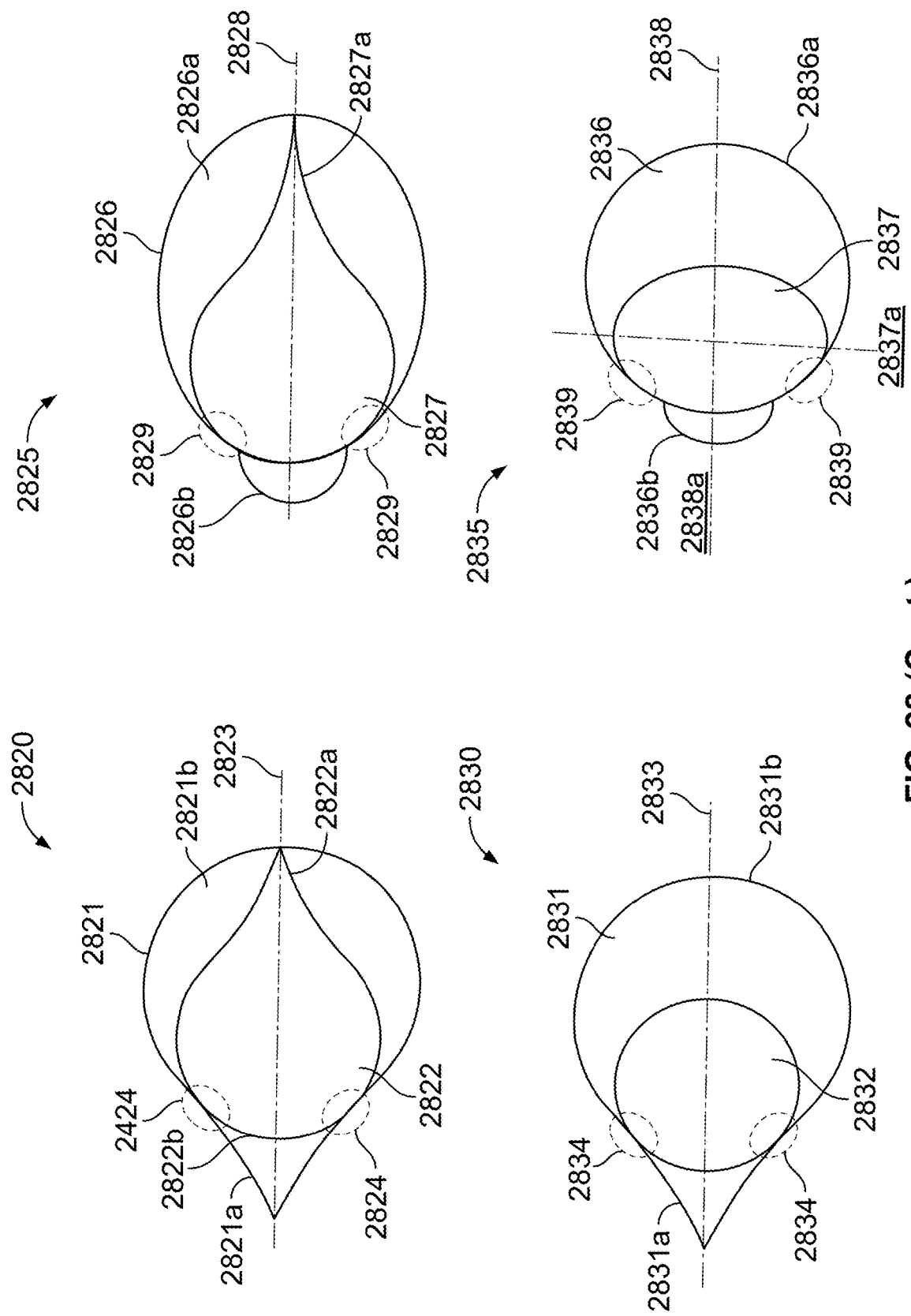

FIG. 28 shows a plurality of double balloon configurations, in accordance with some embodiments of the present specification. FIG. 28 shows first, second, third, fourth, fifth, sixth and seventh double balloon configurations 2805, 2810, 2815, 2820, 2825, 2830, 2835, in fully expanded states. The first configuration 2805 illustrates an outer balloon 2806 that has a compound shape comprising a substantially spherical proximal portion 2806a transitioning into a substantially elliptical distal portion 2806b. The inner balloon 2807 is substantially spherical. In an embodiment, the outer and/or inner balloons 2806, 2807 include a radio-opaque marker 2808 identifying an ablation or hot zone where the inner balloon 2807 contacts the outer balloon 2806 when both are in fully expanded states.

The second configuration 2810 illustrates an outer balloon 2811 that has a compound shape comprising a short substantially spherical proximal portion 2811a, a substantially cylindrical middle portion 2811b and a short substantially conical or tapered distal portion 2811c. The inner balloon 2812 has a substantially tear-drop or droplet shape having its apex or vertex 2812a directed towards a proximal end of the configuration 2810. In an embodiment, the outer and/or inner balloons 2811, 2812 include a radio-opaque marker 2813 identifying an ablation or hot zone where the inner balloon 2811 contacts the outer balloon 2812 when both are in fully expanded states.

The third configuration 2815 illustrates an outer balloon 2816 that has a substantially tear-drop or droplet shape such that an apex or vertex 2816a forms a distal end while a bulbous end 2816b forms a proximal end of the outer balloon 2816. The inner balloon 2817 also has a substantially tear-drop or droplet shape such that an apex or vertex 2817a is directed towards the proximal end and a bulbous end 2817b is directed towards the distal end of the outer balloon 2816. In an embodiment, the outer and/or inner balloons 2816, 2817 include a radio-opaque marker 2818 identifying an ablation or hot zone where the inner balloon 2817 contacts the outer balloon 2816 when both are in fully expanded states.

The fourth configuration 2820 illustrates an outer balloon 2821 that has a substantially tear-drop or droplet shape such that an apex or vertex 2821a forms a distal end while a bulbous end 2821b forms a proximal end of the outer balloon 2821. The inner balloon 2822 also has a substantially tear-drop or droplet shape such that an apex or vertex 2822a is directed towards the proximal end and a bulbous end 2822b is directed towards the distal end of the outer balloon 2821. The outer and inner balloons 2821, 2822 are shown attached to a distal end of an elongate body 2823. An ablation or hot zone 2824 is formed where the inner balloon 2822 contacts the outer balloon 2821 when both are in fully expanded states. In some embodiments, the inner balloon 2822 occupies a smaller area of the inside of the outer balloon 2821 of the fourth configuration 2820 when compared to the balloons 2816, 2817 shown in the third configuration 2815.

The fifth configuration 2825 illustrates an outer balloon 2826 that has a substantially elliptical proximal portion 2826a transitioning into a relatively smaller substantially elliptical distal portion 2826b. The inner balloon 2827 has a substantially tear-drop or droplet shape having its apex or vertex 2827a directed towards a proximal end of the outer balloon 2826. The outer and inner balloons 2826, 2827 are shown attached to a distal end of an elongate body 2828. An ablation or hot zone 2829 is formed where the inner balloon 2827 contacts the outer balloon 2826 when both are in fully expanded states. In some embodiments the elliptical distal portion 2826b comprises a third balloon that is independently operated from a separate elliptical proximal balloon 2826a and can either be inflated with a coolant/insulating fluid or an ablative agent such as water vapor.

The sixth configuration 2830 illustrates an outer balloon 2831 that has a substantially tear-drop or droplet shape such that an apex or vertex 2831a forms a distal end while a bulbous end 2831b form a proximal end of the outer balloon 2831. The inner balloon 2832 has a substantially spherical shape. The outer and inner balloons 2831, 2832 are shown attached to a distal end of an elongate body 2833. An ablation or hot zone 2834 is formed where the inner balloon 2831 contacts the outer balloon 2832 when both are in fully expanded states.

The seventh configuration 2835 illustrates an outer balloon 2836 that has a compound shape comprising a substantially spherical proximal portion 2836a transitioning into a relatively smaller substantially spherical distal portion 2836b. The inner balloon 2837 has a substantially elliptical shape such that a long axis 2837a of the inner balloon 2837 is substantially orthogonal to a longitudinal axis 2838a of the configuration 2835. The outer and inner balloons 2836, 2837 are shown attached to a distal end of an elongate body 2838. An ablation or hot zone 2839 is formed where the inner balloon 2836 contacts the outer balloon 2835 when both are in fully expanded states. In some embodiments, the spherical distal portion 2836b comprises a third balloon that is independently operated from a separate spherical proximal balloon 2836a and can either be inflated with a coolant/ insulating fluid or an ablative agent such as water vapor.

Figure 29:
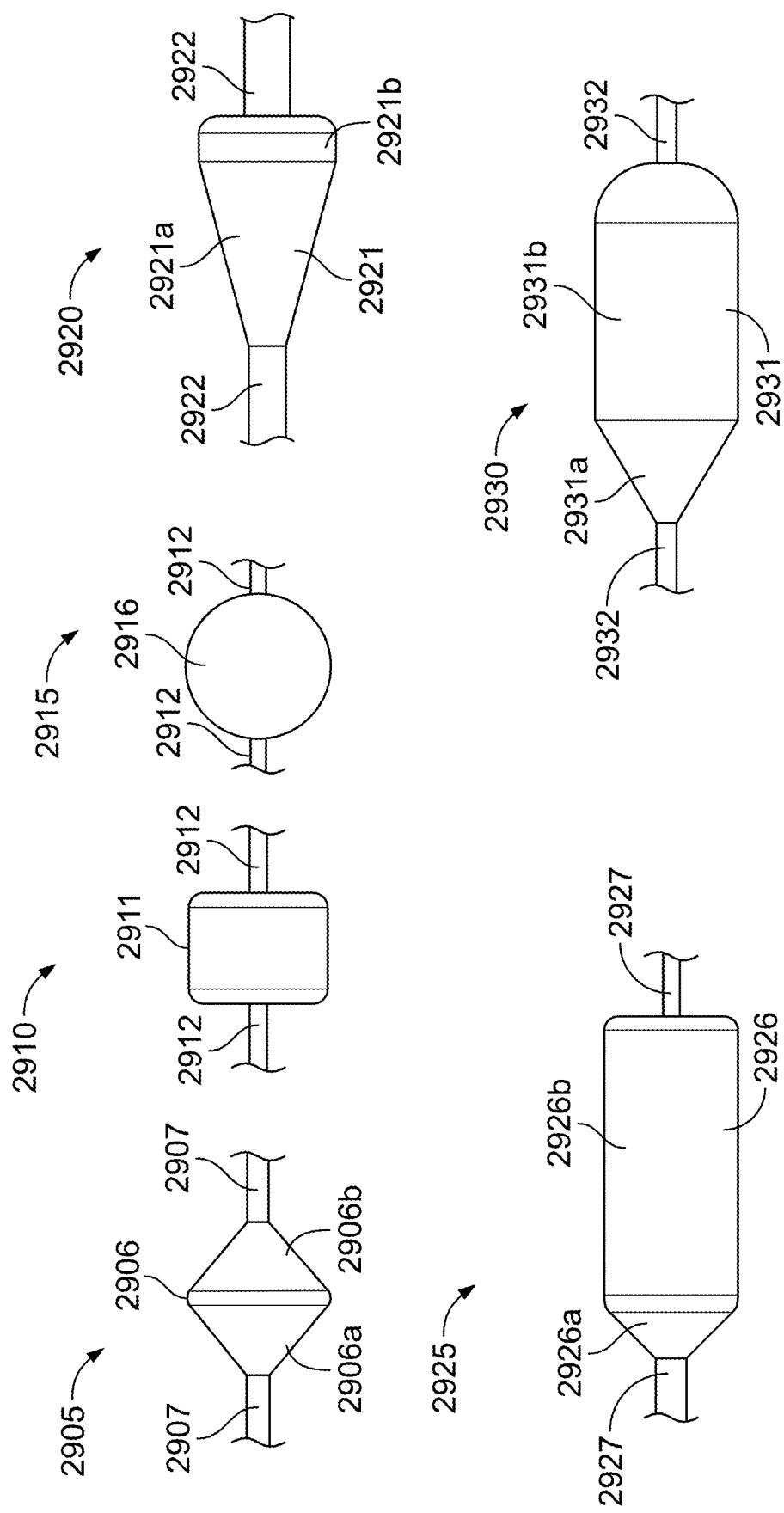
Figure 29:
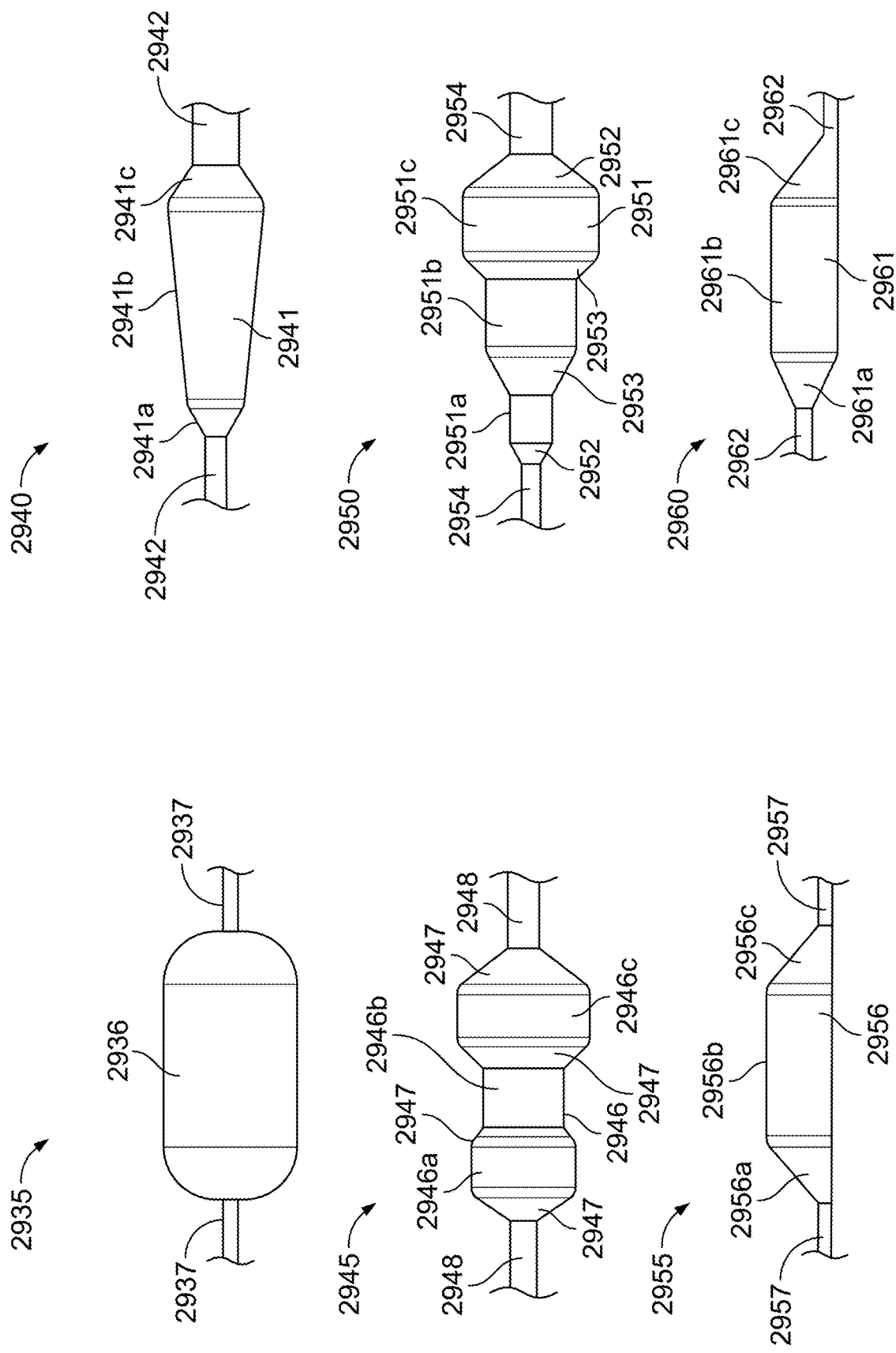

FIG. 29 shows a plurality of exemplary shapes of an outer or inner balloon of a dual balloon catheter, in accordance with some embodiments of the present specification. A first view 2905 shows a conical or twin-conical balloon 2906 comprising first and second conical portions 2906a, 2906b coupled at their bases. Proximal and distal ends of the balloon 2906 extend into tube like structures or necks 2907, which help in keeping the catheter in place when it is passed through the balloon.

A second view 2910 shows a square balloon 2911. It should be appreciated that the qualifier 'square' is indicative of the substantially right-angled or squared ends or corners of the balloon 2911. Proximal and distal ends of the balloon 2911 extend into tube like structures or necks 2912, which help in keeping the catheter in place when it is passed through the balloon. A third view 2915 shows a spherical balloon 2916. Proximal and distal ends of the balloon 2916 extend into tube like structures or necks 2917, which help in keeping the catheter in place when it is passed through the balloon.

A fourth view 2920 shows a conical-cylindrical (short) balloon 2921 comprising a conical first portion 2921a coupled at its base to a short cylindrical second portion 2921b having substantially right-angled or squared ends or corners (similar to the square balloon 2911). A length of the second portion 2921b is substantially shorter than a length of the first portion 2921a. Proximal and distal ends of the balloon 2921 extend into tube like structures or necks 2922, which help in keeping the catheter in place when it is passed through the balloon. It should be appreciated that the qualifier 'short' is indicative of the second portion 2921b being stunted or short.

A fifth view 2925 shows a conical-cylindrical (long) balloon 2926 comprising a conical first portion 2926a coupled at its base to a long cylindrical first portion 2926b having substantially right-angled or squared ends or corners (similar to the square balloon 2911). A length of the cylindrical second portion 2926b is substantially longer than a length of the conical first portion 2926a. Proximal and distal ends of the balloon 2926 extend into tube like structures or necks 2927, which help in keeping the catheter in place when it is passed through the balloon. It should be appreciated that the qualifier 'long' is indicative of the second portion 2931b being elongated.

A sixth view 2930 shows a conical-cylindrical (long) balloon 2931 comprising a conical first portion 2931a coupled at its base to a long cylindrical second portion 2931b having substantially spherical or rounded ends or corners. A length of the second portion 2931b is substantially longer than a length of the first portion 2931a. Proximal and distal ends of the balloon 2931 extend into tube like structures or necks 2932, which help in keeping the catheter in place when it is passed through the balloon. It should be appreciated that the qualifier 'long' is indicative of the second portion 2931b being elongated.

A seventh view 2935 shows a long cylindrical balloon 2936 having substantially spherical or rounded ends or corners. Proximal and distal ends of the balloon 2931 extend into tube like structures or necks 2937, which help in keeping the catheter in place when it is passed through the balloon. It should be appreciated that the qualifier 'long' is indicative of the balloon 2936 being elongated.

An eighth view 2940 shows a tapered balloon 2941 comprising first and second tapered or conical ends 2941a, 2941b of a tapering cylindrical portion 2941c. Proximal and distal ends of the balloon 2941 extend into tube like structures or necks 2942, which help in keeping the catheter in place when it is passed through the balloon.

A ninth view 2945 shows a dog-bone balloon 2946. The balloon 2946 has a compound shape that resembles a dog biscuit or dog-bone toy with first, second and third cylindrical portions 2946a, 2946b, 2946c such that a diameter of the middle/second cylindrical portion 2946b is lesser than the first and third cylindrical portions 2946a, 2946c that form ends of the middle/second cylindrical portion 2946b. Each of the first and third cylindrical portions 2946a, 2946c has tapering or conical ends 2947. Proximal and distal ends of the balloon 2946 extend into tube like structures or necks 2948, which help in keeping the catheter in place when it is passed through the balloon.

A tenth view 2950 shows a stepped balloon 2951 comprising first, second and third cylindrical portions 2951a, 2951b, 2951c wherein a diameter of the second portion 2951b is greater than a diameter of the first portion 2951a and a diameter of the third portion 2951c is greater than the diameter of the second portion 2951b. The balloon 2950 has tapering or conical proximal and distal ends 2952. Tapering or conical portions 2953 are included between the first and second portions 2951a, 2951b and between the second and third portions 2951b, 2951c. Proximal and distal ends 2952 of the balloon 2946 extend into tube like structures or necks 2954, which help in keeping the catheter in place when it is passed through the balloon.

An eleventh view 2955 shows an offset balloon 2956. The offset shape of the balloon 2956 comprises a longitudinal half of a compound shape having tapering or conical ends 2956a, 2956c of a middle cylindrical portion 2956b. Proximal and distal ends of the balloon 2956 extend into tube like structures or necks 2957, which help in keeping the catheter in place when it is passed through the balloon.

A twelfth view 2960 shows a conical-offset balloon 2961. The balloon 2961 comprises a full cylindrical portion 2961b that has a full conical or tapering first end 2961a and a longitudinally halved conical or tapering second end 2961c. Proximal and distal ends of the balloon 2961 extend into tube like structures or necks 2962, which help in keeping the catheter in place when it is passed through the balloon.

Figure 30:
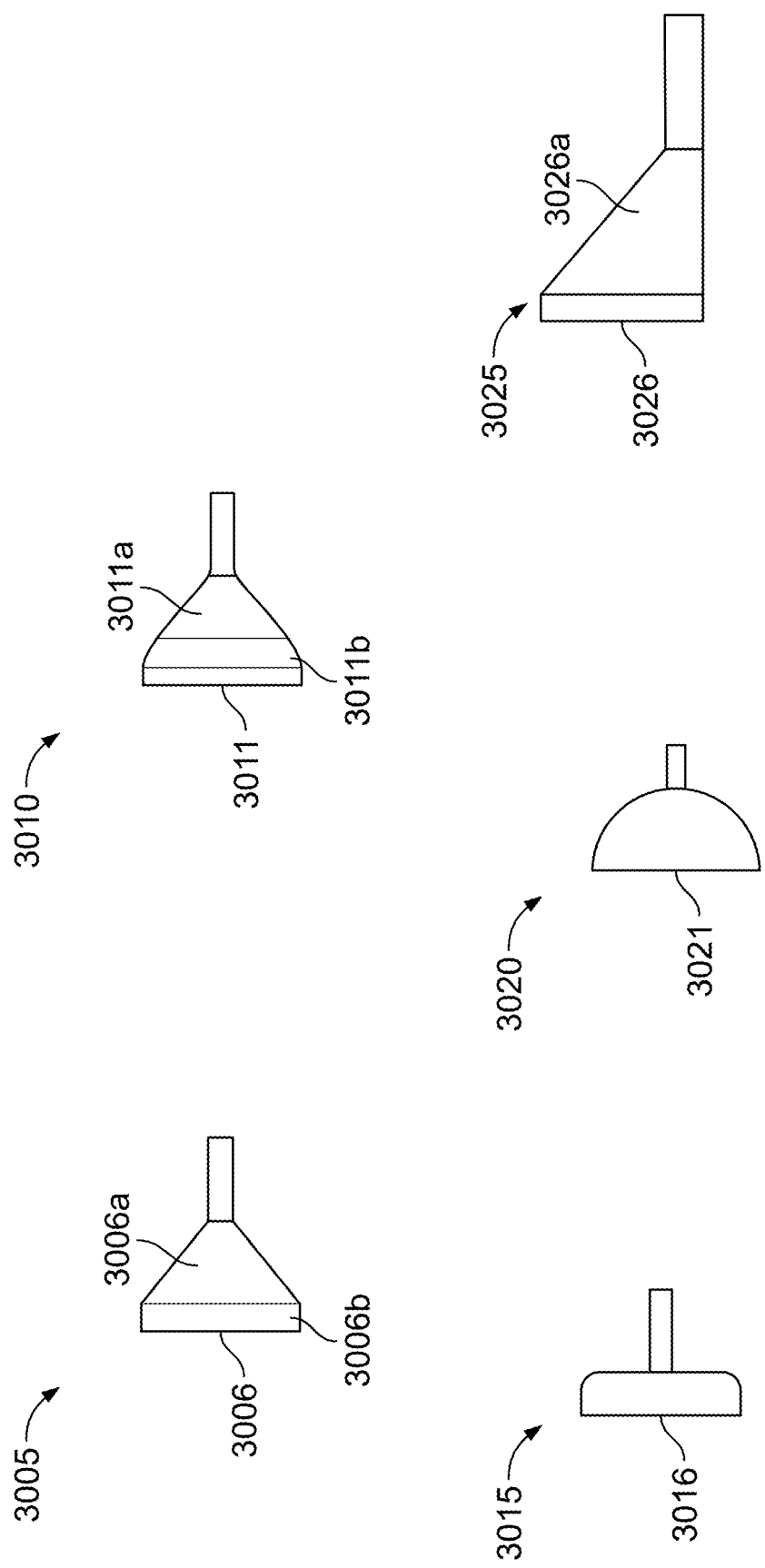

FIG. 30 shows a plurality of exemplary balloon ends or corners, in accordance with some embodiments of the present specification. A first view 3005 shows a conical sharp corner 3006 having a conical or tapering portion 3006a that has a base 3006b with squared or sharp corners. A second view 3010 shows a conical radius corner 3011 having a conical or tapering portion 3011a that has a base 3011b with spherical or rounded corners. A third view 3015 shows a square end 3016 having squared or sharp corners. A fourth view 3020 shows a spherical end 3021 having spherical or rounded corners. A fifth view 3025 shows an offset neck 3026 that is a longitudinal half of a tapering or conical portion 3026a.

Figure 31:
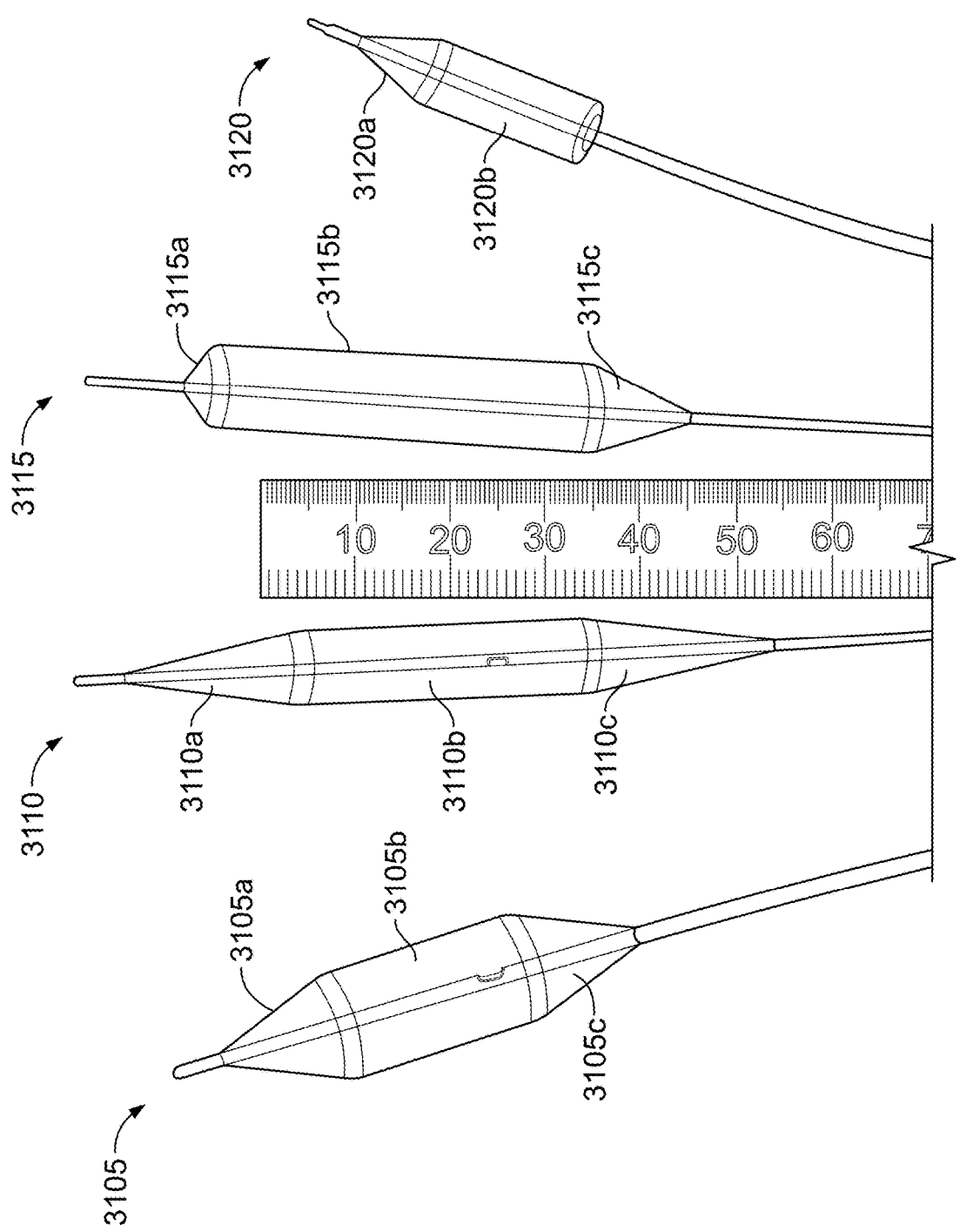

FIG. 31 shows a plurality of balloon shapes having at least one substantially tapering or conical end, in accordance with some embodiments of the present specification. The figure shows first, second, third and fourth balloons 3105, 3110, 3115, 3120. The first balloon 3105 has a compound shape comprising proximal and distal tapering or conical ends 3105a, 3105c with a substantially cylindrical middle portion 3105b. Each of the proximal and distal tapering or conical ends 3105a, 3105c has a first cone angle. The second balloon 3110 also has a compound shape comprising proximal and distal tapering or conical ends 3110a, 3110c with a substantially cylindrical middle portion 3110b. Each of the proximal and distal tapering or conical ends 3110a, 3110c has a second cone angle. The third balloon 3115 also has a compound shape comprising proximal and distal tapering or conical ends 3115a, 3115c with a substantially cylindrical middle portion 3115b. Each of the proximal and distal tapering or conical ends 3115a, 3115c has a third cone angle. The fourth balloon 3120 also has a compound shape comprising a distal tapering or conical end 3120a and a substantially cylindrical proximal portion 3120b. The distal tapering or conical end 3120a has a fourth cone angle.

In embodiments, the different first, second, third and fourth cone angles enable the respective balloons to meet different taper requirements.

Figure 32:
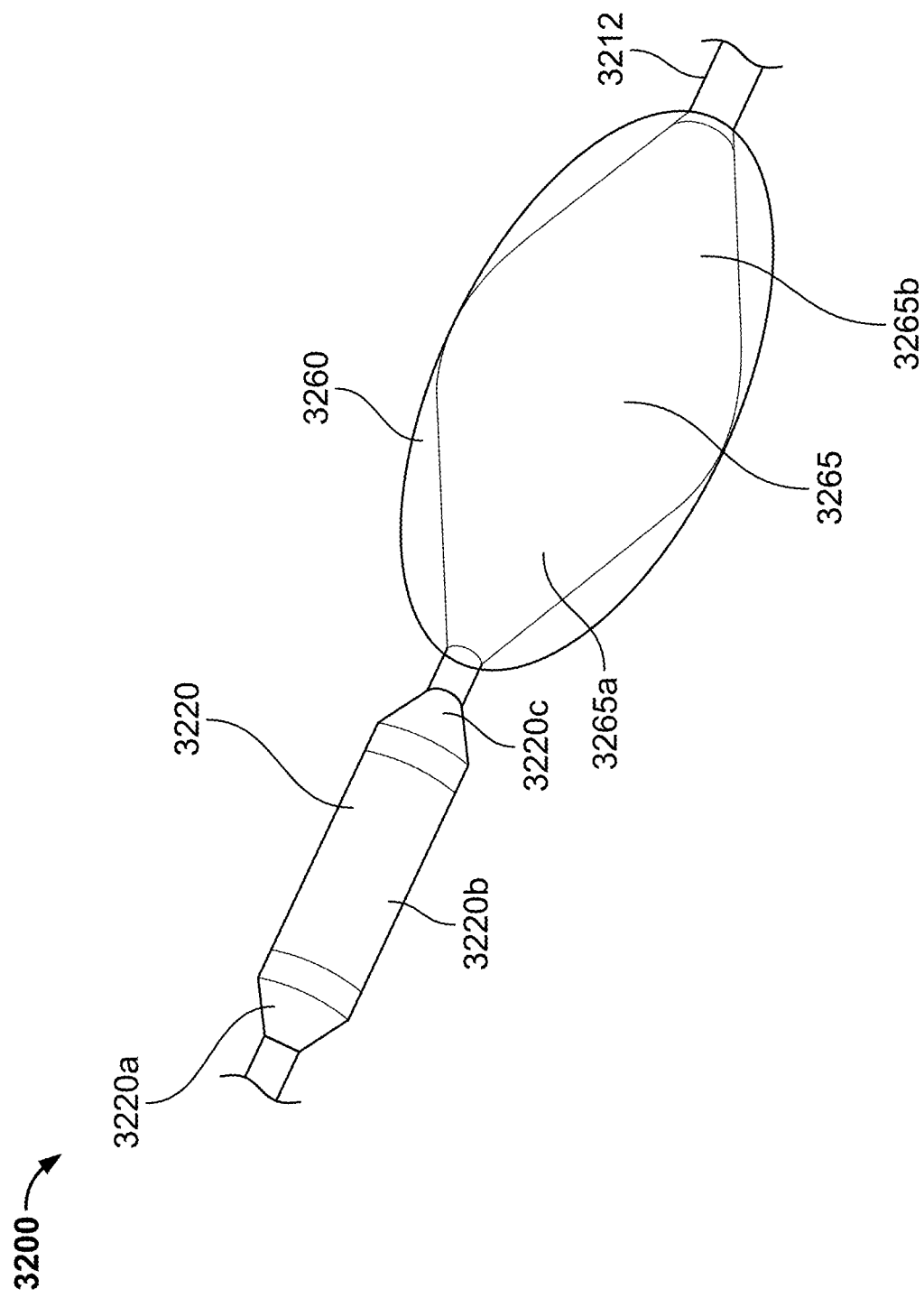

FIG. 32 shows a double balloon catheter 3200 having an inflatable dilation balloon 3220, in accordance with an embodiment of the present specification. The catheter 3200 has an elongate body 3212. An inflatable outer balloon 3260 is attached proximate a distal end of the elongate body 3212. An inflatable inner balloon 3265 is also attached proximate the distal end of the elongate body 3212 such that the inner balloon 3265 is positioned within the outer balloon 3260. The inflatable dilation balloon 3220 is attached to the distal end of the elongate body 3212 such that the balloon 3220 is positioned distal to the outer balloon 3260.

During operation, a cooling fluid such as, but not limited to, water or air, is infused into the balloon 3220 to inflate the balloon 3220 and dilate or enlarge an opening or puncture created in, for example, an atrial septum. In an embodiment, the dilation balloon 3220 has a compound shape comprising proximal and distal substantially tapering or conical ends 3220a, 3220c and a substantially cylindrical middle portion 3220b when in fully expanded state.

Once the catheter 3200 is positioned proximate a target tissue—such as in a pulmonary vein, a fluid is circulated into the outer balloon 3260 while an ablation fluid, such as steam, is infused into the inner balloon 3265 to respectively inflate the outer and inner balloons 3260, 3265. In an embodiment, the outer balloon 3260 is substantially elliptical, in a fully expanded state. In an embodiment, when fully inflated, the inner balloon 3265 has a twin-conical shape comprising first and second conical portions 3265a, 3265b coupled or fused at their bases.

Figure 33:
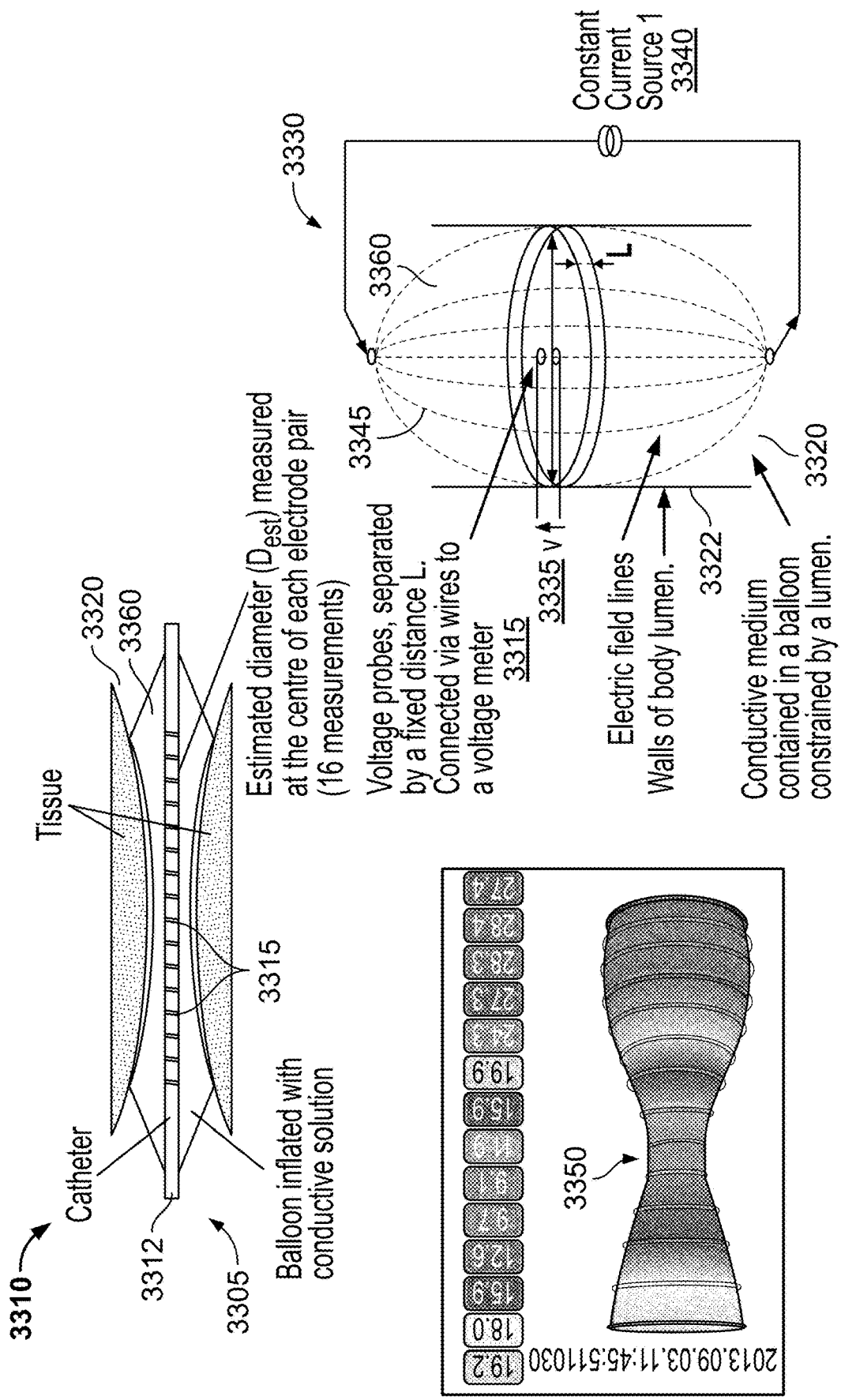

FIG. 33 illustrates a balloon catheter 3310 to measure geometry of a body lumen, in accordance with some embodiments of the present specification. Referring to view 3305, the catheter 3310 includes an elongate body 3312 having an inflatable compliant balloon 3360 mounted on a distal end of the body 3312. The body 3312 has at least one lumen in fluid communication with the balloon 3360. The balloon 3360 houses a plurality of electrode pairs 3315, spaced throughout a longitudinal length of the balloon 3360 that measure voltages. The catheter 3310 uses these voltages to estimate the diameter at a plurality of points (such as, for example, 16 points in one embodiment) along a body lumen 3320. Optionally, a solid-state pressure transducer may also be positioned at a distal end of the balloon 3360.

To estimate a shape and size (geometry) of the body lumen 3320, the catheter 3310 is positioned within the body lumen 3320 and the balloon 3360 is inflated with a conductive solution. The catheter 3310 measures a plurality (such as, 16) of luminal cross-sectional areas (thereby estimating shape and size) along the body lumen 3320 as well as pressure during controlled volumetric expansion of the balloon 3360 within the body lumen.

In some embodiments, the catheter 3310 uses impedance planimetry to characterize geometry (shape and size) of the body lumen 3320. Impedance planimetry uses alternating current (AC) voltage measurements made between electrode pairs to estimate a diameter of a medium (conductive fluid) at a mid-point between those electrodes. The voltage measurements can be obtained provided the voltage drop across the medium is generated from a constant AC current source and the conductivity of the medium is constant and known for a given temperature.

Referring now to view 3330, the balloon 3360 is shown inflated, with the conductive solution, within the body lumen 3320. A pair of electrodes 3315 is shown separated by a fixed distance (L) and is connected via wires to a voltage meter 3335. A constant current source 3340 is applied, and an electric field (represented with a plurality of electric field lines 3345) is generated in the conductive medium contained in the inflated balloon 3360 constrained by walls 3322 of the body lumen 3320.

Now, resistance (R) or impedance can be determined by:

$$V/I = R$$
$$= L/(A\sigma)$$
$$= L/[\Pi(D_{est}/2)^2 \cdot \sigma]$$

where, R is resistance (impedance), given by V/I, σ is the conductivity of the medium, L is the distance between the pair of electrodes 3315, A is a cylinder area and $D_{est}$ is the cylinder diameter. R, the resistance (impedance), can be calculated as the AC current (I) is known and is fixed, and the AC voltage (V) is measured across the pair of electrodes. Since, L is a fixed distance between the electrodes, and the medium conductivity (σ) is known for a given temperature, then $D_{est}$ can be determined. An estimate of the balloon or cylinder diameter ($D_{est}$) at a given electrode position is derived from the measured cylinder area (A) using an assumption that the balloon 3360 is symmetrical about its longitudinal axis at that electrode position.

Thus, once the balloon 3360 is filled with the conductive solution, 16 intraluminal cross-sectional areas (CSA) are measured by the impedance measuring electrodes 3315, whereas the pressure transducer provides the corresponding intra-balloon pressure. The diameter $D_{est}$ and intra-balloon pressure measurements are exported to a software application to generate and display a topography plot 3350. The plot 3350 displays the calculated cross-sectional areas (CSAs) as a cylinder of varying diameters. The geometry of the body lumen can be used to direct the amount of ablative agent needed to be delivered to achieve effective ablation.

Figure 34:
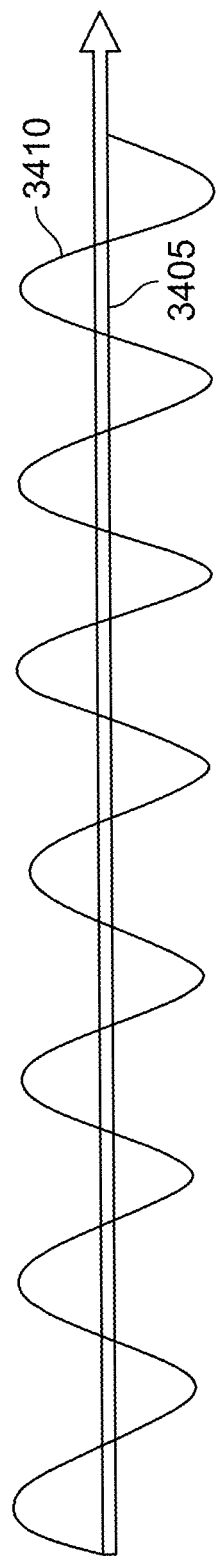

FIG. 34 illustrates relative flow paths of cooling and ablation fluids in an ablation catheter, in accordance with some embodiments of the present specification. As shown, in various ablation catheters of the present specification, the ablation fluid (such as, for example, steam or vapor) flows in a first path 3405 while a second fluid (such as, for example, water, air or carbon-dioxide) flows in a second path 3410.

In some embodiments, the first path 3405 is substantially linear while the second path 3410 is substantially spiral or helical around the first path 3405.

In some embodiments, the first path 3405 is 1.1 to 10 times longer than the second path 3410. In some embodiments, a ratio between a length of the first and second paths 3405, 3410 is π.

Figure 35A:
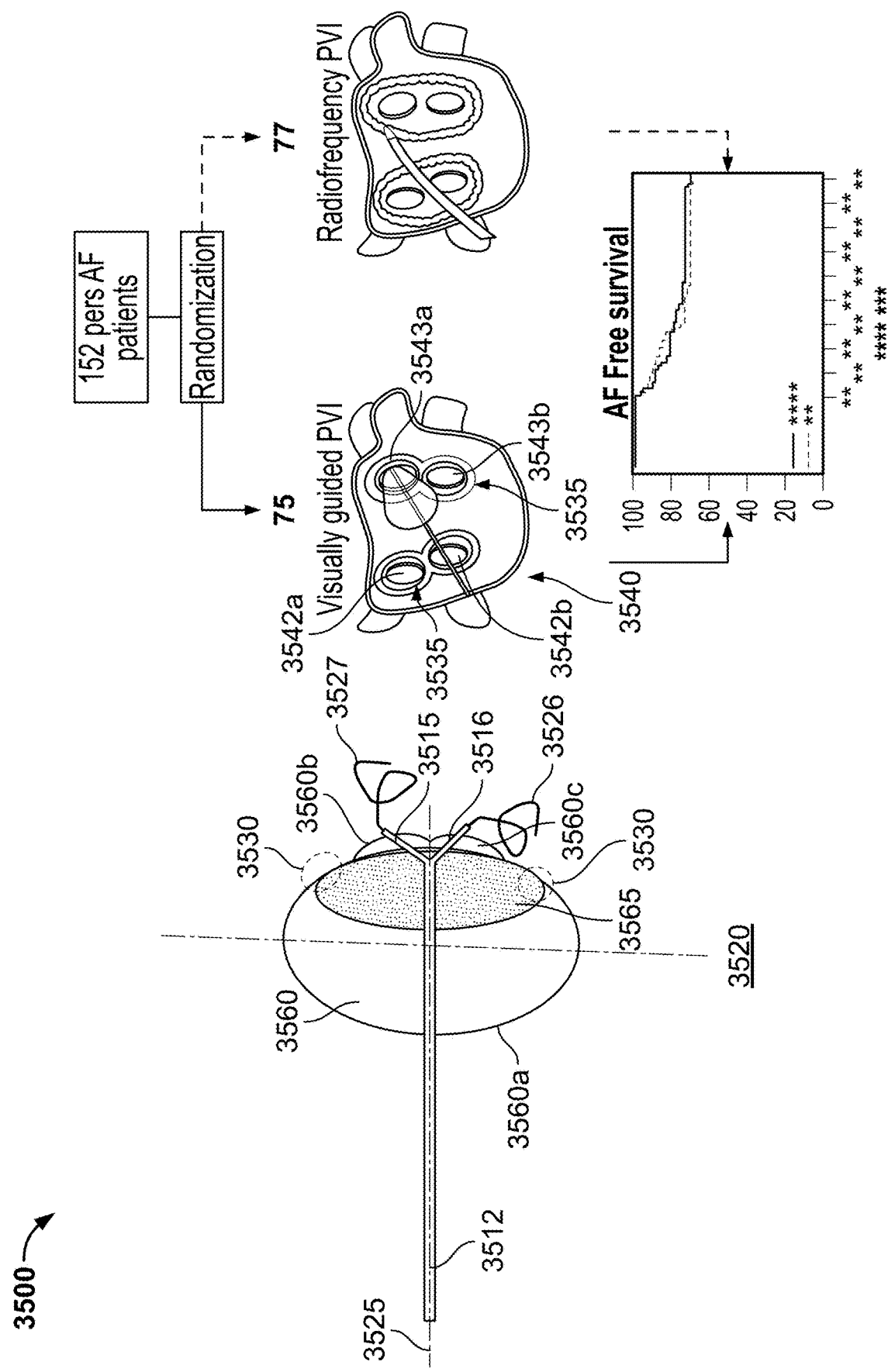

FIG. 35A illustrates a bicornuate cardiac ablation catheter 3500, in accordance with some embodiments of the present specification. The catheter 3500 has an elongate body 3512 having a proximal end and a distal end. The elongate body 3512 bifurcates into first and second branches 3515, 3516 at the distal end. An inflatable outer balloon 3560 is attached to the distal end while an inflatable inner balloon 3565 is also attached to the distal end and positioned within the outer balloon 3560.

In accordance with an aspect, in fully expanded state, the outer balloon 3560 has a compound shape comprising of a substantially elliptical proximal portion 3560a along with first and second substantially spherical or elliptical distal cornuates or portions 3560b, 3560c. In an embodiment, a long axis 3520 of the substantially elliptical proximal portion 3560a is substantially orthogonal to a longitudinal axis 3525 of the elongate body 3512. The first branch 3515 is directed into the first distal cornuate 3560b of the outer balloon 3560 while the second branch 3516 is directed into the second distal cornuate 3560c of the outer balloon 3560. In some embodiments, the first branch 3515 includes a mapping member 3527 extending distally therefrom and the second branch 3516 extends a second mapping member 3526 extending distally therefrom.

In some embodiments, the elongate body 3512 includes a first cooling fluid infusion lumen and a second cooling fluid suction lumen—both of which are in fluid communication with the outer balloon 3560 including the cornuates 3560b, 3560c. During operation, a cooling fluid pump which is in data communication with, and controlled by, a controller enables a cooling fluid to be pumped into the outer balloon 3560 through the cooling fluid infusion lumen and allows the cooling fluid to be pumped out of the outer balloon 3560 through the cooling fluid suction lumen.

In some embodiments, the elongate body 3512 also includes a water/vapor lumen that is in fluid communication with the inner balloon 3565 via a plurality of vapor infusion ports. In some embodiments, at least one flexible heating chamber (such as those described with reference to FIGS. 19A through 19D), comprising a plurality of electrodes, is positioned in-line within the water/vapor lumen. In some embodiments, the at least one flexible heating chamber is positioned in-line within the central water/vapor lumen such that the plurality of electrodes are at least partially inside the inner balloon 3565. During operation, a water/vapor pump which is also in data communication with, and controlled by, the controller pumps water from a sterile water reservoir through the water/vapor lumen to enter a proximal end of the at least one flexible heating chamber. The at least one flexible heating chamber coverts water into vapor that exits through the plurality of vapor infusion ports to inflate the inner balloon 3565 and contact the outer balloon 3560 proximate an area of ablation.

An ablation zone or hot zone 3530 is created at the area of contact between the inner balloon 3565 and the outer balloon 3560, such that thermal energy from the inner balloon 3565 passes through the outer balloon 3560 to an area of ablation. The elongate body 3512 and portions of the outer balloon 3560, excluding the hot zone, remain cool owing to the circulating cooling fluid.

In accordance with an embodiment, the ablation or hot zone 3530 forms an area of ablation or lesion 3535 that is shaped approximately in the form of '8', as shown in view 3540. During operation (such as during a pulmonary vein isolation procedure of view 3540), the catheter 3500 is guided into the left atrium such that the first and second cornuates 3560b, 3560c are positioned in respective first and second pulmonary veins 3542a, 3542b or third and fourth pulmonary veins 3543a, 3543b. The left atrium between the two pulmonary veins 3542a, 3542b or 3543a, 3543b prevents the balloon 3560 from slipping into the pulmonary veins. Thus, simultaneous ablation at the two pulmonary veins 3542a, 3542b or 3543a, 3543b can be carried out using the bicornuate catheter 3500 resulting in the area of ablation or lesion 3535 resembling the figure '8'. In embodiments, simultaneous ablation of two pulmonary veins, using the bicornuate catheter 3500, reduces ablation time by 50%.

In accordance with an aspect, an inflatable ablation balloon, of a balloon cardiac ablation catheter such as the catheter 1442 of FIG. 14A, is multilayered comprising of outer and inner balloon layers fused together. A plurality of ablation fluid channels or paths are defined and sandwiched between the outer and inner layers. During operation, the balloon is inflated to contact target tissue and steam/vapor is allowed to circulate through the plurality of ablation fluid channels to create a deep burn in the target tissue without causing contiguous circumferential scarring. This results in thermal energy non-contiguously spreading over the tissue area in a manner that is controlled and can be circulated and does not lead to contiguous circumferential scarring and hence stricture formation.

In various embodiments, the plurality of ablation fluid channels are configured into a plurality of patterns or contours (such as, but not limited to, a wave, series of lines, sine wave, square wave) such that the circulating steam/vapor creates ablation proximate the area of the channels without any ablation in the remaining area (that is, area devoid of the channels) of the balloon. In an exemplary application of PV (pulmonary vein) ablation, the plurality of channels create a pattern of ablation in a PV sufficient to block conduction of electrical activity from a PV to a Left Atrium (LA) without causing a significant stricture in the PV, wherein a length of the circumferential pattern of ablation is greater than the circumference of the PV proximate the ablation. In some embodiments, a length or width of the circumferential pattern of ablation is 1.2 times greater than a width of a circumference of the PV or another organ being ablated proximate the ablation. Therefore, in an embodiment, if a width of the circumference of a PV is 10 mm, the width of a circumference of ablation will be 12 mm or greater. In some embodiments, a distance between two adjacent circumferential ablation patterns is greater than two times the thickness of the PV or the thickness of the wall or layer of the wall of an organ being ablated.

Figure 35B:
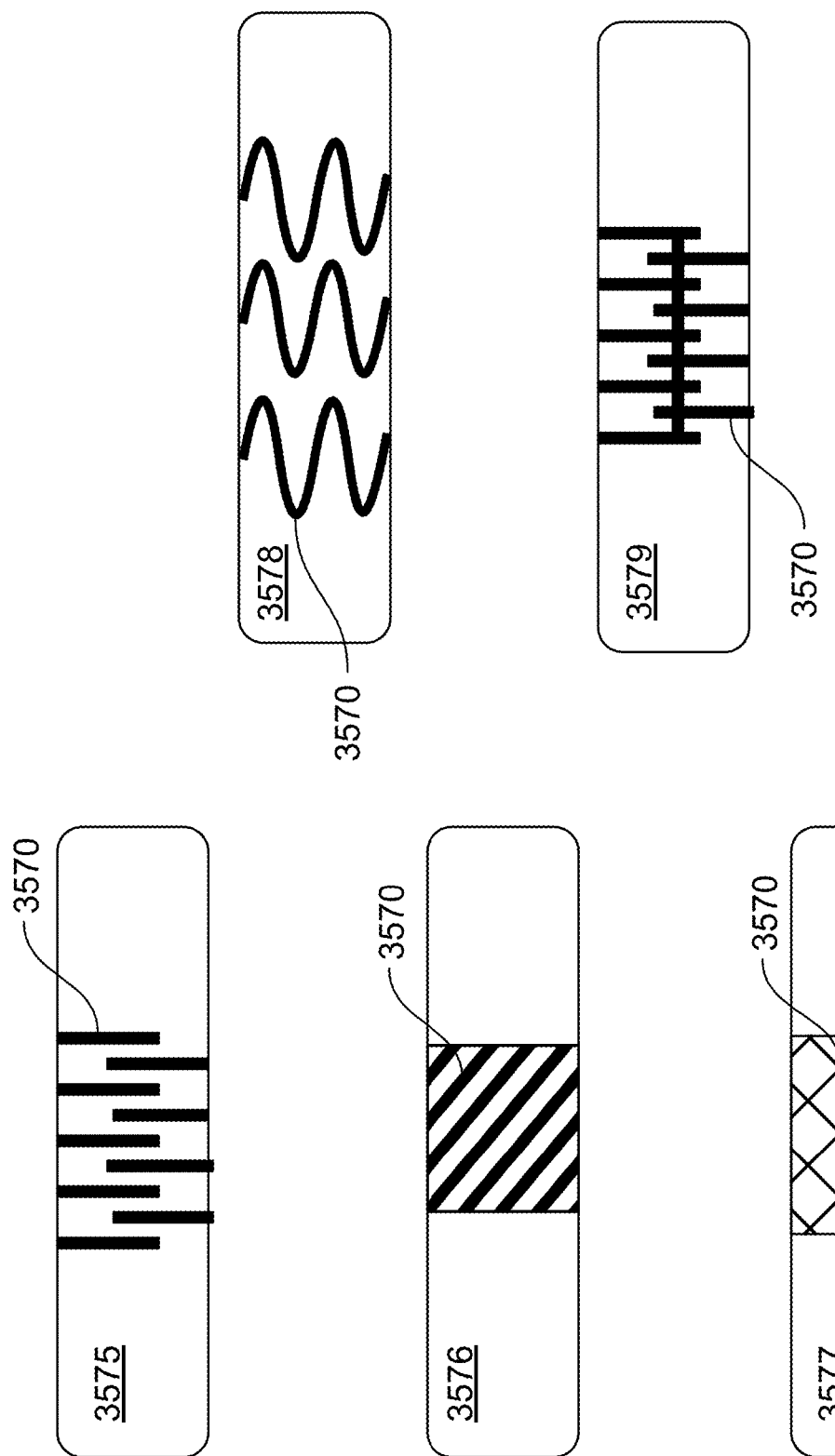

FIG. 35B illustrates a plurality of patterns of the ablation fluid channels or paths 3570 defined in a multilayered balloon of an ablation catheter, in accordance with various embodiments of the present specification. The figure shows first, second, third, fourth, and fifth exemplary patterns 3575, 3576, 3577, 3578 and 3579. The patterns of the channels 3570 determine the ablation contour or pattern.

In various embodiments, balloon pressure of the inner and outer balloons of the ablation catheters of the present specification is managed as steam is produced. In some embodiments, the catheters include a plurality of ports at the proximal end for delivery and removal of inflating agents and ablation agents. In some embodiments, the ablation catheters include at least one ablative agent 'in' port, at least one ablative agent 'out' port, at least one inflating agent 'in' port, and at least one inflating agent 'out' port. In various embodiments, the ablative agent is vapor and the inflating agent is $CO_2$. Each port is in fluid communication with a corresponding lumen within the catheter.

In some embodiments, every port—vapor in, vapor out, $CO_2$ in, $CO_2$ out—is actively managed by a controller, which also actively manages the steam/vapor generator. In some embodiments, each port may be opened or closed in response to instructions from the controller. Controlling the open and close states of the ports prevents leakage and also ensures the out ports will be closed, and/or controlled, during vapor delivery. In some embodiments, the outflow of vapor or steam is controlled by a fluid column which is backloaded into the steam or vapor 'out' lumen. The level the fluid is managed by pressure and volume controlled in and out pumps at the proximal end of the catheter. In various embodiments, actively managing the ports comprises sensing for pressure and temperature at each port and then changing the inputs at each port based on a desired range of values. In various embodiments, each port comprises a valve configured to be opened or closed by the controller.

In various embodiments, the catheters are configured to deliver and/or remove/aspirate fluid in any orientation. Air in the lumens to the balloons expands the balloons at least initially. Vapor can only expand once the temperature inside the balloon reaches >100° C. and steam stops condensing. The pressure in the outer balloon will rise as the inner balloon inflates. In some embodiments, the outer balloon is actively deflated, as the inner balloon is inflated with heated vapor, to maintain a constant pressure. In some embodiments, an amount of air pre-existing in the catheter lumen expands due to heat from the vapor or steam being delivered and causes some inflation of the inner balloon. In some embodiments, the inner balloon is inflated with $CO_2$ partially before inflating with steam, while the inner balloon is maintained at a constant pressure. In some embodiments, the catheter includes an additional port for separately injecting $CO_2$ to assist with inner balloon inflation. In another embodiment the $CO_2$ is mixed with the saline (carbonated saline) and is released simultaneous to the vaporization of the saline and assist with inflation of the internal balloon.

In some embodiments, the inner and outer balloons are inflated according to specific protocols to ensure proper functioning of the ablation catheters. In some embodiments, the inflation protocol comprises: inflating an outer balloon to a first pressure level in a range of 0.5 to 100 psi, inflating an inner balloon first with $CO_2$ to a second pressure level or volume at least 5% less than the first pressure level, inflating the inner balloon with steam to a third pressure level or volume greater than the first and second pressure level, and monitoring a pressure level of the outer balloon and removing or adding $CO_2$ to maintain that level. In another embodiment, the third pressure level of the inner balloon is monitored and maintained by allowing the $CO_2$ or vapor in the inner balloon to escape out of the catheter.

In various embodiments, the catheter bodies of the present specification comprise an extruded shaft with multiple lumens within. In other embodiments, the catheter bodies of the present specification comprise a single lumen with a plurality of bundled liners within said single lumen. The bundled liners are configured to function as separate independent lumens for the various functions of the catheter, including inflating agent delivery and suction and ablative agent delivery and suction. In various embodiments, each of the plurality of bundled liners has a different diameter. The separate lumens provide easier identification of each lumen, greater independence for the inner balloon, and air gaps between the bundled liners for insulation. In one embodiment, a vapor delivery lumen further includes an insulation liner at its distal end. In one embodiment, the insulation liner comprises a braided polyimide/Pebax shaft.

In embodiments, the ablation zone is created when an opposing pressure to the outer balloon is greater than 0.1 psi against the outer balloon. The ablation zone is not created if blood flow across a portion of the ablation zone is greater than 1 ml/min. In some embodiments, the ablation zone is not created if blood flow across a portion of the ablation zone is greater than 10 ml/min, or is greater than 100 ml/min. In embodiments, the blood flow stated here refers to the flow of blood between the outer balloon's external surface and the tissue to be ablated. In one embodiment the blood flow is out of the pulmonary vein to be ablated into a left atrium.

In embodiments, steam for ablation is generated within a certain distance range from the tissue to be ablated. Therefore, in some embodiments, the area that contacts the tissue, or the ablation zone, is away from a source of production of steam at a distance in a range of 0 mm to 100 mm. In some embodiments, the balloon is stretchable, and may be expanded through a controller in the handle.

In some embodiments, the catheter is configured to have a temperature differential between an exterior surface of the catheter and an interior surface of the lumen where heated vapor is generated that is no less than 40 degrees Celsius. More specifically, the exterior surface of the catheter should be less than 60 degrees Celsius and preferably less than 45 degrees Celsius. In some embodiments, the catheter shaft is insulated with a guide sheath and a constant saline flow. The insulation prevents conduction from increasing shaft temperatures during steam generation.

In various embodiments, the outer balloon comprises silicone. In various embodiments, the inner balloon comprises med-durometer urethane, PET, or Pebax. In various embodiments, the inner balloon comprises a material configured to be semi-compliant while also heat tolerant.

FIG. 36A is a flowchart of a plurality of exemplary steps of inflating the balloons of a cardiac ablation catheters and managing pressure within the balloons during an ablation procedure, in accordance with an embodiment of the present specification. After a distal end of a cardiac ablation catheter in accordance with the embodiments of the present specification has been advanced to a pulmonary vein of a patient, an outer balloon is inflated with fluid to a first pressure P1 at step 3610. In various embodiments, P1 is in a range of 0.01 to 5 atm.

At step 3612, pulmonary vein occlusion is documented. In various embodiments, pulmonary vein occlusion is documented radiologically, via ultrasound, or endoscopically. Optionally, occlusion is not documented at all. Unlike other treatment approaches, if there is no occlusion, the ablation zone will not have any effect, i.e. will not ablate tissue, because no counterpressure is being applied against the ablation zone surface area. In the absence of counterpressure against the ablation zone surface, heat transfer out of the ablation zone surface area sufficient to cause tissue ablation will not occur. Hence, in one embodiment, the present invention is directed toward a method of ablating cardiac tissue wherein, in the absence of counterpressure against the ablation zone surface in excess of a threshold value, heat transfer out of the ablation zone surface area sufficient to cause tissue ablation will not occur.

At step 3614, an inner balloon is inflated to a first volume V1. In various embodiments, the inner balloon is inflated with air or $CO_2$. Vapor is infused at 100° C. or higher temperature to raise a temperature of the inner balloon to equal to or greater than 100° C. and raise a volume of the balloon to a second volume V2 at step 3616. Then, at step 3618, vapor is continued to be infused at 100° C. to raise the volume of the balloon to a third volume V3, wherein V3 is equal to or greater than V2, and maintain V3 for a predetermined period of time T1, wherein T1 is sufficient to ablate a portion of the pulmonary vein, pulmonary vein ostium, or an atrium, or wherein T1 is between 1 sec and 5 minutes. It should be appreciated that this step causes an ablation zone, as described herein, to be formed, together with transition zones positioned proximally and distally. A transition zone is an area, defined at least in part by the surface of the outer balloon and adjacent the ablation zone (either proximally, distally or both) in which the temperature of that surface area is equal to no more than 95% of the temperature of the ablation zone, preferably no more than 80%, and even more preferably no more than 60%, or any increment between 30% and 95%. Insulation zone is an area, defined at least in part by the surface of the outer balloon and adjacent the ablation zone (either proximally, distally or both) in which a material or fluid, including but not limited to gas, liquid, air, or $CO_2$, is positioned between the inner surface of the outer balloon and outer surface of the inner balloon, thereby causing a separation, or gap, between the heated surface of the inner balloon and the outer balloon. Gap or separation is the space enclosed by the outer balloon and defined by a distance between the inner surface of the outer balloon and outer surface of the inner balloon which, in the ablation zone, is 0 and outside the ablation zone is greater than 0.

Pressure in the outer balloon is maintained between 0.01 atm and 5 atm at step 3620. At step 3622, the flow of vapor is stopped, allowing the vapor to condense and the inner balloon to deflate to a volume V4 wherein V1<V4<V2/V3. At step 3624, fluid and water created by condensation of the vapor from the inner balloon are removed or aspirated to bring the volume of the inner balloon to the pre-inflation volume or <V1. The outer balloon is deflated to a pressure <P1 reversal of the pulmonary vein occlusion is optionally documented at step 3626. At step 3628, the cycle is repeated in the same or separate pulmonary vein.

FIG. 36B is a flowchart of a plurality of exemplary steps of a method of performing atrial fibrillation ablation, in accordance with some embodiments of the present specification. At step 3630, a guide wire or pacing catheter is placed into a pulmonary vein of a patient. In various embodiments, a lumen of the pacing catheter or pacing wire is configured to eject contrast while the pacing catheter or wire occupies a lumen. In some embodiments, the pacing wire lumen has a diameter of 0.045 inches. At step 3632, a double balloon catheter of the present specification is placed over the guide wire or pacing catheter into the pulmonary vein. In various embodiments, the catheter is introduced via a femoral insertion location and navigated to the treatment area and includes a length sufficient to reach a pulmonary vein from said femoral insertion location. In some embodiments, a distal tip of the catheter has a specific angle of approach to a pulmonary vein from a left atrium. In various embodiments, the angle is in a range of 0 to 180 degrees. In some embodiments, a distal tip of the catheter is configured to deflect 180 degrees about a 1 inch radius. In another embodiment, a distal tip of the catheter is configured to deflect 180 degrees about a 2 inch radius. In some embodiments, a distal tip of the catheter is configured to deflect 150 degrees about a 0.5 inch to 2.5 inch radius.

Now, at step 3634, an outer balloon of the double balloon catheter is inflated with an insulating fluid such as, for example, carbon dioxide to occlude the pulmonary vein. In some embodiments, the inflated outer balloon is in physical contact with an entirety of a pulmonary vein ostia. In other embodiments, the inflated outer balloon is in contact with a portion of a pulmonary vein ostia. In some embodiments, a pear shaped balloon is configured to contact the pulmonary vein ostia. In some embodiments, the inflated outer balloon occludes at least a portion of a pulmonary vein 2-15 mm distal to a pulmonary vein ostia. In some embodiments, prior to inflating the inner balloon, a distance or physical gap between the inflated outer balloon and uninflated inner balloon is in a range of 5-15 mm. In some embodiments, a gap in a range of 0.1 mm to 10 mm is present between a proximal end of the inflated outer balloon and the uninflated inner balloon. In some embodiments, a gap of at least 5 mm is present between a proximal end of the inflated outer balloon and the uninflated inner balloon.

Contrast is injected into the lumen to ensure that the outer balloon is occluding the pulmonary vein. In an embodiment, occlusion of the pulmonary vein is documented and confirmed radiologically. Thereafter, at step 3636, an inner balloon of the double balloon catheter is inflated with steam or water vapor so that the inflated inner balloon contacts the inflated outer balloon at an ablation zone. In some embodiments, the inflated inner balloon contacts at least 2-15 mm along a 360 degree circumference of the inflated outer balloon where the outer balloon is in contact with the ostium axial surface. In some embodiments, the contact between the inner and outer balloons is constant during therapy. In various embodiments, the inner balloon is disc or ball shaped. In some embodiments, the inner balloon is radiopaque. In some embodiments, the inner balloon includes a barium coating. Subsequently, at step 3638, heat energy is transmitted from the inner balloon through the outer balloon to ablate the pulmonary vein, a pulmonary vein ostium or a left atrium. Finally, at step 3640, the pulmonary vein is stimulated through the pacing catheter to document complete pulmonary vein isolation (PVI). At step 3641, after each cycle of therapy, a sufficient amount of fluid is evacuated from the inner balloon and the outer balloon is deflated to allow the catheter to be removed.

FIG. 36C is a flowchart of a plurality of exemplary steps of another method of performing atrial fibrillation ablation, in accordance with some embodiments of the present specification. At step 3642, a right atrium of a patient's heart is accessed through a venous puncture. Then, at step 3644, a left atrium of the patient's heart is accessed through a trans-septal puncture. At step 3646, a guide wire or pacing catheter is placed into a pulmonary vein using fluoroscopic guidance. At step 3648, a double balloon catheter of the present specification is placed over the guide wire or pacing catheter into the pulmonary vein. Now, at step 3650, an outer balloon of the double balloon catheter is inflated with an insulating fluid such as, for example, carbon dioxide to occlude the pulmonary vein and displace blood in the left atrium away from an ablation site. In an embodiment, occlusion of the pulmonary vein is documented and confirmed radiologically through dye study. The pressure and volume of the inflated outer balloon are monitored. In an embodiment, the pressure of the inflated outer balloon is maintained below 5 atm.

Thereafter, at step 3652, an inner balloon of the double balloon catheter is inflated with steam or water vapor so that the inflated inner balloon contacts the inflated outer balloon at an ablation zone. In some embodiments, contact of the inner and outer balloons at the ablation zone is documented and confirmed using fluoroscopy, 3D mapping and/or endoscopy. In some embodiments, one or more sensors in the ablation zone are utilized to monitor contact of the inner and outer balloons. In embodiments, the temperature or a pressure of the inner balloon is monitored.

Subsequently, at step 3654, heat energy is transmitted from the inner balloon through the outer balloon to ablate the pulmonary vein, a pulmonary vein ostium or a left atrium. The temperature and pressure in the outer balloon are monitored to maintain at desired therapeutic values. At step 3656, heat is delivered to the pulmonary vein, pulmonary vein ostium or left atrium for a first duration. In some embodiments, the first duration ranges from 5 seconds to 5 minutes.

Now, at step 3658, the pulmonary vein is stimulated through the pacing catheter to document complete pulmonary vein isolation (PVI). Optionally, at step 3660, the ablation step 3656 is repeated (if required) wherein heat is delivered for a second duration. In some embodiments, the second duration ranges between 50% and 250% of the first duration.

FIG. 36D is a flowchart of a plurality of exemplary steps of a method of performing left atrial appendage ablation, in accordance with some embodiments of the present specification. At step 3662, a guide wire or pacing catheter is placed into a left atrial appendage of a patient. At step 3664, a double balloon catheter of the present specification is placed over the guide wire or pacing catheter into the left atrial appendage.

Now, at step 3666, an outer balloon of the double balloon catheter is inflated with an insulating fluid such as, for example, carbon dioxide to occlude the left atrial appendage. In an embodiment, occlusion of the left atrial appendage is documented and confirmed radiologically. Thereafter, at step 3668, an inner balloon of the double balloon catheter is inflated with steam or water vapor so that the inflated inner balloon contacts the inflated outer balloon at an ablation zone. Subsequently, at step 3670, heat energy is transmitted from the inner balloon through the outer balloon to ablate the left atrial appendage. Finally, at step 3672, the left atrial appendage is filled with an acellular matrix to promote cell growth and occlusion of the left atrial appendage. In one embodiment, a third balloon distal to the double balloon is used to ablate the left atrial appendage. In another embodiment, the third balloon distal to the double balloon is inflated to displace the blood out of the left atrial appendage. In yet another embodiment, the left atrial appendage is flushed with fluid to evacuate the blood out of the left atrial appendage. In another embodiment, suction is applied into the occluded left atrial appendage to generate vacuum in order to better approximate the wall of the left atrial appendage with an ablative surface of the balloon.

FIG. 36E is a flowchart of a plurality of exemplary steps of another method of performing left atrial appendage ablation, in accordance with some embodiments of the present specification. At step 3674, a right atrium of a patient's heart is accessed through a venous puncture. Then, at step 3676, a left atrium of the patient's heart is accessed through a trans-septal puncture. At step 3678, a guide wire or pacing catheter is placed into a left atrial appendage using fluoroscopic guidance. At step 3680, a double balloon catheter of the present specification is placed over the guide wire or pacing catheter into the left atrial appendage.

Now, at step 3682, an outer balloon of the double balloon catheter is inflated with an insulating fluid such as, for example, carbon dioxide to occlude a portion of the left atrial appendage and displace blood in the left atrial appendage away from an ablation site. In an embodiment, occlusion of the left atrial appendage is documented and confirmed radiologically through dye study. The pressure and volume of the inflated outer balloon are monitored. In an embodiment, the pressure of the inflated outer balloon is maintained below 5 atm.

Thereafter, at step 3684 an inner balloon of the double balloon catheter is inflated with steam or water vapor so that the inflated inner balloon contacts the inflated outer balloon at an ablation zone in the left atrial appendage. In some embodiments, contact of the inner and outer balloons at the ablation zone is documented and confirmed using fluoroscopy, 3D mapping and/or endoscopy. In some embodiments, one or more sensors in the ablation zone are utilized to monitor contact of the inner and outer balloons. In embodiments, the temperature of the inner balloon is monitored.

Subsequently, at step 3686, heat energy is transmitted from the inner balloon through the outer balloon to ablate the left atrial appendage. The temperature and pressure in the outer balloon are monitored to maintain at desired therapeutic values. At step 3688, heat is delivered to the left atrial appendage for a first duration. In some embodiments, the first duration ranges from 5 seconds to 5 minutes.

Optionally, at step 3690, the ablation step 3688 is repeated wherein heat is delivered for a second duration. In some embodiments, the second duration ranges between 50% and 250% of the first duration.

Now, at step 3692, the left atrial appendage is optionally filled with an acellular matrix. Finally, at step 3694, tissue ingrowth is allowed into the acellular matrix to occlude the left atrial appendage. In another embodiment, a stent structure or a scaffolding is inserted into the left atrial appendage to facilitate re-epithelialization or tissue growth.

In some embodiments, the balloon catheter does not have the inner balloon but comprises a distal balloon which is used for ablation of the left atrial appendage while the proximal balloon is used for occlusion of the left atrial appendage ostium. The distal ablating balloon and the inner ablating balloon for this application are either compliant or semi-compliant balloons having a durometer comparable to the outer balloon. In the double balloon configuration, the majority of the anterior hemisphere of the outer balloon occludes the left atrial appendage ostium.

FIG. 36F is a flowchart of a plurality of exemplary steps of a method of performing vessel or bronchus ablation, in accordance with some embodiments of the present specification. At step 3695a, a guide wire is placed into a target vessel or organ (such as, for example, a pulmonary artery or lung) of a patient. At step 3695b, a balloon catheter of the present specification is placed over the guide wire or through an endoscope into the target organ.

Now, at step 3695c, a balloon of the balloon catheter is inflated with an insulating fluid such as, for example, carbon dioxide to obtain contact with and occlusion of a target site. In an embodiment, occlusion of the target site is documented and confirmed radiologically or through pressure monitoring in the balloon, wherein the pressure is maintained below 5 atm.

Thereafter, at step 3695d, steam or water vapor is passed through a channel in the wall of the balloon to create ablation in the target site or tissue in a desired pattern (such as those shown with reference to FIG. 36A). Optionally, at step 3695e, the ablation step 3695d is repeated—if desired.

FIG. 36I illustrates a left atrium 3601 depicting a left atrial appendage 3603 in a wall 3605 of the left atrium 3601. FIG. 36J illustrates a plurality of left atrial appendages 3611, 3613, 3615, 3617 depicting a variety of shapes of the left atrial appendages 3611, 3613, 3615, 3617.

In various embodiments, blood is evacuated from the treatment area prior to initiating therapy with the ablation catheters of the present specification in order to prevent the coagulation of blood. In some embodiments, during an ablation procedure, an amount of blood has been evacuated from the treatment area such that the treatment area, defined as the area of cardiac tissue to be ablated, is covered by less than 100 mL of blood, preferably less than 75 mL of blood, and even more preferably less than 50 mL of blood. In some embodiments, prior to an ablation procedure, a treatment area has 25-100% of blood removed.

In some embodiments, ablation provided by the ablation catheters of the present specification are configured to ablate a treatment area defined as having a width of 1 to 15 mm, and, more preferably, 5 to 10 mm, and having a curved band shape extending around an inner surface of a pulmonary vein and comprising a pulmonary vein ostium.

In some embodiments, in order to manage the shape of the treatment area, the expandable member or outer balloon of the ablation catheters of the present specification, when fully expanded, are configured to exert a pressure in a range of 0.01 to 5 atm within a range of 0 to 10 cm from a central axis of the catheter. In embodiments, where multiple balloons are provided, either balloon may be inflated first.

In embodiments, a saline flow rate in a range of 1 ml/min to 25 ml/min is used to deliver the saline. In embodiments, the power delivered to the electrodes for generating vapor is within a range of 10 W to 800 W. In embodiments, the ablation is performed for a time within a range of 1 second to 600 seconds.

In embodiments, at least a contiguous 25% circumference of a pulmonary vein ostium or atrium around the pulmonary vein is ablated and at least 25% of the thickness of the left atrial wall or pulmonary vein ostium or a portion of pulmonary vein is ablated.

Additionally, in various embodiments, the ablation catheters of the present specification are configured to insulate non-target tissues and blood against excessive heat. In some embodiments, during operation, tissue and/or blood outside the treatment area but within 5 cm of the treatment area experiences a temperature increase of no greater than 20° C. and tissue and/or blood at least 5 cm from the treatment area experiences a temperature increase of no greater than 10° C. for a duration greater than 10 seconds.

In various embodiments, ablation therapy provided by the vapor ablation systems of the present specification is delivered to achieve at least one of the following therapeutic objectives or endpoints for cardiac ablation:

Maintain a tissue temperature at 110° C. or less;
Ablate a cardiac tissue without damaging an esophageal tissue;
At least 10% of patients revert to normal sinus rhythm for at least 1 week;
At least 10% of patients remain in normal sinus rhythm for at least 1 week;
Decrease the number of atrial arrhythmia episodes by at least 5% relative to the number of pre-treatment atrial arrhythmia episodes;
Decrease the number of supraventricular arrhythmia episodes by at least 5% relative to the number of pre-treatment supraventricular arrhythmia episodes;
Decrease the number of ventricular arrhythmia episodes by at least 5% relative to the number of pre-treatment ventricular arrhythmia episodes;
An increase in esophageal mucosal temperature at any time during or post treatment is less than 8° C. or an esophageal mucosal temperature at any time during or post treatment is less than 45° C.;
Raise the temperature of a portion of a cardiac tissue along a circumference to greater than or equal to 60 degrees Celsius;
Maintain the temperature of an epicardium to less than or equal to 100 degrees Celsius, a phrenic nerve to less than or equal to 75 degrees Celsius or an esophagus to less than or equal to 60 degrees Celsius;
Raise the temperature of 25% of an endocardium around a circumference to greater than or equal to 60 degrees Celsius and maintain that temperature for more than 10 seconds;
Raise the temperature of 25% of a myocardium around a circumference to greater than or equal to 60 degrees Celsius and maintain that temperature for more than 10 seconds;
Reduce the number of episodes of an arrhythmia by at least 25% relative to the number of episodes of an arrhythmia prior to treatment in at least 25% of treated patients;
Reduce the need for arrhythmia medication by at least 25% relative to a need for arrhythmia medication prior to treatment in at least 25% of treated patients;
Restoration of normal sinus rhythm in at least 25% of treated patients;
Reduce incidence of permanent phrenic nerve injury post ablation to less than or equal to 25%; and
Reduce incidence of transmural permanent esophageal injury post ablation to less than or equal to 25%
Ablate the tissue to a depth of at least 25% of a contiguous circumference and at least 25% of a contiguous thickness of a PV or a left atrial wall.

The method of using a double-balloon cardiac ablation catheter in accordance with the various embodiments of the present specification may be broadly described under the tasks of positioning the catheter, occluding, pushing the blood away, creating an ablation zone, and finally monitoring with pacing. FIG. 36G is a flow chart illustrating exemplary steps under each of these tasks, which may be performed to implement a process of using the double balloon cardiac ablation catheter in accordance with the various embodiments of the present specification. These steps are mentioned under each task and provide an exemplary method of use.

Positioning

At step 36102, a contrast material is injected intravenously so as to enhance real-time imaging of blood flow. At 36104, a guide rail, such as in the form of a wire, may be passed through the vascular system of the patient, into the heart, across the septum, and into the upper pulmonary vein. This wire acts as a guide rail for the subsequent catheters. At 36106, a guide sheath is passed over the guide rail. The purpose of the guide sheath is to provide a constrained path for the ablation catheter. Using a guide sheath provides one dimension of steerability of the catheter, and is therefore useful. The ablation catheter may be forced through an S-shaped path and, when it comes out the other end, the distal tip may be curved in order to provide a second dimension of steerability. At 36108, the ablation catheter is passed over the guide rail and inside the guide sheath. When the distal tip of the ablation catheter is positioned in an antrum, just before the pulmonary vein (PV) ostium (and a guide wire is positioned inside the PV), the guide sheath is retracted to reveal the balloons.

Occlusion

At 36110, the outer balloon is inflated to a pressure within the range of 0.1 to 10 psi, and preferably in a range of 0.5 to 1 psi. Inflation greater than the given range may result in the air or $CO_2$ flowing back through the catheter via an outlet check valve. At 36112, the outer balloon is positioned into mouth of the pulmonary vein by pushing using the guide sheath or shaft of the ablation catheter. At 36114, more contrast may be added to enhance the real-time imaging. The contrast imaging may help determine if the outer balloon is in the right place and if the blood flow is effectively being occluded. An image with having a predefined color, such as white or black, may confirm absence of blood. Radiopaque markers on the surface of the outer balloon or the catheter, if present in accordance with some embodiments of the present specification, allows for visualizing the occlusion under fluoroscopy. Markers may be positioned anywhere. In some embodiments, a marker is positioned on a proximal part of the catheter where the balloon proximally attaches to the catheter, on a distal part of the catheter where the balloon distally attaches to the catheter, or along a length of the catheter between those two points and on the outside of the outer balloon. In an embodiment, a ring of markers extends around where the ablation zone may be. In an embodiment, occlusion of the pulmonary vein is documented and confirmed radiologically.

Pushing Blood Away

At 36116, the guide rail is removed and replaced with a mapping catheter. The mapping (monitoring) catheter is an extended wire with a loop at the end of the wire that is configured to sense electrically active cells. In some embodiments, a pacing catheter is used in place of the mapping catheter. A monitoring catheter passively detects electrical signals. A pacing catheter provides an electrical pulse (pacing pulse) and monitors how that signal propagates through the pulmonary vein. In both cases, the goal is to determine if the ablation has been successful in creating an electrical isolation. In an alternative approach, the mapping/pacing electrode is configured to deploy from a tip of the ablation catheter. The guide rail may be moved through the ablation catheter tip and then retracted. While retracting the guide rail, the guide rail hooks and causes the mapping/pacing electrode to deploy.

Creating Ablation Zone

Once the guide sheath, ablation catheter, and mapping/pacing catheter are in place and the outer balloon is inflated, the inner balloon is then inflated at step 36118. A physician or any other person operating the system in accordance with the present specification, may trigger inflation of the inner balloon by pressing a switch, a button, or a pedal. In response, some amount of air or $CO_2$ may be provided to partially inflate the inner balloon and/or the outer balloon. In case where they are both inflated, they may be inflated either concurrently or sequentially. In some embodiments, the outer balloon is inflated to a pressure in a range of 0.1 to 10 psi. In some embodiments, the inner balloon is inflated to a pressure in a range of 0.5 to 20 psi, and preferably within a range of 2.5 to 3.5 psi. In embodiments, the pressure within the inner balloon is always greater than that of the outer balloon during the step of ablation. In embodiments, the outer balloon is greater in volume to the inner balloon by 3 to 75 cc, and an air gap is present on the distal and proximal ends between the outer balloon and the inner balloon. The air gap provides for an insulation zone distal and proximal to the ablation zone. In embodiments, the insulation zone has a distance ranging from 0.01 mm to 20 mm.

Once the inner balloon is inflated, a generator actives a pump that pushes saline (0.9% saline) through tubing and into the ablation catheter. The amount of saline pushed is sufficient to first wet the electrodes but insufficient to fill the inner balloon. The RF electrodes are then activated to heat the saline. Steam enters the inner balloon and pushes $CO_2$ out of the inner balloon through a one-way check valve. The inner balloon further inflates, due to the influx of steam, and forms a specifically defined ablation zone with the outer balloon. The ablation zone is a portion of the outer balloon surface area that achieves a sufficient temperature to cause the ablation of tissue upon contacting that tissue. The outer balloon surface outside the ablation zone may have a temperature in a range of 37 to 60° C., and preferably in a range of 37 to 40° C., while temperature in the ablation zone may be in a range of 80 to 150° C., and preferably from 90 to 110° C. In embodiments, the ablation zone surface area is less than 50% of outer balloon surface area and at least 5% of outer balloon surface area. In some embodiments, the at least 25% of the surface area of the outer balloon is within the ablation zone.

At step 13120, steam is produced for a pre-defined period of time. The time period may be pre-defined to be in a range from a few seconds to a few minutes. In some embodiments, the range is from 15 seconds to two minutes. In one embodiment, the time period is defined to be of 20 seconds. After the pre-defined period of time, the system shuts off and stops the generation and supply of steam. A therapeutic endpoint to define the period of steaming is to raise endothelium to above 85° C., or to raise temperature of a portion of outer surface of atrium to 45° C. or more, or to a point when pacing is abrupted for more than 2 seconds and, preferably, permanently. The temperature is preferably raised to less than 10% above the esophageal temperature for no more than one minute, for safety purposes. Once therapeutic, safety, or time endpoint is reached, first the electrodes are shut off and then saline is shut off. In some embodiments, a power of 60 W is used by the generator to operate the steam and supply the saline. The wattage may be increased or modified depending on the electrode. In some embodiments, the temperature of the steam may be controlled based on the flow of the saline. As a result, if the flow rate of saline is low, the energy level is adjusted and lowered to prevent low impedance faults.

The saline flow rate may also depend on size of the electrode, including the length, width, and periphery of the electrode; and the power supplied. Generation of steam results in transfer of heat energy from the inner balloon through the outer balloon to ablate the target tissue. In some embodiments, contact of the inner and outer balloons at the ablation zone is documented and confirmed using fluoroscopy, 3D mapping and/or endoscopy. In some embodiments, one or more sensors in the ablation zone are utilized to monitor contact of the inner and outer balloons. In embodiments, the temperature of the inner balloon is monitored. During and after ablation, the temperature and pressure in the outer balloon is monitored to maintain at desired therapeutic values.

At step 36122, electrodes/saline are shut off, resulting in an almost instant collapse of the inner balloon. In some embodiments, at this point $CO_2$ may be automatically injected to maintain a volume of or a pressure in the outer balloon. Volume of the outer balloon is maintained so that the ablation step is repeated (if required) wherein heat is delivered for a second duration. In some embodiments, the second duration ranges between 50% and 250% of the first duration. In one embodiment, the inner balloon is configured to decrease in volume, without applying negative pressure, after terminating RF energy to the electrodes/or flow of saline. In one embodiment, the outer balloon is configured to automatically receive an input of fluid (such as $CO_2$) after terminating electrodes/saline without measuring for pressure, temperature, or volume changes.

Monitoring Through Pacing

At step 13224, successful ablation is confirmed by mapping/pacing. The mapping catheter passively detects electrical signals. The pacing catheter provides an electrical pulse (pacing pulse) and monitors how that signal propagates through the pulmonary vein. In both cases, the goal is to determine if the ablation has been successful in creating an electrical isolation.

At step 13226, the ablation catheter is re-sheathed and positioned out of the way. The guide rail is then repositioned for a different pulmonary vein, in order to repeat the whole process, if required.

In some embodiments, another balloon, in addition to the two (inner and outer) balloons is used for ablation. Referring now to FIG. 36H, an elongate catheter body 36212 has a proximal end, a distal end, an outer catheter 36215 and an inner catheter 36250. A handle is disposed at the proximal end of the body 36212. In some embodiments, the outer and inner catheters 36215, 36250 are coaxial. In alternate embodiments, the outer and inner catheters 36215, 36250 are eccentric. In another embodiment the outer and inner catheters 36215, 36250 are replaced by MLE. In an embodiment, the configuration of the different system components of FIG. 36H is similar to those described in context of FIGS. 26A to 26O. The similar components are not described again here, for the sake of brevity.

The configuration of FIG. 36H has an additional element in the form of a second balloon 36290 at a distal end 36280 of catheter arrangement 36210. FIG. 36D discussed a flowchart of a plurality of exemplary steps of a method of performing left atrial appendage ablation (LAA), in accordance with some embodiments of the present specification. Embodiments of FIG. 36H are used within the process described in FIG. 36D. In embodiments, the second balloon 36290 is configured for ablation, similar to inner balloon 36265. The two balloons 36290, 36265 can be operated simultaneously or in any particular order. The second ablation balloon 36290 is inflated to a pressure between 0.5 and 10 psi and is an elongated balloon to fit a LAA anatomy. The diameter of the second ablation balloon 36290 is between 5 mm and 25 mm and the length is between 20 mm and 50 mm. The second ablation balloon 36290 can be operated using the same lumen as the inner balloon or have an independent lumen for operation. The second balloon 36290 is of a material that is more compliant than inner balloon 36265. Therefore, while the inner balloon may have a radial expansion of less than 10% at 1 atm pressure, the second balloon 36290 may have a radial expansion in a range of 10-25% at 1 atm. The second balloon 36290 is inflated with an ablative agent to ablate a portion of the LAA, in addition to the ablation performed by the inner 36265 an outer 36260 balloons. Their combined ablation function may achieve a reduction in the size of LAA cavity of greater than or equal to 5%. In different embodiments, the reduction in size of up to 10%, 20%, or 25% may be achieved, through the combined ablation of the dual balloon arrangement and the second balloon 36290.

Example Case Study

In one exemplary case study multiple ablation procedures were conducted in a frozen pig heart. The ablation procedures were conducted using a double balloon cardiac ablation test catheter 3700, shown in FIGS. 37A through 37C. Referring now to FIGS. 37A through 37C, the catheter 3700 comprises an elongate body 3712 having a proximal end 3701, a distal end 3720 and a plurality of lumens.

An insufflation port 3720 (at the proximal end of the elongate body 3712) is in fluid communication, via a cooling fluid infusion and suction lumen, with an inflatable outer balloon 3760 attached to the distal end of the elongate body. During operation, a cooling fluid pump which is in data communication with, and controlled by, a controller enables a cooling fluid (such as, but not limited to, water, air or carbon-dioxide) to be pumped into and out of the outer balloon 3760 through the cooling fluid infusion and suction lumen.

A vapor port 3725 (at the proximal end of the elongate body 3712) is in fluid communication, via a vapor lumen, with an inflatable inner balloon 3765 attached to the distal end of the elongate body and positioned within the outer balloon 3760. During operation, a vapor pump which is also in data communication with, and controlled by, the controller enables steam to be infused into the inner balloon 3765 via a plurality of vapor infusion ports positioned on the elongate body 3712 within the inner balloon 3765 causing the inner balloon 3765 to inflate and contact the inflated outer balloon 3760 proximate an area of ablation, thereby creating a hot zone on the outer balloon 3760. A guide wire 3730, shown in FIG. 37C, is inserted through a proximal opening of a guide wire lumen to enable the balloons 3760, 3765 to be positioned for ablation.

FIG. 37D shows ablation being carried out in a frozen pig heart 3740 using the catheter 3700. When both balloons 3760, 3765 were fully inflated, the hot zone on the surface of the outer balloon 3760 approached temperatures in the range of 98 to 102 degree Celsius. Since pulmonary veins were missing therefore multiple atrial ablation treatments were conducted and results obtained as follows:

One 20 second treatment resulted in an approximate treatment depth of 1 mm (that is, tissue ablated to 1 mm depth).

One 30 second treatment resulted in an approximate treatment depth of 1.75 mm.

Two 15 second treatments resulted in an approximate treatment depth of 1 mm.

Two 20 second treatments resulted in an approximate treatment depth of 2 mm.

The outer balloon 3760 did not stick to the target tissue during any of the ablation treatments. FIG. 37E shows a circumferential ablated tissue 3770 (lighter colored tissue) as a result of an ablation treatment using the catheter 3700.

In another ablation treatment, the inflated balloons 3760, 3765 were placed in an atrial appendage to create a 30 second ablation (until white discoloration of the tissue was visible). This resulted in full thickness ablation of the target tissue with stiffening of wall and collagen denaturation (at approximately 70 degrees Celsius). During the treatment, surface temperature of the outer balloon 3760 ranged from 85 to 100 degree Celsius.

Further, a macroscopic assessment of the circularity of the ablations was conducted on multiple animal-derived samples. In all cases the ablations were identified to be greater than 75% of the circumference complete, with larger than 50% ablation in the remaining tissue. At least three defined slices of tissue were used for microscopic assessment. The assessment was scored by the following ablation-related coagulation extent (Necrosis/Coagulation) according to the following scale shown in Table 3, reflecting the ablation success:

TABLE 3

0 Absent.
1 Affects up to 25% of the RSPV/left atrial myocardium wall thickness; minimal.
2 Affects between 26% and 50% of the RSPV/left atrial myocardium wall thickness; mild.
3 Affects between 51% and 75% of the RSPV/left atrial myocardium wall thickness; moderate.
4 Affects over 76% of the RSPV/left atrial myocardium wall thickness; marked.

In the sampled animals, maximal success was found with ablations of 45 seconds (s) and 60 s. Only one attempt of 45 s achieved less than maximal success, owing to a technical malfunction. The results are provided in Table 4, provided below.

TABLE 4

| Animal # | Coating | Ablation Duration | Circumferential Ablation | Depth of Necrosis | Adverse Side Effects |
|---|---|---|---|---|---|
| 53530 | BioCoat | 45 s/45 s | 4 | 4, 4, 4 | 0 |
| 53531 | KY | 45 s/45 s | 4 | 1, 4, 1 | 0 |
| 53532 | BioCoat | 60 s/60 s | 4 | 4, 4, 3 | 0 |
| 53533 | BioCoat | 30 s/30 s | 0 | 0 | n/a |

The data collected in the above research indicated that ablation scars grow in survival animals for about 48 hours, suggesting that the scores indicated in Table 4 would be closer to complete success in real life.

FIG. 38 illustrates another test catheter 3800 for performing ablation in a frozen pig heart, in accordance with some embodiments of the present specification. The catheter 3800 has an elongate body 3812 with a proximal end, a distal end and a water/vapor lumen 3815. An inflatable balloon 3860 is attached to the distal end of the body 3812. The balloon 3860 is in fluid communication with the lumen 3815 via a plurality of vapor infusion ports formed in a portion of the body 3812 lying within the balloon 3860.

At least one flexible heating chamber 3830 (such as those described with reference to FIGS. 19A through 19D), comprising a plurality of electrodes 3835, is positioned in-line within the lumen 3815. During operation, a water/vapor pump which is in data communication with, and controlled by, a controller—pumps water/saline from a sterile saline reservoir through the lumen 3815 to enter a proximal end of the at least one flexible heating chamber 3830. The at least one flexible heating chamber 3830 coverts water/saline into vapor that exits through the at least one vapor infusion port to inflate the balloon 3860. The vapor inflated balloon 3860 is enables ablation of target tissue proximate the balloon 3860.

FIG. 39 illustrates a catheter 3900, in accordance with some embodiments of the present specification. The catheter 3900 has an elongate body 3912, a proximal end and a distal end. The proximal end of the body 3912 has an inlet 3930 for a steam catheter 3925. The distal end of the body 3912 has an outlet 3935 for water/saline. An inflatable balloon 3960 is mounted proximate the distal end of the body 3912. The body 3912 has a lumen 3920 and a plurality of ports 3925 positioned within the balloon 3960. The steam catheter 3925 is introduced within the lumen 3920 via the inlet 3930.

Trans-Arterial Vapor Ablation

FIG. 40 illustrates a trans-arterial vapor ablation catheter 4000, in accordance with some embodiments of the present specification. The catheter 4000 has an elongate body 4012 having a proximal end and a distal end. An electrical cable 4050 supplies electrical power at a handle 4025 at the proximal end of the body 4012. A positioning or occlusion element such as, for example, an inflatable balloon 4060 is attached proximate the distal end of the elongate body 4012. The inflatable balloon 4060 is in fluid communication, via a first lumen, with a balloon inflation/deflation port 4020 at the handle 4025. During operation, a fluid pump which is in data communication with, and controlled by, a controller enables a fluid (such as, but not limited to, water, air or carbon-dioxide) to be pumped into and out of the balloon 4060 through the first lumen.

At least one vapor delivery port 4030 is located at the distal end of the body 4012 and distal to the balloon 4060. The vapor delivery port 4030 is in fluid communication, via a second lumen, with a saline port 4035 at the handle 4025. In some embodiments, at least one flexible heating chamber 4040 (such as those described with reference to FIGS. 19A through 19D), comprising a plurality of electrodes 4042, is positioned in-line within the second lumen. During operation, a water/vapor pump which is also in data communication with, and controlled by, the controller pumps water/saline from a sterile saline reservoir through the second lumen to enter a proximal end of the at least one flexible heating chamber 4040. The at least one flexible heating chamber 4040 coverts water/saline into vapor that exits through the vapor delivery port 4030 to ablate target tissue proximate the port 4030.

In some embodiments, the at least one flexible heating chamber 4040 is positioned in-line within the second lumen such that the proximal end of the heating chamber 4040 lies proximal from a proximal end of the balloon 4060 and a distal end of the heating chamber 4040 lies distal to a distal end of the balloon 4060. In other words, the proximal and distal ends of the chamber 4040 extend beyond the respective proximal and distal ends of the balloon 4060, in some embodiments. In some embodiments, the at least one flexible heating chamber 4040 is positioned in-line within the second lumen such that the plurality of electrodes 4042 are at least partially inside the balloon 4060.

FIG. 41A is a flowchart of a plurality of exemplary steps of a method of performing trans-arterial vapor ablation of a tumor, in accordance with some embodiments of the present specification. At step 4105, a trans-arterial vapor ablation catheter, such as catheter 4000 of FIG. 40, is placed into an artery supplying blood to a tumor. FIG. 41B illustrates the catheter 4000 (of FIG. 40) being deployed into an artery 4106 supplying blood to a tumor 4107 in a liver 4108, in accordance with an embodiment of the present specification.

At step 4110, the balloon 4060 of the catheter 4000 is inflated to occlude a flow of blood into the artery 4106. Optionally, at step 4115, a radiopharmaceutical dye is injected to obtain an arteriogram to check accurate placement of the catheter, to obtain a perfusion scan of the tumor 4107 and to highlight the tumor vasculature. At step 4120, vapor is administered to ablate the artery 4106 supplying blood to the tumor 4107 and an adequacy of ablation is ascertained by measuring the degree of washout of the radiopharmaceutical dye from the tumor vasculature. Optionally, at step 4125, a radiopharmaceutical dye is injected to obtain an arteriogram or perfusion scan to check for adequacy of ablation. If needed, vapor ablation of step 4120 is repeated.

Optionally, at step 4130, a chemotherapeutic, an embolizing or a radioactive agent is administered in conjunction with vapor ablation. Optionally, at step 4135, pressure in the artery 4106 is maintained below 5 atm. In one embodiment, liquid $CO_2$ is insufflated to displace the blood before insufflating vapor. In another embodiment, carbonated saline is used to generate vapor and $CO_2$ simultaneously to ablate an artery. The above device and method can be used to ablate an artery, a vein or a cardiac stricture such as a left atrial appendage.

FIG. 42A illustrates a mapping member 4200 in a loop configuration in accordance with some embodiments of the present specification. The mapping member 4200 comprises a semi-flexible, elongate wire or catheter 4201 with a plurality of electrodes 4202 positioned on the wire or catheter 4201. The mapping member 4200 is configured in a loop or lasso-loop shape.

FIG. 42B illustrates a flexible, loop shaped mapping member 4210 extending from a distal end of a double balloon catheter 4215, in accordance with some embodiments of the present specification. The mapping member 4210 includes a flexible wire or catheter 4211 with a plurality of electrodes 4212 and extends distally away from an outer surface of the outer balloon 4217.

Too great of a distance of the mapping member from an ablation zone may cause difficulty in pacing or sensing while ablating due to a short length of excitable tissue in the pulmonary vein. Therefore, in some embodiments, a mapping member is configured to be positioned such that the pacing/sensing electrodes are closer to the ablation zone, proximate an upper hemisphere of the outer balloon. FIG. 42C illustrates a flexible mapping member 4230 comprising a flexible wire or catheter 4231 having a vertical loop 4233 and a horizontal loop 4234 with a plurality of electrodes 4232 on the wire or catheter 4231, in accordance with some embodiments of the present specification. In embodiments, the electrodes 4232 are positioned on the horizontal loop 4234. The vertical loop has a first diameter D1 that, in some embodiments, is in a range of 5 mm to 20 mm. The horizontal loop has a second diameter D2 that, in some embodiments, is in a range of 10 mm to 40 mm. In some embodiments, diameter D1 is equal to approximately half of diameter D2. The configuration of the mapping member 4230 allows a user to pull the horizontal loop 4234 over the upper hemisphere of an outer balloon (or "nose" of a catheter) to be able to pace and sense close to the ablation zone.

FIG. 42D illustrates a flexible mapping member 4240, comprising a flexible wire or catheter 4241 having a vertical loop 4243 and a horizontal loop 4244 with a plurality of electrodes 4242 on the wire or catheter 4241, extending from a distal end of a double balloon catheter 4245, in accordance with some embodiments of the present specification. In embodiments, the electrodes 4242 are positioned on the horizontal loop 4244. In embodiments, the mapping member is slowly retracted to pull the horizontal loop 4244 over the "nose" of the catheter 4245 or upper hemisphere of the outer balloon 4247 to get close to an ablation zone 4249. The outer balloon 4247 has a spherical shape.

FIG. 42E illustrates a flexible mapping member 4250, comprising a flexible wire or catheter 4251 having a vertical loop 4253 and a horizontal loop 4254 with a plurality of electrodes 4252 on the wire or catheter 4251, being pulled down onto a distal end of a double balloon catheter 4255, in accordance with some embodiments of the present specification. In embodiments, the electrodes 4252 are positioned on the horizontal loop 4254. In embodiments, the mapping member is slowly retracted to pull the horizontal loop 4254 over the "nose" of the catheter 4255 or upper hemisphere of the outer balloon 4257 to get close to an ablation zone 4259. The outer balloon 4257 has a pear shape, allowing the electrodes 4252 of the horizontal loop 2554 to get close to the ablation zone 4259.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of ablating cardiac tissue, the method comprising:

positioning a catheter proximate a cardiac tissue of a patient, wherein the catheter comprises an elongate body having a lumen, a proximal end and a distal end and wherein an outer balloon and an inner balloon are positioned at the distal end such that the inner balloon is positioned within the outer balloon;

inflating the outer balloon with a first fluid to increase a pressure of the outer balloon to a first outer balloon pressure;

infusing heated vapor into the inner balloon to increase a pressure of the inner balloon to a first inner balloon pressure, wherein infusing heated vapor into the inner balloon creates an ablation zone and wherein a surface area of the ablation zone is defined by a portion of the inner balloon contacting a portion of the outer balloon to thereby allow for heat transfer from the heated vapor in the inner balloon through the ablation zone to the cardiac tissue;

maintaining the first inner balloon pressure for a first period of time to ablate the cardiac tissue;

stopping the infusion of heated vapor, wherein stopping the infusion of heated vapor causes the pressure of the inner balloon to decrease to a second inner balloon pressure; and deflating the outer balloon to a second outer balloon pressure.

2. The method of claim 1, wherein the cardiac tissue is a pulmonary vein, a portion of a pulmonary vein, a pulmonary vein ostium, an atrium, tissue proximate to a pulmonary vein antrum, or a left atrial appendage.

3. The method of claim 2, further comprising documenting a degree of pulmonary vein occlusion achieved by inflating the outer balloon.

4. The method of claim 1, wherein the first outer balloon pressure is between 0.01 atm and 5 atm.

5. The method of claim 1, further comprising inflating the inner balloon with a second fluid prior to infusing the heated vapor into the inner balloon, wherein the second fluid is air or $CO_2$.

6. The method of claim 1, wherein the first period of time is between 1 second and 5 minutes.

7. The method of claim 6, wherein the first outer balloon pressure is maintained for the first period of time.

8. The method of claim 1, wherein the surface area of the ablation zone is a function of a surface area of tissue positioned at a junction between the patient's pulmonary vein and the patient's left atrium.

9. The method of claim 1, further comprising removing a fluid created by a condensation of the heated vapor in the inner balloon, wherein the removal of the fluid decreases the pressure of the inner balloon to a third inner balloon pressure and wherein the third inner balloon pressure is less than or equal to the first inner balloon pressure.

10. The method of claim 1, wherein the catheter comprises a plurality of electrodes positioned proximate the distal end and wherein the heated vapor is generated by directing saline through the lumen and over the plurality of electrodes.

11. The method of claim 1, further comprising documenting a degree of removing an occlusion of the pulmonary vein after deflating the outer balloon.

12. The method of claim 1 wherein the first fluid is air or $CO_2$.

13. The method of claim 1, wherein the heated vapor comprises steam and wherein a temperature of the ablation zone is between 60° C. to 110° C.

14. The method of claim 1, further comprising placing a guide wire or pacing catheter into a heart of the patient and placing the catheter over the guide wire or pacing catheter.

15. The method of claim 14, further comprising sensing or stimulating a pulmonary vein using the guide wire or pacing catheter to determine a degree of pulmonary vein isolation.

16. The method of claim 1, wherein a distal tip of the catheter is configured to deflect from a linear configuration to a curved configuration, wherein the curved configuration is defined by the distal tip being adapted to turn up to 150 degrees through a radius ranging from 0.5 to 2.5 inches.

17. The method of claim 1, wherein the inflated outer balloon is in contact with a portion of an ostium of a pulmonary vein and occludes at least a portion of the pulmonary vein 2 mm to 15 mm distal to the pulmonary vein ostium.

18. The method of claim 1, wherein the ablation zone has a width of 2 mm to 15 mm and wherein the ablation zone has a curved length at least partially defined by an extent of contact between the inflated outer balloon and a surface of the cardiac tissue.

19. The method of claim 1, wherein a distance between an outer surface of the inflated outer balloon and an outer surface of the uninflated inner balloon is in a range of 1 mm to 25 mm.

20. The method of claim 1, further comprising using at least one of fluoroscopy, three dimensional mapping, or an endoscopic procedure to determine an extent of contact of between at least two of the inner balloon, the outer balloon, and the cardiac tissue.

21. The method of claim 1, wherein the catheter further comprises at least one sensor.

22. The method of claim 21, wherein the at least one sensor is configured to monitor contact of the inner balloon with the outer balloon or configured to monitor a temperature or pressure of the outer balloon or a temperature or pressure of the inner balloon.

23. The method of claim 1, further comprising introducing the catheter through a venous puncture in a femoral vein of the patient and advancing the catheter into a left atrium of the patient and into a pulmonary vein or left atrial appendage through a trans-septal puncture.

24. The method of claim 1, wherein the ablation zone is positioned away from a source of production of the heated vapor no further than 100 mm.

25. The method of claim 1, wherein the ablation zone is only created when a pressure opposing a surface of the outer balloon is greater than 0.1 psi.

26. The method of claim 1, further comprising repeating steps to ablate cardiac tissue for a second period of time, wherein the second period of time is equal to 50% to 250% of the first period of time.

27. The method of claim 1, wherein the ablation is performed to treat atrial fibrillation or ablate a left atrial appendage in the patient.

28. The method of claim 1, wherein, upon being inflated, the outer balloon has a pear-shaped configuration, wherein the pear-shaped configuration comprises a proximal body that narrows into a tapered distal end.

29. The method of claim 1, wherein: upon being inflated, a shape of the outer balloon is defined by a curve of a surface of the outer balloon that is further defined by a plane intersecting an entire length of the catheter, wherein the curve is characterized by a first point, a second point, and a third point sequentially positioned, and extending along the length of the catheter, between a proximal point and a distal point, wherein a first slope between the proximal point and first point has a first value, a second slope between the first point and second point has a second value, a third slope between the second point and the third point has a third value, a fourth slope between the third point and distal point has a fourth value, and wherein an absolute value of the first value is greater than an absolute value of the second value, an absolute value of the third value or an absolute value of the fourth value, the absolute value of the second value is greater than the absolute value of the third value, and the absolute value of the fourth value is greater than the absolute value of the third value; and wherein, when inflated, the inner balloon has the shape of an oblate spheroid where the minor axis, or short axis, coincides with the longitudinal axis of the catheter and the major axis, or long axis, is perpendicular to the catheter.

30. The method of claim 1, wherein, upon the inner balloon and outer balloon being inflated, the ablation zone has a width and curved length defined by an extent of contact between the outer balloon and a portion of the cardiac tissue.

* * * * *